(12) United States Patent
Flohr et al.

(10) Patent No.: US 9,394,311 B2
(45) Date of Patent: Jul. 19, 2016

(54) TRIAZOLO COMPOUNDS AS PDE10 INHIBITORS

(71) Applicant: Hoffmann-La Roche Inc., Little Falls, NJ (US)

(72) Inventors: Alexander Flohr, Loerrach (DE); Katrin Groebke Zbinden, Liestal (CH); Bernd Kuhn, Reinach BL (CH); Christian Lerner, Binningen (CH); Markus Rudolph, Basel (CH); Herve Schaffhauser, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/552,837

(22) Filed: Nov. 25, 2014

(65) Prior Publication Data

US 2015/0148332 A1    May 28, 2015

Related U.S. Application Data

(63) Continuation of application No. PCT/EP2013/060838, filed on May 27, 2013.

(30) Foreign Application Priority Data

May 30, 2012  (EP) ..................... 12169954

(51) Int. Cl.
| C07D 249/08 | (2006.01) |
| C07D 403/06 | (2006.01) |
| C07D 403/04 | (2006.01) |
| C07D 487/04 | (2006.01) |
| C07D 471/04 | (2006.01) |

(52) U.S. Cl.
CPC ............ *C07D 487/04* (2013.01); *C07D 403/06* (2013.01); *C07D 471/04* (2013.01); *C07D 249/08* (2013.01); *C07D 403/04* (2013.01)

(58) Field of Classification Search
CPC .. C07D 249/08; C07D 233/56; C07D 231/12; C07D 249/12; A01N 43/653
USPC ................... 548/262.2; 514/210.21; 546/119; 540/599
See application file for complete search history.

(56) References Cited

U.S. PATENT DOCUMENTS 2,744,116 A    5/1956    Shreve et al.

FOREIGN PATENT DOCUMENTS

| GB | WO 2006123242 A1 * | 11/2006 | .......... C07D 401/04 |
| WO | 2008/103357 | 8/2008 | |
| WO | 2009/152825 A1 | 12/2009 | |
| WO | 2011/072697 | 6/2011 | |
| WO | 2011/150156 | 12/2011 | |
| WO | 2012/054366 A2 | 4/2012 | |
| WO | WO 2012054366 A2 * | 4/2012 | |

OTHER PUBLICATIONS

Lipinski, C., "Bioisoteric Design of conformationally restricted Pyridyltriazole Histamine H2-Receptor Antagonists" J. Med. Chem. 1983, 26 (1): pp. 1-6.*
International Search Report issued in International Application No. PCT/EP2013/060838, dated Jul. 22, 2013, in 2 pages.
Lipinski, "Bioisosteric Design of Conformationally Restricted Pyridyltriazole Histamine H2-receptor Antagonists" J. Med. Chem. 26:1-6 ( 1983).
Chemical Abstract No. 64:67832.
Japanese Laid Open Patent (Kohyo) Publication No. 2009-504592.
Japanese Laid-open Patent (Kohyo) Publication No. 2002-534519.
Japanese Laid-open Patent (Kohyo) Publication No. 2010-528991.

* cited by examiner

*Primary Examiner* — Alicia L Otton
*Assistant Examiner* — Sagar Patel

(57) ABSTRACT

The present invention provides compounds of formula (Ia) and (Ib)

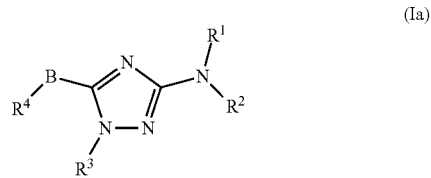

(Ia)

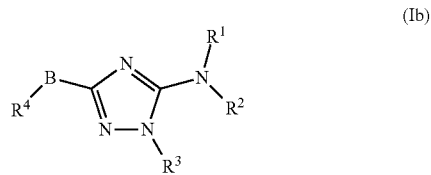

(Ib)

wherein $R^1$, $R^2$, $R^3$ and $R^4$ are as defined in the description and in the claims, as well as physiologically acceptable salts thereof. These compounds inhibit PDE10A and can be used as medicaments.

9 Claims, No Drawings

US 9,394,311 B2

TRIAZOLO COMPOUNDS AS PDE10 INHIBITORS

CROSS REFERENCE TO RELATED APPLICATIONS

This application is a continuation of PCT/EP2013060838 filed on May 27, 2013, 2013, which claims priority to EP Patent Application No. 12169954.0 filed on May 30, 2012, the disclosures of which are all incorporated herein by reference in their entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry*, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234(1): 109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J. S., et al., Eur. J. Neuroscience 2005, 2: 1070-1076). In addition

SUMMARY OF THE INVENTION

The present invention relates to compounds of formula (Ia) and (Ib)

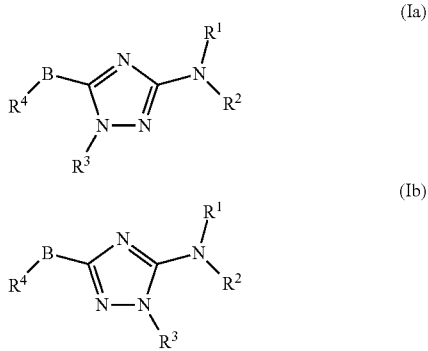

wherein

B is $C_1$-$C_4$-alkylene, $C_2$-$C_4$-alkenylene, $C_2$-$C_4$-alkynylene, $C_3$-$C_5$-cycloalkyl, $R^1$ and $R^2$, are independently selected from hydrogen, $C_1$-$C_7$-alkyl optionally substituted by $C_3$-$C_5$-cycloalkyl; $C_1$-$C_7$-hydroxyalkyl, $C_1$-$C_7$-alkoxyalkyl, $C_1$-$C_7$-haloalkyl, $C_3$-$C_5$-cycloalkyl, $R^1$ and $R^2$ together with the nitrogen atom to which they are attached, form a azaspirocycloalkyl, a bicyclic ring or heterocycloalkyl which can be substituted by 1 to 3 substituents independently selected from the group consisting of halogen, $C_1$-$C_7$-alkyl optionally substituted by $C_1$-$C_7$-alkoxy; $C_1$-$C_7$-hydroxyalkyl, $C_1$-$C_7$-alkoxy, $C_1$-$C_7$-haloalkyl, hydroxyl, —$NR^9R^{10}$ and oxo;

$R^3$ is selected from hydrogen, $C_3$-$C_5$-cycloalkyl, $C_1$-$C_7$-alkoxyalkyl, $C_1$-$C_7$-haloalkyl, heterocycloalkyl, —$(CH_2)_{0,1,2}$-aryl optionally substituted by $C_1$-$C_7$-alkoxy and $C_1$-$C_7$-alkyl optionally substituted by $C_3$-$C_5$-cycloalkyl;

$R^4$ is selected from heteroaryl optionally substituted by 1 to 3 substituents selected from halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, —$SO_2R^8$, $C_1$-$C_2$-alkoxy optionally substituted by halogen, $C_1$-$C_2$-alkoxy, heterocycloalkyl, $R^6$ and $R^8$ are selected from $C_1$-$C_7$-alkyl, $R^7$ is selected from heterocycloalkyl, $R^9$ and $R^{10}$ are independently selected from hydrogen, $C_1$-$C_7$-alkyl, C(O)—O—$C_1$-$C_7$-alkyl.

Further, the invention is concerned with a process for the manufacture of the above compounds, pharmaceutical preparations which contain such compounds as well as the use of these compounds for the production of pharmaceutical preparations.

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

DETAILED DESCRIPTION OF THE INVENTION

Unless otherwise indicated, the following definitions are set forth to illustrate and define the meaning and scope of the various terms used to describe the invention herein.

The terms "compound(s) of the formula (Ia) and (Ib)", "compound(s) of formula (Ia) and (Ib)", "compound(s) of this invention" or "compound(s) of the present invention" refer to any compound selected from the genus of compounds as defined by the formula (Ia) and (Ib) including stereoisomers, tautomers, solvates, and salts (e.g. pharmaceutically acceptable salts) thereof.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "optional" or "optionally" denotes that a subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "halogen" refers to fluorine, chlorine, bromine and iodine, more superficially fluorine, chlorine and bromine.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, hexylene.

The term "alkenylene" denotes a linear divalent hydrocarbon chain of 2 to 7 carbon atoms or a branched divalent hydrocarbon chain of 3 to 7 carbon atoms with at least one double bond. Exemplary alkenylene include ethenylene, 2,2-dimethylethenylene, propenylene, 2-methylpropenylene, butenylene, and pentenylene.

The term "alkynylene" denotes a linear divalent hydrocarbon chain of 2-6 carbon atoms or a branched divalent hydrocarbon chain of 3-6 carbon atoms with at least one triple bond. Exemplary alkynylene include ethynylene, 2,2-dimethylethynylene, propynylene, 2-methylpropynylene, butynylene, and pentynylene.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "alkoxy" denotes a group of the formula —O—R', wherein R' is an alkyl group. Examples of alkoxy moieties include methoxy, ethoxy, isopropoxy, and tert-butoxy.

The term "alkoxyalkyl" denotes an alkyl group wherein at least one of the hydrogen atoms of the alkyl group has been replaced by an alkoxy group. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "aryl" denotes a monovalent aromatic carbocyclic mono- or bicyclic ring system comprising 6 to 10 carbon ring atoms. Examples of aryl moieties include phenyl and naphthyl The term "amino" refers to a monovalent group that has a nitrogen atom with two hydrogen atoms (represented by —$NH_2$).

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "azaspirocycloalkyl" refers to a monovalent saturated 7- to 11-membered bicyclic moiety with the rings connected through one atom, containing one, two or three N heteroatoms, the remaining ring atoms being carbon atoms, wherein the point of attachment can be through either a carbon atom or a heteroatom.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The definitions described herein apply irrespective of whether the terms in question appear alone or in combination. It is contemplated that the definitions described herein may be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

Compounds of formula (Ia) and (Ib) can form pharmaceutically acceptable salts. Examples of such pharmaceutically acceptable salts are salts of compounds of formula (Ia) and (Ib) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

It will be appreciated that the compounds of general formula (Ia) and (Ib) in this invention may be derivatised at functional groups to provide derivatives which are capable of conversion back to the parent compound in vivo.

The present invention relates to compounds of formula (Ia) and (Ib)

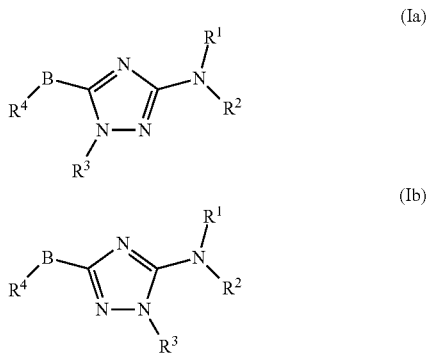

wherein

B is $C_1$-$C_4$-alkylene, $C_2$-$C_4$-alkenylene, $C_2$-$C_4$-alkynylene, $C_3$-$C_5$-cycloalkyl, $R^1$ and $R^2$, are independently selected from hydrogen, $C_1$-$C_7$-alkyl optionally substituted by $C_3$-$C_5$-cycloalkyl; $C_1$-$C_7$-hydroxyalkyl, $C_1$-$C_7$-alkoxyalkyl, $C_1$-$C_7$-haloalkyl, $C_3$-$C_5$-cycloalkyl, $R^1$ and $R^2$ together with the nitrogen atom to which they are attached, form a azaspirocycloalkyl, a bicyclic ring or heterocycloalkyl which can be substituted by 1 to 3 substituents independently selected from the group consisting of halogen, $C_1$-$C_7$-alkyl optionally substituted by $C_1$-$C_7$-alkoxy; $C_1$-$C_7$-hydroxyalkyl, $C_1$-$C_7$-alkoxy, $C_1$-$C_7$-haloalkyl, hydroxyl, —$NR^9R^{10}$ and oxo;

$R^3$ is selected from hydrogen, $C_3$-$C_5$-cycloalkyl, $C_1$-$C_7$-alkoxyalkyl, $C_1$-$C_7$-haloalkyl, heterocycloalkyl, —$(CH_2)_{0,1,2}$-aryl optionally substituted by $C_1$-$C_7$-alkoxy and $C_1$-$C_7$-alkyl optionally substituted by $C_3$-$C_5$-cycloalkyl;

$R^4$ is selected from heteroaryl optionally substituted by 1 to 3 substituents selected from halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, —$SO_2R^8$, $C_1$-$C_2$-alkoxy optionally substituted by halogen, $C_1$-$C_2$-alkoxy and heterocycloalkyl, $R^6$ and $R^8$ are selected from $C_1$-$C_7$-alkyl, $R^7$ is selected from heterocycloalkyl, $R^9$ and $R^{10}$ are independently selected from hydrogen, $C_1$-$C_7$-alkyl, C(O)—O— $C_1$-$C_7$-alkyl.

In a particular embodiment the present invention relates to compounds of formula (Ia):

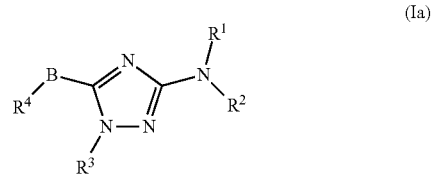

In a particular embodiment the present invention relates to compounds of formula (Ib):

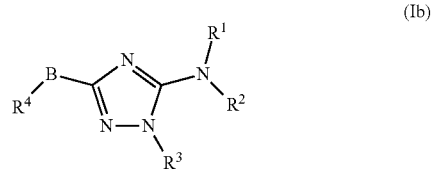

In a particular embodiment the invention relates to compounds of formula (Ia) and (Ib) wherein:

B is $C_1$-$C_4$-alkylene, $C_2$-$C_4$-alkenylene, $C_2$-$C_4$-alkynylene.

$R^1$ and $R^2$, are independently selected from hydrogen, $C_1$-$C_7$-alkyl, $C_1$-$C_7$-hydroxyalkyl, $C_1$-$C_7$-alkoxyalkyl, $C_1$-$C_7$-haloalkyl, $(CH_2)_{0,1}$—$C_3$-$C_8$-cycloalkyl, $R^1$ and $R^2$ together with the nitrogen atom to which they are attached, form a heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$-haloalkyl, hydroxyl and oxo;

$R^3$ is selected from hydrogen, $C_1$-$C_7$-alkyl, $C_1$-$C_7$-alkoxyalkyl, $C_1$-$C_7$-haloalkyl, $(CH_2)_{1,2}$—$C_3$-$C_5$-cycloalkyl, —$(CH_2)_{1,2}$-aryl optionally substituted by $C_1$-$C_7$-alkoxy, $R^4$ is selected from heteroaryl optionally substituted by 1 to 3 substituents selected from halogen, $C_1$-$C_7$-alkyl, $C_1$-$C_7$-haloalkyl, $C_1$-$C_2$-alkoxy optionally substituted by halogen, $C_3$-$C_5$-cycloalkyl, cyano.

In a particular embodiment the invention relates to compounds of formula (Ia) and (Ib) wherein, B is selected from the group consisting of $C_2$-alkylene, $C_2$-alkenylene, $C_2$-alkynylene, preferably ethylene or ethenylene.

In a particular embodiment the invention relates to compounds of formula (Ia) and (Ib) wherein, $R^1$ and $R^2$, together with the nitrogen atom to which they are attached, form a 4 to 7 membered heterocycloalkyl, preferably azetidinyl, pyrrolidinyl, piperidinyl, azepanyl.

In a particular embodiment the invention relates to compounds of formula (Ia) and (Ib) wherein $R^4$ is selected from the group consisting of:

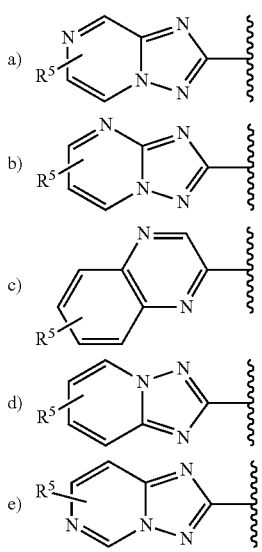

wherein R⁵ is selected from halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—R⁶—C(O)—R⁷, —SO₂R⁸, $C_1$-$C_2$-alkoxy optionally substituted by halogen, $C_1$-$C_2$-alkoxy or heterocycloalkyl, R⁶ and R⁸ are independently selected from $C_1$-$C_7$-alkyl,
R⁷ is selected from heterocycloalkyl.

In a particular embodiment the invention relates to compounds of formula (Ia) and (Ib) wherein, R⁵ is selected from hydrogen, halogen, $C_1$-$C_7$-alkyl, $C_1$-$C_7$-haloalkyl, $C_1$-$C_7$-alkoxy, cyano.

In a particular embodiment the invention relates to compounds of formula (Ia) and (Ib) wherein, R⁴ is selected from the group consisting of

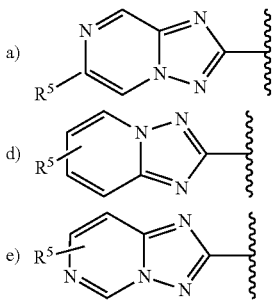

Particular compounds of the invention are selected from the group consisting of:
2-[2-(2-Ethyl-5-pyrrolidin-1-yl-2H-[1,2,4]triazol-3-yl)-vinyl]-5,8-dimethyl-[1,2,4]triazolo[1,5-a]pyrazine
2-[2-(2-Ethyl-5-pyrrolidin-1-yl-2H-[1,2,4]triazol-3-yl)-ethyl]-5,8-dimethyl-[1,2,4]triazolo[1,5-a]pyrazine
2-[2-(2-Ethyl-5-pyrrolidin-1-yl-2H-[1,2,4]triazol-3-yl)-vinyl]-5,8-dimethyl-[1,2,4]triazolo[1,5-a]pyrimidine
2-[2-(2-Ethyl-5-pyrrolidin-1-yl-2H-[1,2,4]triazol-3-yl)-ethyl]-5,7-dimethyl-[1,2,4]triazolo[1,5-a]pyrimidine
{5-[2-(5,8-Dimethyl-[1,2,4]triazolo[1,5-a]pyrazin-2-yl)-vinyl]-1-ethyl-1H-[1,2,4]triazol-3-yl}-dimethyl-amine
{5-[2-(5,8-Dimethyl-[1,2,4]triazolo[1,5-a]pyrazin-2-yl)-ethyl]-1-methyl-1H-[1,2,4]triazol-3-yl}-dimethyl-amine
5,8-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrazine
5,8-Dimethyl-2-[2-(5-pyrrolidin-1-yl-2H-[1,2,4]triazol-3-yl)-ethyl]-[1,2,4]triazolo[1,5-a]pyrazine
2-[2-(5-Azetidin-1-yl-2-methyl-2H-[1,2,4]triazol-3-yl)-vinyl]-5,8-dimethyl-[1,2,4]triazolo[1,5-a]pyrazine
2-[2-(5-Azetidin-1-yl-2-methyl-2H-[1,2,4]triazol-3-yl)-ethyl]-5,8-dimethyl-[1,2,4]triazolo[1,5-a]pyrazine
Cyclopropyl-{5-[2-(5,8-dimethyl-[1,2,4]triazolo[1,5-a]pyrazin-2-yl)-vinyl]-1-methyl-1H-[1,2,4]triazol-3-yl}-methyl-amine
Cyclopropyl-{5-[2-(5,8-dimethyl-[1,2,4]triazolo[1,5-a]pyrazin-2-yl)-ethyl]-1-methyl-1H-[1,2,4]triazol-3-yl}-methyl-amine
5,8-Dimethyl-2-[2-(2-methyl-5-pyrrolidin-1-yl-2H-[1,2,4]triazol-3-yl)-vinyl]-[1,2,4]triazolo[1,5-a]pyrazine
5,8-Dimethyl-2-[2-(2-methyl-5-pyrrolidin-1-yl-2H-[1,2,4]triazol-3-yl)-ethyl]-[1,2,4]triazolo[1,5-a]pyrazine
2-Methyl-3-[2-(2-methyl-5-pyrrolidin-1-yl-2H-[1,2,4]triazol-3-yl)-vinyl]-quinoxaline
2-Methyl-3-[2-(2-methyl-5-pyrrolidin-1-yl-2H-[1,2,4]triazol-3-yl)-ethyl]-quinoxaline
5,8-Dimethyl-2-[2-(1-methyl-5-pyrrolidin-1-yl-1H-[1,2,4]triazol-3-yl)-vinyl]-[1,2,4]triazolo[1,5-a]pyrazine
5,8-Dimethyl-2-[2-(1-methyl-5-pyrrolidin-1-yl-1H-[1,2,4]triazol-3-yl)-ethyl]-[1,2,4]triazolo[1,5-a]pyrazine
7-Chloro-2-[1-(4-methoxy-benzyl)-5-pyrrolidin-1-yl-1H-[1,2,4]triazol-3-ylethynyl]-[1,2,4]triazolo[1,5-a]pyridine
2-{2-[2-(4-Methoxy-benzyl)-5-pyrrolidin-1-yl-2H-[1,2,4]triazol-3-yl]-ethyl}-5,8-dimethyl-[1,2,4]triazolo[1,5-a]pyrazine
2-[2-(5-Azetidin-1-yl-2-methyl-2H-[1,2,4]triazol-3-yl)-ethyl]-5,7-dimethyl-[1,2,4]triazolo[1,5-a]pyrimidine
5,7-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrimidine
{5-[2-(5,8-Dimethyl-[1,2,4]triazolo[1,5-a]pyrazin-2-yl)-ethyl]-1-methyl-1H-[1,2,4]triazol-3-yl}-ethyl-methyl-amine
5,7-dimethyl-2-(2-(1-methyl-3-(pyrrolidin-1-yl)-1H-1,2,4-triazol-5-yl)ethyl)-[1,2,4]triazolo[1,5-a]pyrimidine
N-cyclopropyl-5-(2-(5,8-dimethyl-[1,2,4]triazolo[1,5-a]pyrazin-2-yl)ethyl)-N,1-dimethyl-1H-1,2,4-triazol-3-amine
6-Chloro-2-(2-(1-methyl-3-(pyrrolidin-1-yl)-1H-1,2,4-triazol-5-yl)ethyl)-[1,2,4]triazolo[1,5-a]pyridine
6-Chloro-5-methyl-2-(2-(1-methyl-3-(pyrrolidin-1-yl)-1H-1,2,4-triazol-5-yl)ethyl)-[1,2,4]triazolo[1,5-a]pyridine
6-Chloro-5-methyl-2-[2-(1-methyl-5-pyrrolidin-1-yl-1H-[1,2,4]triazol-3-yl)-ethyl]-[1,2,4]triazolo[1,5-a]pyridine
5-Methyl-2-(2-(1-methyl-3-(pyrrolidin-1-yl)-1H-1,2,4-triazol-5-yl)ethyl)-[1,2,4]triazolo[1,5-a]pyridine
Cyclopropyl-{5-[2-(5,7-dimethyl-[1,2,4]triazolo[1,5-a]pyrimidin-2-yl)-vinyl]-1-methyl-1H-[1,2,4]triazol-3-yl}-methyl-amine
7,8-Dimethyl-2-(2-(1-methyl-3-(pyrrolidin-1-yl)-1H-1,2,4-triazol-5-yl)ethyl)-[1,2,4]triazolo[1,5-a]pyridine
7,8-Dimethyl-2-(2-(1-methyl-5-(pyrrolidin-1-yl)-1H-1,2,4-triazol-3-yl)ethyl)-[1,2,4]triazolo[1,5-a]pyridine
2-[2-(2-Ethyl-5-pyrrolidin-1-yl-2H-[1,2,4]triazol-3-yl)-ethyl]-3-methyl-quinoxaline
Cyclopropyl-{5-[2-(5,7-dimethyl-[1,2,4]triazolo[1,5-a]pyrimidin-2-yl)-ethyl]-1-methyl-1H-[1,2,4]triazol-3-yl}-methyl-amine
6-Chloro-5,8-dimethyl-2-(2-(1-methyl-5-(pyrrolidin-1-yl)-1H-1,2,4-triazol-3-yl)vinyl)-[1,2,4]triazolo[1,5-a]pyridine 6-Chloro-5,8-dimethyl-2-(2-(1-methyl-5-(pyrrolidin-1-yl)-1H-1,2,4-triazol-3-yl)ethyl)-[1,2,4]triazolo[1,5-a]pyridine
5,8-Dimethyl-2-(2-(1-methyl-3-(pyrrolidin-1-yl)-1H-1,2,4-triazol-5-yl)ethyl)-[1,2,4]triazolo[1,5-a]pyridine
6-Chloro-5,8-dimethyl-2-(2-(1-methyl-3-(pyrrolidin-1-yl)-1H-1,2,4-triazol-5-yl)ethyl)-[1,2,4]triazolo[1,5-a]pyridine
2-{2-(5-(3-Fluoro-azetidin-1-yl)-2-methyl-2H-[1,2,4]triazol-3-yl)-ethyl}-5,8-dimethyl-[1,2,4]triazolo[1,5-a]pyrazine
5,6-Dimethyl-2-(2-(1-methyl-3-(pyrrolidin-1-yl)-1H-1,2,4-triazol-5-yl)ethyl)-[1,2,4]triazolo[1,5-a]pyridine
5,6,8-Trimethyl-2-(2-(1-methyl-3-(pyrrolidin-1-yl)-1H-1,2,4-triazol-5-yl)ethyl)-[1,2,4]triazolo[1,5-a]pyrazine
5,7,8-Trimethyl-2-(2-(1-methyl-3-(pyrrolidin-1-yl)-1H-1,2,4-triazol-5-yl)ethyl)-[1,2,4]triazolo[1,5-c]pyrimidine
2-{2-[5-(3-Methoxy-pyrrolidin-1-yl)-2-methyl-2H-[1,2,4]triazol-3-yl]-ethyl}-5,8-dimethyl-[1,2,4]triazolo[1,5-a]pyrazine
8-Chloro-5,7-dimethyl-2-(2-(1-methyl-3-(pyrrolidin-1-yl)-1H-1,2,4-triazol-5-yl)ethyl)-[1,2,4]triazolo[1,5-c]pyrimidine
5,7-Dimethyl-2-(2-(1-methyl-3-(pyrrolidin-1-yl)-1H-1,2,4-triazol-5-yl)ethyl)-[1,2,4]triazolo[1,5-c]pyrimidine
6-Chloro-5,8-dimethyl-2-[(1S,2S)-2-(2-methyl-5-pyrrolidin-1-yl-2H-[1,2,4]triazol-3-yl)-cyclopropyl]-[1,2,4]triazolo[1,5-a]pyridine
2-((1-Ethyl-5-(pyrrolidin-1-yl)-1H-1,2,4-triazol-3-yl)ethynyl)-5,8-dimethyl-[1,2,4]triazolo[1,5-a]pyrazine
2-(2-(1-Ethyl-5-(pyrrolidin-1-yl)-1H-1,2,4-triazol-3-yl)ethyl)-5,8-dimethyl-[1,2,4]triazolo[1,5-a]pyrazine
5,8-Dimethyl-2-[2-(2-methyl-5-piperidin-1-yl-2H-[1,2,4]triazol-3-yl)-ethyl]-[1,2,4]triazolo[1,5-a]pyrazine
5-Ethyl-8-methyl-2-(2-(1-methyl-3-(pyrrolidin-1-yl)-1H-1,2,4-triazol-5-yl)ethyl)-[1,2,4]triazolo[1,5-c]pyrimidine
5,8-Dimethyl-2-{2-[2-methyl-5-(2-methyl-pyrrolidin-1-yl)-2H-[1,2,4]triazol-3-yl]-ethyl}-[1,2,4]triazolo[1,5-a]pyrazine
6,8-Dichloro-5-methyl-2-[2-(2-methyl-5-pyrrolidin-1-yl-2H-[1,2,4]triazol-3-yl)-ethyl]-[1,2,4]triazolo[1,5-a]pyridine
2-(2-(1-Methyl-3-(pyrrolidin-1-yl)-1H-1,2,4-triazol-5-yl)ethyl)-[1,2,4]triazolo[1,5-a]pyridine-6-carbonitrile
8-Chloro-2-(2-(1-methyl-3-(pyrrolidin-1-yl)-1H-1,2,4-triazol-5-yl)ethyl)-6-(trifluoromethyl)-[1,2,4]triazolo[1,5-a]pyridine
7-Methyl-2-(2-(1-methyl-3-(pyrrolidin-1-yl)-1H-1,2,4-triazol-5-yl)ethyl)-8-nitro-[1,2,4]triazolo[1,5-a]pyridine
2-(2-(1-Methyl-3-(pyrrolidin-1-yl)-1H-1,2,4-triazol-5-yl)ethyl)-[1,2,4]triazolo[1,5-a]quinoline
5-Methyl-2-(2-(1-methyl-3-(pyrrolidin-1-yl)-1H-1,2,4-triazol-5-yl)ethyl)-[1,2,4]triazolo[1,5-a]pyrazine
5,8-Dimethyl-2-[2-(2-methyl-5-pyrrolidin-1-yl-2H-[1,2,4]triazol-3-yl)-ethyl]-[1,2,4]triazolo[1,5-c]pyrimidine
{5-[2-(5,8-Dimethyl-[1,2,4]triazolo[1,5-a]pyrazin-2-yl)-ethyl]-1-methyl-1H-[1,2,4]triazol-3-yl}-diethyl-amine
Cyclopropyl-{5-[2-(5,8-dimethyl-[1,2,4]triazolo[1,5-a]pyrazin-2-yl)-ethyl]-1-methyl-1H-[1,2,4]triazol-3-yl}-ethyl-amine
6,8-Dichloro-2-{2-[2-(4-methoxy-benzyl)-5-pyrrolidin-1-yl-2H-[1,2,4]triazol-3-yl]-ethyl}-5-methyl-[1,2,4]triazolo[1,5-a]pyridine
6,8-Dichloro-2-(2-(1-(4-methoxybenzyl)-5-(pyrrolidin-1-yl)-1H-1,2,4-triazol-3-yl)ethyl)-5-methyl-[1,2,4]triazolo[1,5-a]pyridine
6-Fluoro-2-(2-(1-methyl-3-(pyrrolidin-1-yl)-1H-1,2,4-triazol-5-yl)ethyl)-7-(trifluoromethyl)-[1,2,4]triazolo[1,5-a]pyridin-5-amine
2-(2-(1-Methyl-3-(pyrrolidin-1-yl)-1H-1,2,4-triazol-5-yl)ethyl)-5-(trifluoromethyl)-[1,2,4]triazolo[1,5-a]pyridine
8-Bromo-2-(2-(1-methyl-3-(pyrrolidin-1-yl)-1H-1,2,4-triazol-5-yl)ethyl)-6-(trifluoromethyl)-[1,2,4]triazolo[1,5-a]pyridine
2-(2-(1-Methyl-3-(pyrrolidin-1-yl)-1H-1,2,4-triazol-5-yl)ethyl)-7-(trifluoromethyl)-[1,2,4]triazolo[1,5-a]pyridine
2-(2-(1-Methyl-3-(pyrrolidin-1-yl)-1H-1,2,4-triazol-5-yl)ethyl)-[1,2,4]triazolo[1,5-a]pyridine-7-carbonitrile
6,8-Dichloro-5-methyl-2-[2-(5-pyrrolidin-1-yl-1H-[1,2,4]triazol-3-yl)-ethyl]-[1,2,4]triazolo[1,5-a]pyridine
6-Chloro-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine
5-Methyl-2-(2-(1-methyl-3-(pyrrolidin-1-yl)-1H-1,2,4-triazol-5-yl)ethyl)-[1,2,4]triazolo[1,5-a]pyridine-6-carbonitrile
8-Bromo-6-chloro-5-methyl-2-[2-(2-methyl-5-pyrrolidin-1-yl-2H-[1,2,4]triazol-3-yl)-ethyl]-[1,2,4]triazolo[1,5-a]pyridine
6-Bromo-8-chloro-5-methyl-2-(2-(1-methyl-3-(pyrrolidin-1-yl)-1H-1,2,4-triazol-5-yl)ethyl)-[1,2,4]triazolo[1,5-a]pyridine
6-Chloro-8-methanesulfonyl-5-methyl-2-[2-(2-methyl-5-pyrrolidin-1-yl-2H-[1,2,4]triazol-3-yl)-ethyl]-[1,2,4]triazolo[1,5-a]pyridine
8-Chloro-5-methyl-2-[2-(2-methyl-5-pyrrolidin-1-yl-2H-[1,2,4]triazol-3-yl)-ethyl]-[1,2,4]triazolo[1,5-a]pyridine-6-carbonitrile
8-Ethyl-5-methyl-2-(2-(1-methyl-3-(pyrrolidin-1-yl)-1H-1,2,4-triazol-5-yl)ethyl)-[1,2,4]triazolo[1,5-c]pyrimidine
6-Chloro-8-methoxy-5-methyl-2-[2-(2-methyl-5-pyrrolidin-1-yl-2H-[1,2,4]triazol-3-yl)-ethyl]-[1,2,4]triazolo[1,5-a]pyridine
6-Chloro-8-cyclopropyl-5-methyl-2-[2-(2-methyl-5-pyrrolidin-1-yl-2H-[1,2,4]triazol-3-yl)-ethyl]-[1,2,4]triazolo[1,5-a]pyridine
5-Methyl-2-[2-(2-methyl-5-pyrrolidin-1-yl-2H-[1,2,4]triazol-3-yl)-ethyl]-[1,2,4]triazolo[1,5-a]pyridine-6,8-dicarbonitrile
6-Chloro-5-methyl-2-[2-(2-methyl-5-pyrrolidin-1-yl-2H-[1,2,4]triazol-3-yl)-ethyl]-[1,2,4]triazolo[1,5-a]pyridine-8-carbonitrile
2-{6-Chloro-5-methyl-2-[2-(2-methyl-5-pyrrolidin-1-yl-2H-[1,2,4]triazol-3-yl)-ethyl]-[1,2,4]triazolo[1,5-a]pyridin-8-yl}-propan-2-ol
2-[(E)-2-(5-Azetidin-1-yl-2-methyl-2H-[1,2,4]triazol-3-yl)-vinyl]-5,8-dimethyl-[1,2,4]triazolo[1,5-c]pyrimidine
6-Bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine
5-Methyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine-6-carbonitrile
5,6-Dimethyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine
6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-ol
6-Ethyl-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine 1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-2-one
6-Chloro-2-{2-[5-(3,3-difluoro-pyrrolidin-1-yl)-2-methyl-2H-[1,2,4]triazol-3-yl]-ethyl}-5-methyl-8-trifluoromethyl-[1,2,4]triazolo[1,5-a]pyridine
5,8-Dimethyl-2-{2-[2-methyl-5-(3-methyl-azetidin-1-yl)-2H-[1,2,4]triazol-3-yl]-ethyl}-[1,2,4]triazolo[1,5-a]pyrazine
2-{2-[5-(3,3-Difluoro-azetidin-1-yl)-2-methyl-2H-[1,2,4]triazol-3-yl]-ethyl}-5,8-dimethyl-[1,2,4]triazolo[1,5-a]pyrazine
6-Chloro-5-methyl-2-(2-methyl-5-pyrrolidin-1-yl-2H-[1,2,4]triazol-3-ylethynyl)-8-trifluoromethyl-[1,2,4]triazolo[1,5-a]pyridine
2-{2-[5-(5-Aza-spiro[2.4]hept-5-yl)-2-methyl-2H-[1,2,4]triazol-3-yl]-ethyl}-5,8-dimethyl-[1,2,4]triazolo[1,5-a]pyrazine
2-{2-[5-(3,3-Difluoro-pyrrolidin-1-yl)-2-methyl-2H-[1,2,4]triazol-3-yl]-ethyl}-5,8-dimethyl-[1,2,4]triazolo[1,5-a]pyrazine
2-{2-[5-((S)-3-Fluoro-pyrrolidin-1-yl)-2-methyl-2H-[1,2,4]triazol-3-yl]-ethyl}-5,8-dimethyl-[1,2,4]triazolo[1,5-a]pyrazin
6-Chloro-8-difluoromethoxy-5-methyl-2-[2-(2-methyl-5-pyrrolidin-1-yl-2H-[1,2,4]triazol-3-yl)-ethyl]-[1,2,4]triazolo[1,5-a]pyridine
2-{2-[5-((R)-3-Fluoro-pyrrolidin-1-yl)-2-methyl-2H-[1,2,4]triazol-3-yl]-ethyl}-5,8-dimethyl-[1,2,4]triazolo[1,5-a]pyrazine
Cyclopropylmethyl-{5-[(E)-2-(5,8-dimethyl-[1,2,4]triazolo[1,5-a]pyrazin-2-yl)-vinyl]-1-methyl-1H-[1,2,4]triazol-3-yl}-methyl-amine
6-Chloro-5-methyl-2-[2-(2-methyl-5-pyrrolidin-1-yl-2H-[1,2,4]triazol-3-yl)-ethyl]-8-(2,2,2-trifluoro-ethoxy)-[1,2,4]triazolo[1,5-a]pyridine
2-{2-[5-(3-Aza-bicyclo[3.2.0]hept-3-yl)-2-methyl-2H-[1,2,4]triazol-3-yl]-ethyl}-5,8-dimethyl-[1,2,4]triazolo[1,5-a]pyrazine
5,8-Dimethyl-2-{2-[2-methyl-5-((S)-2-methyl-pyrrolidin-1-yl)-2H-[1,2,4]triazol-3-yl]-ethyl}-[1,2,4]triazolo[1,5-a]pyrazine
5,8-Dimethyl-2-{2-[2-methyl-5-((R)-2-methyl-pyrrolidin-1-yl)-2H-[1,2,4]triazol-3-yl]-ethyl}-[1,2,4]triazolo[1,5-a]pyrazine
2-[(E)-2-(5-Azepan-1-yl-2-methyl-2H-[1,2,4]triazol-3-yl)-vinyl]-5,8-dimethyl-[1,2,4]triazolo[1,5-a]pyrazine
7,8-Dimethyl-2-(2-(1-methyl-3-(pyrrolidin-1-yl)-1H-1,2,4-triazol-5-yl)ethyl)-5-(trifluoromethyl)-[1,2,4]triazolo[1,5-c]pyrimidine
1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-ol
6-Chloro-5-methyl-2-[2-(1-methyl-5-pyrrolidin-1-yl-1H-[1,2,4]triazol-3-yl)-ethyl]-8-trifluoromethyl-[1,2,4]triazolo[1,5-a]pyridine
6-Chloro-8-difluoromethoxy-5-methyl-2-[2-(1-methyl-5-pyrrolidin-1-yl-1H-[1,2,4]triazol-3-yl)-ethyl]-[1,2,4]triazolo[1,5-a]pyridine
((R)-1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-yl)-carbamic acid tert-butyl ester
5,8-Dimethyl-2-(2-methyl-5-pyrrolidin-1-yl-2H-[1,2,4]triazol-3-ylethynyl)-[1,2,4]triazolo[1,5-a]pyrazine
5,8-Dimethyl-2-[2-(2-phenyl-5-pyrrolidin-1-yl-2H-[1,2,4]triazol-3-yl)-ethyl]-[1,2,4]triazolo[1,5-a]pyrazine
2-{2-[2-(2,2-Difluoro-ethyl)-5-pyrrolidin-1-yl-2H-[1,2,4]triazol-3-yl]-ethyl}-5,8-dimethyl-[1,2,4]triazolo[1,5-a]pyrazine
5,8-Dimethyl-2-{2-[2-methyl-5-(2-methyl-pyrrolidin-1-yl)-2H-[1,2,4]triazol-3-yl]-ethyl}-[1,2,4]triazolo[1,5-c]pyrimidine
5,8-Dimethyl-2-{2-[2-methyl-5-((S)-2-methyl-pyrrolidin-1-yl)-2H-[1,2,4]triazol-3-yl]-ethyl}-[1,2,4]triazolo[1,5-c]pyrimidine
5,8-Dimethyl-2-{2-[2-methyl-5-((R)-2-methyl-pyrrolidin-1-yl)-2H-[1,2,4]triazol-3-yl]-ethyl}-[1,2,4]triazolo[1,5-c]pyrimidine
5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-a]pyrazine
5,8-Dimethyl-2-{2-[2-methyl-5-((S)-3-methyl-pyrrolidin-1-yl)-2H-[1,2,4]triazol-3-yl]-ethyl}-[1,2,4]triazolo[1,5-a]pyrazine
5,8-Dimethyl-2-{2-[2-methyl-5-((R)-3-methyl-pyrrolidin-1-yl)-2H-[1,2,4]triazol-3-yl]-ethyl}-[1,2,4]triazolo[1,5-a]pyrazine
2-[2-(2-Cyclopropylmethyl-5-pyrrolidin-1-yl-2H-[1,2,4]triazol-3-yl)-ethyl]-5,8-dimethyl-[1,2,4]triazolo[1,5-a]pyrazine
2-[2-(1-Cyclopropylmethyl-5-pyrrolidin-1-yl-1H-[1,2,4]triazol-3-yl)-ethyl]-5,8-dimethyl-[1,2,4]triazolo[1,5-a]pyrazine (b)
5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-c]pyrimidine
6-Chloro-8-(2-methoxyethoxy)-5-methyl-2-[2-(2-methyl-5-pyrrolidin-1-yl-1,2,4-triazol-3-yl)ethyl]-[1,2,4]triazolo[1,5-a]pyridine
6-Chloro-5-methyl-2-(2-(1-methyl-3-(pyrrolidin-1-yl)-1H-1,2,4-triazol-5-yl)ethyl)-8-(tetrahydro-2H-pyran-4-yloxy)-[1,2,4]triazolo[1,5-a]pyridine
4-[2-[[6-Chloro-5-methyl-2-[2-(2-methyl-5-pyrrolidin-1-yl-1,2,4-triazol-3-yl)ethyl]-[1,2,4]triazolo[1,5-a]pyridin-8-yl]oxy]ethyl]morpholine
6-Chloro-5-methyl-2-(2-(3-(pyrrolidin-1-yl)-1-(tetrahydro-2H-pyran-4-yl)-1H-1,2,4-triazol-5-yl)ethyl)-8-(trifluoromethyl)-[1,2,4]triazolo[1,5-a]pyridine
2-[2-(2-Cyclopropyl-5-pyrrolidin-1-yl-2H-[1,2,4]triazol-3-yl)-ethyl]-5,8-dimethyl-[1,2,4]triazolo[1,5-a]pyrazine
2-[2-(1-Cyclopropyl-5-pyrrolidin-1-yl-1H-[1,2,4]triazol-3-yl)-ethyl]-5,8-dimethyl-[1,2,4]triazolo[1,5-a]pyrazine (b)
2-{2-[5-((R)-2-Methoxymethyl-pyrrolidin-1-yl)-2-methyl-2H-[1,2,4]triazol-3-yl]-ethyl}-5,8-dimethyl-[1,2,4]triazolo[1,5-a]pyrazine
2-(6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-yloxy)-1-morpholinoethanone
(+5,8-Dimethyl-2-(2-(1-methyl-3-(pyrrolidin-1-yl)-1H-1,2,4-triazol-5-yl)propyl)-[1,2,4]triazolo[1,5-a]pyrazine
(R)-6-Chloro-2-(2-(3-(3-fluoropyrrolidin-1-yl)-1-methyl-1H-1,2,4-triazol-5-yl)ethyl)-5-methyl-8-(trifluoromethyl)-[1,2,4]triazolo[1,5-a]pyridine
6-Chloro-5-methyl-2-(2-(3-(pyrrolidin-1-yl)-1H-1,2,4-triazol-5-yl)ethyl)-8-(trifluoromethyl)-[1,2,4]triazolo[1,5-a]pyridine
2-{2-[5-(3-Difluoromethyl-pyrrolidin-1-yl)-2-methyl-2H-[1,2,4]triazol-3-yl]-ethyl}-5,8-dimethyl-[1,2,4]triazolo[1,5-a]pyrazine
6-Chloro-8-(difluoromethyl)-5-methyl-2-(2-(1-methyl-3-(pyrrolidin-1-yl)-1H-1,2,4-triazol-5-yl)ethyl)-[1,2,4]triazolo[1,5-a]pyridine
6-Chloro-2-(2-(1-cyclopropyl-5-(pyrrolidin-1-yl)-1H-1,2,4-triazol-3-yl)ethyl)-5-methyl-8-(trifluoromethyl)-[1,2,4]triazolo[1,5-a]pyridine 6-Chloro-2-(2-(1-cyclopropyl-3-(pyrrolidin-1-yl)-1H-1,2,4-triazol-5-yl)ethyl)-5-methyl-8-(trifluoromethyl)-[1,2,4]triazolo[1,5-a]pyridine 7-chloro-2-((1-(4-methoxybenzyl)-5-(pyrrolidin-1-yl)-1H-1,2,4-triazol-3-yl)ethynyl)quinoxaline 7-chloro-2-(2-(5-(pyrrolidin-1-yl)-1H-1,2,4-triazol-3-yl)ethyl)quinoxaline 6-Chloro-3-methyl-2-(2-methyl-5-pyrrolidin-1-yl-2H-[1,2,4]triazol-3-ylethynyl)-quinoxaline 6-Chloro-2-methyl-3-(2-methyl-5-pyrrolidin-1-yl-2H-[1,2,4]triazol-3-ylethynyl)-quinoxaline The compounds of the present invention are useful for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The compounds of the present invention are useful for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The compounds of the present invention are useful for the treatment or prophylaxis of psychotic disorders, schizophrenia, positive, negative and/or cognitive symptoms associated with schizophrenia, delusional disorder, substance-induced psychotic disorder, anxiety disorders, panis disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

In a further embodiment the present invention relates to a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound of the present invention.

In a further embodiment the present invention relates to a process for the manufacture of compounds of the present invention, which process comprises a) reacting a compound of formula (Id)

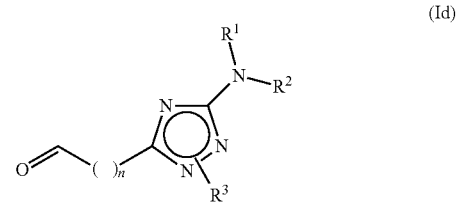

with b) a compound of formula (4a)

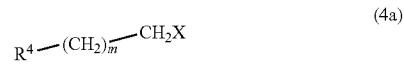

to a compound of formula (Ie)

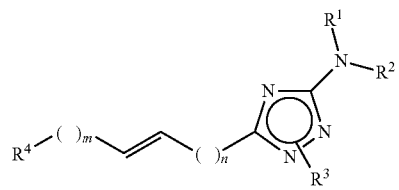

wherein n and m are 0 or 1, $R^1$, $R^2$, $R^3$, $R^4$ and X are as defined above.

General Procedures:

Compounds of formula 1 can be prepared from compound 2 according to scheme 1, typically by catalytic hydrogenation. Compound 2 can be prepared from building blocks 3 and 4 according to scheme 1. The conversion, commonly known as Wittig reaction, can be achieved in several ways. In one method, the halogenide 4 is activated by reaction with a suitable phosphine such as triphenylphosphine. The formed phosphonium salt is then reacted with the aldehyde 3 and a suitable base such as n-butyllithium, hexamethyldisilazane or DBU to the desired product 2.

Scheme 1

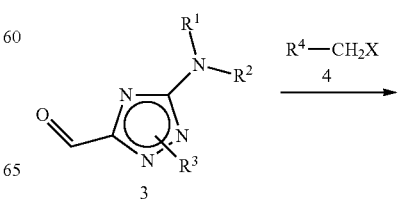

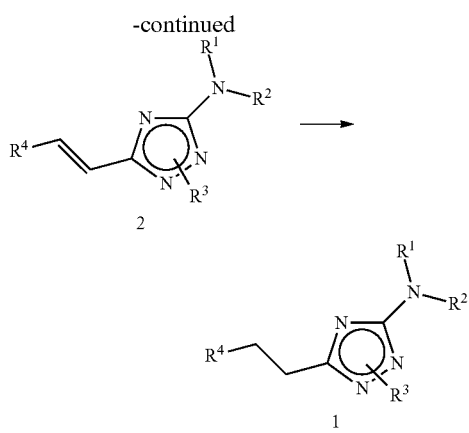

Compounds of formula 3 can be prepared according to Scheme 2: 3-Methyl-but-2-enoyl chloride is reacted with sodium isothiocyanate to form 3-methyl-but-2-enoyl isothiocyanate 8 which is then reacted with a suitable substituted amine 6 to form thiourea 9. Compound 9 is activated with an alkylation reagent such as methyl iodide and then reacted with a suitable substituted hydrazine 7 to form triazole 11. Triazole 11 is then oxidized with a suitable reagent such as ozone or potassium periodate/osmium tetroxide to form the desired aldehyde 3. If isomers are formed during the formation of 11, these can be separated by methods known in the art. Alternatively, compound 10 is reacted with hydrazine to form compound 11c which is alkylated with a suitable substituted alkylating reagent 12 to form compound 11b which is then converted in the described way to aldehyde 3b.

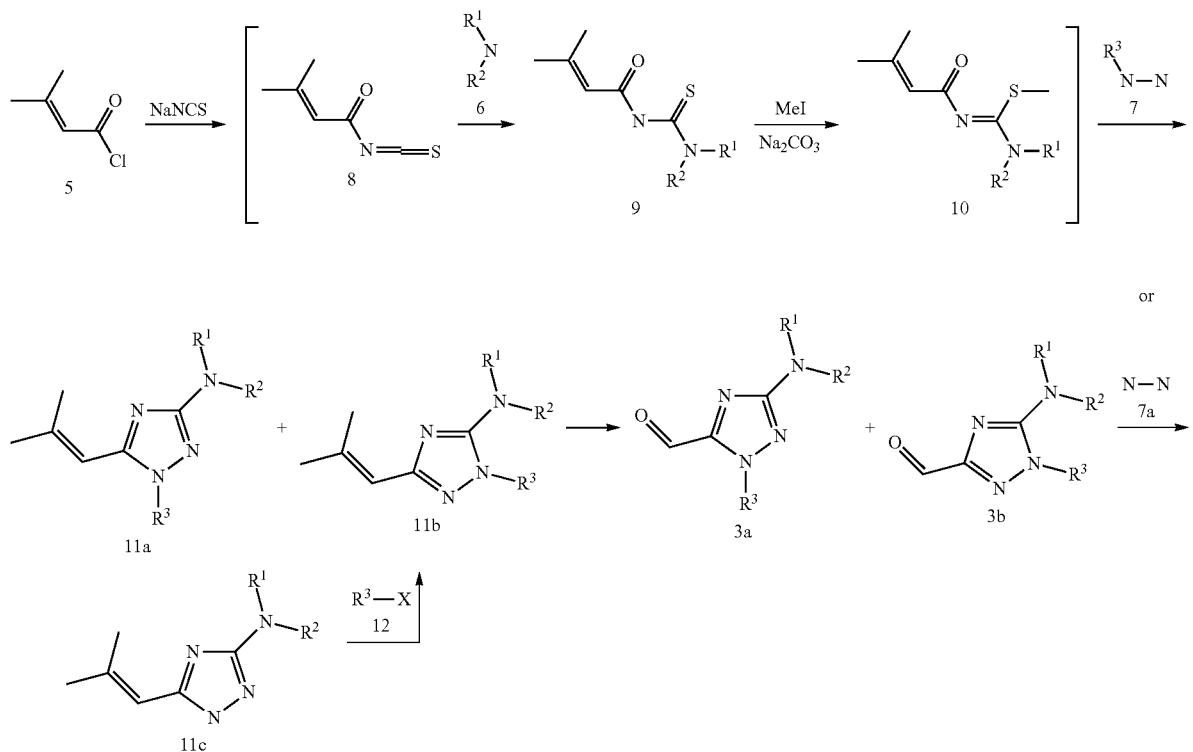

Scheme 2

Another method for preparing compounds of formula 1 is depicted in scheme 3: 3,5-Dibromo-1H-[1,2,4]triazole 13 is alkylated with a suitable substituted alkylating reagent 12 to form 14 by methods well known in the art. For example, if X is an alkylsulfonate, iodide or bromide, 12 can be deprotonated with a suitable base such as sodium hydride and then be reacted with 13. Compound 14 is then deprotonated with a suitable base such as n-butyllithium and reacted with dimethylformamide to yield aldehyde 15. Aldehyde 15 is the reacted with a suitable substituted halogenide 4 in the same way as described for compound 2 (scheme 1) to form compound 16. Compound 16 can be used in a palladium-catalyzed cross coupling reaction using a suitable substituted amine 6 and a suitable ligand, such as Xantphos, to yield the desired compound 2.

Scheme 3

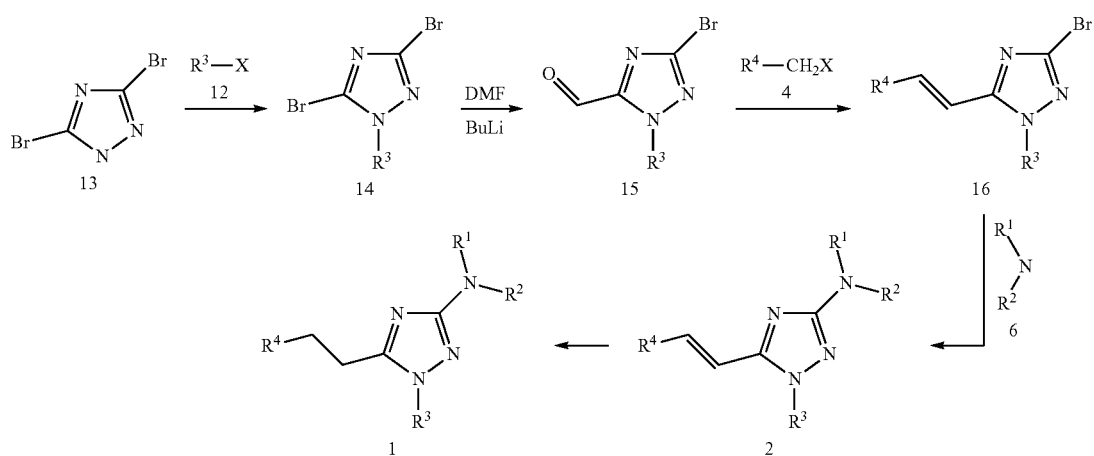

Another method for preparing compounds of formula 1 is depicted in scheme 3: A compound of formula 17 is used in a palladium-catalyzed cross coupling reaction using a suitable substituted arylhalogenide 18 and a suitable ligand, such as Xantphos, to form compound 19. Compound 19 is then converted to compound 1 by methods well known in the art. For example, 19 can by hydrogenated with a suitable catalysts such as Palladium to yield compound 1.

Scheme 4

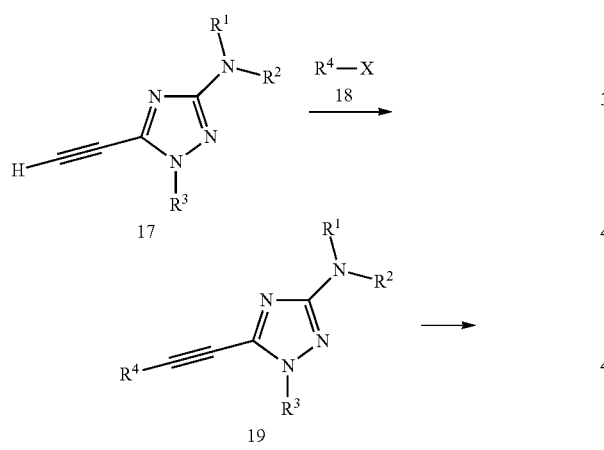

-continued

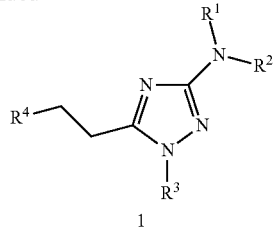

Compounds of formula 17 can be prepared according to Scheme 5: But-2-ynoyl chloride 20 is reacted with sodium isothiocyanate to form but-2-ynoyl isothiocyanate 21 which is then reacted with a suitable substituted amine 6 to form thiourea 22. Compound 22 is activated with an alkylation reagent such as methyl iodide and then reacted with a suitable substituted hydrazine 7 to form triazole 24. Triazole 11 is then deprotected with a suitable base such as sodium hydroxide to form compound 17.

Scheme 5

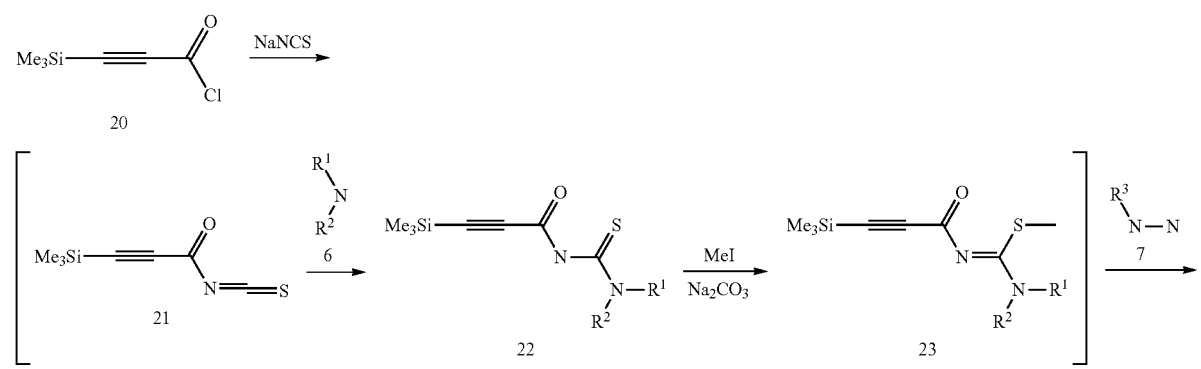

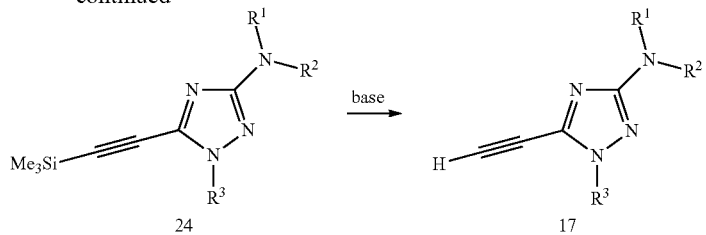

3-Methyl-but-2-enoyl chloride 5, sodium isothiocyanate, 3,5-dibromo-1H-[1,2,4]triazole 13 and but-2-ynoyl chloride 20 are commercially available. Halogenides 4 and 18, amines 6, hydrazines 7 and alkylating reagents 12 are either commercially available, or can be prepared by methods well known in the art.

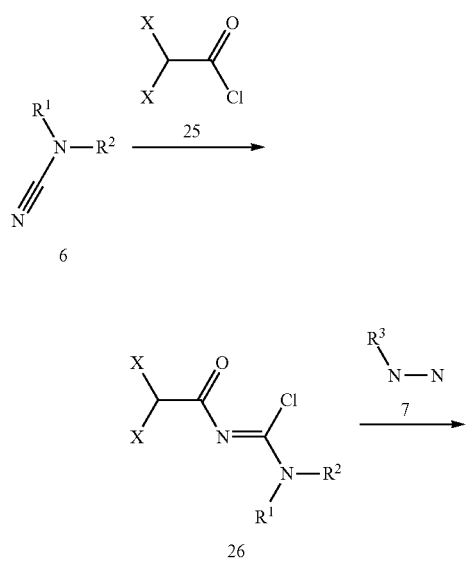

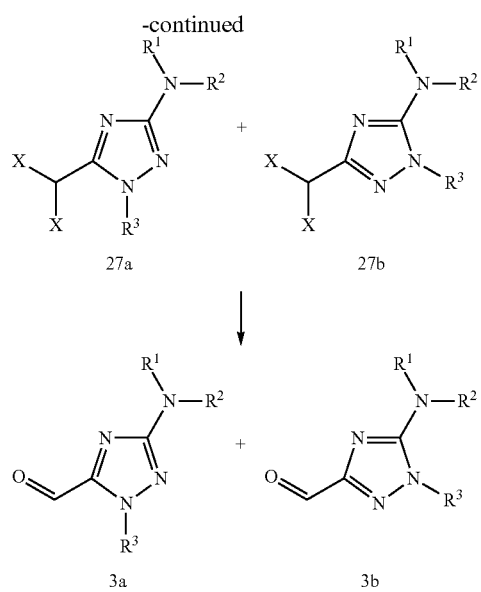

Another method for preparing compounds of formula 3 is shown in scheme 6: A compound of formula 6 is reacted with an acid chloride containing a masked aldehyde of formula 25 to obtain an intermediate of formula 26. A suitable method is to protect the aldehyde as a geminal dihalide such as X=Cl. The molecule of formula 26 is reacted with a substituted hydrazine derivative of formula 7, in presence of a suitable base, to give intermediates of formula 27a or formula 27b. Deprotection of the aldehyde by methods well known in the art gives compounds of formula 3a or formula 3b.

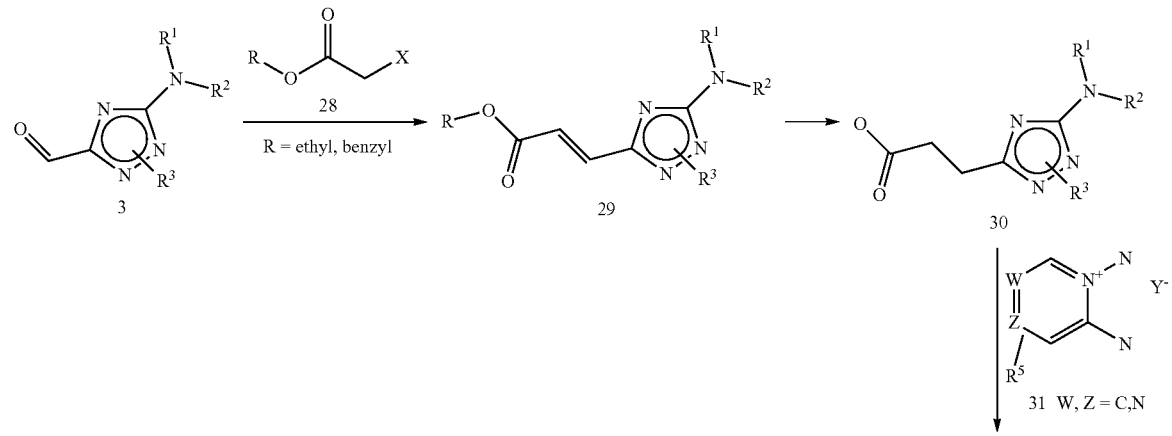

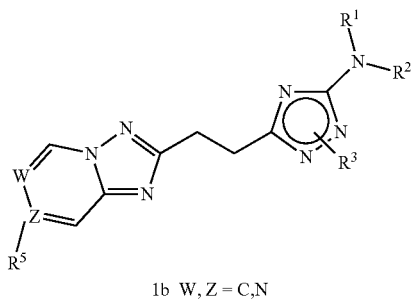

1b W, Z = C,N

Scheme 7 shows a method for the preparation of compounds of the formula 1b: A compound of the formula 3 is reacted with a suitable ester of formula 28 in a conversion commonly known as Wittig (using a phospine) or Horner-Wadsworth-Emmons (using a phosphonate) reaction to give an alkene of formula 29. Alkenes of formula 29 are then reduced and hydrolyzed to an acid of formula 30. Acids of formula 30 are reacted with salts of formula 31 in presence of a suitable coupling agent such as 0-(7-azabenzotriazol-1-yl)-N,N,N',N-tetramethyluronium hexafluorophosphate (HATU) in presence of a suitable base to give compounds of formula 1b.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (Ia) and (Ib) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation Scheme 8

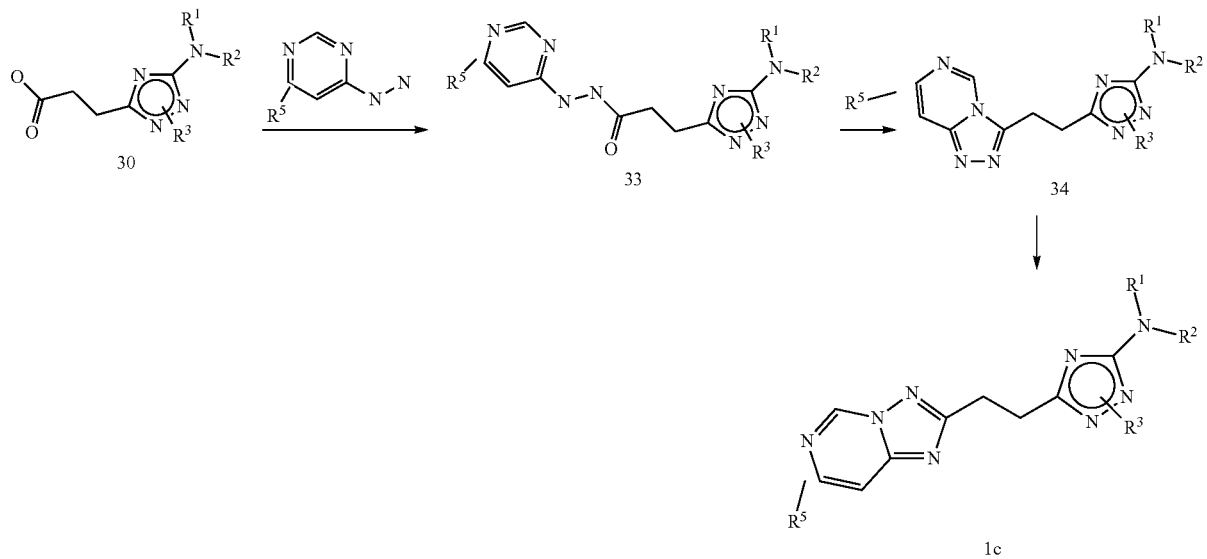

Scheme 8 shows a method for the preparation of compounds of the formula 1c: Acids of formula 30 are reacted with compounds of formula 32 in presence of a suitable coupling agent such as 0-(7-azabenzotriazol-1-yl)-N,N,N',N-tetramethyluronium hexafluorophosphate (HATU) in presence of a suitable base to give compounds of formula 33. Compounds of formula 33 are then cyclized in presence of a suitable dehydrating agent such as methyl N-(triethylammoniumsulfonyl)carbamate (Burgess reagent) to compounds of formula 34. Compounds of formula 34 are then rearranged in presence of a suitable reagent, typically an acid such as hydrochloric acid or base in a reaction commonly known as Dimroth rearrangement to compounds of formula 1c.

depends mainly on the particular use and the concentration of compound, but preferably ranges anywhere from about 3 to about 8. In one example, a compound of formula (Ia) and (Ib) is formulated in an acetate buffer, at pH 5. In another embodiment, the compounds of formula (Ia) and (Ib) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of adminis tration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount may be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (Ia) and (Ib), or a stereoisomer or pharmaceutically acceptable salt thereof. In a further embodiment includes a pharmaceutical composition comprising a compound of Formula (Ia) and (Ib), or a stereoisomer or pharmaceutically acceptable salt thereof, together with a pharmaceutically acceptable carrier or excipient.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM MgCl2/0.05 mg/ml BSA (Sigma cat. # A-7906), 50 nM cGMP (Sigma, cat. # G6129) and 50 nM [3H]-cGMP (GE Healthcare, cat. # TRK392 S.A. 13.2 Ci/mmol), 3.75 ng/well PDE10A enzyme (Enzo Life Science, Lausen, Switzerland cat # SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 µl of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer Top-Count Scintillation plate reader.

The compounds according to formula (Ia) and (Ib) have an $IC_{50}$ value below 10 µM, more specifically below 5 µM, yet more specifically below 1 µM. The following table shows data for some examples.

| Example | $IC_{50}$ [nM] |
| --- | --- |
| 1 | 11.88 |
| 2 | 5.57 |
| 3 | 205.12 |
| 4 | 10.87 |
| 6 | 334.23 |
| 7 | 17.01 |
| 8 | 1.87 |
| 10 | 1.4 |
| 11 | 42.26 |
| 12 | 263.09 |
| 13 | 27.68 |
| 14 | 5.76 |
| 15 | 104.8 |
| 16 | 61.41 |
| 17 | 6.72 |
| 18 | 2.68 |
| 19 | 476.78 |
| 20 | 5.00 |
| 21 | 91.55 |
| 22 | 20.41 |
| 23 | 103.21 |
| 24 | 23.56 |
| 25 | 42.26 |
| 26 | 62.68 |
| 27 | 0.98 |
| 28 | 2.13 |
| 29 | 55.9 |
| 30 | 57.86 |

| Example | IC$_{50}$ [nM] |
|---|---|
| 31 | 4.49 |
| 32 | 7.23 |
| 33 | 54.96 |
| 34 | 128.45 |
| 35 | 0.15 |
| 36 | 0.58 |
| 37 | 4.21 |
| 38 | 0.28 |
| 39 | 55.57 |
| 40 | 10.25 |
| 41 | 37.26 |
| 42 | 13.63 |
| 43 | 84.3 |
| 44 | 9.41 |
| 45 | 58.83 |
| 46 | 4.98 |
| 47 | 4.48 |
| 48 | 28.49 |
| 49 | 31.65 |
| 50 | 4.9 |
| 51 | 28.43 |
| 52 | 0.63 |
| 53 | 380.76 |
| 54 | 104.77 |
| 55 | 94.65 |
| 56 | 29.2 |
| 57 | 251.42 |
| 58 | 8.21 |
| 59 | 50.57 |
| 60 | 185.98 |
| 61 | 0.72 |
| 62 | 3.23 |
| 63 | 32.35 |
| 64 | 56.59 |
| 65 | 36.51 |
| 66 | 330.99 |
| 67 | 317.27 |
| 68 | 0.22 |
| 69 | 0.5 |
| 70 | 3.47 |
| 71 | 1.01 |
| 72 | 1.22 |
| 73 | 86.93 |
| 74 | 2.16 |
| 75 | 3.78 |
| 76 | 0.44 |
| 77 | 9.99 |
| 78 | 30.63 |
| 79 | 2.22 |
| 80 | 76.34 |
| 81 | 74.41 |
| 82 | 0.48 |
| 83 | 6.84 |
| 84 | 1.45 |
| 85 | 4.22 |
| 86 | 3.44 |
| 87 | 287.66 |
| 88 | 9.78 |
| 89 | 108.21 |
| 90 | 475.46 |
| 91 | 0.88 |
| 92 | 13.94 |
| 93 | 166.38 |
| 94 | 121.96 |
| 95 | 0.23 |
| 96 | 10.65 |
| 97 | 79.33 |
| 98 | 0.51 |
| 99 | 273.37 |
| 100 | 5.5 |
| 101 | 57.63 |
| 102 | 179.4 |
| 103 | 10.18 |
| 104 | 131.25 |
| 105 | 0.44 |
| 106 | 0.55 |
| 107 | 171.18 |
| 108 | 0.8 |
| 109 | 0.29 |
| 110 | 3.25 |
| 111 | 18.44 |
| 112 | 9 |
| 113 | 131.01 |
| 114 | 34.21 |
| 115 | 5.46 |
| 116 | 8.94 |
| 117a | 1.32 |
| 117b | 6.69 |
| 118 | 27.38 |
| 119 | 0.23 |
| 120 | 0.36 |
| 121 | 1.37 |
| 122 | 0.35 |
| 123a | 2.03 |
| 123b | 8.2 |
| 124 | 14.1 |
| 125 | 2.07 |
| 126 | 321.27 |
| 127 | 2.71 |
| 128 | 0.72 |
| 129 | 48.1 |
| 130 | 0.89 |
| 131 | 1.58 |
| 132 | 0.72 |
| 133 | 17.79 |
| 134 | 33.05 |
| 135 | 10.74 |
| 136 | 5.17 |

EXAMPLES

Example 1

2-[2-(2-Ethyl-5-pyrrolidin-1-yl-2H-[1,2,4]triazol-3-yl)-vinyl]-5,8-dimethyl-[1,2,4]triazolo[1,5-a]pyrazine

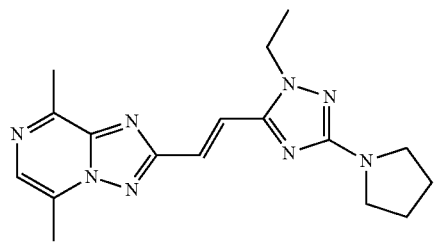 [SMILES: CCn1nc(N2CCCC2)nc1/C=C/c1nc2c(C)ncc(C)n2n1]

a) 3-Methyl-but-2-enoyl isothiocyanate

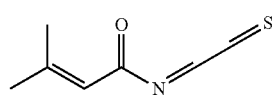

To a solution of potassium thiocyanate (10 g, 101 mmol, Eq: 1.00) and hexaethylene glycol monomethyl ether (896 mg, 830 µl, 3.02 mmol, Eq: 0.03) in dry dichloromethane (120 ml) was added dropwise at 0° C. a solution of 3-methylbut-2-enoyl chloride (12.0 g, 11.2 ml, 101 mmol, Eq: 1.00) in dry dichloromethane (20.0 ml) over 1 hour under argon atmosphere. After the addition was completed, the mixture (now light brown & turbid) was allowed to warm to 25° C. and was stirred for additional 3 hours. The mixture was filtrated, the filtrate was evaporated the residue was distilled under reduced pressure affording 3-methyl-but-2-enoyl isothiocyanate (9.989 g/70.2%) as a yellow liquid. GC-MS: m/ei=141 (M)/bp: 86° C./2 mbar b) 3-Methyl-but-2-enoic acid (pyrrolidine-1-carbothioyl)-amide

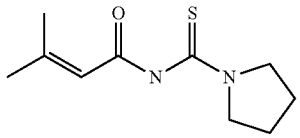

To a solution of 3-methylbut-2-enoyl isothiocyanate (500 mg, 3.54 mmol, Eq: 1.00) in benzene (10.0 ml) was added a solution of pyrrolidine (252 mg, 293 µl, 3.54 mmol, Eq: 1.00) in benzene (5.00 ml). The mixture was stirred for 30 minutes. The solvent was evaporated affording 3-methyl-but-2-enoic acid (pyrrolidine-1-carbothioyl)-amide (824 mg/110%) as a light yellow solid. MS: m/e=213.1 (M+H+)

c) 3-Methyl-but-2-enoic acid 1-methylsulfanyl-1-pyrrolidin-1-yl-meth-(Z)-ylideneamide

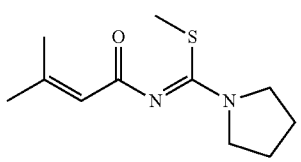

A mixture of 3-methyl-N-(pyrrolidine-1-carbonothioyl) but-2-enamide (230 mg, 1.08 mmol, Eq: 1.00), sodium carbonate (121 mg, 1.14 mmol, Eq: 1.05) and iodomethane (769 mg, 339 µl, 5.42 mmol, Eq: 5) in tetrahydrofuran (7 ml) was stirred for 18 hours at 70° C. The crude material was applied on silicagel and purified by flash chromatography over a 20 g silicagel column using heptane/ethyl acetate 50-100% as eluent affording 3-methyl-but-2-enoic acid 1-methylsulfanyl-1-pyrrolidin-1-yl-meth-(Z)-ylideneamide (119 mg/48.5%) as a light yellow liquid. MS: m/e=227.1 (M+H+)

d) 1-Ethyl-5-(2-methyl-propenyl)-3-pyrrolidin-1-yl-1H-[1,2,4]triazole

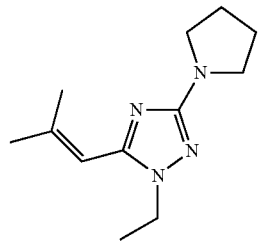 [SMILES: CCn1nc(N2CCCC2)nc1C=C(C)C]

A mixture of (Z)-methyl N-3-methylbut-2-enoylpyrrolidine-1-carbimidothioate (1.19 g, 5.26 mmol, Eq: 1.00), ethylhydrazine oxalate (2.37 g, 15.8 mmol, Eq: 3) and N,N-diisopropylethylamine (5.44 g, 7.15 ml, 42.1 mmol, Eq: 8) in dioxane (20 ml) was heated to 100° C., the resulting suspension was stirred for 3 hours at 100° C. The mixture was diluted with ethyl acetate and washed with water for 3 times. The organic layer was separated, dried over magnesium sulfate, filtrated and evaporated. The crude material was applied on silicagel and purified by flash chromatography over a 20 g silicagel column using heptane/ethyl acetate 30-70% as eluent affording 1-ethyl-5-(2-methyl-propenyl)-3-pyrrolidin-1-yl-1H-[1,2,4]triazole (441 mg/38.1%) as a light yellow oil. MS: m/e=221.0 (M+H+)

e) 2-Ethyl-5-pyrrolidin-1-yl-2H-[1,2,4]triazole-3-carbaldehyde

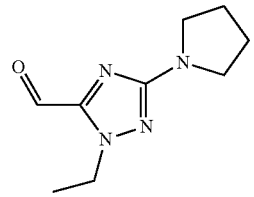

A mixture of 1-ethyl-5-(2-methylprop-1-enyl)-3-(pyrrolidin-1-yl)-1H-1,2,4-triazole (441 mg, 2.00 mmol, Eq: 1.00), osmium(VIII) oxide (382 mg, 382 µl, 60.1 µmol, Eq: 0.03), sodium periodate (1.71 g, 8.01 mmol, Eq: 4) and benzyltriethylammonium chloride (182 mg, 801 µmol, Eq: 0.4) in dioxane (21 ml) and water (6.3 ml) was stirred for 2 hours at 120° C. The mixture was diluted with ethyl acetate and washed with 2× water and brine. The organic layer was separated, dried over magnesium sulfate, filtrated and evaporated affording 2-Ethyl-5-pyrrolidin-1-yl-2H-[1,2,4]triazole-3-carbaldehyde (268 mg/69.2%) as a dark green viscous oil. MS: m/e=195.4 (M+H+)

f) (5,8-Dimethyl-[1,2,4]triazolo[1,5-a]pyrazin-2-ylmethyl)-triphenyl-phosphonium chloride

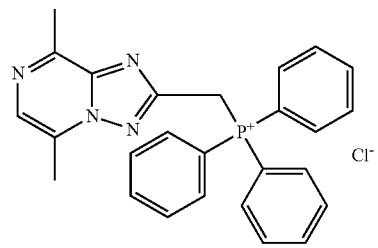 [SMILES: Cc1ncc(C)n2nc(C[P+](c3ccccc3)(c3ccccc3)c3ccccc3)nc12 ; [Cl-]]

A mixture of 2-(chloromethyl)-5,8-dimethyl-[1,2,4]triazolo[1,5-a]pyrazine (prepared as described in WO2009152825) (500 mg, 2.54 mmol, Eq: 1.00) and triphenylphosphine (667 mg, 2.54 mmol, Eq: 1.00) in acetonitrile (24.9 ml) was refluxed for 18 hours under argon atmosphere.

The solvent was evaporated the light pink solid was triturated with ether, the solid was filtered off, washed with ether and dried in vacuo affording (5,8-dimethyl-[1,2,4]triazolo[1,5-a]pyrazin-2-ylmethyl)-triphenyl-phosphonium chloride (1.292 g, 72.5%) as a light pink solid. MS-Cl: m/e=423 (M+H+)

g) 2-[2-(2-Ethyl-5-pyrrolidin-1-yl-2H-[1,2,4]triazol-3-yl)-vinyl]-5,8-dimethyl-[1,2,4]triazolo[1,5-a]pyrazine

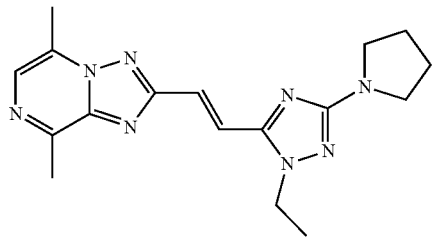 [SMILES: CCn1nc(N2CCCC2)nc1/C=C/c1nc2c(C)ncc(C)n2n1]

A mixture of ((5,8-dimethyl-[1,2,4]triazolo[1,5-a]pyrazin-2-yl)methyl)triphenylphosphonium chloride (125 mg, 272 µmol, Eq: 1.00), 1-ethyl-3-(pyrrolidin-1-yl)-1H-1,2,4-triazole-5-carbaldehyde (52.9 mg, 272 µmol, Eq: 1.00) and 1,8-diazabicyclo[5.4.0]undec-7-ene (104 mg, 103 µl, 681 µmol, Eq: 2.5) in tetrahydrofuran (6 ml) was stirred for 18 hours at 25° C. under nitrogen atmosphere. The crude material was applied on silicagel and purified by flash chromatography over a 50 g silicagel column using ethyl acetate methanol 0-10% as eluent affording 2-[2-(2-ethyl-5-pyrrolidin-1-yl-2H-[1,2,4]triazol-3-yl)-vinyl]-5,8-dimethyl-[1,2,4]triazolo[1,5-a]pyrazine (37 mg/40.1%) as a bright yellow viscous oil. MS: m/e=339.5 (M+H+)

Example 2

2-[2-(2-Ethyl-5-pyrrolidin-1-yl-2H-[1,2,4]triazol-3-yl)-ethyl]-5,8-dimethyl-[1,2,4]triazolo[1,5-a]pyrazine

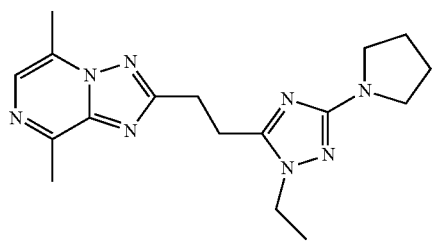 [SMILES: CCn1nc(N2CCCC2)nc1CCc1nc2c(C)ncc(C)n2n1]

A mixture of 2-(2-(1-ethyl-3-(pyrrolidin-1-yl)-1H-1,2,4-triazol-5-yl)vinyl)-5,8-dimethyl-[1,2,4]triazolo[1,5-a]pyrazine (33 mg, 97.5 µmol, Eq: 1.00) and palladium on carbon 10% (10.4 mg, 9.75 µmol, Eq: 0.1) in methanol (30 ml) was stirred for 5 hours under hydrogen atmosphere at 25° C. The catalyst was filtered off and the filtrate was evaporated affording 2-[2-(2-Ethyl-5-pyrrolidin-1-yl-2H-[1,2,4]triazol-3-yl)-ethyl]-5,8-dimethyl-[1,2,4]triazolo[1,5-a]pyrazine (32 mg 96.4%) as a yellow oil. MS: m/e=341.5 (M+H+)

Example 3

2-[2-(2-Ethyl-5-pyrrolidin-1-yl-2H-[1,2,4]triazol-3-yl)-vinyl]-5,8-dimethyl-[1,2,4]triazolo[1,5-a]pyrimidine

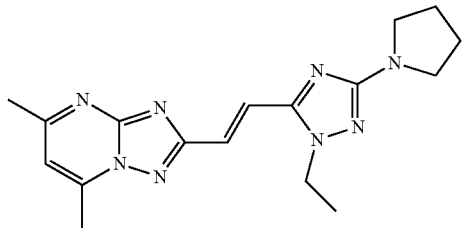 [SMILES: CCn1nc(N2CCCC2)nc1/C=C/c1nc2nc(C)cc(C)n2n1]

a) (5,7-Dimethyl-[1,2,4]triazolo[1,5-a]pyrimidin-2-ylmethyl)-triphenyl-phosphonium chloride

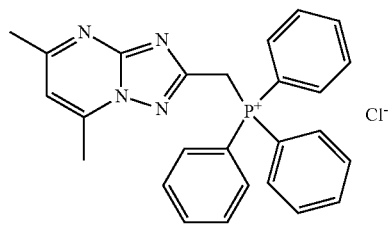 [SMILES: Cc1cc(C)n2nc(C[P+](c3ccccc3)(c3ccccc3)c3ccccc3)nc2n1 ; [Cl-]]

Was prepared in the same manner as described in General Procedure Example 1f) using 2-(chloromethyl)-5,7-dimethyl-[1,2,4]triazolo[1,5-a]pyrimidine (prepared as described in WO2009152825) (120 mg, 610 µmol, Eq: 1.00) affording (5,7-dimethyl-[1,2,4]triazolo[1,5-a]pyrimidin-2-ylmethyl)-triphenyl-phosphonium chloride (249 mg, 88.9%) as an off-white solid. MS-Cl: m/e=423.2 (M+H+), mp: 220.5 b) 2-[2-(2-Ethyl-5-pyrrolidin-1-yl-2H-[1,2,4]triazol-3-yl)-vinyl]-5,8-dimethyl-[1,2,4]triazolo[1,5-a]pyrimidine

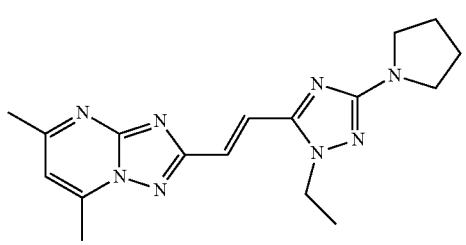 [SMILES: CCn1nc(N2CCCC2)nc1/C=C/c1nc2nc(C)cc(C)n2n1]

Was prepared in the same manner as described in General Procedure Example 1g) using ((5,7-dimethyl-[1,2,4]triazolo[1,5-a]pyrimidin-2-yl)methyl)triphenylphosphonium chloride (85 mg, 185 µmol, Eq: 1.00) and 1-ethyl-3-(pyrrolidin-1-yl)-1H-1,2,4-triazole-5-carbaldehyde (36.0 mg, 185 µmol, Eq: 1.00) as starting materials. Chromatography afforded 2-[2-(2-ethyl-5-pyrrolidin-1-yl-2H-[1,2,4]triazol-3-yl)-vinyl]-5,8-dimethyl-[1,2,4]triazolo[1,5-a]pyrazine (28 mg/44.7%) as a bright yellow viscous oil. MS: m/e=339.5 (M+H+)

Example 4

2-[2-(2-Ethyl-5-pyrrolidin-1-yl-2H-[1,2,4]triazol-3-yl)-ethyl]-5,7-dimethyl-[1,2,4]triazolo[1,5-a]pyrimidine

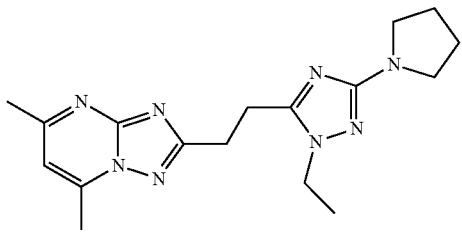 [SMILES: CCn1nc(N2CCCC2)nc1CCc1nc2nc(C)cc(C)n2n1]

Was prepared in the same manner as described in General Procedure Example 2 using 2-(2-(1-ethyl-3-(pyrrolidin-1-yl)-1H-1,2,4-triazol-5-yl)vinyl)-5,7-dimethyl-[1,2,4]triazolo[1,5-a]pyrimidine (24 mg, 70.9 µmol, Eq: 1.00). Filtration and evaporation of the solvent afforded 2-[2-(2-ethyl-5-pyrrolidin-1-yl-2H-[1,2,4]triazol-3-yl)-ethyl]-5,7-dimethyl-[1,2,4]triazolo[1,5-a]pyrimidine (10 mg/41.4%) as a white solid. MS: m/e=341.1 (M+H+)

Example 5

{5-[2-(5,8-Dimethyl-[1,2,4]triazolo[1,5-a]pyrazin-2-yl)-vinyl]-1-ethyl-1H-[1,2,4]triazol-3-yl}-dimethyl-amine

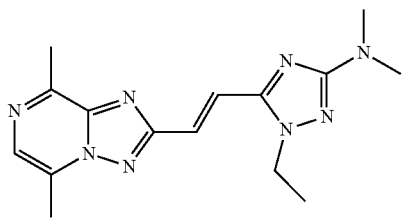 [SMILES: CCn1nc(N(C)C)nc1/C=C/c1nc2c(C)ncc(C)n2n1]

a) 1,1-Dimethyl-3-(3-methyl-but-2-enoyl)-thiourea

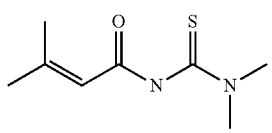

Was prepared in the same manner as described in General Procedure Example 1b) using 3-methylbut-2-enoyl isothiocyanate (2 g, 14.2 mmol, Eq: 1.00) and dimethylamine solution 2M in THF (7.08 ml, 14.2 mmol, Eq: 1.00). Evaporation of the solvent afforded 1,1-dimethyl-3-(3-methyl-but-2-enoyl)-thiourea (2.239 g/84.9%) as a yellow oil which was used without further purification in the next step. MS: m/e=187.4 (M+H+)

b) 1,1,2-Trimethyl-3-(3-methyl-but-2-enoyl)-isothiourea

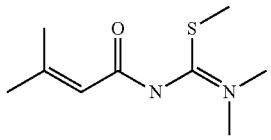

Was prepared in the same manner as described in General Procedure Example 1c) using N-(dimethylcarbamothioyl)-3-methylbut-2-enamide (2.24 g, 12.0 mmol, Eq: 1.00) as starting material. Filtration and evaporation of the solvents afforded 1,1,2-trimethyl-3-(3-methyl-but-2-enoyl)-isothiourea (3.17 g/154%) as a red oil, which was used without further purification in the next step. MS: m/e=201.4 (M+H+)

c) 5-Dimethylamino-2-methyl-2H-[1,2,4]triazole-3-carbaldehyde

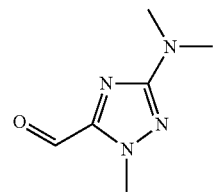

A mixture of (Z)-methyl N,N-dimethyl-N'-(3-methylbut-2-enoyl)carbamimidothioate (2.41 g, 12.0 mmol, Eq: 1.00) and methylhydrazine (5.54 g, 6.34 ml, 120 mmol, Eq: 10) was heated to 100° C. for 30 minutes. The mixture was dissolved in ethyl acetate and washed with water 3 times and once with brine. The organic layer was separated, dried over magnesium sulfate, filtrated and evaporated affording dimethyl-[1-methyl-5-(2-methyl-propenyl)-1H-[1,2,4]triazol-3-yl]-amine (824 mg/38.0%) as a yellow liquid. A mixture of N,N,1-trimethyl-5-(2-methylprop-1-enyl)-1H-1,2,4-triazol-3-amine (824 mg, 4.57 mmol, Eq: 1.00), osmium tetroxide 4% aq. (872 mg, 872 µl, 137 µmol, Eq: 0.03), sodium periodate (3.91 g, 18.3 mmol, Eq: 4) and benzyltriethylammonium chloride (416 mg, 1.83 mmol, Eq: 0.4) in dioxane (42 ml) and water (13 ml) was stirred for 2 hours at 60° C. The mixture was diluted with ethyl acetate and washed with 2× water and brine. The organic layer was separated, dried over magnesium sulfate, filtrated and evaporated affording 1.0 g dark brown oil. The crude material was applied on silicagel and purified by flash chromatography over a 50 g silicagel column using ethyl acetate/methanol 0-10% as eluent affording 5-dimethylamino-2-methyl-2H-[1,2,4]triazole-3-carbaldehyde (127 mg/60.0%) as a brown oil. MS: m/e=155.3 (M+H+)

d) {5-[2-(5,8-Dimethyl-[1,2,4]triazolo[1,5-a]pyrazin-2-yl)-vinyl]-1-ethyl-1H-[1,2,4]triazol-3-yl}-dimethyl-amine

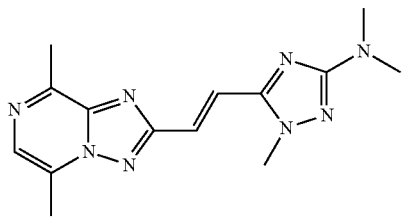 [SMILES: Cc1ncc(C)n2nc(/C=C/c3nc(N(C)C)nn3C)nc12]

Was prepared in the same manner as described in General Procedure Example 1g) using ((5,8-dimethyl-[1,2,4]triazolo[1,5-a]pyrazin-2-yl)methyl)triphenylphosphonium chloride (100 mg, 218 µmol, Eq: 1.00), 3-(dimethylamino)-1-methyl-1H-1,2,4-triazole-5-carbaldehyde (33.6 mg, 218 µmol, Eq: 1.00) as starting materials. Chromatography afforded {5-[2-(5,8-dimethyl-[1,2,4]triazolo[1,5-a]pyrazin-2-yl)-vinyl]-1-ethyl-1H-[1,2,4]triazol-3-yl}-dimethyl-amine (16 mg 24.6%) as a bright yellow viscous oil. MS: m/e=299.4 (M+H+)

Example 6

{5-[2-(5,8-Dimethyl-[1,2,4]triazolo[1,5-a]pyrazin-2-yl)-ethyl]-1-methyl-1H-[1,2,4]triazol-3-yl}-dimethyl-amine

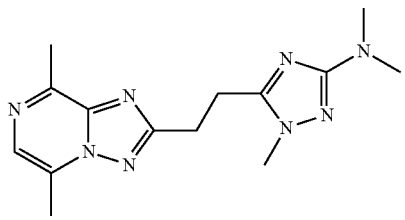 [SMILES: Cc1ncc(C)n2nc(CCc3nc(N(C)C)nn3C)nc12]

Was prepared in the same manner as described in General Procedure Example 2 using 5-(2-(5,8-dimethyl-[1,2,4]triazolo[1,5-a]pyrazin-2-yl)vinyl)-N,N,1-trimethyl-1H-1,2,4-triazol-3-amine (16 mg, 53.6 µmol, Eq: 1.00) as starting material. Filtration and evaporation of the solvent afforded {5-[2-(5,8-dimethyl-[1,2,4]triazolo[1,5-a]pyrazin-2-yl)-ethyl]-1-methyl-1H-[1,2,4]triazol-3-yl}-dimethyl-amine (12 mg/74.5%) as a colorless viscous oil. MS: m/e=301.9 (M+H+)

Example 7

5,8-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrazine

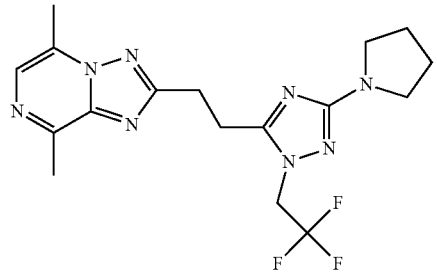 [SMILES: Cc1ncc(C)n2nc(CCc3nc(N4CCCC4)nn3CC(F)(F)F)nc12]

a) 5-(2-Methyl-propenyl)-3-pyrrolidin-1-yl-1-(2,2,2-trifluoro-ethyl)-1H-[1,2,4]triazole

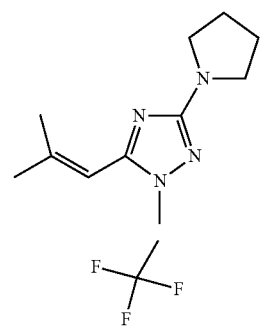

A mixture of (Z)-methyl N-3-methylbut-2-enoylpyrrolidine-1-carbimidothioate (2.515 g, 11.1 mmol, Eq: 1.00) and (2,2,2-trifluoroethyl)hydrazine (5 g, 30.7 mmol, Eq: 2.76) was stirred for 1 hour at 100° C. The mixture was dissolved in ethyl acetate and washed with water 3 times and once with brine. The organic layer was separated, dried over magnesium sulfate, filtrated and evaporated affording 5-(2-methyl-propenyl)-3-pyrrolidin-1-yl-1-(2,2,2-trifluoro-ethyl)-1H-[1,2,4]triazole (1.599 g/52.5%) as an off-white waxy solid. MS: m/e=275.4 (M+H+)

b) 5-Pyrrolidin-1-yl-2-(2,2,2-trifluoro-ethyl)-2H-[1,2,4]triazole-3-carbaldehyde

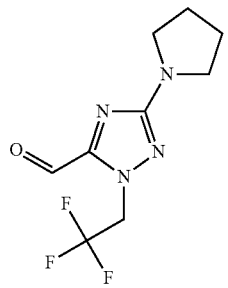 [SMILES: O=Cc1nc(N2CCCC2)nn1CC(F)(F)F]

Was prepared in the same manner as described in General Procedure Example 1e) using 5-(2-methylprop-1-enyl)-3-(pyrrolidin-1-yl)-1-(2,2,2-trifluoroethyl)-1H-1,2,4-triazole (1.599 g, 5.83 mmol, Eq: 1.00) as starting material. Extraction and evaporation of the solvents afforded 5-pyrrolidin-1-yl-2-(2,2,2-trifluoro-ethyl)-2H-[1,2,4]triazole-3-carbaldehyde (1.134 g/78.4%) as a dark brown waxy solid. MS: m/e=249.4 (M+H+)

c) 5,8-Dimethyl-2-{2-[5-pyrrolidin-1-yl-2-(2,2,2-trifluoro-ethyl)-2H-[1,2,4]triazol-3-yl]-vinyl}-[1,2,4]triazolo[1,5-a]pyrazine

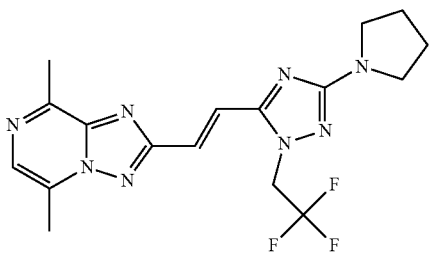 [SMILES: Cc1ncc(C)n2nc(/C=C/c3nc(N4CCCC4)nn3CC(F)(F)F)nc12]

Was prepared in the same manner as described in General Procedure Example 1g) using ((5,8-dimethyl-[1,2,4]triazolo[1,5-a]pyrazin-2-yl)methyl)triphenylphosphonium chloride (85 mg, 185 µmol, Eq: 1.00), 3-(pyrrolidin-1-yl)-1-(2,2,2-trifluoroethyl)-1H-1,2,4-triazole-5-carbaldehyde (50.6 mg, 204 µmol, Eq: 1.1) as starting materials. Chromatography afforded 5,8-dimethyl-2-{2-[5-pyrrolidin-1-yl-2-(2,2,2-trifluoro-ethyl)-2H-[1,2,4]triazol-3-yl]-vinyl}-[1,2,4]triazolo[1,5-a]pyrazine (20 mg/27.5%) as a white viscous oil. MS: m/e=393.5 (M+H+)

d) 5,8-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrazine

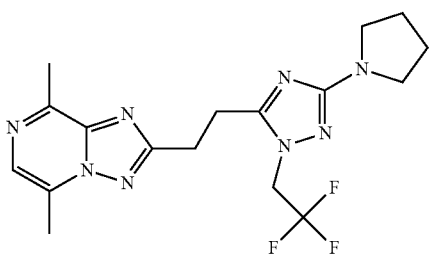 [SMILES: Cc1ncc(C)n2nc(CCc3nc(N4CCCC4)nn3CC(F)(F)F)nc12]

Was prepared in the same manner as described in General Procedure Example 2 using 5,8-dimethyl-2-(2-(3-(pyrrolidin-1-yl)-1-(2,2,2-trifluoroethyl)-1H-1,2,4-triazol-5-yl)vinyl)-[1,2,4]triazolo[1,5-a]pyrazine (20 mg, 51.0 µmol, Eq: 1.00) as starting material. The crude material was applied on a 5 g silicagel column using ethyl acetate/methanol 0-10% as eluent affording 5,8-dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrazine (11 mg/52.4%) as a white solid. MS: m/e=395.8 (M+H+)

Example 8

5,8-Dimethyl-2-[2-(5-pyrrolidin-1-yl-2H-[1,2,4]triazol-3-yl)-ethyl]-[1,2,4]triazolo[1,5-a]pyrazine

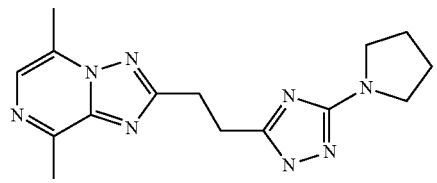 [SMILES: Cc1ncc(C)n2nc(CCc3nc(N4CCCC4)n[nH]3)nc12]

2-(2-(1-(4-methoxybenzyl)-3-(pyrrolidin-1-yl)-1H-1,2,4-triazol-5-yl)ethyl)-5,8-dimethyl-[1,2,4]triazolo[1,5-a]pyrazine (13.6 mg, 31.4 µmol, Eq: 1.00) was stirred with trifluoroacetic acid (143 mg, 96.3 µl, 1.26 mmol, Eq: 40) and anisole (61.2 mg, 61.8 µl, 566 µmol, Eq: 18) in Dichloromethane (400 µl) overnight at room-temperature. The reaction mixture was extracted with aq. sodium borohydride sat. and dichloromethane three times, dried over magnesium sulfate, filtered and evaporated to give 5,8-Dimethyl-2-[2-(5-pyrrolidin-1-yl-2H-[1,2,4]triazol-3-yl)-ethyl]-[1,2,4]triazolo[1,5-a]pyrazine (6.6 mg, 67.2%) as off-white solid.

Example 9

2-[2-(5-Azetidin-1-yl-2-methyl-2H-[1,2,4]triazol-3-yl)-vinyl]-5,8-dimethyl-[1,2,4]triazolo[1,5-a]pyrazine

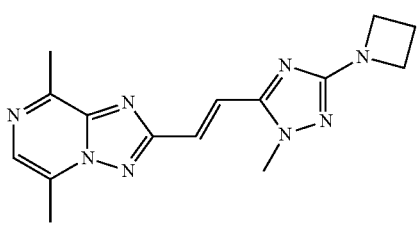 [SMILES: Cc1ncc(C)n2nc(/C=C/c3nc(N4CCC4)nn3C)nc12]

a) 2-[(E)-2-(5-Bromo-2-methyl-2H-[1,2,4]triazol-3-yl)-vinyl]-5,8-dimethyl-[1,2,4]triazolo[1,5-a]pyrazine

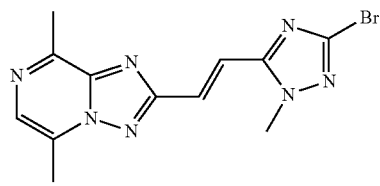 [SMILES: Cc1ncc(C)n2nc(/C=C/c3nc(Br)nn3C)nc12]

Was prepared in the same manner as described in Example 1g) using 3-bromo-1-methyl-1H-1,2,4-triazole-5-carbaldehyde (218 mg, 1.15 mmol, Eq: 1.00) and ((5,8-dimethyl-[1,2,4]triazolo[1,5-a]pyrazin-2-yl)methyl)triphenylphosphonium chloride (527 mg, 1.15 mmol, Eq: 1.00) as starting materials. Chromatography afforded 2-[(E)-2-(5-bromo-2-methyl-2H-[1,2,4]triazol-3-yl)-vinyl]-5,8-dimethyl-[1,2,4]triazolo[1,5-a]pyrazine (258 mg/67.3%) as a white solid. MS: m/e=336.0334.1 (M+H+), mp: 199.4° C.

b) 2-[2-(5-Azetidin-1-yl-2-methyl-2H-[1,2,4]triazol-3-yl)-vinyl]-5,8-dimethyl-[1,2,4]triazolo[1,5-a]pyrazine

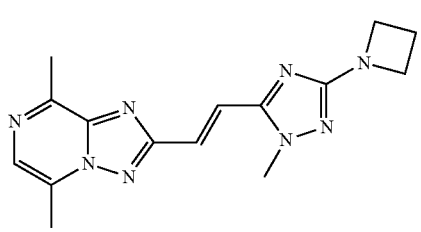

A solution of 2-(2-(3-bromo-1-methyl-1H-1,2,4-triazol-5-yl)vinyl)-5,8-dimethyl-[1,2,4]triazolo[1,5-a]pyrazine (28 mg, 83.8 µmol, Eq: 1.00) in dioxane (1 ml) was purged with argon, then sodium phenoxide (14.6 mg, 126 µmol, Eq: 1.5), 4,5-bis(diphenylphosphino)-9,9-dimethylxanthene (xantphos) (3.88 mg, 6.7 µmol, Eq: 0.08), tris(dibenzylideneacetone)dipalladium chloroform complex/Pd2(dba)3CHCl3 (3.47 mg, 3.35 µmol, Eq: 0.04) and azetidine (9.57 mg, 11.3 µl, 168 µmol, Eq: 2) were added. The vial was capped and irradiated at 140° C. for 30 minutes in the microwave oven. The crude material was applied on silicagel and purified by chromatography over a 5 g silicagel column using ethyl acetate/methanol 0-10% as eluent affording 2-[2-(5-azetidin-1-yl-2-methyl-2H-[1,2,4]triazol-3-yl)-vinyl]-5,8-dimethyl-[1,2,4]triazolo[1,5-a]pyrazine (4 mg/15.4%) as a light yellow solid. MS: m/e=311.4 (M+H+)

Example 10

2-[2-(5-Azetidin-1-yl-2-methyl-2H-[1,2,4]triazol-3-yl)-ethyl]-5,8-dimethyl-[1,2,4]triazolo[1,5-a]pyrazine

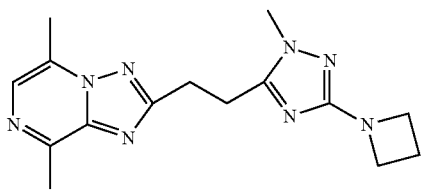 [SMILES: Cc1ncc(C)n2nc(CCc3nc(N4CCC4)nn3C)nc12]

Was prepared in the same manner as described in General Procedure Example 2 using 2-(2-(3-(azetidin-1-yl)-1-methyl-1H-1,2,4-triazol-5-yl)vinyl)-5,8-dimethyl-[1,2,4]triazolo[1,5-a]pyrazine (10 mg, 32.2 µmol, Eq: 1.00) as starting material. Filtration and evaporation afforded 2-[2-(5-Azetidin-1-yl-2-methyl-2H-[1,2,4]triazol-3-yl)-ethyl]-5,8-dimethyl-[1,2,4]triazolo[1,5-a]pyrazine (15 mg/149%) as a white solid. MS: m/e=313.4 (M+H+), mp: 103-107° C.

Example 11

Cyclopropyl-{5-[2-(5,8-dimethyl-[1,2,4]triazolo[1,5-a]pyrazin-2-yl)-vinyl]-1-methyl-1H-[1,2,4]triazol-3-yl}-methyl-amine

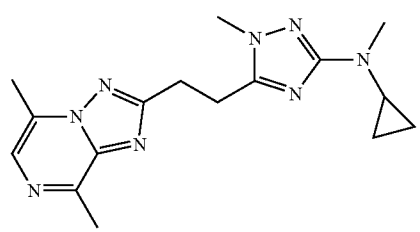 [SMILES: Cc1ncc(C)n2nc(CCc3nc(N(C)C4CC4)nn3C)nc12]

a) Cyclopropyl-methyl-[1-methyl-5-(2-methyl-propenyl)-1H-[1,2,4]triazol-3-yl]-amine

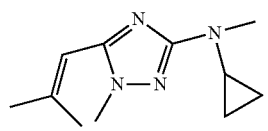

To a solution of 3-methylbut-2-enoyl isothiocyanate (500 mg, 3.54 mmol, Eq: 1.00) in Tetrahydrofuran (3.5 ml) was added a solution of N-methylcyclopropanamine (264 mg, 3.72 mmol, Eq: 1.05) in Tetrahydrofuran (3.5 ml). The mixture was stirred for 30 minutes. Sodium carbonate (394 mg, 3.72 mmol, Eq: 1.05) and iodomethane (1.01 g, 443 µl, 7.08 mmol, Eq: 2) was added and stirred overnight at 70° C. The solvent was evaporated. Methylhydrazine (1.63 g, 1.86 ml, 35.4 mmol, Eq: 10) was added and the mixture was stirred for 2 hours at 100° C. MS showed just product peak. The crude material was applied on silica gel and purified by column chromatography using heptane/ethyl acetate (0-40% ethyl acetate) as eluent affording Cyclopropyl-methyl-[1-methyl-5-(2-methyl-prop enyl)-1H-[1,2,4]triazol-3-yl]-amine (305 mg, 41.8%) as light yellow oil. MS: m/z=207.0 (M+H+)

b) 5-(Cyclopropyl-methyl-amino)-2-methyl-2H-[1,2,4]triazole-3-carbaldehyde

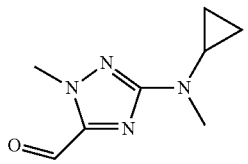

Was prepared in the same manner as described in General Procedure Example 1e) using N-cyclopropyl-N,1-dimethyl-5-(2-methylprop-1-enyl)-1H-1,2,4-triazol-3-amine (150 mg, 727 µmol, Eq: 1.00) as starting material. Extraction and evaporation of the solvents afforded 5-(Cyclopropyl-methyl-amino)-2-methyl-2H-[1,2,4]triazole-3-carbaldehyde (105 mg/80.1%) as a black semisolid.

c) Cyclopropyl-{5-[2-(5,8-dimethyl-[1,2,4]triazolo[1,5-a]pyrazin-2-yl)-vinyl]-1-methyl-1H-[1,2,4]triazol-3-yl}-methyl-amine

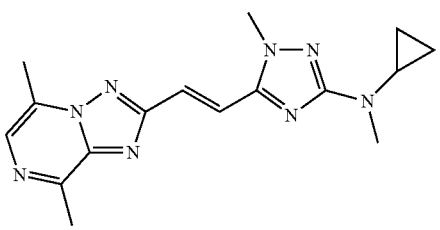 [SMILES: Cc1ncc(C)n2nc(/C=C/c3nc(N(C)C4CC4)nn3C)nc12]

Was prepared in the same manner as described in General Procedure Example 1g) using ((5,8-dimethyl-[1,2,4]triazolo[1,5-a]pyrazin-2-yl)methyl)triphenylphosphonium chloride (127 mg, 277 µmol, Eq: 1.00) and 3-(cyclopropyl(methyl)amino)-1-methyl-1H-1,2,4-triazole-5-carbaldehyde (50 mg, 277 µmol, Eq: 1.00) as starting materials. Chromatography afforded Cyclopropyl-{5-[2-(5,8-dimethyl-[1,2,4]triazolo[1,5-a]pyrazin-2-yl)-vinyl]-1-methyl-1H-[1,2,4]triazol-3-yl}-methyl-amine (30 mg, 33.3%) as light yellow waxy solid. MS: m/z=325.5 (M+H+)

Example 12

Cyclopropyl-{5-[2-(5,8-dimethyl-[1,2,4]triazolo[1,5-a]pyrazin-2-yl)-ethyl]-1-methyl-1H-[1,2,4]triazol-3-yl}-methyl-amine

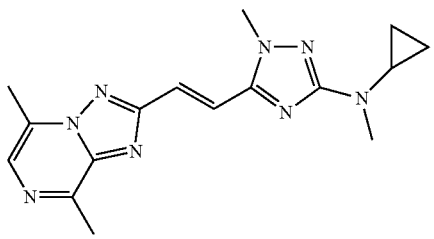 [SMILES: Cc1ncc(C)n2nc(/C=C/c3nc(N(C)C4CC4)nn3C)nc12]

Was prepared in the same manner as described in General Procedure Example 2 using N-cyclopropyl-5-(2-(5,8-dimethyl-[1,2,4]triazolo[1,5-a]pyrazin-2-yl)vinyl)-N,1-dimethyl-1H-1,2,4-triazol-3-amine (23 mg, 70.9 µmol, Eq: 1.00) as starting material. Filtration and evaporation of the solvent afforded Cyclopropyl-{5-[2-(5,8-dimethyl-[1,2,4]triazolo[1,5-a]pyrazin-2-yl)-ethyl]-1-methyl-1H-[1,2,4]triazol-3-yl}-methyl-amine (15 mg/64.8%) as a white waxy solid. MS: m/z=327.5 (M+H+)

Example 13

5,8-Dimethyl-2-[2-(2-methyl-5-pyrrolidin-1-yl-2H-[1,2,4]triazol-3-yl)-vinyl]-[1,2,4]triazolo[1,5-a]pyrazine

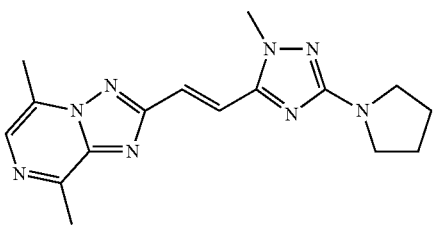 [SMILES: Cc1ncc(C)n2nc(/C=C/c3nc(N4CCCC4)nn3C)nc12]

a) 1-Methyl-5-(2-methyl-propenyl)-3-pyrrolidin-1-yl-1H-[1,2,4]triazole

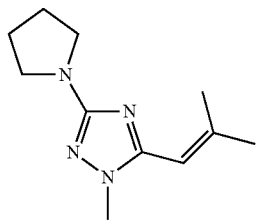

Was prepared in the same manner as described in General procedure 1d, using 3-Methyl-but-2-enoic acid 1-methylsulfanyl-1-pyrrolidin-1-yl-meth-(Z)-ylideneamide and methylhydrazine as starting materials. Extraction and evaporation of the solvents afforded 1-Methyl-5-(2-methyl-propenyl)-3-pyrrolidin-1-yl-1H-[1,2,4]triazole (261 mg/106%) as yellow oil. MS: m/z=207.1 (M+H+)

b) 2-Methyl-5-pyrrolidin-1-yl-2H-[1,2,4]triazole-3-carbaldehyde

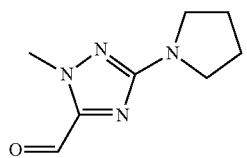

Was prepared in the same manner as described in General procedure 1e, using 1-methyl-5-(2-methylprop-1-enyl)-3-(pyrrolidin-1-yl)-1H-1,2,4-triazole (1.346 g, 6.52 mmol, Eq: 1.00) as starting material. Extraction and evaporation of the solvents afforded 2-Methyl-5-pyrrolidin-1-yl-2H-[1,2,4]triazole-3-carbaldehyde (599 mg/50.9%) as yellow solid. MS: m/z=181.4 (M+H+), mp: 64.7° C.

c) 5,8-Dimethyl-2-[2-(2-methyl-5-pyrrolidin-1-yl-2H-[1,2,4]triazol-3-yl)-vinyl]-[1,2,4]triazolo[1,5-a]pyrazine

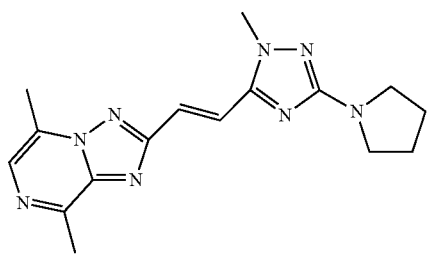 [SMILES: Cc1ncc(C)n2nc(/C=C/c3nc(N4CCCC4)nn3C)nc12]

Was prepared in the same manner as described in General Procedure Example 1g) using 1-methyl-3-(pyrrolidin-1-yl)-1H-1,2,4-triazole-5-carbaldehyde (75 mg, 416 µmol, Eq: 1.00) and ((5,8-dimethyl-[1,2,4]triazolo[1,5-a]pyrazin-2-yl)methyl)triphenylphosphonium chloride (191 mg, 416 µmol, Eq: 1.00) as starting materials. Chromatography afforded Cyclopropyl-{5-[2-(5,8-dimethyl-[1,2,4]triazolo[1,5-a]pyrazin-2-yl)-vinyl]-1-methyl-1H-[1,2,4]triazol-3-yl}-methyl-amine (71 mg, 52.6%) as light yellow solid. MS: m/z=325.4 (M+H+), mp: 196.4° C.

Example 14

5,8-Dimethyl-2-[2-(2-methyl-5-pyrrolidin-1-yl-2H-[1,2,4]triazol-3-yl)-ethyl]-[1,2,4]triazolo[1,5-a]pyrazine

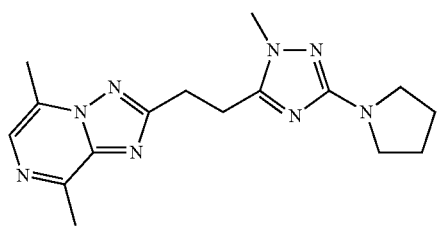 [SMILES: Cc1ncc(C)n2nc(CCc3nc(N4CCCC4)nn3C)nc12]

Was prepared in the same manner as described in General Procedure Example 2 using 5,8-dimethyl-2-(2-(1-methyl-3-(pyrrolidin-1-yl)-1H-1,2,4-triazol-5-yl)vinyl)-[1,2,4]triazolo[1,5-a]pyrazine (65 mg, 200 µmol, Eq: 1.00) as starting material. Filtration and evaporation of the solvent afforded Cyclopropyl-{5-[2-(5,8-dimethyl-[1,2,4]triazolo[1,5-a]pyrazin-2-yl)-ethyl]-1-methyl-1H-[1,2,4]triazol-3-yl}-methyl-amine (45 mg/68.6%) as a white solid. MS: m/z=327.3 (M+H+), mp: 126.5° C.

Example 15

2-Methyl-3-[2-(2-methyl-5-pyrrolidin-1-yl-2H-[1,2,4]triazol-3-yl)-vinyl]-quinoxaline

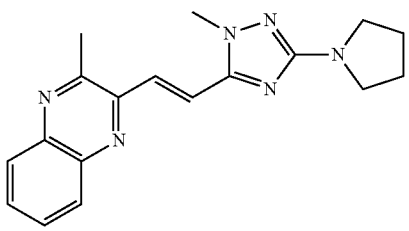 [SMILES: Cc1nc2ccccc2nc1/C=C/c1nc(N2CCCC2)nn1C]

a) (3-Methyl-quinoxalin-2-ylmethyl)-triphenyl-phosphonium chloride

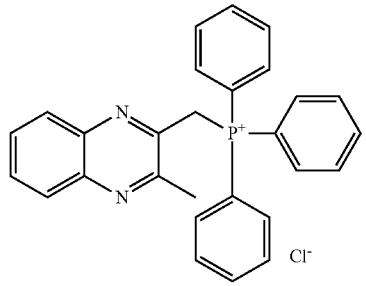 [SMILES: Cc1nc2ccccc2nc1C[P+](c1ccccc1)(c1ccccc1)c1ccccc1 ; [Cl-]]

Was prepared in same manner as described in General Procedure Example 10 using 2-(chloromethyl)-3-methylquinoxaline (350 mg, 1.82 mmol, Eq: 1.00) as starting material affording (3-Methyl-quinoxalin-2-ylmethyl)-triphenyl-phosphonium chloride (724 mg, 87.6%) as light brown solid. MS: m/z=419.5 (M−Cl+H+), mp: 155.4 b) 2-Methyl-3-[2-(2-methyl-5-pyrrolidin-1-yl-2H-[1,2,4]triazol-3-yl)-vinyl]-quinoxaline

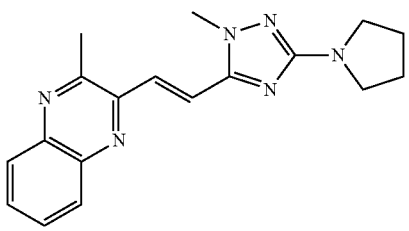 [SMILES: Cc1nc2ccccc2nc1/C=C/c1nc(N2CCCC2)nn1C]

Was prepared in the same manner as described in General Procedure Example 1g) using 1-methyl-3-(pyrrolidin-1-yl)-1H-1,2,4-triazole-5-carbaldehyde (50 mg, 277 µmol, Eq: 1.00) and ((3-methylquinoxalin-2-yl)methyl)triphenylphosphonium chloride (126 mg, 277 µmol, Eq: 1.00) as starting materials. Chromatography afforded 2-Methyl-3-[2-(2-methyl-5-pyrrolidin-1-yl-2H-[1,2,4]triazol-3-yl)-vinyl]-quinoxaline (50 mg, 56.2%) as light yellow solid. MS: m/z=321.4 (M+H+)

Example 16

2-Methyl-3-[2-(2-methyl-5-pyrrolidin-1-yl-2H-[1,2,4]triazol-3-yl)-ethyl]-quinoxaline

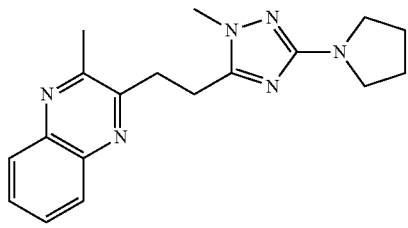 [SMILES: Cc1nc2ccccc2nc1CCc1nc(N2CCCC2)nn1C]

Was prepared in the same manner as described in General Procedure Example 2 using 2-methyl-3-(2-(1-methyl-3-(pyrrolidin-1-yl)-1H-1,2,4-triazol-5-yl)vinyl)quinoxaline (45 mg, 140 µmol, Eq: 1.00) as starting material. Filtration and evaporation of the solvent afforded 2-Methyl-3-[2-(2-methyl-5-pyrrolidin-1-yl-2H-[1,2,4]triazol-3-yl)-ethyl]-quinoxaline (15 mg/33.1%) as a light yellow solid. MS: m/z=323.4 (M+H+)

Example 17

5,8-Dimethyl-2-[2-(1-methyl-5-pyrrolidin-1-yl-1H-[1,2,4]triazol-3-yl)-vinyl]-[1,2,4]triazolo[1,5-a]pyrazine

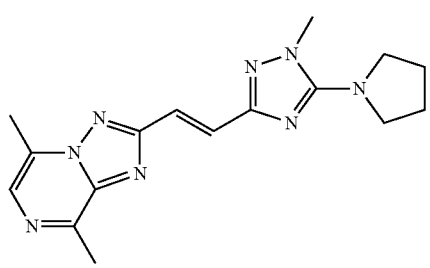 [SMILES: Cc1ncc(C)n2nc(/C=C/c3nc(N4CCCC4)n(C)n3)nc12]

a) 5-(2-Methyl-propenyl)-3-pyrrolidin-1-yl-1H-[1,2,4]triazole

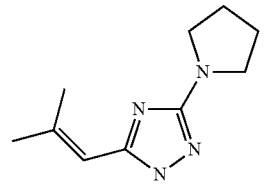

Was prepared in the same manner as described in General Procedure Example 2, using (Z)-methyl N-3-methylbut-2-enoylpyrrolidine-1-carbimidothioate (3.69 g, 16.3 mmol, Eq: 1.00) and hydrazine 1M in THF (16.3 ml, 16.3 mmol, Eq: 1.00). Chromatography afforded 5-(2-Methyl-propenyl)-3-pyrrolidin-1-yl-1H-[1,2,4]triazole (695 mg, 22.2%) as white waxy solid. MS: m/z=193.1 (M+H+)

b) 1-Methyl-3-(2-methyl-propenyl)-5-pyrrolidin-1-yl-1H-[1,2,4]triazole

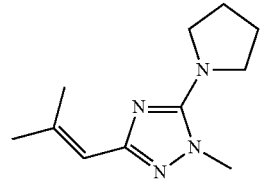

5-(2-methylprop-1-enyl)-3-(pyrrolidin-1-yl)-1H-1,2,4-triazole (220 mg, 1.14 mmol, Eq: 1.00) was solved in DMF (4.5 ml) and cooled in a icebath to 0° C. sodium hydride (54.9 mg, 1.37 mmol, Eq: 1.2) was added and stirring was continued for 30 min. iodomethane (325 mg, 143 µl, 2.29 mmol, Eq: 2) was added under ice cooling. The cooling bath was removed after 15 min. and stirring was continued overnight. Water was added and extracted two times with ethyl acetate, dried over magnesium sulfate, filtered and evaporated. Separation of the isomers afforded
1-Methyl-3-(2-methyl-propenyl)-5-pyrrolidin-1-yl-1H-[1,2,4]triazole (51 mg, 21.6%) as light yellow solid. MS: m/z=193.1 (M+H+)

c) 1-Methyl-5-pyrrolidin-1-yl-1H-[1,2,4]triazole-3-carbaldehyde

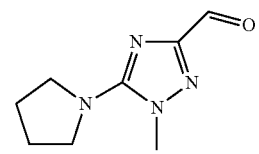

Was prepared in the same manner as described in General procedure 1e, using 1-methyl-3-(2-methylprop-1-enyl)-5-

(pyrrolidin-1-yl)-1H-1,2,4-triazole (48 mg, 233 μmol, Eq: 1.00) as starting material. Extraction and evaporation of the solvents afforded 1-Methyl-5-pyrrolidin-1-yl-1H-[1,2,4]triazole-3-carbaldehyde (47 mg/112%) as light brown oil.

d) 5,8-Dimethyl-2-[2-(1-methyl-5-pyrrolidin-1-yl-1H-[1,2,4]triazol-3-yl)-vinyl]-[1,2,4]triazolo[1,5-a]pyrazine

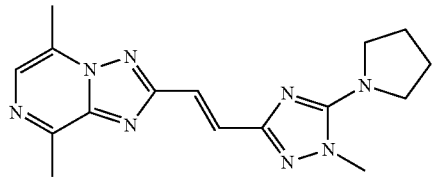 [SMILES: Cc1ncc(C)n2nc(/C=C/c3nc(N4CCCC4)n(C)n3)nc12]

Was prepared in the same manner as described in General Procedure Example 1g) using 1-methyl-5-(pyrrolidin-1-yl)-1H-1,2,4-triazole-3-carbaldehyde (45 mg, 250 μmol, Eq: 1.00) and ((5,8-dimethyl-[1,2,4]triazolo[1,5-a]pyrazin-2-yl)methyl)triphenylphosphonium chloride (115 mg, 250 μmol, Eq: 1.00) as starting materials. Chromatography afforded 5,8-Dimethyl-2-[2-(1-methyl-5-pyrrolidin-1-yl-1H-[1,2,4]triazol-3-yl)-vinyl]-[1,2,4]triazolo[1,5-a]pyrazine (32 mg, 39.5%) as white solid. MS: m/z=325.5 (M+H+)

Example 18

5,8-Dimethyl-2-[2-(1-methyl-5-pyrrolidin-1-yl-1H-[1,2,4]triazol-3-yl)-ethyl]-[1,2,4]triazolo[1,5-a]pyrazine

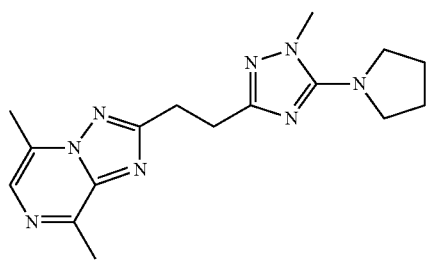 [SMILES: Cc1ncc(C)n2nc(CCc3nc(N4CCCC4)n(C)n3)nc12]

Was prepared in the same manner as described in General Procedure Example 2 using 5,8-dimethyl-2-(2-(1-methyl-5-(pyrrolidin-1-yl)-1H-1,2,4-triazol-3-yl)vinyl)-[1,2,4]triazolo[1,5-a]pyrazine (25 mg, 77.1 μmol, Eq: 1.00) as starting material. Filtration and evaporation of the solvent afforded 5,8-Dimethyl-2-[2-(1-methyl-5-pyrrolidin-1-yl-1H-[1,2,4]triazol-3-yl)-ethyl]-[1,2,4]triazolo[1,5-a]pyrazine (20.1 mg/79.9%) as a white waxy solid. MS: m/z=326.4 (M+H+)

Example 19

7-Chloro-2-[1-(4-methoxy-benzyl)-5-pyrrolidin-1-yl-1H-[1,2,4]triazol-3-ylethynyl]-[1,2,4]triazolo[1,5-a]pyridine

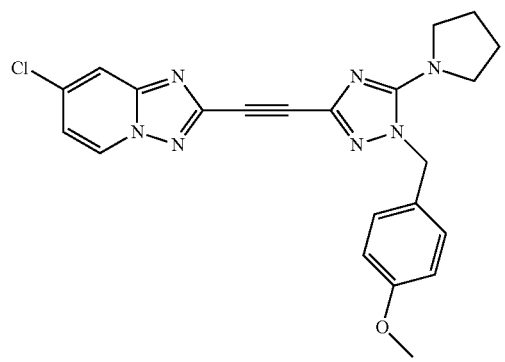 [SMILES: COc1ccc(Cn2nc(C#Cc3nc4cc(Cl)ccn4n3)nc2N2CCCC2)cc1]

a) 3,5-Dibromo-1-(4-methoxy-benzyl)-1H-[1,2,4]triazole

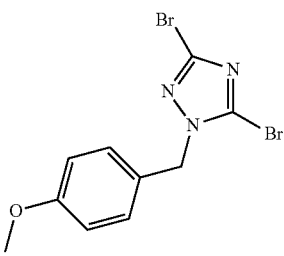 [SMILES: COc1ccc(Cn2nc(Br)nc2Br)cc1]

3,5-dibromo-1H-1,2,4-triazole (1.5 g, 6.61 mmol, Eq: 1.00), potassium iodide (110 mg, 661 μmol, Eq: 0.10), 4-methoxybenzyl chloride (1.14 g, 990 μl, 7.27 mmol, Eq: 1.1) and N,N-diisopropylethylamine (1.71 g, 2.31 ml, 13.2 mmol, Eq: 2.0) was stirred in acetonitrile (23.0 ml) overnight at room temperature. The crude material was applied on silica gel and purified by column chromatography using heptane/ethyl acetate gradient as eluent to afford 3,5-dibromo-1-(4-methoxy-benzyl)-1H-[1,2,4]triazole (1.79 g/78.0%) as a white solid. MS: m/e=345685051 (M+H+), mp: 75.7° C.

b) 3-Bromo-1-(4-methoxy-benzyl)-5-pyrrolidin-1-yl-1H-[1,2,4]triazole

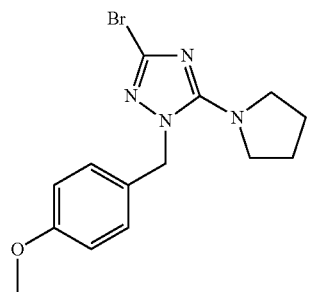 [SMILES: COc1ccc(Cn2nc(Br)nc2N2CCCC2)cc1]

A mixture of 3,5-dibromo-1-(4-methoxybenzyl)-1H-1,2,4-triazole (1.268 g, 3.65 mmol, Eq: 1.00) and pyrrolidine (273 mg, 317 µl, 3.84 mmol, Eq: 1.05) in dimethyl formamide (12 ml) was heated for 18 hours to 110° C. under argon atmosphere. The crude material was applied on silicagel and purified by flash chromatography over a 50 g silicagel column using heptane/ethyl acetate 30-50% as eluent affording 3-bromo-1-(4-methoxy-benzyl)-5-pyrrolidin-1-yl-1H-[1,2,4]triazole (608 mg/49.3%) as a colorless oil. MS: m/e=338339 (M+H+)

c) 1-(4-Methoxy-benzyl)-5-pyrrolidin-1-yl-3-trimethylsilanylethynyl-1H-[1,2,4]triazole

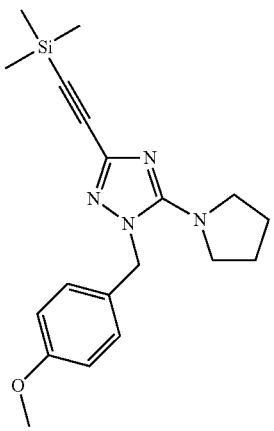 [SMILES: COc1ccc(Cn2nc(C#C[Si](C)(C)C)nc2N2CCCC2)cc1]

A mixture of 3-bromo-1-(4-methoxybenzyl)-5-(pyrrolidin-1-yl)-1H-1,2,4-triazole (197 mg, 584 µmol, Eq: 1.00), ethynyltrimethylsilane (115 mg, 164 µl, 1.17 mmol, Eq: 2) and triethylamine (88.7 mg, 122 µl, 876 µmol, Eq: 1.5) in tetrahydrofuran (3 ml) was purged for 5 minutes with nitrogen. Then copper (I) iodide (1.11 mg, 5.84 µmol, Eq: 0.01), bis(triphenylphosphine) palladium(II) chloride (4.1 mg, 5.84 µmol, Eq: 0.01) and triphenylphosphine (1.53 mg, 5.84 µmol, Eq: 0.01) were added, the vessel was capped and heated to 75° C. for 18 hours. The crude material was applied on silicagel and purified by flash chromatography over a 20 g silicagel column using heptane/ethyl acetate 10-30% as eluent affording 1-(4-methoxy-benzyl)-5-pyrrolidin-1-yl-3-trimethylsilanylethynyl-1H-[1,2,4]triazole (95 mg/45.9%) as an orange oil. MS: m/e=355.4 (M+H+)

d) 3-Ethynyl-1-(4-methoxy-benzyl)-5-pyrrolidin-1-yl-1H-[1,2,4]triazole

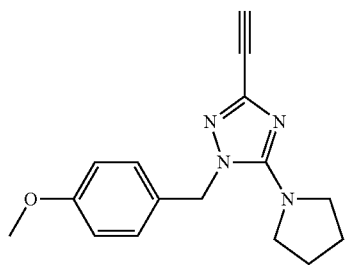 [SMILES: C#Cc1nc(N2CCCC2)n(Cc2ccc(OC)cc2)n1]

A mixture of 1-(4-methoxybenzyl)-5-(pyrrolidin-1-yl)-3-((trimethylsilyl)ethynyl)-1H-1,2,4-triazole (95 mg, 268 µmol, Eq: 1.00) and sodium hydroxide sol. 1N (0.1 ml) in methanol (3 ml) was stirred for 18 hours at 25° C. The mixture was diluted with ethyl acetate and washed with water, the organic layer was separated, dried over magnesium sulfate, filtrated and evaporated affording 3-ethynyl-1-(4-methoxy-benzyl)-5-pyrrolidin-1-yl-1H-[1,2,4]triazole (83 mg/110%) as a yellow oil. MS: m/e=283.4 (M+H+)

e) 1-Ethoxycarbonyl-3-(4-chloro-pyridin-2-yl)-thiourea

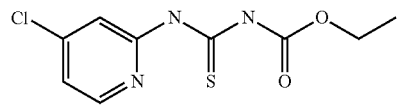 [SMILES: CCOC(=O)NC(=S)Nc1cc(Cl)ccn1]

To a solution of 4-chloropyridin-2-amine (2.16 g, 16.8 mmol, Eq: 1.00) in dioxane (70 ml) was added O-ethyl carbonisothiocyanatidate (2.2 g, 1.9 ml, 16.8 mmol, Eq: 1.00) at 25° C. The resulting mixture was stirred for 2 hours at 25° C. The mixture was diluted with ethyl acetate and washed with water and brine, the organic layer was separated, dried over magnesium sulfate, filtrated and evaporated affording 1-ethoxycarbonyl-3-(4-chloro-pyridin-2-yl)-thiourea (4.02 g/92.1%) as a green waxy solid. MS: m/e=257.9 (M−H+)

f) 7-Chloro-[1,2,4]triazolo[1,5-a]pyridin-2-ylamine

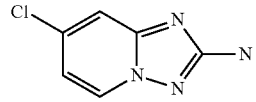 [SMILES: Nc1nc2cc(Cl)ccn2n1]

A mixture of hydroxylamine hydrochloride (5.35 g, 77.0 mmol, Eq: 5) and N-ethyldiisopropylamine (5.97 g, 8.07 ml, 46.2 mmol, Eq: 3) in ethanol (80 ml) was stirred for a few minutes at 25° C., then the mixture was added to 1-ethoxycarbonyl-3-(4-chloro-pyridin-2-yl)-thiourea (4.0 g, 15.4 mmol, Eq: 1.00) and the resulting mixture was refluxed for 2.5 days (over the weekend). The crude material was applied on SiO2 and purified by flash chromatography over a 20 g SiO2 column using ethyl acetate 100% as eluent affording 7-chloro-[1,2,4]triazolo[1,5-a]pyridin-2-ylamine (2.03 g/78.2%) as a white solid. MS: m/e=169.1 (M+H+), mp: 189-190° C.

g) 2-Bromo-7-chloro-[1,2,4]triazolo[1,5-a]pyridine

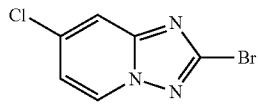 [SMILES: Clc1ccn2nc(Br)nc2c1]

A solution of copper(II) bromide (1.43 g, 6.39 mmol, Eq: 1.1) and tert-butyl nitrite (733 mg, 845 µl, 6.39 mmol, Eq: 1.1) in acetonitrile (29.4 ml) (dark green) was heated to 75° C., then 7-chloro-[1,2,4]triazolo[1,5-a]pyridin-2-amine (980 mg, 5.81 mmol, Eq: 1.00) was added in small portions. The resulting mixture was stirred for 2 hours at 75° C. The mixture was diluted with dichloromethane and washed 3 times with water, the organic layers were combined, dried over magnesium sulfate filtrated and evaporated. The crude material was applied on SiO2 and purified by flash chromatography over a 20 g SiO2 column using heptane/ethyl acetate 10-40% as eluent affording 2-bromo-7-chloro-[1,2,4]triazolo[1,5-a]pyridine (434 mg/32.1%) as a white solid. MS: m/e=230 (M+H+)

h) 7-Chloro-2-[1-(4-methoxy-benzyl)-5-pyrrolidin-1-yl-1H-[1,2,4]triazol-3-ylethynyl]-[1,2,4]triazolo[1,5-a]pyridine

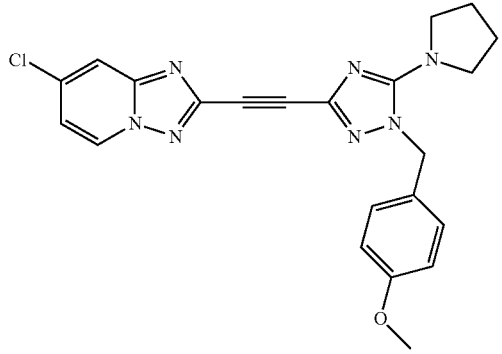 [SMILES: COc1ccc(Cn2nc(C#Cc3nc4cc(Cl)ccn4n3)nc2N2CCCC2)cc1]

A mixture of 3-ethynyl-1-(4-methoxybenzyl)-5-(pyrrolidin-1-yl)-1H-1,2,4-triazole (75 mg, 266 µmol, Eq: 1.00), 2-bromo-7-chloro-[1,2,4]triazolo[1,5-a]pyridine (67.9 mg, 292 µmol, Eq: 1.1) and triethylamine (40.3 mg, 55.5 µl, 398 µmol, Eq: 1.5) in tetrahydrofuran (2 ml) was purged with argon, then copper (I) iodide (1.01 mg, 5.31 µmol, Eq: 0.02), bis(triphenylphosphine) palladium(II) chloride (3.73 mg, 5.31 µmol, Eq: 0.02) and triphenylphosphine (1.39 mg, 5.31 µmol, Eq: 0.02) were added, the vessel was capped and heated for 18 hours to 75° C. Still starting material. The mixture was cooled, purged with argon and another portion of copper (I) iodide (1.01 mg, 5.31 µmol, Eq: 0.02), bis(triphenylphosphine) palladium(II) chloride (3.73 mg, 5.31 µmol, Eq: 0.02) and triphenylphosphine (1.39 mg, 5.31 µmol, Eq: 0.02) was added and the mixture was stirred again over night at 75° C. The crude material was applied on silicagel and purified by flash chromatography over a 20 g silicagel column using ethyl acetate/methanol 0-10% as eluent affording 7-chloro-2-[1-(4-methoxy-benzyl)-5-pyrrolidin-1-yl-1H-[1,2,4]triazol-3-ylethynyl]-[1,2,4]triazolo[1,5-a]pyridine (33 mg 26.8%) as an orange oil. MS: m/e=434.4 (M+H+)

Example 20

2-{2-[2-(4-Methoxy-benzyl)-5-pyrrolidin-1-yl-2H-[1,2,4]triazol-3-yl]-ethyl}-5,8-dimethyl-[1,2,4]triazolo[1,5-a]pyrazine

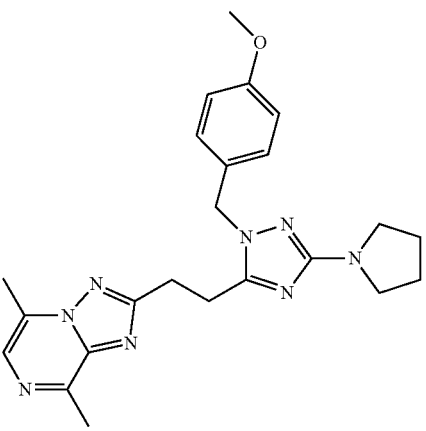 [SMILES: COc1ccc(Cn2nc(N3CCCC3)nc2CCc2nc3c(C)ncc(C)n3n2)cc1]

a) 5-Bromo-2-(4-methoxy-benzyl)-2H-[1,2,4]triazole-3-carbaldehyde

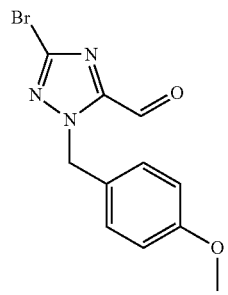 [SMILES: COc1ccc(Cn2nc(Br)nc2C=O)cc1]

Was prepared in the same manner as described in General Procedure Example 8a) using 3,5-dibromo-1-(4-methoxy-benzyl)-1H-1,2,4-triazole (150 mg, 432 µmol, Eq: 1.00) as starting material. Extraction and evaporation of the solvents afforded 1-Methyl-5-pyrrolidin-1-yl-1H-[1,2,4]triazole-3-carbaldehyde (150 mg/117%) as dark green oil.

b) 2-{2-[5-Bromo-2-(4-methoxy-benzyl)-2H-[1,2,4]triazol-3-yl]-vinyl}-5,8-dimethyl-[1,2,4]triazolo[1,5-a]pyrazine

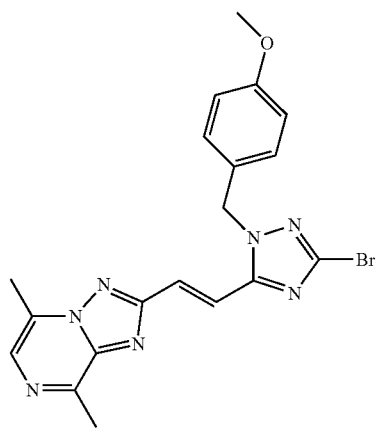 [SMILES: COc1ccc(Cn2nc(Br)nc2/C=C/c2nc3c(C)ncc(C)n3n2)cc1]

Was prepared in the same manner as described in General Procedure Example 1g) using 3-bromo-1-(4-methoxybenzyl)-1H-1,2,4-triazole-5-carbaldehyde (50 mg, 169 μmol, Eq: 1.00) and ((5,8-dimethyl-[1,2,4]triazolo[1,5-a]pyrazin-2-yl)methyl)triphenylphosphonium chloride (77.5 mg, 169 μmol, Eq: 1.00) as starting materials. Chromatography afforded 2-{2-[5-Bromo-2-(4-methoxy-benzyl)-2H-[1,2,4]triazol-3-yl]-vinyl}-5,8-dimethyl-[1,2,4]triazolo[1,5-a]pyrazine (50 mg, 35.4%) as a white solid. MS: m/z=442.3 (M+H+)

c) 2-{2-[2-(4-Methoxy-benzyl)-5-pyrrolidin-1-yl-2H-[1,2,4]triazol-3-yl]-vinyl}-5,8-dimethyl-[1,2,4]triazolo[1,5-a]pyrazine

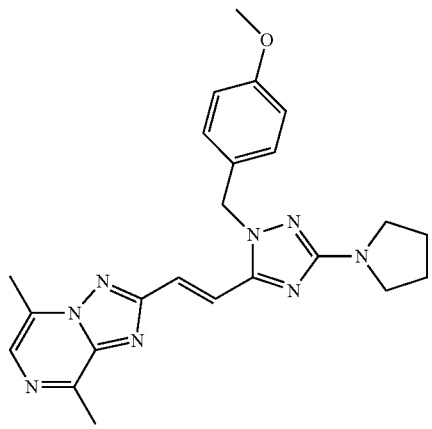 [SMILES: COc1ccc(Cn2nc(N3CCCC3)nc2/C=C/c2nc3c(C)ncc(C)n3n2)cc1]

Was prepared in the same manner as described in General Procedure Example 9 using 2-(2-(3-bromo-1-(4-methoxy-benzyl)-1H-1,2,4-triazol-5-yl)vinyl)-5,8-dimethyl-[1,2,4]triazolo[1,5-a]pyrazine (55 mg, 125 μmol, Eq: 1.00) and pyrrolidine (17.8 mg, 20.7 μl, 250 μmol, Eq: 2) as starting materials. Chromatography afforded 2-{2-[2-(4-Methoxy-benzyl)-5-pyrrolidin-1-yl-2H-[1,2,4]triazol-3-yl]-vinyl}-5,8-dimethyl-[1,2,4]triazolo[1,5-a]pyrazine (23 mg, 42.8%) as a light yellow solid. MS: m/z=431.5 (M+H+)

d) 2-{2-[2-(4-Methoxy-benzyl)-5-pyrrolidin-1-yl-2H-[1,2,4]triazol-3-yl]-ethyl}-5,8-dimethyl-[1,2,4]triazolo[1,5-a]pyrazine

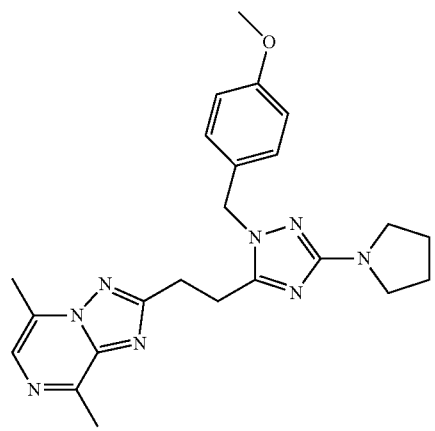 [SMILES: COc1ccc(Cn2nc(N3CCCC3)nc2CCc2nc3c(C)ncc(C)n3n2)cc1]

Was prepared in the same manner as described in General Procedure Example 2 using 2-(2-(1-(4-methoxybenzyl)-3-(pyrrolidin-1-yl)-1H-1,2,4-triazol-5-yl)vinyl)-5,8-dimethyl-[1,2,4]triazolo[1,5-a]pyrazine (21 mg, 48.8 μmol, Eq: 1.00) as starting material. Filtration and evaporation of the solvent afforded 2-{2-[2-(4-Methoxy-benzyl)-5-pyrrolidin-1-yl-2H-[1,2,4]triazol-3-yl]-ethyl}-5,8-dimethyl-[1,2,4]triazolo[1,5-a]pyrazine (17 mg/80.6%) as a colorless oil. MS: m/z=433.5 (M+H+)

Example 21

2-[2-(5-Azetidin-1-yl-2-methyl-2H-[1,2,4]triazol-3-yl)-ethyl]-5,7-dimethyl-[1,2,4]triazolo[1,5-a]pyrimidine

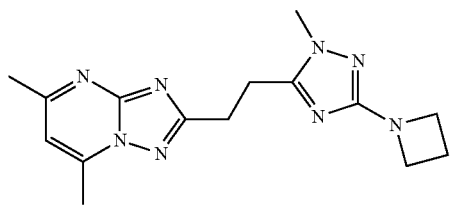 [SMILES: Cc1cc(C)n2nc(CCc3nc(N4CCC4)nn3C)nc2n1]

a)
5-Bromo-2-methyl-2H-[1,2,4]triazole-3-carbaldehyde

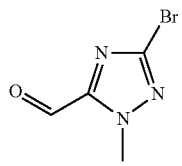

To a solution of 3,5-dibromo-1-methyl-1H-1,2,4-triazole (500 mg, 2.08 mmol, Eq: 1.00) in tetrahydrofuran (5 ml) was added dropwise at −45° C. under argon atmosphere n-butyl-lithium 1.6 M in hexane (1.56 ml, 2.49 mmol, Eq: 1.2). The resulting mixture was stirred for 30 minutes at −45° C. and was then cooled to −70° C. Then dimethyl formamide (197 mg, 209 μl, 2.7 mmol, Eq: 1.3) was added dropwise. After 15 minutes the cooling bath was removed and the mixture was allowed to reach 25° C. The mixture was stirred for additional 2 hours at 25° C. The mixture was poured on water and extracted twice with ethyl acetate, the organic layers were combined, washed with water and brine, dried over magnesium sulfate, filtrated and evaporated, affording 5-bromo-2-methyl-2H-[1,2,4]triazole-3-carbaldehyde (218 mg/55.3%) as an orange semi solid. MS: m/e=189 (M+H+)

b) 2-[2-(5-Bromo-2-methyl-2H-[1,2,4]triazol-3-yl)-vinyl]-5,7-dimethyl-[1,2,4]triazolo[1,5-a]pyrimidine

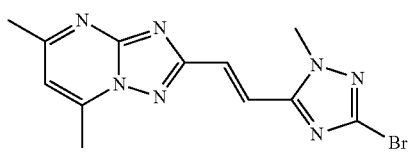 [SMILES: Cc1cc(C)n2nc(/C=C/c3nc(Br)nn3C)nc2n1]

A mixture of 3-bromo-1-methyl-1H-1,2,4-triazole-5-carbaldehyde (193 mg, 1.02 mmol, Eq: 1.00), ((5,7-dimethyl-[1,2,4]triazolo[1,5-a]pyrimidin-2-yl)methyl)triphenylphosphonium chloride (466 mg, 1.02 mmol, Eq: 1.00) and DBU (387 mg, 383 μl, 2.54 mmol, Eq: 2.5) in tetrahydrofuran (12 ml) was stirred for 18 hours at 25° C. under argon atmosphere. Chromatography afforded) 2-[2-(5-bromo-2-methyl-2H-[1,2,4]triazol-3-yl)-vinyl]-5,7-dimethyl-[1,2,4]triazolo[1,5-a]pyrimidine (161 mg/47.4%) as a white solid. MS: m/z=334336 (M+H+), mp: 277.4° C.

c) 2-[2-(5-Azetidin-1-yl-2-methyl-2H-[1,2,4]triazol-3-yl)-vinyl]-5,7-dimethyl-[1,2,4]triazolo[1,5-a]pyrimidine

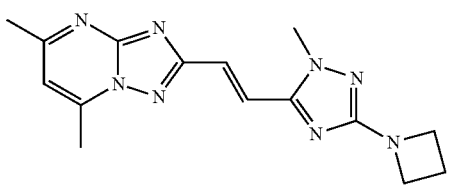 [SMILES: Cc1cc(C)n2nc(/C=C/c3nc(N4CCC4)nn3C)nc2n1]

A solution of 2-(2-(3-bromo-1-methyl-1H-1,2,4-triazol-5-yl)vinyl)-5,7-dimethyl-[1,2,4]triazolo[1,5-a]pyrimidine (59 mg, 177 μmol, Eq: 1.00) in dioxane (2.11 ml) was purged with argon, then azetidine (15.1 mg, 17.8 μl, 265 μmol, Eq: 1.5), 4,5-bis(diphenylphosphino)-9,9-dimethylxanthene (8.17 mg, 14.1 μmol, Eq: 0.08), tris(dibenzylideneacetone)dipalladium chloroform complex (7.31 mg, 7.06 μmol, Eq: 0.04) and sodium phenolate (20.5 mg, 177 μmol, Eq: 1.00) were added. The vial was capped and irradiated at 140° C. for 60 minutes in the microwave oven. Chromatography afforded 2-[2-(5-azetidin-1-yl-2-methyl-2H-[1,2,4]triazol-3-yl)-vinyl]-5,7-dimethyl-[1,2,4]triazolo[1,5-a]pyrimidine (15 mg/27.4%) as a light yellow solid. MS: m/z=311.4 (M+H+).

d) 2-[2-(5-Azetidin-1-yl-2-methyl-2H-[1,2,4]triazol-3-yl)-ethyl]-5,7-dimethyl-[1,2,4]triazolo[1,5-a]pyrimidine

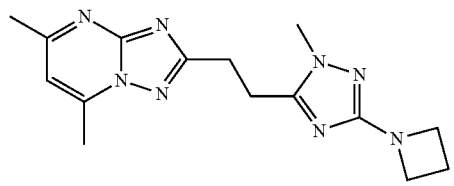 [SMILES: Cc1cc(C)n2nc(CCc3nc(N4CCC4)nn3C)nc2n1]

A mixture of 2-(2-(3-(azetidin-1-yl)-1-methyl-1H-1,2,4-triazol-5-yl)vinyl)-5,7-dimethyl-[1,2,4]triazolo[1,5-a]pyrimidine (15 mg, 48.3 μmol, Eq: 1.00) and palladium on carbon 10% (5.14 mg, 4.83 μmol, Eq: 0.1) in methanol (15 ml) was stirred for 6 hours at 25° C. under hydrogen atmosphere. The catalyst was filtered off, evaporation of the solvent afforded 2-[2-(5-azetidin-1-yl-2-methyl-2H-[1,2,4]triazol-3-yl)-ethyl]-5,7-dimethyl-[1,2,4]triazolo[1,5-a]pyrimidine (14.3 mg/94.7%) as a light yellow solid. MS: m/z=313.4 (M+H+).

Example 22

5,7-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrimidine

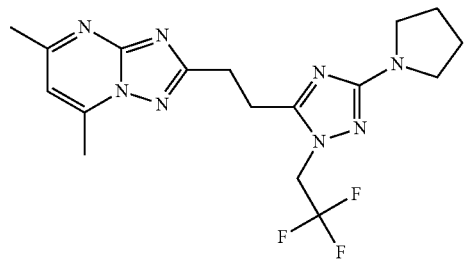 [SMILES: Cc1cc(C)n2nc(CCc3nc(N4CCCC4)nn3CC(F)(F)F)nc2n1]

a) 5,7-Dimethyl-2-{2-[5-pyrrolidin-1-yl-2-(2,2,2-trifluoro-ethyl)-2H-[1,2,4]triazol-3-yl]-vinyl}-[1,2,4]triazolo[1,5-a]pyrimidine

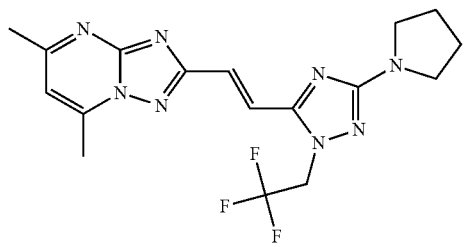 [SMILES: Cc1cc(C)n2nc(/C=C/c3nc(N4CCCC4)nn3CC(F)(F)F)nc2n1]

A mixture of 3-(pyrrolidin-1-yl)-1-(2,2,2-trifluoroethyl)-1H-1,2,4-triazole-5-carbaldehyde (54 mg, 218 μmol, Eq: 1.00), ((5,7-dimethyl-[1,2,4]triazolo[1,5-a]pyrimidin-2-yl)methyl)triphenylphosphonium chloride (99.8 mg, 218 μmol, Eq: 1.00) and 2,3,4,6,7,8,9,10-octahydropyrimido[1,2-a]azepine (82.8 mg, 544 μmol, Eq: 2.5) in tetrahydrofuran (3.36 ml) was stirred for 18 hours at 25° C. under argon atmosphere. Chromatography afforded 5,7-dimethyl-2-{2-[5-pyrrolidin-1-yl-2-(2,2,2-trifluoro-ethyl)-2H-[1,2,4]triazol-3-yl]-vinyl}-[1,2,4]triazolo[1,5-a]pyrimidine (20 mg/23.4%) as a light yellow viscous oil. MS: m/z=393.4 (M+H+).

b) 5,7-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrimidine

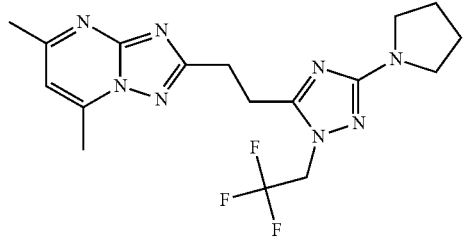 [SMILES: Cc1cc(C)n2nc(CCc3nc(N4CCCC4)nn3CC(F)(F)F)nc2n1]

A mixture of 5,7-dimethyl-2-(2-(3-(pyrrolidin-1-yl)-1-(2,2,2-trifluoroethyl)-1H-1,2,4-triazol-5-yl)vinyl)-[1,2,4]triazolo[1,5-a]pyrimidine (19 mg, 48.4 μmol, Eq: 1.00) and palladium on carbon 10% (5.15 mg, 4.84 μmol, Eq: 0.1) in methanol (15 ml) was stirred for 6 hours at 25° C. under hydrogen atmosphere. Evaporation of the solvent afforded 5,7-dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrimidine (19 mg/99.5%) as a white solid. MS: m/z=395.5 (M+H+), mp: 180.2° C.

Example 23

{5-[2-(5,8-Dimethyl-[1,2,4]triazolo[1,5-a]pyrazin-2-yl)-ethyl]-1-methyl-1H-[1,2,4]triazol-3-yl}-ethyl-methyl-amine

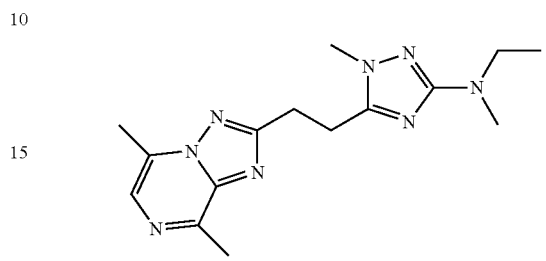

A mixture of 5-(2-(5,8-dimethyl-[1,2,4]triazolo[1,5-a]pyrazin-2-yl)vinyl)-N-ethyl-N,1-dimethyl-1H-1,2,4-triazol-3-amine (7 mg, 22.4 μmol, Eq: 1.00) and palladium on carbon 10% (4.77 mg, 4.48 μmol, Eq: 0.2) in methanol (1 ml) was stirred for 14 hours at 25° C. under hydrogen atmosphere. TLC (CH2Cl2/MeOH 19:1/UV 254 nm) showed complete reaction (spot to spot). palladium was filtered off and the filtrate was evaporated and applied on silica gel. Purification by column chromatography over 10 g SiO2 using ethyl acetate/methanol (0-10% MeOH) as eluent to give {5-[2-(5,8-Dimethyl-[1,2,4]triazolo[1,5-a]pyrazin-2-yl)-ethyl]-1-methyl-1H-[1,2,4]triazol-3-yl}-ethyl-methyl-amine (3.5 mg, 49.7%) as off-white solid

Example 24

5,7-dimethyl-2-(2-(1-methyl-3-(pyrrolidin-1-yl)-1H-1,2,4-triazol-5-yl)ethyl)-[1,2,4]triazolo[1,5-a]pyrimidine

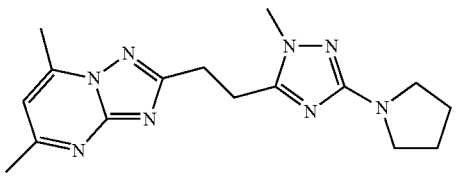 [SMILES: Cc1cc(C)n2nc(CCc3nc(N4CCCC4)nn3C)nc2n1]

A mixture of 5,7-dimethyl-2-(2-(1-methyl-3-(pyrrolidin-1-yl)-1H-1,2,4-triazol-5-yl)vinyl)-[1,2,4]triazolo[1,5-a]pyrimidine (65 mg, 200 μmol, Eq: 1.00) and palladium on carbon 10% (42.6 mg, 40.1 μmol, Eq: 0.2) in methanol (10.0 ml) was stirred for 14 hours at 25° C. under hydrogen atmosphere. TLC (CH2Cl2/MeOH 19:1/UV 254 nm) showed complete reaction (spot to spot). palladium was filtered off and the filtrate was evaporated and dried under high vacuum to give 5,7-Dimethyl-2-[2-(2-methyl-5-pyrrolidin-1-yl-2H-[1,2,4]triazol-3-yl)-ethyl]-[1,2,4]triazolo[1,5-a]pyrimidine (34 mg, 52%) as viscous oil

Example 25

N-cyclopropyl-5-(2-(5,8-dimethyl-[1,2,4]triazolo[1,5-a]pyrazin-2-yl)ethyl)-N,1-dimethyl-1H-1,2,4-triazol-3-amine

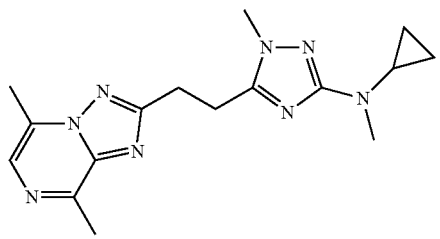 [SMILES: Cc1ncc(C)n2nc(CCc3nc(N(C)C4CC4)nn3C)nc12]

A mixture of N-cyclopropyl-5-(2-(5,8-dimethyl-[1,2,4]triazolo[1,5-a]pyrazin-2-yl)vinyl)-N,1-dimethyl-1H-1,2,4-triazol-3-amine (23 mg, 70.9 µmol, Eq: 1.00) and palladium on carbon 10% (7.55 mg, 7.09 µmol, Eq: 0.1) in methanol (3.5 ml) was stirred for 14 hours at 25° C. under hydrogen atmosphere. Palladium was filtered off, the crude material was applied on silica gel and purified by column chromatography using ethy acetate/methanol (0-10% methanol) as eluent to give N-cyclopropyl-5-(2-(5,8-dimethyl-[1,2,4]triazolo[1,5-a]pyrazin-2-yl)ethyl)-N,1-dimethyl-1H-1,2,4-triazol-3-amine (15 mg, 64.8%) as white waxy solid

Example 26

6-Chloro-2-(2-(1-methyl-3-(pyrrolidin-1-yl)-1H-1,2,4-triazol-5-yl)ethyl)-[1,2,4]triazolo[1,5-a]pyridine

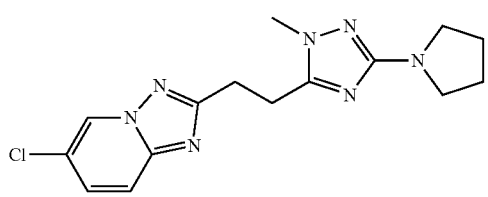 [SMILES: Cn1nc(N2CCCC2)nc1CCc1nc2ccc(Cl)cn2n1]

a) O-(mesitylsulfonyl)hydroxylamine

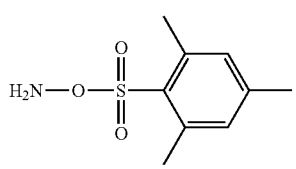

70% aq. perchloric acid (4.34 g, 2.6 ml, 43.2 mmol, Eq: 4.12) was added to ethyl N-mesitylsulfonyloxyacetimidate (2.99 g, 10.5 mmol, Eq: 1.00) in THF (4 ml) at 0° C. The reaction mixture was stirred for 1 h at 0° C. The mixture was poured into water (60 ml) and extracted with CH2Cl2 (20 ml+2×10 ml). The combined organic layers were dried over Na2SO4. The solution was used without further purification in the next step.

b) 1-Amino-5-chloropyridin-2(1H)-iminium 2,4,6-trimethylbenzenesulfonate

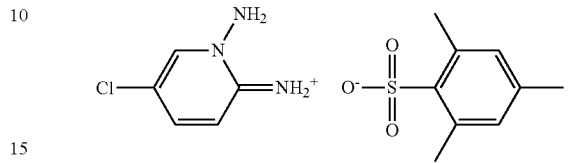

The fresh solution of O-(mesitylsulfonyl)hydroxylamine (2.14 g, 9.96 mmol, Eq: 1.00) in CH2Cl2 prepared in the previous step was added dropwise at 0° C. to a solution of 5-chloropyridin-2-amine (1.28 g, 9.96 mmol, Eq: 1.00) in CH2Cl2 (20 ml). The suspension was stirred for 20 min and then filtered. The residue was washed with DCM and dried under high vacuum to give the desired product as a white powder (2.5 g, 73%). MS m/z=144.03 (M−MsO+H+)

c) 6-Chloro-2-(chloromethyl)-[1,2,4]triazolo[1,5-a]pyridine

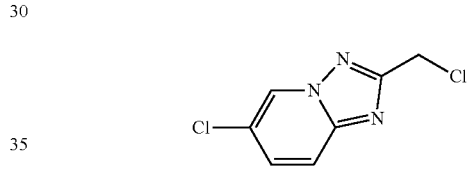

A mixture of 1-amino-5-chloropyridin-2(1H)-iminium 2,4,6-trimethylbenzenesulfonate (500 mg, 1.45 mmol, Eq: 1.00), 2-chloroacetyl chloride (172 mg, 122 µl, 1.53 mmol, Eq: 1.05) and pyridine (242 mg, 247 µl, 3.05 mmol, Eq: 2.1) in DMF (5.00 ml) was stirred at 90° C. for 2 h. The mixture was poured on 20 ml half saturated aq. NaHCO3 and extracted with EtOAc. The combined organic phases were dried over Na2SO4, filtered and concentrated to an oil. Purification by column chromatography (SiO2, 0 to 80% EtOAc in n-heptane) gave the desired product (68 mg, 23%) as a white solid. MS m/z=202.1 (M+H+)

d) ((6-Chloro-[1,2,4]triazolo[1,5-a]pyridin-2-yl)methyl)triphenylphosphonium chloride

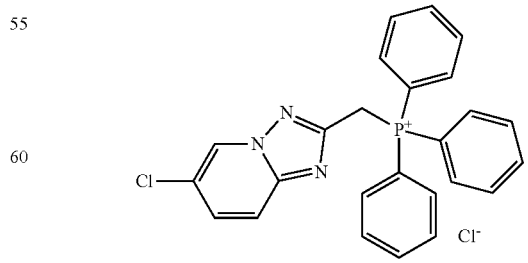

The desired product (225 mg, 75%) was obtained as a white solid in analogy to Example 1f) from 6-chloro-2-(chloromethyl)-[1,2,4]triazolo[1,5-a]pyridine (98 mg, 485 µmol, Eq: 1.00). MS m/z=428.3 (M−Cl+H+)

e) 6-Chloro-2-(2-(1-methyl-3-(pyrrolidin-1-yl)-1H-1,2,4-triazol-5-yl)vinyl)-[1,2,4]triazolo[1,5-a]pyridine

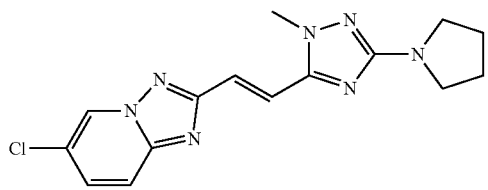 [SMILES: Cn1nc(N2CCCC2)nc1/C=C/c1nc2ccc(Cl)cn2n1]

The desired product was prepared in analogy to Example 1 g) from ((6-chloro-[1,2,4]triazolo[1,5-a]pyridin-2-yl)methyl)triphenylphosphonium chloride (170 mg, 366 µmol, Eq: 1.00) and 1-methyl-3-(pyrrolidin-1-yl)-1H-1,2,4-triazole-5-carbaldehyde (66.0 mg, 366 µmol, Eq: 1.00). 110 mg (91%) of the desired product were obtained as a light yellow solid. MS: m/z=330.4 (M+H+)

f) 6-Chloro-2-(2-(1-methyl-3-(pyrrolidin-1-yl)-1H-1,2,4-triazol-5-yl)ethyl)-[1,2,4]triazolo[1,5-a]pyridine

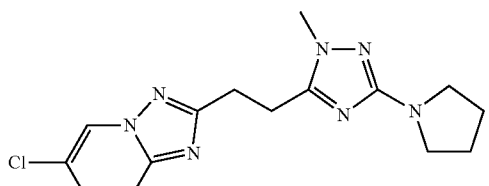

A suspension of 6-chloro-2-(2-(1-methyl-3-(pyrrolidin-1-yl)-1H-1,2,4-triazol-5-yl)vinyl)-[1,2,4]triazolo[1,5-a]pyridine (50 mg, 152 µmol, Eq: 1.00) and 5% Pd on Ba2SO4 (150 mg) in EtOAc (5 ml) was stirred under hydrogen (1 atm) for 2 h. The mixture was filtered over Celite and the residue purified by prep. HPLC to give the desired product (7.7 mg, 15%) as a white solid. MS: m/z=331.9 (M+H+)

Example 27

6-Chloro-5-methyl-2-(2-(1-methyl-3-(pyrrolidin-1-yl)-1H-1,2,4-triazol-5-yl)ethyl)-[1,2,4]triazolo[1,5-a]pyridine

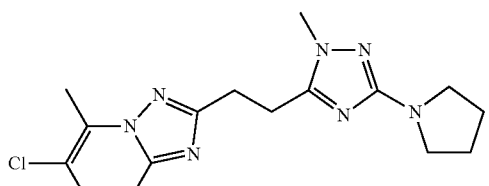

The product (6.9 mg) was obtained from 5-chloro-6-methylpyridin-2-amine in analogy to Example 26 as a light yellow solid. MS: m/z=346.5 (M+H+)

Example 28

6-Chloro-5-methyl-2-[2-(1-methyl-5-pyrrolidin-1-yl-1H-[1,2,4]triazol-3-yl)-ethyl]-[1,2,4]triazolo[1,5-a]pyridine

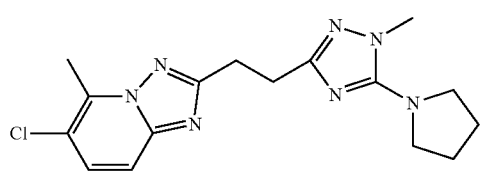 [SMILES: Cc1c(Cl)ccc2nc(CCc3nc(N4CCCC4)n(C)n3)nn12]

The product (7 mg) was obtained as a light yellow powder in analogy to Example 26 using 5-chloro-6-methylpyridin-2-amine (step b) and 1-methyl-5-pyrrolidin-1-yl-1H-[1,2,4]triazole-3-carbaldehyde (step e) as starting materials. MS: m/z=346.5 (M+H+)

Example 29

5-Methyl-2-(2-(1-methyl-3-(pyrrolidin-1-yl)-1H-1,2,4-triazol-5-yl)ethyl)-[1,2,4]triazolo[1,5-a]pyridine

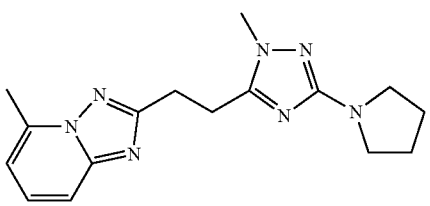

a) 6-chloro-5-methyl-2-(2-(1-methyl-3-(pyrrolidin-1-yl)-1H-1,2,4-triazol-5-yl)vinyl)-[1,2,4]triazolo[1,5-a]pyridine

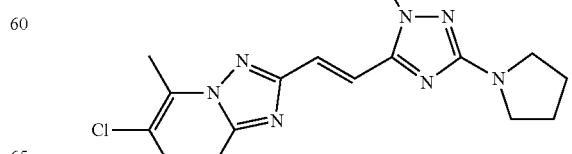

The product (36 mg) was obtained as a light yellow solid from 5-chloro-6-methylpyridin-2-amine in analogy to Example 26, steps b-e. MS: m/z=344.3 (M+H+)

b) 5-methyl-2-(2-(1-methyl-3-(pyrrolidin-1-yl)-1H-1,2,4-triazol-5-yl)ethyl)-[1,2,4]triazolo[1,5-a]pyridine

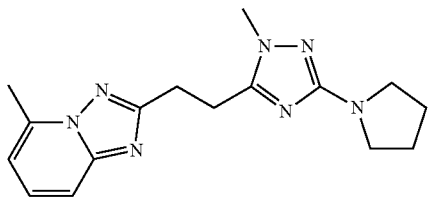 [SMILES: Cc1cccc2nc(CCc3nc(N4CCCC4)nn3C)nn12]

A mixture of 6-chloro-5-methyl-2-(2-(1-methyl-3-(pyrrolidin-1-yl)-1H-1,2,4-triazol-5-yl)vinyl)-[1,2,4]triazolo[1,5-a]pyridine (5 mg, 14.5 µmol, Eq: 1.00), palladium on carbon (10.0 mg, 94.0 µmol, Eq: 6.46) and triethylamine (0.02 ml) in ethanol (3 ml) was stirred 1 h under hydrogen (1 atm). The mixture was filtered over Celite and then concentrated to an oil. The residue was dissolved in DCM (15 ml) and Na2CO3 (50 mg) was added. The mixture was stirred for 5 min and then filtered over Celite and concentrated to give the desired product (5 mg) as a colorless oil. MS: m/z=312.3 (M+H+)

Example 30

Cyclopropyl-{5-[2-(5,7-dimethyl-[1,2,4]triazolo[1,5-a]pyrimidin-2-yl)-vinyl]-1-methyl-1H-[1,2,4]triazol-3-yl}-methyl-amine

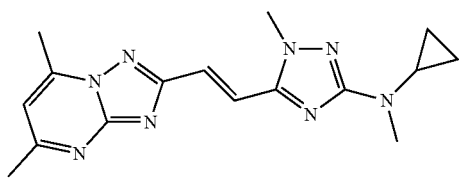 [SMILES: Cc1cc(C)n2nc(/C=C/c3nc(N(C)C4CC4)nn3C)nc2n1]

To a solution of 3-(cyclopropyl(methyl)amino)-1-methyl-1H-1,2,4-triazole-5-carbaldehyde (45 mg, 250 µmol, Eq: 1.00) in tetrahydrofuran (2.3 ml) were added ((5,7-dimethyl-[1,2,4]triazolo[1,5-a]pyrimidin-2-yl)methyl)triphenylphosphonium chloride (115 mg, 250 µmol, Eq: 1.00) and DBU (95.0 mg, 94.1 µl, 624 µmol, Eq: 2.5). The resulting mixture was stirred for 18 hours at 25° C. TLC (Hep/EtOAC 1:1/UV 254 nm) showed no starting material left and new product spot. MS showed product peak also. The crude material was applied on silicagel and purified by flash chromatography over a 20 g silicagel column using heptane/ethyl acetate 1:1 as eluent to give Cyclopropyl-{5-[2-(5,7-dimethyl-[1,2,4]triazolo[1,5-a]pyrimidin-2-yl)-vinyl]-1-methyl-1H-[1,2,4]triazol-3-yl}-methyl-amine (30 mg, 37%) as light yellow waxy solid Example 31

7,8-Dimethyl-2-(2-(1-methyl-3-(pyrrolidin-1-yl)-1H-1,2,4-triazol-5-yl)ethyl)-[1,2,4]triazolo[1,5-a]pyridine

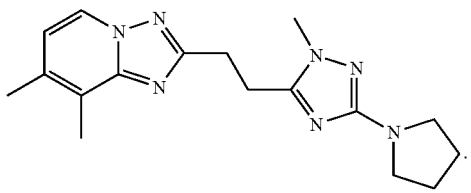 [SMILES: Cc1ccn2nc(CCc3nc(N4CCCC4)nn3C)nc2c1C]

The desired product (12.2 mg) was obtained as a light yellow solid in analogy to Example 29 from 5-bromo-3,4-dimethylpyridin-2-amine. MS: m/z=328.5 (M+H+)

Example 32

7,8-Dimethyl-2-(2-(1-methyl-5-(pyrrolidin-1-yl)-1H-1,2,4-triazol-3-yl)ethyl)-[1,2,4]triazolo[1,5-a]pyridine

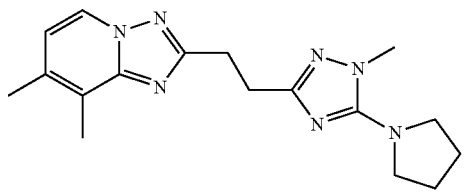 [SMILES: Cc1ccn2nc(CCc3nc(N4CCCC4)n(C)n3)nc2c1C]

a) 6-bromo-7,8-dimethyl-2-(2-(1-methyl-5-(pyrrolidin-1-yl)-1H-1,2,4-triazol-3-yl)vinyl)-[1,2,4]triazolo[1,5-a]pyridine

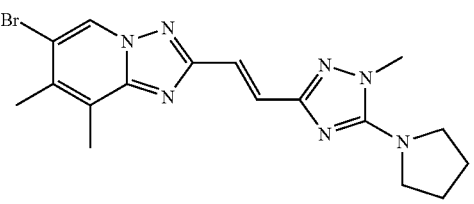 [SMILES: Cc1c(Br)cn2nc(/C=C/c3nc(N4CCCC4)n(C)n3)nc2c1C]

The desired product (26 mg) was obtained as a light yellow solid in analogy to Example 26 steps a-e using 5-bromo-3,4-dimethylpyridin-2-amine (step b) and 1-methyl-5-pyrrolidin-1-yl-1H-[1,2,4]triazole-3-carbaldehyde (step e) as starting materials. MS: m/z=404.4 (M+H+)

b) 7,8-Dimethyl-2-(2-(1-methyl-5-(pyrrolidin-1-yl)-1H-1,2,4-triazol-3-yl)ethyl)-[1,2,4]triazolo[1,5-a]pyridine

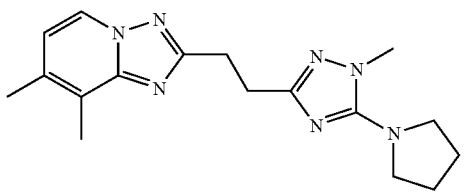 [SMILES: Cc1ccn2nc(CCc3nc(N4CCCC4)n(C)n3)nc2c1C]

The desired product (10.1 mg) was obtained in analogy to Example 29b from 6-bromo-7,8-dimethyl-2-(2-(1-methyl-5-(pyrrolidin-1-yl)-1H-1,2,4-triazol-3-yl)vinyl)-[1,2,4]triazolo[1,5-a]pyridine as a light yellow solid. MS: m/z=326.5 (M+H+)

Example 33

2-[2-(2-Ethyl-5-pyrrolidin-1-yl-2H-[1,2,4]triazol-3-yl)-ethyl]-3-methyl-quinoxaline

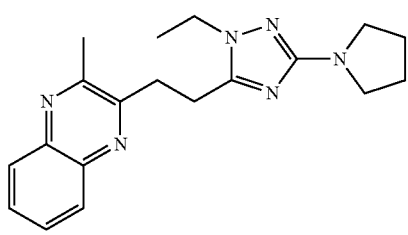 [SMILES: CCn1nc(N2CCCC2)nc1CCc1nc2ccccc2nc1C]

2-(2-(1-ethyl-3-(pyrrolidin-1-yl)-1H-1,2,4-triazol-5-yl)vinyl)-3-methylquinoxaline (10 mg, 29.9 μmol, Eq: 1.00) was stirred in Ethyl acetate (6 ml) using 5% Pd on Ba2SO4 (3 mg, 30.8 μmol, Eq: 1.00) as catalyst in a hydrogen atmosphere. The mixture was stirred at room temperature for totally 12 h. TLC showed nearly complete conversion. The crude material was applied on silica gel an purified by column chromatography using ethyl acetate/methanol (0-5% methanol) as eluent to give 2-[2-(2-Ethyl-5-pyrrolidin-1-yl-2H-[1,2,4]triazol-3-yl)-ethyl]-3-methyl-quinoxaline (3.2 mg, 31.8%) as off-white semisolid Example 34

Cyclopropyl-{5-[2-(5,7-dimethyl-[1,2,4]triazolo[1,5-a]pyrimidin-2-yl)-ethyl]-1-methyl-1H-[1,2,4]triazol-3-yl}-methyl-amine

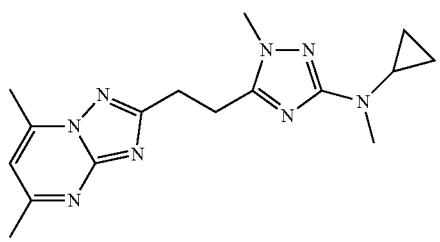 [SMILES: Cc1cc(C)n2nc(CCc3nc(N(C)C4CC4)nn3C)nc2n1]

N-cyclopropyl-5-(2-(5,7-dimethyl-[1,2,4]triazolo[1,5-a]pyrimidin-2-yl)vinyl)-N,1-dimethyl-1H-1,2,4-triazol-3-amine (10 mg, 30.8 μmol, Eq: 1.00) was stirred in Ethyl acetate (6 ml) using 5% Pd on Ba2SO4 (3 mg, 30.8 μmol, Eq: 1.00) as catalyst in a hydrogen atmosphere. The mixture was stirred at room temperature for 4 h. No reaction. Palladium on activated charcoal 10% (5 mg, 30.8 μmol, Eq: 1.00) was added an stirring was continued for 4 h. TLC showed new product but still starting material left. Palladium on activated charcoal 10% (4 mg, 30.8 μmol, Eq: 1.00) was added and stirring was continued for 4 h again. TLC showed nearly complete conversion. The crude material was applied on silica gel an purified by column chromatography using ethyl acetate/methanol (0-5% methanol) as eluent to give Cyclopropyl-{5-[2-(5,7-dimethyl-[1,2,4]triazolo[1,5-a]pyrimidin-2-yl)-ethyl]-1-methyl-1H-[1,2,4]triazol-3-yl}-methyl-amine (8.4 mg, 83.5%) as off-white semisolid.

Example 35

6-Chloro-5,8-dimethyl-2-(2-(1-methyl-5-(pyrrolidin-1-yl)-1H-1,2,4-triazol-3-yl)vinyl)-[1,2,4]triazolo[1,5-a]pyridine

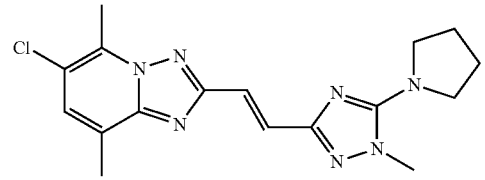 [SMILES: Cc1cc(Cl)c(C)n2nc(/C=C/c3nc(N4CCCC4)n(C)n3)nc12]

a) 5-Chloro-3,6-dimethylpyridin-2-amine

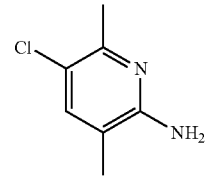

NCS (3.28 g, 24.6 mmol, Eq: 1.00) was added at 15° C. in one portion to a solution of 3,6-dimethylpyridin-2-amine (3 g, 24.6 mmol, Eq: 1.00) in ethyl acetate (130 mL). The temperature was maintained between 20-24° C. for 1 h. The red mixture was stirred overnight. The mixture was filtered. The filtrate was washed with 40% aq. sodium bisulfite solution (100 ml) and brine.

The aqueous phase was extracted with EtOAc (2×100 ml). The combined organic layers were dried over Na2SO4 and then concentrated to an oil. The residue was purified by column chromatography (70 g SiO2, 0 to 50% EtOAc/n-heptane) to afford 5-chloro-3,6-dimethylpyridin-2-amine (1.16 g, 30.2%) as a light yellow-brown product. MS: m/z=157.1 (M+H+)

b) 6-chloro-5,8-dimethyl-2-(2-(1-methyl-5-(pyrrolidin-1-yl)-1H-1,2,4-triazol-3-yl)vinyl)-[1,2,4]triazolo[1,5-a]pyridine

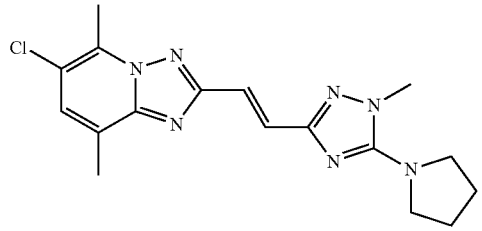 [SMILES: Cc1cc(Cl)c(C)n2nc(/C=C/c3nc(N4CCCC4)n(C)n3)nc12]

Using 5-chloro-3,6-dimethylpyridin-2-amine as starting material, the product (87 mg) was obtained in analogy to Example 26, steps b-e as a light yellow solid. MS: m/z=358.5 (M+H+)

Example 36

6-Chloro-5,8-dimethyl-2-(2-(1-methyl-5-(pyrrolidin-1-yl)-1H-1,2,4-triazol-3-yl)ethyl)-[1,2,4]triazolo[1,5-a]pyridine

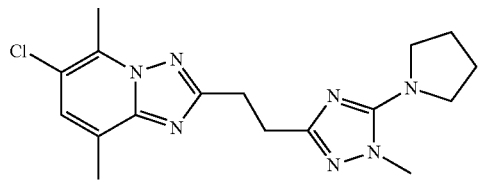 [SMILES: Cc1cc(Cl)c(C)n2nc(CCc3nc(N4CCCC4)n(C)n3)nc12]

Example 37

5,8-Dimethyl-2-(2-(1-methyl-3-(pyrrolidin-1-yl)-1H-1,2,4-triazol-5-yl)ethyl)-[1,2,4]triazolo[1,5-a]pyridine

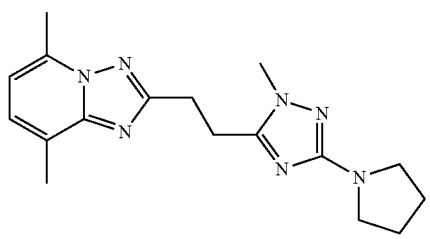 [SMILES: Cc1ccc(C)n2nc(CCc3nc(N4CCCC4)nn3C)nc12]

The product (35 mg, 91.1%) was obtained as a white solid in analogy to Example 29b from (E)-6-chloro-5,8-dimethyl-2-(2-(1-methyl-3-(pyrrolidin-1-yl)-1H-1,2,4-triazol-5-yl)vinyl)-[1,2,4]triazolo[1,5-a]pyridine. MS: m/z=326.5 (M+H+)

Example 38

6-Chloro-5,8-dimethyl-2-(2-(1-methyl-3-(pyrrolidin-1-yl)-1H-1,2,4-triazol-5-yl)ethyl)-[1,2,4]triazolo[1,5-a]pyridine

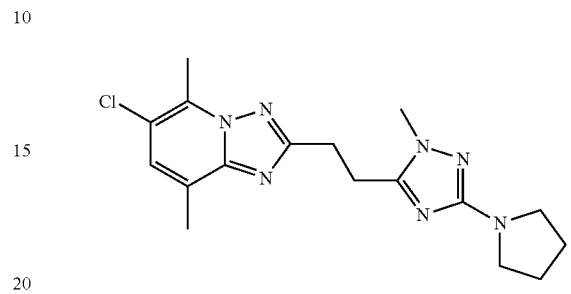

Ethyl acetate was added to (E)-6-chloro-5,8-dimethyl-2-(2-(1-methyl-3-(pyrrolidin-1-yl)-1H-1,2,4-triazol-5-yl)vinyl)-[1,2,4]triazolo[1,5-a]pyridine (15 mg). Palladium (5 wt. %) on barium sulfate (20 mg) was added. The mixture was stirred for 5 h under a hydrogen atmosphere and then filtered over Celite. The mixture was concentrated and purified by preparative HPLC to give the desired product (10.2 mg, 67.8%) as a light yellow powder. MS: m/z=360.5 (M+H+)

Example 39

2-{2-[5-(3-Fluoro-azetidin-1-yl)-2-methyl-2H-[1,2,4]triazol-3-yl]-ethyl}-5,8-dimethyl-[1,2,4]triazolo[1,5-a]pyrazine

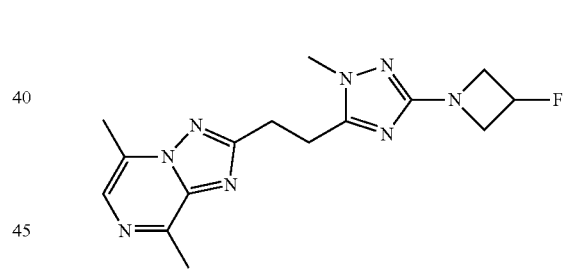

a) 2-{(E)-2-[5-(3-Fluoro-azetidin-1-yl)-2-methyl-2H-[1,2,4]triazol-3-yl]-vinyl}-5,8-dimethyl-[1,2,4]triazolo[1,5-a]pyrazine

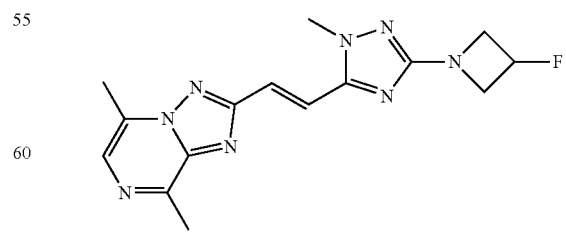

Was prepared in the same manner as described in Example 87a) using 3-fluoroazetidine hydrochloride (26.7 mg, 239 μmol, Eq: 2) instead of pyrrolidin-2-one affording 2-{(E)-2-

[5-(3-Fluoro-azetidin-1-yl)-2-methyl-2H-[1,2,4]triazol-3-yl]-vinyl}-5,8-dimethyl-[1,2,4]triazolo[1,5-a]pyrazine (12.3 mg, 31.3%) as off-white solid. MS: m/z=329.4 (M+H⁺)

b) 2-{2-[5-(3-Fluoro-azetidin-1-yl)-2-methyl-2H-[1,2,4]triazol-3-yl]-ethyl}-5,8-dimethyl-[1,2,4]triazolo[1,5-a]pyrazine

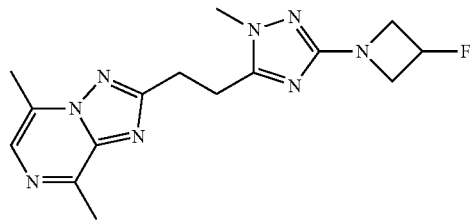 [SMILES: Cc1ncc(C)n2nc(CCc3nc(N4CC(F)C4)nn3C)nc12]

Was prepared in the same manner as described in Example 87 b) from (E)-2-(2-(3-(3-fluoroazetidin-1-yl)-1-methyl-1H-1,2,4-triazol-5-yl)vinyl)-5,8-dimethyl-[1,2,4]triazolo[1,5-a]pyrazine (10 mg, 30.5 μmol, Eq: 1.00) affording 2-{2-[5-(3-Fluoro-azetidin-1-yl)-2-methyl-2H-[1,2,4]triazol-3-yl]-ethyl}-5,8-dimethyl-[1,2,4]triazolo[1,5-a]pyrazine (10.1 mg, 100%) as off-white waxy solid. MS: m/z=331.4 (M+H⁺)

Example 40

5,6-Dimethyl-2-(2-(1-methyl-3-(pyrrolidin-1-yl)-1H-1,2,4-triazol-5-yl)ethyl)-[1,2,4]triazolo[1,5-a]pyridine

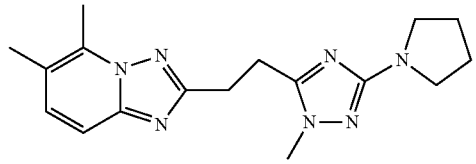

a) (E)-5,6-Dimethyl-2-(2-(1-methyl-3-(pyrrolidin-1-yl)-1H-1,2,4-triazol-5-yl)vinyl)-[1,2,4]triazolo[1,5-a]pyridine

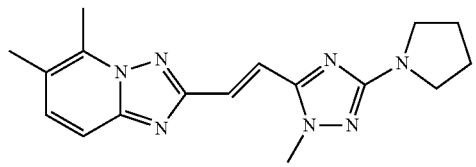 [SMILES: Cc1ccc2nc(/C=C/c3nc(N4CCCC4)nn3C)nn2c1C]

The product (55 mg) was obtained in analogy to Example 26 (steps a-e) from 5,6-dimethylpyridin-2-amine as a yellow solid. MS: m/z=324.19 (M+H+)

b) 5,6-Dimethyl-2-(2-(1-methyl-3-(pyrrolidin-1-yl)-1H-1,2,4-triazol-5-yl)ethyl)-[1,2,4]triazolo[1,5-a]pyridine

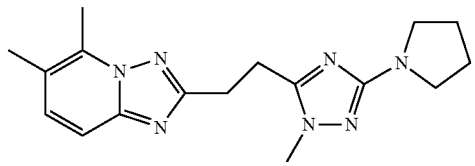 [SMILES: Cc1ccc2nc(CCc3nc(N4CCCC4)nn3C)nn2c1C]

(E)-5,6-Dimethyl-2-(2-(1-methyl-3-(pyrrolidin-1-yl)-1H-1,2,4-triazol-5-yl)vinyl)-[1,2,4]triazolo[1,5-a]pyridine (45 mg) and Pd/C (5 mg) were stirred in acetic acid (0.7 ml) under hydrogen for 1 h. The mixture was filtered and concentrated to give the product (45 mg, 99.4%) as a light yellow solid. MS: m/z=326.2 (M+H+)

Example 41

5,6,8-Trimethyl-2-(2-(1-methyl-3-(pyrrolidin-1-yl)-1H-1,2,4-triazol-5-yl)ethyl)-[1,2,4]triazolo[1,5-a]pyrazine

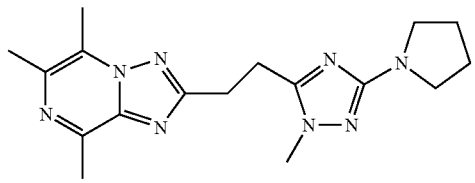 [SMILES: Cc1nc(C)c2nc(CCc3nc(N4CCCC4)nn3C)nn2c1C]

a) (E)-5,6,8-Trimethyl-2-(2-(1-methyl-3-(pyrrolidin-1-yl)-1H-1,2,4-triazol-5-yl)vinyl)-[1,2,4]triazolo[1,5-a]pyrazine

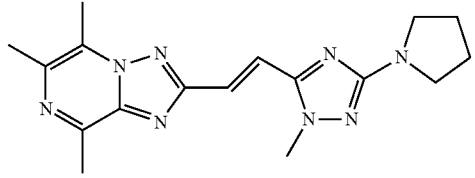 [SMILES: Cc1nc(C)c2nc(/C=C/c3nc(N4CCCC4)nn3C)nn2c1C]

The product (55 mg) was obtained in analogy to Example 26 (steps a-e) from 3,5,6-trimethylpyrazin-2-amine as a yellow solid. MS: m/z=339.20 (M+H+)

b) 5,6,8-Trimethyl-2-(2-(1-methyl-3-(pyrrolidin-1-yl)-1H-1,2,4-triazol-5-yl)ethyl)-[1,2,4]triazolo[1,5-a]pyrazine

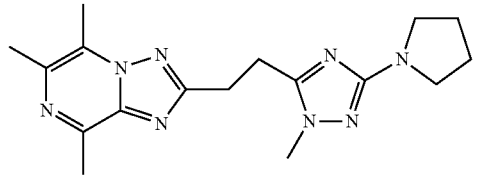 [SMILES: Cc1nc(C)c2nc(CCc3nc(N4CCCC4)nn3C)nn2c1C]

(E)-5,6,8-Trimethyl-2-(2-(1-methyl-3-(pyrrolidin-1-yl)-1H-1,2,4-triazol-5-yl)vinyl)-[1,2,4]triazolo[1,5-a]pyrazine (45 mg, 99.4%) and Pd/C (5 mg) were stirred in acetic acid (0.7 ml) under hydrogen for 1 h. The mixture was filtered and concentrated to give the product (25 mg) as a light brown solid. MS: m/z=341.2 (M+H+)

Example 42

5,7,8-Trimethyl-2-(2-(1-methyl-3-(pyrrolidin-1-yl)-1H-1,2,4-triazol-5-yl)ethyl)-[1,2,4]triazolo[1,5-c]pyrimidine

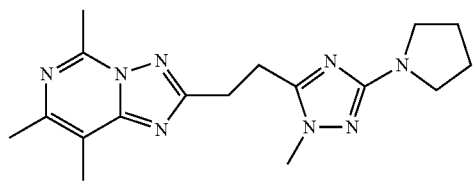 [SMILES: Cc1nc(C)n2nc(CCc3nc(N4CCCC4)nn3C)nc2c1C]

a) (E)-5,7,8-Trimethyl-2-(2-(1-methyl-3-(pyrrolidin-1-yl)-1H-1,2,4-triazol-5-yl)vinyl)-[1,2,4]triazolo[1,5-c]pyrimidine

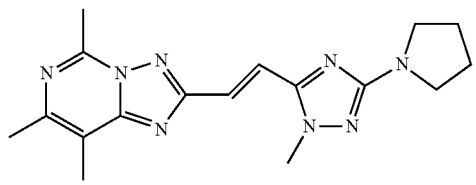 [SMILES: Cc1nc(C)n2nc(/C=C/c3nc(N4CCCC4)nn3C)nc2c1C]

The product (35 mg) was obtained in analogy to Example 26 (steps a-e) from 2,5,6-trimethylpyrimidin-4-amine as a yellow solid. MS: m/z=339.5 (M+H+)

b) 5,7,8-Trimethyl-2-(2-(1-methyl-3-(pyrrolidin-1-yl)-1H-1,2,4-triazol-5-yl)ethyl)-[1,2,4]triazolo[1,5-c]pyrimidine

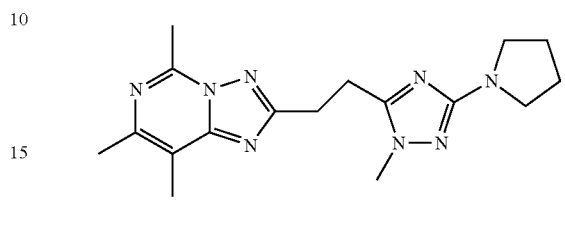

(E)-5,7,8-Trimethyl-2-(2-(1-methyl-3-(pyrrolidin-1-yl)-1H-1,2,4-triazol-5-yl)vinyl)-[1,2,4]triazolo[1,5-c]pyrimidine (32 mg) and Pd/C (10 mg) were stirred in ethanol (0.4 ml) under hydrogen for 1 h. The mixture was filtered and concentrated to give the product (20 mg, 62.5%) as a white waxy solid. MS: m/z=341.4 (M+H+)

Example 43

2-{2-[5-(3-Methoxy-pyrrolidin-1-yl)-2-methyl-2H-[1,2,4]triazol-3-yl]-ethyl}-5,8-dimethyl-[1,2,4]triazolo[1,5-a]pyrazine

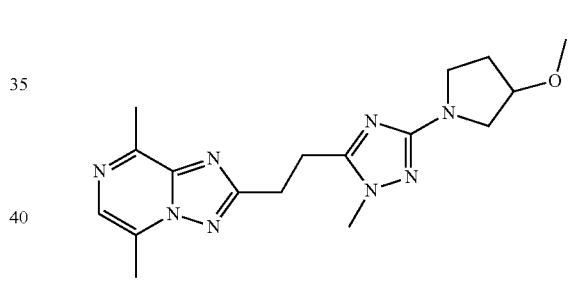

a) 2-{(E)-2-[5-(3-Fluoro-azetidin-1-yl)-2-methyl-2H-[1,2,4]triazol-3-yl]-vinyl}-5,8-dimethyl-[1,2,4]triazolo[1,5-a]pyrazine

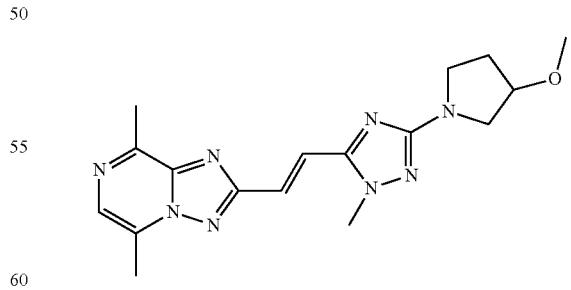

Was prepared in the same manner as described in Example 87a) using 3-methoxypyrrolidine (24.2 mg, 239 μmol, Eq: 2) instead of pyrrolidin-2-one affording 2-{(E)-2-[5-(3-Fluoro-azetidin-1-yl)-2-methyl-2H-[1,2,4]triazol-3-yl]-vinyl}-5,8-dimethyl-[1,2,4]triazolo[1,5-a]pyrazine (15.4 mg, 36.3%) as yellow oil. MS: m/z=355.4 (M+H⁺)

b) 2-{2-[5-(3-Methoxy-pyrrolidin-1-yl)-2-methyl-2H-[1,2,4]triazol-3-yl]-ethyl}-5,8-dimethyl-[1,2,4]triazolo[1,5-a]pyrazine

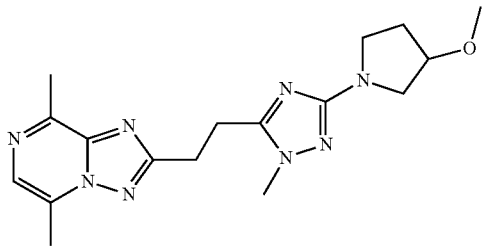 [SMILES: COC1CCN(c2nc(CCc3nc4c(C)ncc(C)n4n3)n(C)n2)C1]

Was prepared in the same manner as described in Example 87 b) from (E)-2-(2-(3-(3-methoxypyrrolidin-1-yl)-1-methyl-1H-1,2,4-triazol-5-yl)vinyl)-5,8-dimethyl-[1,2,4]triazolo[1,5-a]pyrazine (13.5 mg, 38.1 µmol, Eq: 1.00) affording 2-{2-[5-(3-Methoxy-pyrrolidin-1-yl)-2-methyl-2H-[1,2,4]triazol-3-yl]-ethyl}-5,8-dimethyl-[1,2,4]triazolo[1,5-a]pyrazine (4.7 mg, 34.6%) as off-white semisolid. MS: m/z=357.5 (M+H$^+$)

Example 44

8-Chloro-5,7-dimethyl-2-(2-(1-methyl-3-(pyrrolidin-1-yl)-1H-1,2,4-triazol-5-yl)ethyl)-[1,2,4]triazolo[1,5-c]pyrimidine

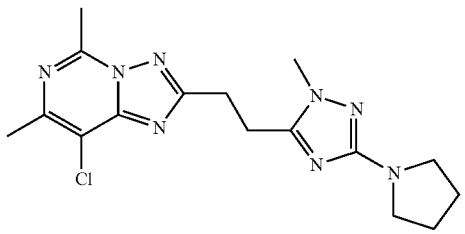 [SMILES: Cc1nc(C)n2nc(CCc3nc(N4CCCC4)nn3C)nc2c1Cl]

The product (6.6 mg) was obtained as a light yellow solid in analogy to Example 26 from 5-chloro-2,6-dimethylpyrimidin-4-amine. MS: m/z=361.5 (M+H+)

Example 45

5,7-Dimethyl-2-(2-(1-methyl-3-(pyrrolidin-1-yl)-1H-1,2,4-triazol-5-yl)ethyl)-[1,2,4]triazolo[1,5-c]pyrimidine

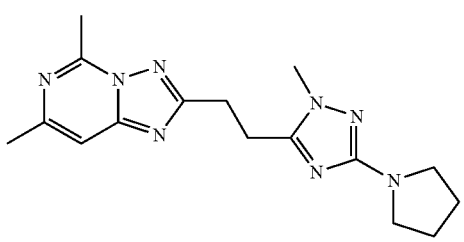 [SMILES: Cc1cc2nc(CCc3nc(N4CCCC4)nn3C)nn2c(C)n1]

The product (7.1 mg, 31.2%) was obtained as a white solid in analogy to Example 29b from 8-chloro-5,7-dimethyl-2-(2-(1-methyl-3-(pyrrolidin-1-yl)-1H-1,2,4-triazol-5-yl)ethyl)-[1,2,4]triazolo[1,5-c]pyrimidine. MS: m/z=327.2 (M+H+)

Example 46

6-Chloro-5,8-dimethyl-2-[(1S,2S)-2-(2-methyl-5-pyrrolidin-1-yl-2H-[1,2,4]triazol-3-yl)-cyclopropyl]-[1,2,4]triazolo[1,5-a]pyridine

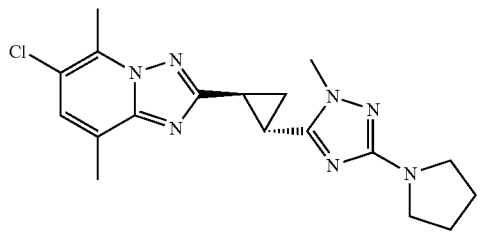 [SMILES: Cc1cc(Cl)c(C)n2nc([C@H]3C[C@@H]3c3nc(N4CCCC4)nn3C)nc12]

a) 1-Amino-5-chloro-3,6-dimethylpyridin-2(1H)-iminium 2,4,6-trimethylbenzenesulfonate

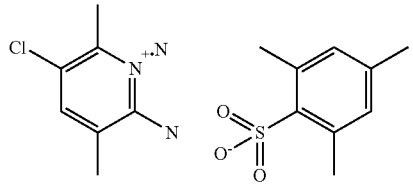

The product (1.5 g, 54.5%) was obtained as a white solid from 5-chloro-3,6-dimethylpyridin-2-amine in analogy to Example 26b. MS: m/z=169.2 (M+), m/z=199.3 (M−)

b) 2-(6-Chloro-5,8-dimethyl-[1,2,4]triazolo[1,5-a]pyridin-2-yl)cyclopropanecarboxylic acid

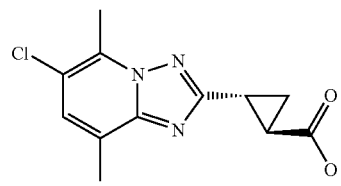 [SMILES: Cc1cc(Cl)c(C)n2nc([C@@H]3C[C@H]3C(=O)O)nc12]

1-Amino-5-chloro-3,6-dimethylpyridin-2(1H)-iminium 2,4,6-trimethylbenzenesulfonate (100 mg, 269 µmol, Eq: 1.00) was added to a solution of ethyl 2-formylcyclopropanecarboxylate (38.2 mg, 269 µmol, Eq: 1.00) in methanol (2 ml). 2 N KOH aq (200 µl, 400 µmol, Eq: 1.49) was added and the yellow mixture was stirred for 1 h at room temperature under air. 1 N LiOH aq (4 mL, 4 mmol, Eq: 14.9) and tetrahydrofuran (8 ml) were added and the mixture was stirred for 30 min at room temperature. Volatile organic solvents were evaporated, water (10 ml) was added and the mixture was washed with diethyl ether (10 ml). The aqueous phase was acidified with 2 N HCl aq and then extracted with ethyl acetate (3×10 ml). The combined organic layers were dried over sodium sulfate and then concentrated to give the desired product (70 mg, 98%) as a white solid. MS: m/z=266.1 (M+H+)

c) 6-Chloro-5,8-dimethyl-2-[(1S,2S)-2-(2-methyl-5-pyrrolidin-1-yl-2H-[1,2,4]triazol-3-yl)-cyclopropyl]-[1,2,4]triazolo[1,5-c]pyridine

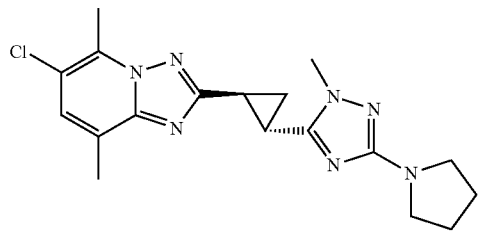 [SMILES: Cc1cc(Cl)c(C)n2nc([C@H]3C[C@@H]3c3nc(N4CCCC4)nn3C)nc12]

Oxalyl chloride (290 mg, 200 µL, 2.28 mmol, Eq: 8.67) was added to 2-(6-chloro-5,8-dimethyl-[1,2,4]triazolo[1,5-a]pyridin-2-yl)cyclopropanecarboxylic acid (70 mg, 263 µmol, Eq: 1.00) in dichloromethane (2 ml), 0.002 ml dimethylformamide was added and the mixture stirred for 30 min. The mixture was concentrated to an oil. The residue was dissolved in acetone (2 mL) and potassium thiocyanate (30.7 mg, 316 µmol, Eq: 1.2) was added. The white suspension was stirred for 30 min and then filtered. The filtrate was concentrated to an oil. The residue was dissolved in toluene (2 mL). Pyrrolidine (22.5 mg, 316 µmol, Eq: 1.2) was added and the mixture was stirred for 1 h. The mixture was concentrated to an oil. The residue was dissolved in tetrahydrofuran, cesium carbonate (172 mg, 527 µmol, Eq: 2) and iodomethane (187 mg, 1.32 mmol, Eq: 5) were added, the mixture was stirred for 5 h at room temperature. The mixture was filtered and concentrated to an oil. The residue was dissolved in methylhydrazine (2 mL) and heated to 100° C. for 1 h. Water (10 ml) was added and the mixture was extracted with dichloromethane (3×10 ml). The organic layer was dried over sodium sulfate and then purified by column chromatography to give the desired product (9.8 mg, 10%) as a colorless oil. MS: m/z=372.5 (M+H+)

Example 47

2-((1-Ethyl-5-(pyrrolidin-1-yl)-1H-1,2,4-triazol-3-yl)ethynyl)-5,8-dimethyl-[1,2,4]triazolo[1,5-a]pyrazine

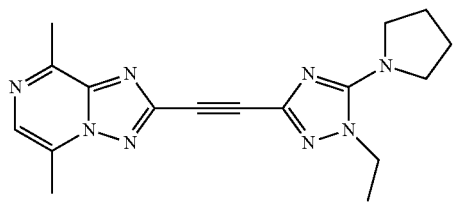 [SMILES: CCn1nc(C#Cc2nc3c(C)ncc(C)n3n2)nc1N1CCCC1]

a) 3,5-Dibromo-1-ethyl-1H-[1,2,4]triazole

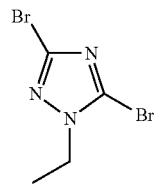

3,5-Dibromo-1H-1,2,4-triazole (2.5 g, 11.0 mmol, Eq: 1.00) was dissolved in dimethylformamide (31.8 ml) and sodium hydride (529 mg, 60% dispersion in mineral oil, 13.2 mmol, Eq: 1.2) was added slowly. Ethyl methanesulfonate (2.74 g, 2.27 ml, 22.0 mmol, Eq: 2) was added to the reaction and the mixture was heated in a microwave oven for 60 minutes at 100° C. The mixture was diluted with water and extracted 3× with ethyl acetate. The organic layer was dried over magnesium sulfate, filtered and the solvent was evaporated to give 3,5-dibromo-1-ethyl-1H-[1,2,4]triazole (2.54 g, 90.4%) as a white powder. MS: m/z=255.9 (M+H+)

b) 3-Bromo-1-ethyl-5-pyrrolidin-1-yl-1H-[1,2,4]triazole

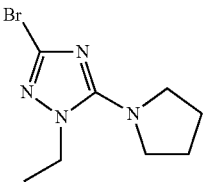

A mixture of 3,5-dibromo-1-ethyl-1H-1,2,4-triazole (462 mg, 1.81 mmol, Eq: 1.00) and pyrrolidine (135 mg, 157 µl, 1.9 mmol, Eq: 1.05) in dimethylformamide (4 ml) was heated for 40 minutes at 110° C. in a microwave oven. Evaporation of the solvent afforded 578 mg of an orange oil. The crude material was applied on silica gel and purified by flash chromatography over a 20 g silica gel column using dichloromethane/methanol 0-10% as eluent to give 3-bromo-1-ethyl-5-pyrrolidin-1-yl-1H-[1,2,4]triazole (240 mg, 54%) as an orange oil. MS: m/z=2-(5247 (M+H+)

c) 1-Ethyl-5-pyrrolidin-1-yl-3-trimethylsilanylethynyl-1H-[1,2,4]triazole

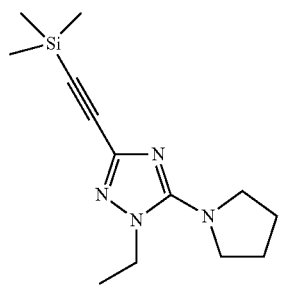 [SMILES: CCn1nc(C#C[Si](C)(C)C)nc1N1CCCC1]

A mixture of 3-bromo-1-ethyl-5-(pyrrolidin-1-yl)-1H-1,2,4-triazole (240 mg, 979 µmol, Eq: 1.00), ethynyltrimethylsilane (192 mg, 275 μl, 1.96 mmol, Eq: 2) and triethylamine (149 mg, 205 μl, 1.47 mmol, Eq: 1.5) in tetrahydrofuran (3.65 ml) was purged for 5 minutes with nitrogen. Then copper (I) iodide (1.86 mg, 9.79 μmol, Eq: 0.01), bis(triphenylphosphine)palladium(II) chloride (6.87 mg, 9.79 μmol, Eq: 0.01) and triphenylphosphine (2.57 mg, 9.79 μmol, Eq: 0.01) were added, the vessel was capped and heated to 120° C. for 1 day. Once more copper (I) iodide (1.86 mg, 9.79 μmol, Eq: 0.01), triphenylphosphine (2.57 mg, 9.79 μmol, Eq: 0.01), bis(triphenylphosphine)palladium(II) chloride (6.87 mg, 9.79 μmol, Eq: 0.01) and ethynyltrimethylsilane (192 mg, 275 μl, 1.96 mmol, Eq: 2) were added, the vial was purged with argon, capped again and stirred for one more day at 120° C. The crude material was applied on silica gel and purified by flash chromatography over a 20 g silica gel column using heptane/ethyl acetate 10-30% as eluent affording 1-ethyl-5-pyrrolidin-1-yl-3-trimethylsilanylethynyl-1H-[1,2,4]triazole (122 mg, 47.5%) as an orange oil. MS: m/z=263.4 (M+H+)

d) 1-Ethyl-3-ethynyl-5-pyrrolidin-1-yl-1H-[1,2,4]triazole

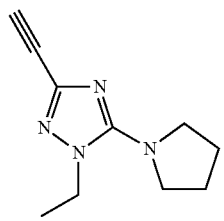

A mixture of 1-ethyl-5-(pyrrolidin-1-yl)-3-((trimethylsilyl)ethynyl)-1H-1,2,4-triazole (122 mg, 465 μmol, Eq: 1.00) in methanol (3 ml) and 1N NaOH aq. (0.1 ml) was stirred for 18 hours at 25° C. under argon atmosphere. The mixture was diluted with ethyl acetate and washed with water. The organic layer was separated, dried over magnesium sulfate, filtered and concentrated affording 1-ethyl-3-ethynyl-5-pyrrolidin-1-yl-1H-[1,2,4]triazole (79 mg, 89.3%) as an orange oil. MS: m/z=191.2 (M+H+)

e) Ethyl-N-[(3,6-dimethylpyrazin-2-yl)carbamothioyl]carbamate

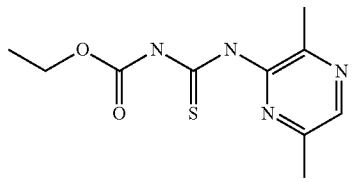 [SMILES: CCOC(=O)NC(=S)Nc1nc(C)cnc1C]

To a solution of 3,6-dimethyl-pyrazin-2-ylamine (5 g, 40.65 mmol) in dioxane (150 ml) was added ethoxycarbonyl isothiocyanate (4.75 ml, 40.65 mmol) at 25° C., and the reaction mixture was stirred for 18 hours at 25° C. Volatiles were removed in vacuo. The resultant residue was dissolved in ethyl acetate, washed with water twice, and brine, dried over anhydrous sodium sulfate, filtered, and evaporated affording ethyl-N-[(3,6-dimethylpyrazin-2-yl)carbamothioyl]carbamate (10 g, 96.73%) as a light yellow solid. MS: m/z=255 (M+H+)

f) 5,8-Dimethyl-[1,2,4]triazolo[1,5-a]pyrazin-2-ylamine

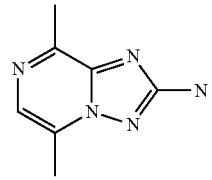

A mixture of hydroxylamine hydrochloride (13.68 g, 196.85 mmol) and N,N-diisopropylethylamine (20.6 ml, 118.11 mmol) in ethanol (200 ml) was stirred for 10 minutes at 25° C. To this mixture was then added ethyl-N-[(3,6-dimethylpyrazin-2-yl)carbamothioyl]carbamate (10 g, 39.37 mmol), and the resultant mixture was heated under reflux for 16 hours. The resultant mixture was diluted with water (100 ml), stirred for 10 min, and extracted twice with ethyl acetate. The combined organic layers were washed with brine, dried over anhydrous sodium sulfate, filtered and evaporated. The crude material thus obtained was triturated with hexane affording 5,8-dimethyl-[1,2,4]triazolo[1,5-a]pyrazin-2-ylamine (2.4 g, 71.87%) as a white solid. MS: m/z=164 (M+H+)

g) 2-Bromo-5,8-dimethyl-[1,2,4]triazolo[1,5-a]pyrazine

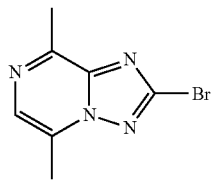

A mixture of 5,8-dimethyl-[1,2,4]triazolo[1,5-a]pyrazin-2-ylamine (2.4 g, 14.71 mmol), sodium nitrite (10.15 g, 147.08 mmol) and benzyltriethylammonium bromide (8 g, 29.42 mmol) in bromoform (76.2 ml, 872.17 mmol) was stirred at 25° C. for 30 minutes. To this mixture was then added dichloroacetic acid (2.43 ml, 29.42 mmol) and the reaction mixture was stirred at 25° C. for further 20 hours. (The reaction flask was wrapped in aluminum foil to protect the mixture from light). Water (100 ml) was added to the reaction mixture, which was then stirred for 30 minutes at 25° C., and finally extracted 4 times with dichloromethane. The combined organic layers were washed twice with water and brine, dried over anhydrous sodium sulfate, filtered and evaporated. The crude material thus obtained was purified by silica gel column chromatography using hexane ethyl acetate 20% as eluent affording 2-bromo-5,8-dimethyl-[1,2,4]triazolo[1,5-a]pyrazine (4.8 g, 74.72%) as an off white solid. MS: m/z=227 (M+H+)

h) 2-((1-Ethyl-5-(pyrrolidin-1-yl)-1H-1,2,4-triazol-3-yl)ethynyl)-5,8-dimethyl-[1,2,4]triazolo[1,5-a]pyrazine

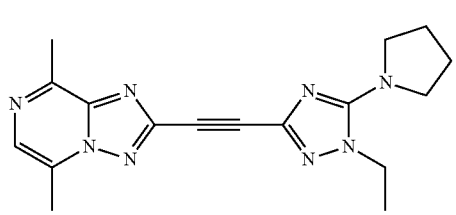 [SMILES: CCn1nc(C#Cc2nc3c(C)ncc(C)n3n2)nc1N1CCCC1]

A mixture of 1-ethyl-3-ethynyl-5-(pyrrolidin-1-yl)-1H-1,2,4-triazole (79 mg, 415 µmol, Eq: 1.00), 2-bromo-5,8-dimethyl-[1,2,4]triazolo[1,5-a]pyrazine (104 mg, 457 µmol, Eq: 1.1) and triethylamine (63.0 mg, 86.8 µl, 623 µmol, Eq: 1.5) in dioxane (2.11 ml) was purged with argon, then copper (I) iodide (1.58 mg, 8.31 µmol, Eq: 0.02), bis(triphenylphosphine)palladium(II) chloride (5.83 mg, 8.31 µmol, Eq: 0.02) and triphenylphosphine (2.18 mg, 8.31 µmol, Eq: 0.02) were added, the vessel was capped and heated for 18 hours to 110° C. The crude material was applied on silica gel and purified by flash chromatography over a 20 g silica gel column using ethyl acetate 100% as eluent affording 2-((1-ethyl-5-(pyrrolidin-1-yl)-1H-1,2,4-triazol-3-yl)ethynyl)-5,8-dimethyl-[1,2,4]triazolo[1,5-a]pyrazine (52 mg, 37.2%) as an orange oil. MS: m/z=337.4 (M+H+)

Example 48

2-(2-(1-Ethyl-5-(pyrrolidin-1-yl)-1H-1,2,4-triazol-3-yl)ethyl)-5,8-dimethyl-[1,2,4]triazolo[1,5-a]pyrazine

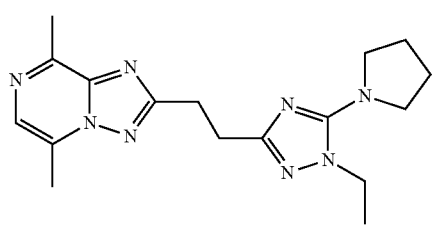 [SMILES: CCn1nc(CCc2nc3c(C)ncc(C)n3n2)nc1N1CCCC1]

A mixture of 2-((1-ethyl-5-(pyrrolidin-1-yl)-1H-1,2,4-triazol-3-yl)ethynyl)-5,8-dimethyl-[1,2,4]triazolo[1,5-a]pyrazine (43 mg, 128 µmol, Eq: 1.00) and palladium on carbon 10% (13.6 mg, 12.8 µmol, Eq: 0.1) in methanol (10 ml) was stirred for 20 hours at 25° C. under hydrogen atmosphere. The catalyst was filtered off, the filtrate was evaporated affording 2-(2-(1-ethyl-5-(pyrrolidin-1-yl)-1H-1,2,4-triazol-3-yl)ethyl)-5,8-dimethyl-[1,2,4]triazolo[1,5-a]pyrazine (42 mg, 96.5%) as an light yellow oil. MS: m/z=341.5 (M+H+)

Example 49

5,8-Dimethyl-2-[2-(2-methyl-5-piperidin-1-yl-2H-[1,2,4]triazol-3-yl)-ethyl]-[1,2,4]triazolo[1,5-a]pyrazine

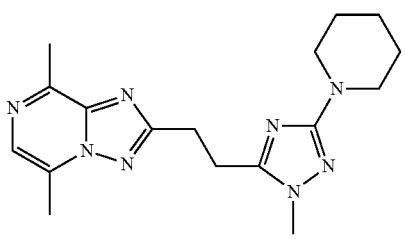 [SMILES: Cc1ncc(C)n2nc(CCc3nc(N4CCCCC4)nn3C)nc12]

a) 3-Methyl-but-2-enoic acid (piperidine-1-carbothioyl)-amide

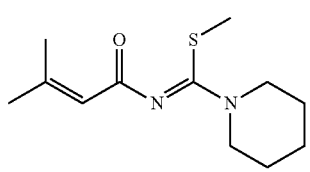 [SMILES: CS/C(=N\C(=O)C=C(C)C)N1CCCCC1]

To a solution of 3-methylbut-2-enoyl isothiocyanate (2 g, 14.2 mmol, Eq: 1.00) in benzene (40.0 ml) was added a solution of piperidine (1.21 g, 1.4 ml, 14.2 mmol, Eq: 1.00) in benzene (20.0 ml). The mixture was stirred for 2 hours. The mixture was evaporated affording 3-methyl-but-2-enoic acid (piperidine-1-carbothioyl)-amide (3.32 g, 104%) as a yellow oil. MS: m/z=227.2 (M+H+)

b) 3-Methyl-but-2-enoic acid 1-methylsulfanyl-1-piperidin-1-yl-meth-(Z)-ylideneamide A mixture of 3-methyl-N-(piperidine-1-carbonothioyl)but-2-enamide (3.21 g, 14.2 mmol, Eq: 1.00), sodium carbonate (1.58 g, 14.9 mmol, Eq: 1.05) and iodomethane (10.1 g, 4.43 ml, 70.9 mmol, Eq: 5) in tetrahydrofuran (100 ml) was stirred for 2.5 days under reflux. The mixture was evaporated, 30 ml of ethyl acetate was added and the mixture was filtrated, the filtrate was evaporated affording 3-methyl-but-2-enoic acid 1-methylsulfanyl-1-piperidin-1-yl-meth-(Z)-ylideneamide (5.137 g, 151%) as an orange-brown semi-solid. MS: m/z=241.2 (M+H+)

c) 1-[1-Methyl-5-(2-methyl-propenyl)-1H-[1,2,4] triazol-3-yl]-piperidine

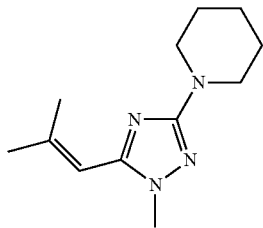 [SMILES: CC(C)=Cc1nc(N2CCCCC2)nn1C]

A mixture of (Z)-methyl N-3-methylbut-2-enoylpiperidine-1-carbimidothioate (3.2 g, 9.32 mmol, Eq: 1.00) and methylhydrazine (4.9 g, 5.6 ml, 106 mmol, Eq: 11.4) was heated for 1.5 hours at 100° C. The mixture was diluted with ethyl acetate and washed 3 times with water. The organic layer was separated, dried over magnesium sulfate, filtrated and evaporated to give 1.135 g of a yellow oil. The crude material was applied on silica gel and purified by flash chromatography over a 50 g silica gel column using heptane/ethyl acetate 10-50% as eluent affording 1-[1-methyl-5-(2-methyl-prop enyl)-1H-[1,2,4]triazol-3-yl]-piperidine (376 mg, 18.3%) as a light yellow oil. MS: m/z=221.2 (M+H+)

d) 2-Methyl-5-piperidin-1-yl-2H-[1,2,4]triazole-3-carbaldehyde

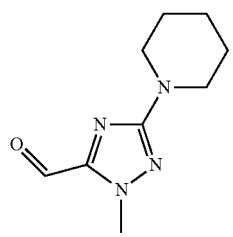

A mixture of 1-(1-methyl-5-(2-methylprop-1-enyl)-1H-1, 2,4-triazol-3-yl)piperidine (376 mg, 1.71 mmol, Eq: 1.00), sodium periodate (1.46 g, 6.83 mmol, Eq: 4), osmium tetroxide 4% aq. (325 mg, 325 µl, 51.2 µmol, Eq: 0.03) and benzyltriethylammonium chloride (155 mg, 683 µmol, Eq: 0.4) in dioxane (17.9 ml) and water (4.12 ml) was stirred for 1.5 hours at 70° C. The mixture was diluted with ethyl acetate and washed 2× with water and brine. The organic layer was separated, dried over magnesium sulfate, filtrated and evaporated affording 2-methyl-5-piperidin-1-yl-2H-[1,2,4]triazole-3-carbaldehyde (331 mg, 99.9%) as a brown waxy solid. MS: m/z=195.4 (M+H+)

e) 5,8-Dimethyl-2-[(E)-2-(2-methyl-5-piperidin-1-yl-2H-[1,2,4]triazol-3-yl)-vinyl]-[1,2,4]triazolo[1,5-a] pyrazine

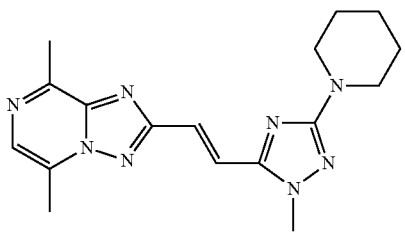 [SMILES: Cc1ncc(C)n2nc(/C=C/c3nc(N4CCCCC4)nn3C)nc12]

A mixture of 1-methyl-3-(piperidin-1-yl)-1H-1,2,4-triazole-5-carbaldehyde (60 mg, 309 µmol, Eq: 1.00), ((5,8-dimethyl-[1,2,4]triazolo[1,5-a]pyrazin-2-yl)methyl)triphenylphosphonium chloride (142 mg, 309 µmol, Eq: 1.00) and DBU (51.7 mg, 51.2 µl, 340 µmol, Eq: 1.1) in tetrahydrofuran (15 ml) was stirred for 18 hours at 25° C. under argon. The crude material was applied on silica gel and purified by flash chromatography over a 20 g silica gel column using ethyl acetate/methanol 0-7% as eluent affording 5,8-dimethyl-2-[(E)-2-(2-methyl-5-piperidin-1-yl-2H-[1,2,4]triazol-3-yl)-vinyl]-[1,2,4]triazolo[1,5-a]pyrazine (56 mg, 53.6%) as a yellow solid. MS: m/z=339.5 (M+H+), MP: 186-188° C.

f) 5,8-Dimethyl-2-[2-(2-methyl-5-piperidin-1-yl-2H-[1,2,4]triazol-3-yl)-ethyl]-[1,2,4]triazolo[1,5-a]pyrazine

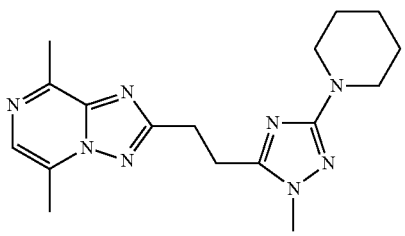 [SMILES: Cc1ncc(C)n2nc(CCc3nc(N4CCCCC4)nn3C)nc12]

A mixture of (E)-5,8-dimethyl-2-(2-(1-methyl-3-(piperidin-1-yl)-1H-1,2,4-triazol-5-yl)vinyl)-[1,2,4]triazolo[1,5-a] pyrazine (52 mg, 154 µmol, Eq: 1.00) and palladium on carbon 10% (16.4 mg, 15.4 µmol, Eq: 0.1) in methanol (20 ml) was stirred for 24 hours at 25° C. under a hydrogen atmosphere. The catalyst was filtered off, the filtrate was evaporated affording 5,8-dimethyl-2-[2-(2-methyl-5-piperidin-1-yl-2H-[1,2,4]triazol-3-yl)-ethyl]-[1,2,4]triazolo[1,5-a]pyrazine (30 mg, 57.4%) as a yellow oil. MS: m/z=341.5 (M+H+)

Example 50

5-Ethyl-8-methyl-2-(2-(1-methyl-3-(pyrrolidin-1-yl)-1H-1,2,4-triazol-5-yl)ethyl)-[1,2,4]triazolo[1,5-c]pyrimidine

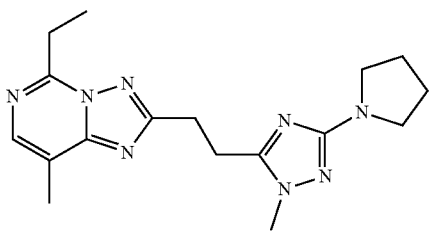 [SMILES: CCc1ncc(C)c2nc(CCc3nc(N4CCCC4)nn3C)nn12]

a) (E)-Benzyl 3-(1-methyl-3-(pyrrolidin-1-yl)-1H-1,2,4-triazol-5-yl)acrylate

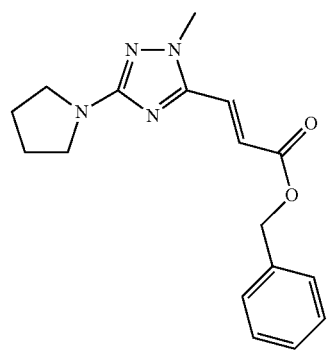 [SMILES: Cn1nc(N2CCCC2)nc1/C=C/C(=O)OCc1ccccc1]

DBU (3.79 g, 3.75 ml, 24.9 mmol, Eq: 1.2) was added to 2-methyl-5-pyrrolidin-1-yl-2H-[1,2,4]triazole-3-carbaldehyde (3.74 g, 20.8 mmol, Eq: 1.00), benzyl 2-(dimethoxyphosphoryl) acetate (6.43 g, 24.9 mmol, Eq: 1.2) and lithium chloride (2.64 g, 62.3 mmol, Eq: 3) in acetonitrile (100 ml). The mixture was stirred for 1 h at room temperature. Half saturated sodium chloride solution (20 ml) was added and the mixture was extracted with dichloromethane. The combined organic layers were dried over sodium sulfate. The product (3.8 g, 58.8%) was obtained as a yellow solid after column chromatography (SiO$_2$, ethyl acetate/n-heptane). MS: m/z=313.3 (M+H+).

b) 3-(1-Methyl-3-(pyrrolidin-1-yl)-1H-1,2,4-triazol-5-yl)propanoic acid

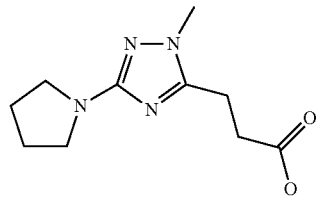 [SMILES: Cn1nc(N2CCCC2)nc1CCC(=O)O]

(E)-Benzyl 3-(1-methyl-3-(pyrrolidin-1-yl)-1H-1,2,4-triazol-5-yl)acrylate was stirred with palladium on carbon (10 wt %, 140 mg) in dioxane (60 ml) under hydrogen for 2 h. Additional palladium on carbon (10 wt %, 250 mg) was added and the mixture was stirred overnight under hydrogen. The mixture was filtered over Celite and concentrated to give the product (1.95 g, 96.7%) as a white solid. MS: m/z=225.2 (M+H+).

c) 3-Amino-2-ethyl-5-methylpyrimidin-4(3H)-iminium 2,4,6-trimethylbenzenesulfonate

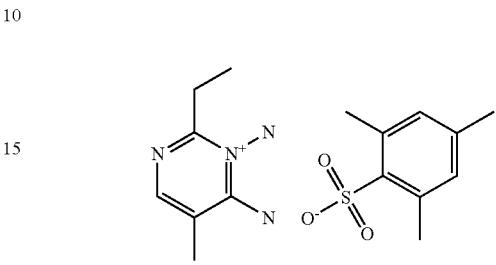

The product (410 mg, 72.5%) was obtained as a white solid in analogy to Example 26b from 2-ethyl-5-methylpyrimidin-4-amine. MS: m/z=153.2 (M+), m/z=199.3 (M−).

d) 5-Ethyl-8-methyl-2-(2-(1-methyl-3-(pyrrolidin-1-yl)-1H-1,2,4-triazol-5-yl)ethyl)-[1,2,4]triazolo[1,5-c]pyrimidine

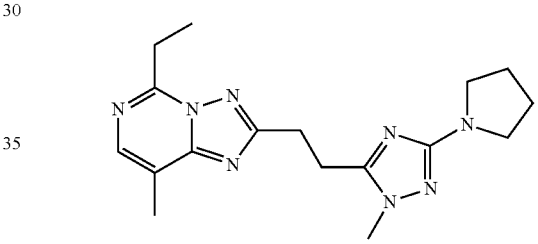

HATU (40.5 mg, 106 μmol, Eq: 1.5) and N,N-diisopropylethylamine (27.5 mg, 37.2 μL, 213 μmol, Eq: 3) were added to 3-(1-methyl-3-(pyrrolidin-1-yl)-1H-1,2,4-triazol-5-yl)propanoic acid in dimethylformamide (1 ml). The mixture was stirred for 10 min at room temperature. 3-Amino-2-ethyl-5-methylpyrimidin-4(3H)-iminium 2,4,6-trimethylbenzenesulfonate was added, and the mixture was stirred at 100° C. for 1 h. The product (2.7 mg, 100%) was obtained as a white solid after purification by preparative HPLC.

Example 51

5,8-Dimethyl-2-{2-[2-methyl-5-(2-methyl-pyrrolidin-1-yl)-2H-[1,2,4]triazol-3-yl]-ethyl}-[1,2,4]triazolo[1,5-a]pyrazine

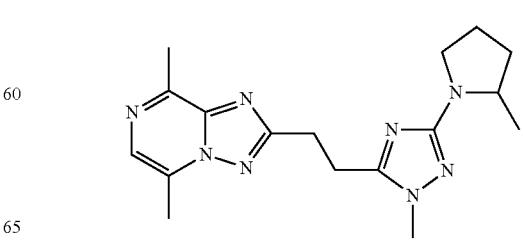

a) 2-Methyl-5-(2-methyl-pyrrolidin-1-yl)-2H-[1,2,4]triazole-3-carbaldehyde

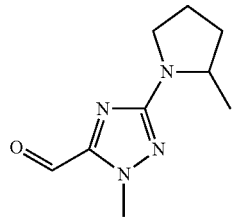

Was prepared in the same manner as described in Example 49 a-d) using 2-methylpyrrolidine instead of piperidine, affording 2-methyl-5-(2-methyl-pyrrolidin-1-yl)-2H-[1,2,4]triazole-3-carbaldehyde (449 mg, 74.9%) as a dark green waxy solid. MS: m/z=195.4 (M+H+)

b) 5,8-Dimethyl-2-{(E)-2-[2-methyl-5-(2-methyl-pyrrolidin-1-yl)-2H-[1,2,4]triazol-3-yl]-vinyl}-[1,2,4]triazolo[1,5-a]pyrazine

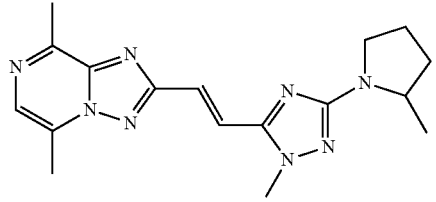 [SMILES: Cc1ncc(C)n2nc(/C=C/c3nc(N4CCCC4C)nn3C)nc12]

Was prepared in the same manner as described in Example 49 e) using 2-methyl-5-(2-methyl-pyrrolidin-1-yl)-2H-[1,2,4]triazole-3-carbaldehyde (60 mg, 309 µmol, Eq: 1.00) as aldehyde, affording 5,8-dimethyl-2-{(E)-2-[2-methyl-5-(2-methyl-pyrrolidin-1-yl)-2H-[1,2,4]triazol-3-yl]-vinyl}-[1,2,4]triazolo[1,5-a]pyrazine (58 mg, 55.5%) as a yellow viscous oil. MS: m/z=339.5 (M+H+)

c) 5,8-Dimethyl-2-{2-[2-methyl-5-(2-methyl-pyrrolidin-1-yl)-2H-[1,2,4]triazol-3-yl]-ethyl}-[1,2,4]triazolo[1,5-a]pyrazine A mixture of (E)-5,8-dimethyl-2-(2-(1-methyl-3-(2-methylpyrrolidin-1-yl)-1H-1,2,4-triazol-5-yl)vinyl)-[1,2,4]triazolo[1,5-a]pyrazine (50 mg, 148 µmol, Eq: 1.00) and palladium on carbon 10% (31.4 mg, 29.5 µmol, Eq: 0.2) in methanol (20 ml) was stirred for 5 hours at 25° C. under hydrogen atmosphere. The catalyst was filtered off, the filtrate was evaporated affording 5,8-dimethyl-2-{2-[2-methyl-5-(2-methyl-pyrrolidin-1-yl)-2H-[1,2,4]triazol-3-yl]-ethyl}-[1,2,4]triazolo[1,5-a]pyrazine (49 mg, 97.4%) as a colorless viscous oil. MS: m/z=341.5

Example 52

6,8-Dichloro-5-methyl-2-[2-(2-methyl-5-pyrrolidin-1-yl-2H-[1,2,4]triazol-3-yl)-ethyl]-[1,2,4]triazolo[1,5-a]pyridine

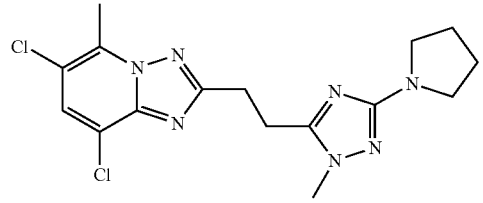

a) 1,2-Diamino-3,5-dichloro-6-methylpyridinium 2,4,6-trimethylbenzenesulfonate

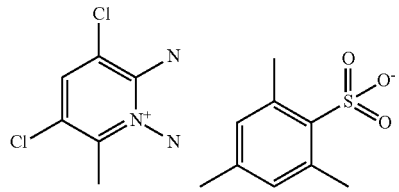

The product (2.2 g, 99.3%) was obtained as a white solid in analogy to Example 26b from 3,5-dichloro-6-methylpyridin-2-amine. MS: m/z=192.1 (M+), m/z=199.2 (M−).

b) 6,8-Dichloro-5-methyl-2-[2-(2-methyl-5-pyrrolidin-1-yl-2H-[1,2,4]triazol-3-yl)-ethyl]-[1,2,4]triazolo[1,5-a]pyridine

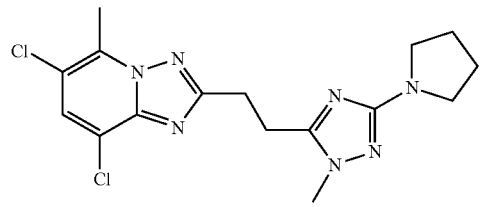 [SMILES: Cc1c(Cl)cc(Cl)c2nc(CCc3nc(N4CCCC4)nn3C)nn12]

The product (22 mg, 95%) was obtained as a light yellow oil in analogy to Example 50d from 1,2-diamino-3,5- dichloro-6-methylpyridinium 2,4,6-trimethylbenzenesulfonate. MS: m/z=380.5 (M+H+)

Example 53

2-(2-(1-Methyl-3-(pyrrolidin-1-yl)-1H-1,2,4-triazol-5-yl)ethyl)-[1,2,4]triazolo[1,5-a]pyridine-6-carbonitrile

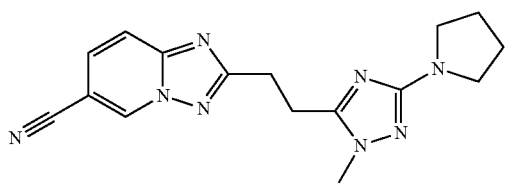 [SMILES: Cn1nc(N2CCCC2)nc1CCc1nc2ccc(C#N)cn2n1]

The desired product (6.1 mg, 18.9%) was obtained in analogy to Example 52 from 6-aminonicotinonitrile. MS: m/z=323.1 (M+H+)

Example 54

8-Chloro-2-(2-(1-methyl-3-(pyrrolidin-1-yl)-1H-1,2,4-triazol-5-yl)ethyl)-6-(trifluoromethyl)-[1,2,4]triazolo[1,5-a]pyridine

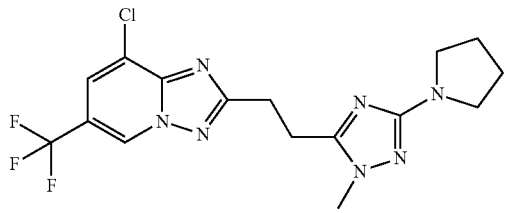 [SMILES: Cn1nc(N2CCCC2)nc1CCc1nc2c(Cl)cc(C(F)(F)F)cn2n1]

The desired product (4 mg, 10%) was obtained in analogy to Example 52 from 3-chloro-5-(trifluoromethyl)pyridin-2-amine. MS: m/z=400.1 (M+H+)

Example 55

7-Methyl-2-(2-(1-methyl-3-(pyrrolidin-1-yl)-1H-1,2,4-triazol-5-yl)ethyl)-8-nitro-[1,2,4]triazolo[1,5-a]pyridine

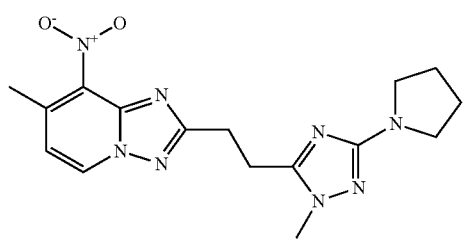 [SMILES: Cc1ccn2nc(CCc3nc(N4CCCC4)nn3C)nc2c1[NH+]([O-])O]

The desired product (1.8 mg, 5%) was obtained in analogy to Example 52 from 4-methyl-3-nitropyridin-2-amine. MS: m/z=357.2 (M+H+)

Example 56

2-(2-(1-Methyl-3-(pyrrolidin-1-yl)-1H-1,2,4-triazol-5-yl)ethyl)-[1,2,4]triazolo[1,5-a]quinoline

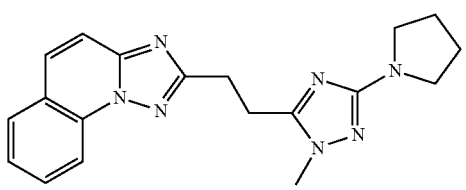 [SMILES: Cn1nc(N2CCCC2)nc1CCc1nc2ccc3ccccc3n2n1]

The desired product (2.2 mg, 6%) was obtained in analogy to Example 52 from quinolin-2-amine. MS: m/z=348.2 (M+H+)

Example 57

5-Methyl-2-(2-(1-methyl-3-(pyrrolidin-1-yl)-1H-1,2,4-triazol-5-yl)ethyl)-[1,2,4]triazolo[1,5-a]pyrazine

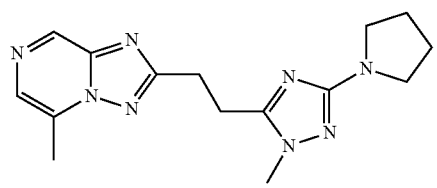 [SMILES: Cc1cncc2nc(CCc3nc(N4CCCC4)nn3C)nn12]

The desired product (1.9 mg, 3.5%) was obtained in analogy to example 52 from 6-methylpyrazin-2-amine. MS: m/z=313.2 (M+H+)

Example 58

5,8-Dimethyl-2-[2-(2-methyl-5-pyrrolidin-1-yl-2H-[1,2,4]triazol-3-yl)-ethyl]-[1,2,4]triazolo[1,5-c]pyrimidine

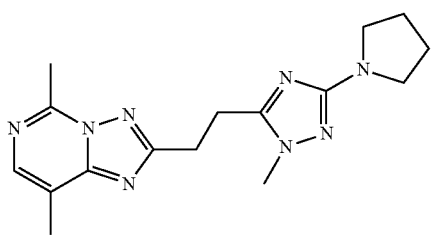 [SMILES: Cc1cnc(C)n2nc(CCc3nc(N4CCCC4)nn3C)nc12]

a) 5,8-Dimethyl-2-[(E)-2-(2-methyl-5-pyrrolidin-1-yl-2H-[1,2,4]triazol-3-yl)-vinyl]-[1,2,4]triazolo[1,5-c]pyrimidine

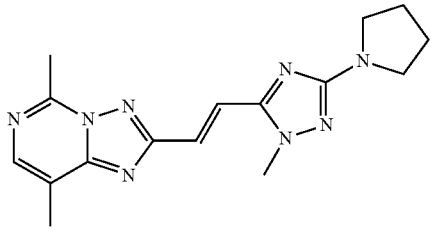 [SMILES: Cc1cnc(C)n2nc(/C=C/c3nc(N4CCCC4)nn3C)nc12]

Was prepared in the same manner as described in Example 81a) using 1-methyl-3-(pyrrolidin-1-yl)-1H-1,2,4-triazole-5-carbaldehyde (30 mg, 166 µmol, Eq: 1.00) and ((5,8-dimethyl-[1,2,4]triazolo[1,5-c]pyrimidin-2-yl)methyl)triphenylphosphonium chloride (76.4 mg, 166 µmol, Eq: 1.00) (prepared as described in WO2011150156, pp 123-125, Expl. 24 g) affording 5,8-dimethyl-2-[(E)-2-(2-methyl-5-pyrrolidin-1-yl-2H-[1,2,4]triazol-3-yl)-vinyl]-[1,2,4]triazolo[1,5-c]pyrimidine (27 mg, 50.0%) as light yellow amorphous. MS: m/z=325.6 (M+H$^+$)

b) 5,8-Dimethyl-2-[2-(2-methyl-5-pyrrolidin-1-yl-2H-[1,2,4]triazol-3-yl)-ethyl]-[1,2,4]triazolo[1,5-c]pyrimidine

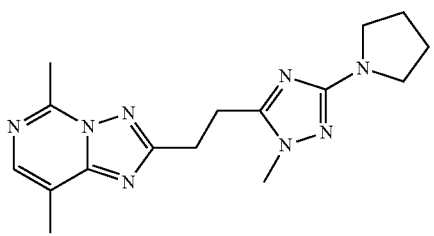

Was prepared in the same manner as described in Example 87 b) from (E)-5,8-dimethyl-2-(2-(1-methyl-3-(pyrrolidin-1-yl)-1H-1,2,4-triazol-5-yl)vinyl)-[1,2,4]triazolo[1,5-c]pyrimidine (23 mg, 70.9 µmol, Eq: 1.00) affording 5,8-dimethyl-2-[2-(2-methyl-5-pyrrolidin-1-yl-2H-[1,2,4]triazol-3-yl)-ethyl]-[1,2,4]triazolo[1,5-c]pyrimidine (16 mg, 69.1%) as light yellow waxy solid. MS: m/z=327.5 (M+H$^+$)

Example 59

{5-[2-(5,8-Dimethyl-[1,2,4]triazolo[1,5-a]pyrazin-2-yl)-ethyl]-1-methyl-1H-[1,2,4]triazol-3-yl}-diethyl-amine

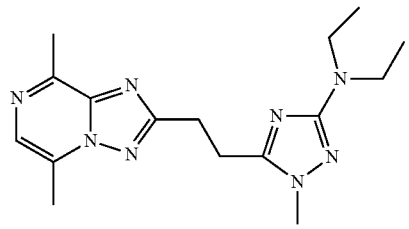 [SMILES: CCN(CC)c1nc(CCc2nc3c(C)ncc(C)n3n2)n(C)n1]

a) 5-Diethylamino-2-methyl-2H-[1,2,4]triazole-3-carbaldehyde

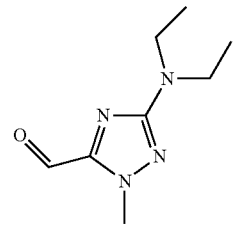

Was prepared in the same manner as described in Example 49 a-d) using diethylamine instead of piperidine, affording 5-diethylamino-2-methyl-2H-[1,2,4]triazole-3-carbaldehyde (792 mg, 79.3%) as a brown liquid. MS: m/z=183.2 (M+H+)

b) {5-[(E)-2-(5,8-Dimethyl-[1,2,4]triazolo[1,5-a]pyrazin-2-yl)-vinyl]-1-methyl-1H-[1,2,4]triazol-3-yl}-diethyl-amine

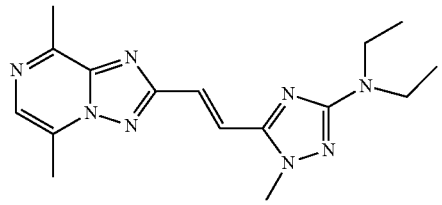 [SMILES: CCN(CC)c1nc(/C=C/c2nc3c(C)ncc(C)n3n2)n(C)n1]

Was prepared in the same manner as described in Example 49 e) using 3-(diethylamino)-1-methyl-1H-1,2,4-triazole-5-carbaldehyde (60 mg, 329 µmol, Eq: 1.00) as aldehyde affording {5-[(E)-2-(5,8-dimethyl-[1,2,4]triazolo[1,5-a]pyrazin-2-yl)-vinyl]-1-methyl-1H-[1,2,4]triazol-3-yl}-diethyl-amine (73 mg, 67.9%) as a yellow solid. MS: m/z=327.5 (M+H+), MP: 162.5° C.

c) {5-[2-(5,8-Dimethyl-[1,2,4]triazolo[1,5-a]pyrazin-2-yl)-ethyl]-1-methyl-1H-[1,2,4]triazol-3-yl}-diethyl-amine

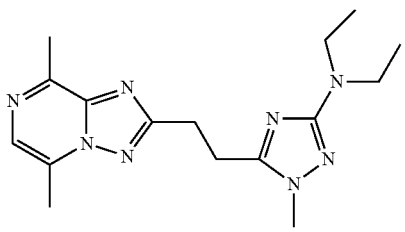 [SMILES: CCN(CC)c1nc(CCc2nc3c(C)ncc(C)n3n2)n(C)n1]

A mixture of (E)-5-(2-(5,8-dimethyl-[1,2,4]triazolo[1,5-a]pyrazin-2-yl)vinyl)-N,N-diethyl-1-methyl-1H-1,2,4-triazol-3-amine (62 mg, 190 µmol, Eq: 1.00) and palladium on carbon 10% (10.1 mg, 9.5 µmol, Eq: 0.05) in methanol (15 ml) was stirred for 5 hours at 25° C. under hydrogen atmosphere. The catalyst was filtered off, the filtrate was evaporated affording {5-[2-(5,8-dimethyl-[1,2,4]triazolo[1,5-a]pyrazin- 2-yl)-ethyl]-1-methyl-1H-[1,2,4]triazol-3-yl}-diethyl-amine (62 mg, 99.4%) as a light yellow viscous oil. MS: m/z=329.5 (M+H+)

Example 60

Cyclopropyl-{5-[2-(5,8-dimethyl-[1,2,4]triazolo[1,5-a]pyrazin-2-yl)-ethyl]-1-methyl-1H-[1,2,4]triazol-3-yl}-ethyl-amine

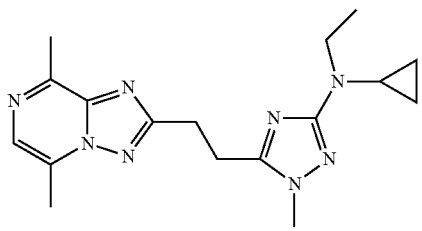 [SMILES: CCN(c1nc(CCc2nc3c(C)ncc(C)n3n2)n(C)n1)C1CC1]

a) 5-(Cyclopropyl-ethyl-amino)-2-methyl-2H-[1,2,4]triazole-3-carbaldehyde

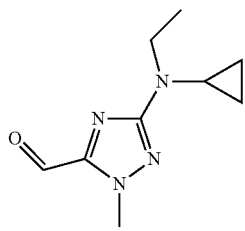

Was prepared in the same manner as described in Example 49 a-d) using N-ethylcyclopropan-amine hydrochloride (861 mg, 7.08 mmol, Eq: 1.00) instead of piperidine and N,N-diisopropyl ethyl-amine (915 mg, 1.2 ml, 7.08 mmol, Eq: 1.00) as base, affording 5-(cyclopropyl-ethyl-amino)-2-methyl-2H-[1,2,4]triazole-3-carbaldehyde (222 mg, 66.4%) as a black waxy solid. MS: m/z=195.2 (M+H+)

b) Cyclopropyl-{5-[(E)-2-(5,8-dimethyl-[1,2,4]triazolo[1,5-a]pyrazin-2-yl)-vinyl]-1-methyl-1H-[1,2,4]triazol-3-yl}-ethyl-amine

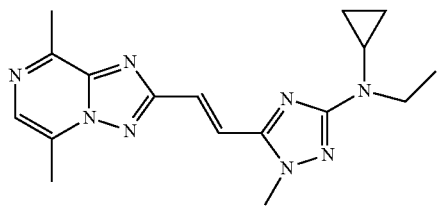 [SMILES: CCN(c1nc(/C=C/c2nc3c(C)ncc(C)n3n2)n(C)n1)C1CC1]

Was prepared in the same manner as described in Example 49 e) using 3-(cyclopropyl(ethyl)amino)-1-methyl-1H-1,2,4-triazole-5-carbaldehyde (60 mg, 309 µmol, Eq: 1.00) as aldehyde affording cyclopropyl-{5-[(E)-2-(5,8-dimethyl-[1,2,4]triazolo[1,5-a]pyrazin-2-yl)-vinyl]-1-methyl-1H-[1,2,4]triazol-3-yl}-ethyl-amine (80 mg, 76.5%) as a yellow viscous oil. MS: m/z=339.5 (M+H+)

c) Cyclopropyl-{5-[2-(5,8-dimethyl-[1,2,4]triazolo[1,5-a]pyrazin-2-yl)-ethyl]-1-methyl-1H-[1,2,4]triazol-3-yl}-ethyl-amine

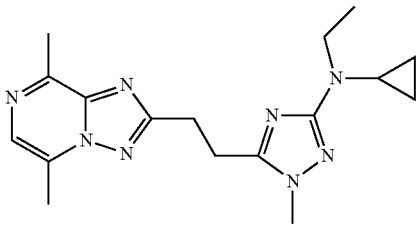 [SMILES: CCN(c1nc(CCc2nc3c(C)ncc(C)n3n2)n(C)n1)C1CC1]

A mixture of (E)-N-cyclopropyl-5-(2-(5,8-dimethyl-[1,2,4]triazolo[1,5-a]pyrazin-2-yl)vinyl)-N-ethyl-1-methyl-1H-1,2,4-triazol-3-amine (75 mg, 222 µmol, Eq: 1.00) and palladium on carbon 10% (11.8 mg, 11.1 µmol, Eq: 0.05) in methanol (15 ml) was stirred for 5 hours at 25° C. under hydrogen atmosphere. The catalyst was filtered off, the filtrate was evaporated affording cyclopropyl-{5-[2-(5,8-dimethyl-[1,2,4]triazolo[1,5-a]pyrazin-2-yl)-ethyl]-1-methyl-1H-[1,2,4]triazol-3-yl}-ethyl-amine (65 mg, 86.2%) as a light yellow viscous oil. MS: m/z=341.5 (M+H+)

Example 61

6,8-Dichloro-2-{2-[2-(4-methoxy-benzyl)-5-pyrrolidin-1-yl-2H-[1,2,4]triazol-3-yl]-ethyl}-5-methyl-[1,2,4]triazolo[1,5-c]pyridine

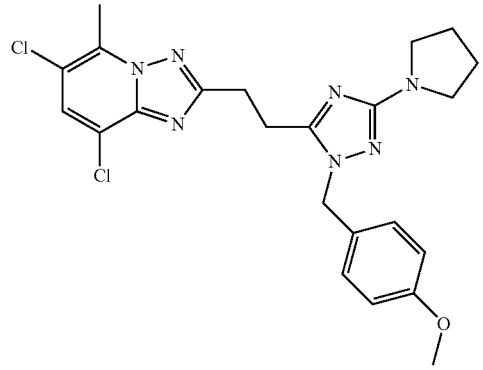 [SMILES: COc1ccc(Cn2nc(N3CCCC3)nc2CCc2nc3c(Cl)cc(Cl)c(C)n3n2)cc1]

a) 5-(Dichloromethyl)-1-(4-methoxybenzyl)-3-(pyrrolidin-1-yl)-1H-1,2,4-triazole and 3-(dichloromethyl)-1-(4-methoxybenzyl)-5-(pyrrolidin-1-yl)-1H-1,2,4-triazole

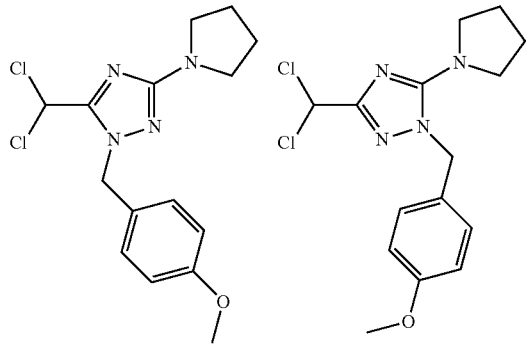

2,2-Dichloroacetyl chloride (662 mg, 433 μL, 4.49 mmol, Eq: 0.9) was added dropwise below 0° C. to pyrrolidine-1-carbonitrile (0.48 g, 505 μL, 4.99 mmol, Eq: 1.00). The mixture was stirred for 15 min at room temperature. Dichloromethane (7.5 mL) was added, followed by N,N-diisopropylethylamine (1.87 g, 2.53 mL, 14.5 mmol, Eq: 2.9) and (4-methoxybenzyl) hydrazine dihydrochloride (1.01 g, 4.49 mmol, Eq: 0.9) at 0° C. The mixture was stirred for 1 h at room temperature and then heated for 2 h under reflux. The reaction mixture was concentrated and then partitioned between aqueous ammonium chloride and ethyl acetate. The combined organic layers were dried over sodium sulfate and then concentrated to an oil. The product (1.6 g, 93%, mixture of isomers) was obtained as a light yellow solid after filtration over silica (eluted with ethyl acetate). MS: m/z=341.4 (M+H+)

b) 1-(4-Methoxybenzyl)-3-(pyrrolidin-1-yl)-1H-1,2,4-triazole-5-carbaldehyde

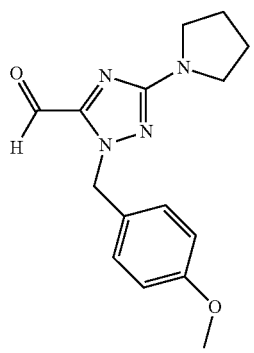 [SMILES: COc1ccc(Cn2nc(N3CCCC3)nc2C=O)cc1]

The mixture of 5-(dichloromethyl)-1-(4-methoxybenzyl)-3-(pyrrolidin-1-yl)-1H-1,2,4-triazole and 3-(dichloromethyl)-1-(4-methoxybenzyl)-5-(pyrrolidin-1-yl)-1H-1,2,4-triazole from the previous step (299 mg, 0.876 mmol, Eq: 1) was suspended in ethanol (5 ml) and water (5 ml). Sodium acetate (180 mg, 2.2 mmol, Eq: 5) was added. The reaction mixture was heated for 16 h at 60° C. The mixture was extracted with ethyl acetate. The combined organic layers were dried over sodium sulfate. The product (74 mg, 29%) was obtained as a yellow solid by column chromatography (SiO2, ethyl acetate n-heptane). MS: m/z=287.3 (M+H+)

c) 6,8-Dichloro-2-{2-[2-(4-methoxy-benzyl)-5-pyrrolidin-1-yl-2H-[1,2,4]triazol-3-yl]-ethyl}-5-methyl-[1,2,4]triazolo[1,5-c]pyridine

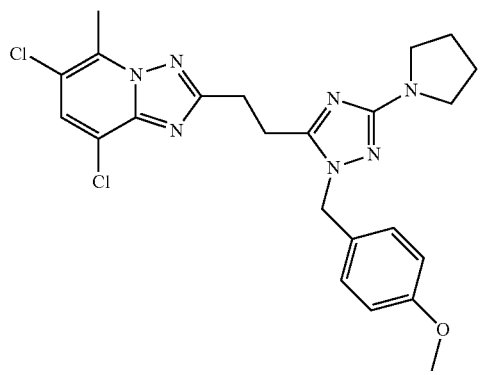 [SMILES: COc1ccc(Cn2nc(N3CCCC3)nc2CCc2nc3c(Cl)cc(Cl)c(C)n3n2)cc1]

The product (40 mg, 22%) was obtained as a light yellow oil in analogy to Example 50 using 1-(4-methoxybenzyl)-3-(pyrrolidin-1-yl)-1H-1,2,4-triazole-5-carbaldehyde and 1,2-diamino-3,5-dichloro-6-methylpyridinium 2,4,6-trimethylbenzenesulfonate as starting materials. MS: m/z=486.2 (M+H+)

Example 62

6,8-Dichloro-2-(2-(1-(4-methoxybenzyl)-5-(pyrrolidin-1-yl)-1H-1,2,4-triazol-3-yl)ethyl)-5-methyl-[1,2,4]triazolo[1,5-a]pyridine

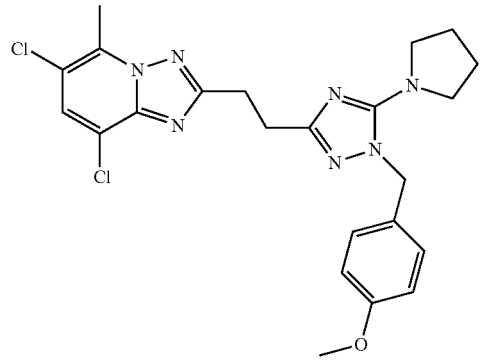 [SMILES: COc1ccc(Cn2nc(CCc3nc4c(Cl)cc(Cl)c(C)n4n3)nc2N2CCCC2)cc1]

a) 1-(4-Methoxybenzyl)-5-(pyrrolidin-1-yl)-1H-1,2,4-triazole-3-carbaldehyde

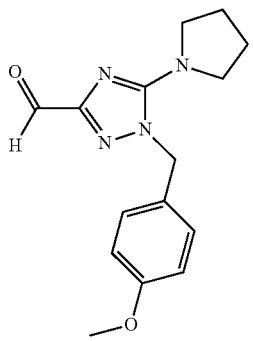 [SMILES: COc1ccc(Cn2nc(C=O)nc2N2CCCC2)cc1]

The product (117 mg, 46%) was obtained as a light yellow oil in the chromatographic separation from Example 61b. MS: m/z=287.15 (M+H+)

b) 6,8-Dichloro-2-(2-(1-(4-methoxybenzyl)-5-(pyrrolidin-1-yl)-1H-1,2,4-triazol-3-yl)ethyl)-5-methyl-[1,2,4]triazolo[1,5-a]pyridine

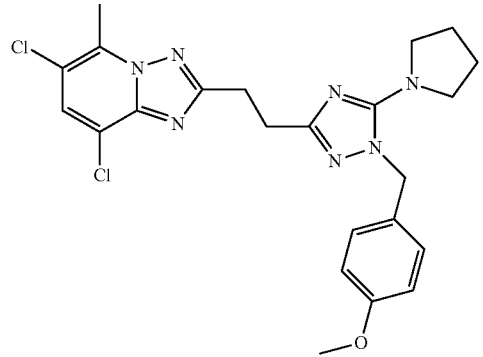 [SMILES: COc1ccc(Cn2nc(CCc3nc4c(Cl)cc(Cl)c(C)n4n3)nc2N2CCCC2)cc1]

The product (65 mg, 39%) was obtained in analogy to Example 61 from 1-(4-methoxybenzyl)-5-(pyrrolidin-1-yl)-1H-1,2,4-triazole-3-carbaldehyde. MS: m/z=486.2 (M+H+)

Example 63

6-Fluoro-2-(2-(1-methyl-3-(pyrrolidin-1-yl)-1H-1,2,4-triazol-5-yl)ethyl)-7-(trifluoromethyl)-[1,2,4]triazolo[1,5-a]pyridin-5-amine

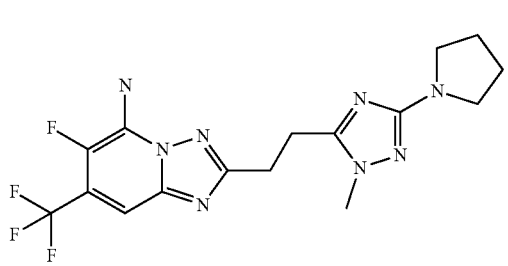 [SMILES: Cn1nc(N2CCCC2)nc1CCc1nc2cc(C(F)(F)F)c(F)c(N)n2n1]

The desired product (9 mg, 12%) was obtained in analogy to Example 52 from 3-fluoro-4-(trifluoromethyl)pyridine-2,6-diamine. MS: m/z=399.4 (M+H+)

Example 64

2-(2-(1-Methyl-3-(pyrrolidin-1-yl)-1H-1,2,4-triazol-5-yl)ethyl)-5-(trifluoromethyl)-[1,2,4]triazolo[1,5-a]pyridine

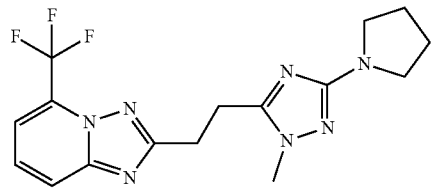 [SMILES: Cn1nc(N2CCCC2)nc1CCc1nc2cccc(C(F)(F)F)n2n1]

The desired product (4 mg, 8%) was obtained in analogy to Example 52 from 6-(trifluoromethyl)pyridin-2-amine. MS: m/z=366.3 (M+H+)

Example 65

8-Bromo-2-(2-(1-methyl-3-(pyrrolidin-1-yl)-1H-1,2,4-triazol-5-yl)ethyl)-6-(trifluoromethyl)-[1,2,4]triazolo[1,5-a]pyridine

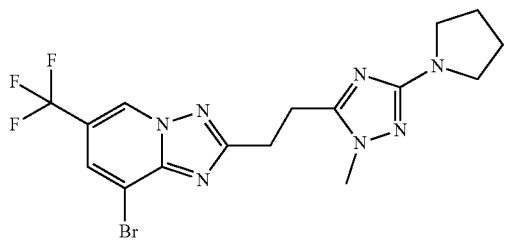 [SMILES: Cn1nc(N2CCCC2)nc1CCc1nc2c(Br)cc(C(F)(F)F)cn2n1]

The desired product (31 mg, 38%) was obtained in analogy to Example 52 from 3-bromo-5-(trifluoromethyl)pyridin-2-amine. MS: m/z=445.3 (M+H+)

Example 66

2-(2-(1-Methyl-3-(pyrrolidin-1-yl)-1H-1,2,4-triazol-5-yl)ethyl)-7-(trifluoromethyl)-[1,2,4]triazolo[1,5-a]pyridine

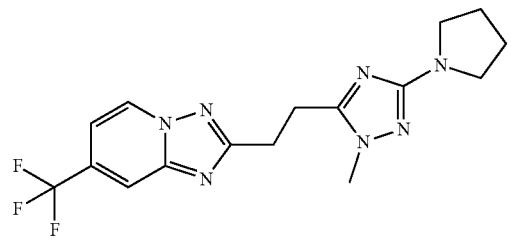 [SMILES: Cn1nc(N2CCCC2)nc1CCc1nc2cc(C(F)(F)F)ccn2n1]

The desired product (13 mg, 19%) was obtained in analogy to Example 52 from 4-(trifluoromethyl)pyridin-2-amine. MS: m/z=366.3 (M+H+)

Example 67

2-(2-(1-Methyl-3-(pyrrolidin-1-yl)-1H-1,2,4-triazol-5-yl)ethyl)-[1,2,4]triazolo[1,5-a]pyridine-7-carbonitrile

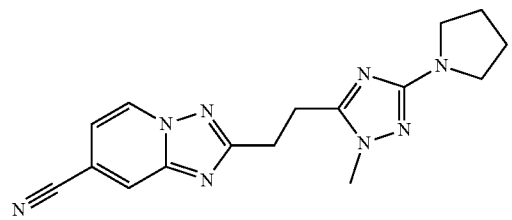 [SMILES: Cn1nc(N2CCCC2)nc1CCc1nc2cc(C#N)ccn2n1]

The desired product (9 mg, 15%) was obtained in analogy to Example 52 from 2-aminoisonicotinonitrile. MS: m/z=323.3 (M+H+)

Example 68

6,8-Dichloro-5-methyl-2-[2-(5-pyrrolidin-1-yl-1H-[1,2,4]triazol-3-yl)-ethyl]-[1,2,4]triazolo[1,5-a]pyridine

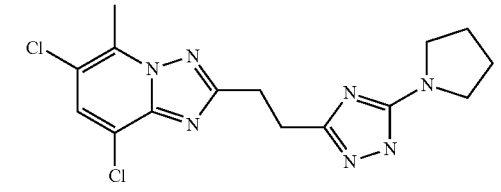 [SMILES: Cc1c(Cl)cc(Cl)c2nc(CCc3n[nH]c(N4CCCC4)n3)nn12]

6,8-Dichloro-2-(2-(1-(4-methoxybenzyl)-5-(pyrrolidin-1-yl)-1H-1,2,4-triazol-3-yl)ethyl)-5-methyl-[1,2,4]triazolo[1,5-a]pyridine (17 mg, 35.0 μmol, Eq: 1.00) in trifluoroacetic acid (539 μl) was heated 3 h under reflux. The product (12.8 mg, 100%) was obtained as a white solid by preparative HPLC. MS: m/z=366.2 (M+H+)

Example 69

6-Chloro-5-methyl-2-[2-(2-methyl-5-pyrrolidin-1-yl-2H-[1,2,4]triazol-3-yl)-ethyl]-8-trifluoromethyl-[1,2,4]triazolo[1,5-c]pyridine

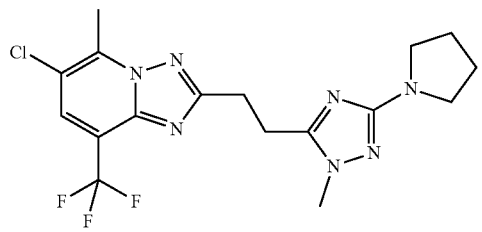 [SMILES: Cc1c(Cl)cc(C(F)(F)F)c2nc(CCc3nc(N4CCCC4)nn3C)nn12]

a) N-(4-Methoxybenzyl)-6-methyl-3-(trifluoromethyl)pyridin-2-amine

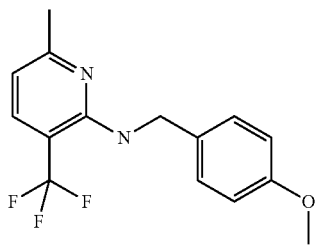

2-Chloro-6-methyl-3-(trifluoromethyl)pyridine (200 mg, 1.02 mmol, Eq: 1.00), (4-methoxyphenyl)methylamine (168 mg, 159 µL, 1.23 mmol, Eq: 1.2) and potassium carbonate (212 mg, 1.53 mmol, Eq: 1.5) were combined in dimethylformamide (1.2 mL) to give a light yellow suspension. The mixture was stirred at 120° C. for 2 h. Additional potassium carbonate (141 mg, 1.02 mmol, Eq: 1) and (4-methoxyphenyl)methanamine (140 mg, 133 µL, 1.02 mmol, Eq: 1) were added and the mixture was stirred at 120° C. for 7 h. Saturated aqueous sodium chloride solution was added and the mixture was extracted with ethyl acetate. The combined organic layers were dried over sodium sulfate and concentrated to an oil. The product (100 mg, 33%) was obtained as a colorless oil by column chromatography (SiO₂, ethyl acetate/n-heptane). MS: m/z=297.3 (M+H+)

b) 6-Methyl-3-(trifluoromethyl)pyridin-2-amine

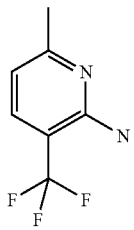

N-(4-Methoxybenzyl)-6-methyl-3-(trifluoromethyl)pyridin-2-amine (100 mg, 338 µmol, Eq: 1.00) in trifluoroacetic acid (2 ml) was heated under reflux for 30 min. The mixture was concentrated. The crude product (120 mg, pink solid) was used in the next step without further purification. MS: m/z=218.2 (M+H+)

c) 5-Chloro-6-methyl-3-(trifluoromethyl)pyridin-2-amine

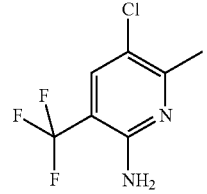

6-Methyl-3-(trifluoromethyl)pyridin-2-amine (59 mg, 335 µmol, Eq: 1.00) was suspended in 37% HCl aq (4.13 ml) and 35% hydrogen peroxide aq (488 mg, 440 µl, 5.02 mmol, Eq: 15) was added dropwise. The mixture was stirred for 20 min. Water (50 ml) was added. The mixture was alkalized by addition of sodium bicarbonate and extracted with dichloromethane. The combined organic layers were dried over sodium sulfate and concentrated to an oil. The product (70 mg, 99.2%) was obtained as a light yellow solid by column chromatography (SiO₂, ethyl acetate/n-heptane). MS: m/z=211.2 (M+H+)

d) 6-Chloro-5-methyl-2-[2-(2-methyl-5-pyrrolidin-1-yl-2H-[1,2,4]triazol-3-yl)-ethyl]-8-trifluoromethyl-[1,2,4]triazolo[1,5-c]pyridine

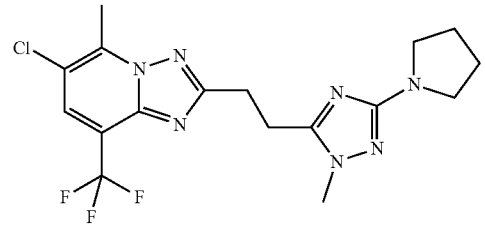 [SMILES: Cc1c(Cl)cc(C(F)(F)F)c2nc(CCc3nc(N4CCCC4)nn3C)nn12]

The desired product (52 mg) was obtained as a white solid in analogy to Example 52 from 5-chloro-6-methyl-3-(trifluoromethyl)pyridin-2-amine. MS: m/z=414.3 (M+H+)

Example 70

5-Methyl-2-(2-(1-methyl-3-(pyrrolidin-1-yl)-1H-1,2,4-triazol-5-yl)ethyl)-[1,2,4]triazolo[1,5-a]pyridine-6-carbonitrile

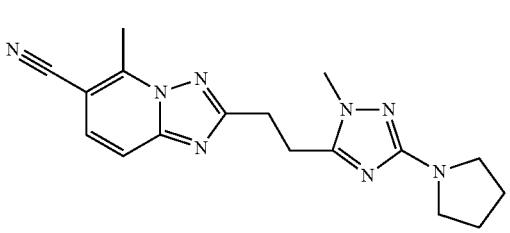 [SMILES: Cc1c(C#N)ccc2nc(CCc3nc(N4CCCC4)nn3C)nn12]

The desired product (25 mg) was obtained as a white powder in analogy to example 52 from 6-amino-2-methylnicotinonitrile. MS: m/z=349.7 (M+H+)

Example 71

8-Bromo-6-chloro-5-methyl-2-[2-(2-methyl-5-pyrrolidin-1-yl-2H-[1,2,4]triazol-3-yl)-ethyl]-[1,2,4]triazolo[1,5-a]pyridine

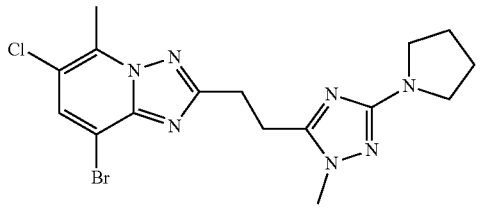 [SMILES: Cc1c(Cl)cc(Br)c2nc(CCc3nc(N4CCCC4)nn3C)nn12]

The desired product (92 mg) was obtained as a white solid in analogy to example 52 from 3-bromo-5-chloro-6-methylpyridin-2-amine. MS: m/z=426.3 (M+H+)

Example 72

6-Bromo-8-chloro-5-methyl-2-(2-(1-methyl-3-(pyrrolidin-1-yl)-1H-1,2,4-triazol-5-yl)ethyl)-[1,2,4]triazolo[1,5-a]pyridine

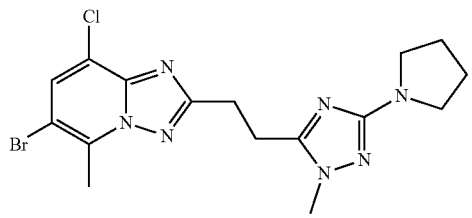 [SMILES: Cc1c(Br)cc(Cl)c2nc(CCc3nc(N4CCCC4)nn3C)nn12]

a) 5-Bromo-3-chloro-6-methylpyridin-2-amine

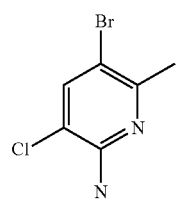

The product (947 mg, 80%) was obtained as an orange solid in analogy to Example 69c from 5-bromo-6-methylpyridin-2-amine. MS: m/z=221.2 (M+H+)

b) 6-Bromo-8-chloro-5-methyl-2-(2-(1-methyl-3-(pyrrolidin-1-yl)-1H-1,2,4-triazol-5-yl)ethyl)-[1,2,4]triazolo[1,5-a]pyridine

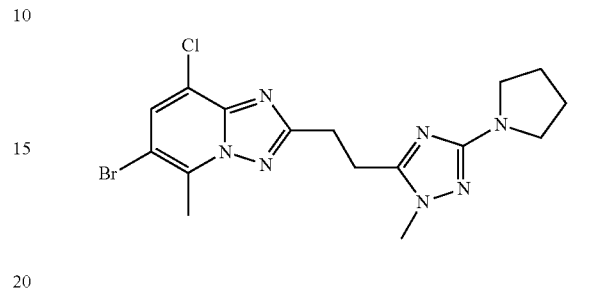

The desired product (123 mg) was obtained as a white solid in analogy to Example 52 from 5-bromo-3-chloro-6-methylpyridin-2-amine. MS: m/z=426.1 (M+H+)

Example 73

6-Chloro-8-methanesulfonyl-5-methyl-2-[2-(2-methyl-5-pyrrolidin-1-yl-2H-[1,2,4]triazol-3-yl)-ethyl]-[1,2,4]triazolo[1,5-a]pyridine

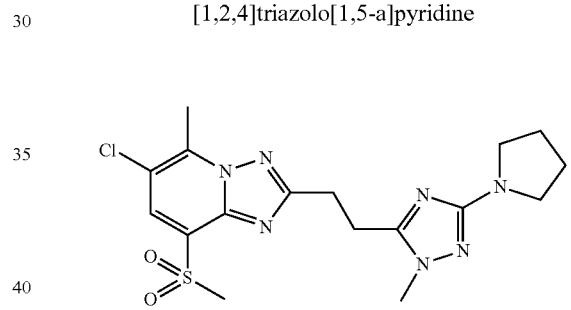

a) 5-Chloro-6-methyl-3-methylsulfanyl-pyridin-2-ylamine

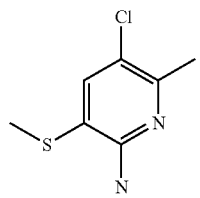

3-Bromo-5-chloro-6-methylpyridin-2-amine (300 mg, 1.35 mmol, Eq: 1.00) was dissolved in tetrahydrofuran (5 ml). 1.6M n-BuLi in hexanes (3.39 ml, 5.42 mmol, Eq: 4) was added at −78° C. The mixture was stirred for 10 min. 1,2-Dimethyldisulfane (510 mg, 481 μl, 5.42 mmol, Eq: 4) was added and mixture allowed to warm to room temperature. The mixture was stirred for 30 min. Water was added and the mixture was extracted with dichloromethane. The combined organic layers were dried over sodium sulfate and concentrated to an oil. The product (158 mg, 61.8%) was obtained as a light yellow solid by chromatography (SiO$_2$, ethyl acetate/n-heptane). MS: m/z=230.1 (M+acetonitrile+H+)

b) 5-Chloro-6-methyl-3-(methylsulfonyl)pyridin-2-amine

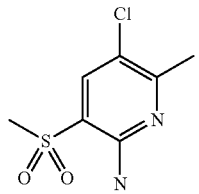

5-Chloro-6-methyl-3-methylsulfanyl-pyridin-2-ylamine (160 mg, 848 μmol, Eq: 1.00) and oxone (1.56 g, 2.54 mmol, Eq: 3) were combined in methanol (15 ml) to give an off-white suspension. The mixture was cooled to 0° C., and water (30 ml) was added dropwise, followed by 39% hydrogen sulfite (1.5 ml) and saturated sodium bicarbonate solution (6 ml). The mixture was stirred for 10 min and then extracted with ethyl acetate. The combined organic layers were dried over sodium sulfate and concentrated to an oil. The product (88 mg, 47%) was obtained as a white solid by chromatography (SiO$_2$, ethyl acetate/n-heptane). MS: m/z=221.2 (M+H+)

c) 6-Chloro-8-methanesulfonyl-5-methyl-2-[2-(2-methyl-5-pyrrolidin-1-yl-2H-[1,2,4]triazol-3-yl)-ethyl]-[1,2,4]triazolo[1,5-a]pyridine

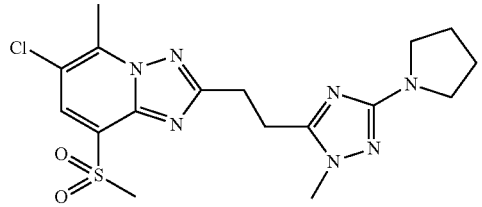 [SMILES: Cc1c(Cl)cc(S(C)(=O)=O)c2nc(CCc3nc(N4CCCC4)nn3C)nn12]

The desired product (24 mg) was obtained as an off-white solid in analogy to Example 52 from 5-chloro-6-methyl-3-(methylsulfonyl)pyridin-2-amine. MS: m/z=424.4 (M+H+)

Example 74

8-Chloro-5-methyl-2-[2-(2-methyl-5-pyrrolidin-1-yl-2H-[1,2,4]triazol-3-yl)-ethyl]-[1,2,4]triazolo[1,5-c]pyridine-6-carbonitrile

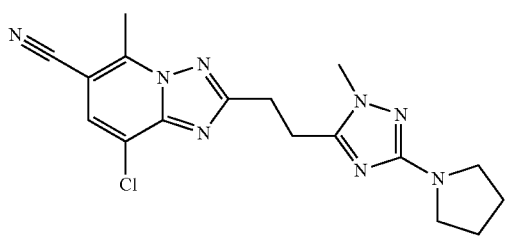 [SMILES: Cc1c(C#N)cc(Cl)c2nc(CCc3nc(N4CCCC4)nn3C)nn12]

a) 6-Amino-5-chloro-2-methylnicotinonitrile

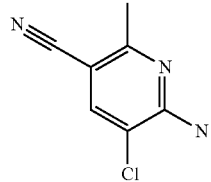

The product (53 mg, 31%) was obtained as a white powder in analogy to Example 69c from 6-amino-2-methylnicotinonitrile. MS: m/z=209.2 (M+acetonitrile+H+)

b) 8-Chloro-5-methyl-2-[2-(2-methyl-5-pyrrolidin-1-yl-2H-[1,2,4]triazol-3-yl)-ethyl]-[1,2,4]triazolo[1,5-c]pyridine-6-carbonitrile The desired product (27 mg) was obtained as a white powder in analogy to Example 52 from 6-amino-5-chloro-2-methylnicotinonitrile. MS: m/z=370.7 (M+H+)

Example 75

8-Ethyl-5-methyl-2-(2-(1-methyl-3-(pyrrolidin-1-yl)-1H-1,2,4-triazol-5-yl)ethyl)-[1,2,4]triazolo[1,5-c]pyrimidine

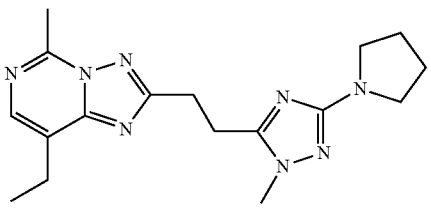 [SMILES: CCc1cnc(C)n2nc(CCc3nc(N4CCCC4)nn3C)nc12]

a) 5-Ethyl-4-hydrazinyl-2-methylpyrimidine

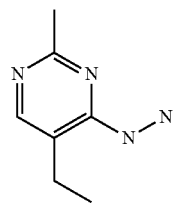

Hydrazine monohydrate (0.398 mL, 5.24 mmol) was added to 4-chloro-5-ethyl-2-methylpyrimidine (216 mg, 1.31 mmol). The reaction mixture was stirred in a sealed tube at room temperature overnight. Remaining hydrazine was evaporated. Purification by column chromatography (SiO$_2$, methanol/ammonia/dichloromethane) to afforded the desired product (136 mg, 68.2%) as an amorphous off-white solid. MS: m/z=153.11 (M+H+)

b) N'-(5-Ethyl-2-methylpyrimidin-4-yl)-3-(1-methyl-3-(pyrrolidin-1-yl)-1H-1,2,4-triazol-5-yl)propanehydrazide

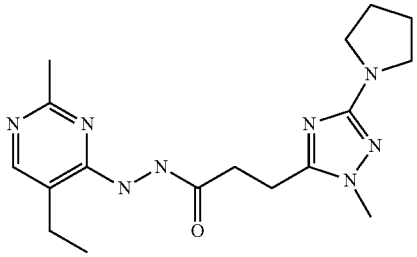 [SMILES: CCc1cnc(C)nc1NNC(=O)CCc1nc(N2CCCC2)nn1C]

3-(1-Methyl-3-(pyrrolidin-1-yl)-1H-1,2,4-triazol-5-yl) propanoic acid (140 mg, 0.624 mmol), HATU (712 mg, 1.87 mmol) and N,N-diisopropylethylamine (600 µl, 3.53 mmol) were dissolved in dimethylformamide (18 mL). The mixture was stirred for 20 minutes. 5-Ethyl-4-hydrazinyl-2-methylpyrimidine (99 mg, 0.655 mmol) was added and the reaction mixture was allowed to stir at room temperature overnight. The mixture was concentrated to an oil. Preparative HPLC afforded the desired product (71 mg, 31%) as a yellow gum. MS: m/z=359.23 (M+H+)

c) 8-Ethyl-5-methyl-3-(2-(1-methyl-3-(pyrrolidin-1-yl)-1H-1,2,4-triazol-5-yl)ethyl)-[1,2,4]triazolo[4,3-c] pyrimidine

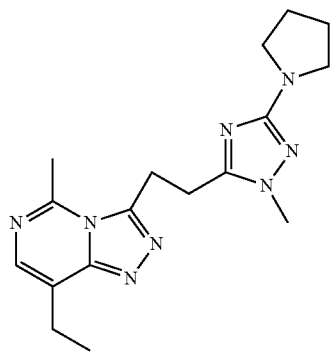 [SMILES: CCc1cnc(C)n2c(CCc3nc(N4CCCC4)nn3C)nnc12]

N'-(5-Ethyl-2-methylpyrimidin-4-yl)-3-(1-methyl-3-(pyrrolidin-1-yl)-1H-1,2,4-triazol-5-yl)propanehydrazide (56.6 mg, 158 µmol) in tetrahydrofuran (4 ml) was added to Burgess reagent (155 mg, 632 µmol). The mixture was heated in a sealed tube at 80° C. for 1 h. Saturated sodium bicarbonate solution was added and extracted with dichloromethane. The organic layers were dried over sodium sulfate and concentrated to an oil to afford the desired product (69 mg) as a yellow solid which was used without further purification in the next step. MS: m/z=341.2 (M+H+)

d) 8-Ethyl-5-methyl-2-(2-(1-methyl-3-(pyrrolidin-1-yl)-1H-1,2,4-triazol-5-yl)ethyl)-[1,2,4]triazolo[1,5-c] pyrimidine

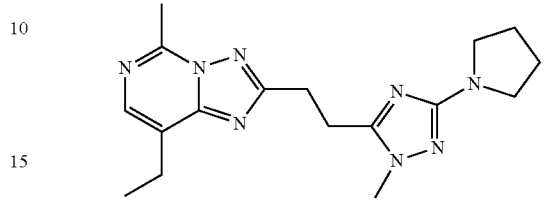

1.25 N HCl in methanol (57.3 µl, 71.7 µmol) was added to a solution of 8-ethyl-5-methyl-3-(2-(1-methyl-3-(pyrrolidin-1-yl)-1H-1,2,4-triazol-5-yl)ethyl)-[1,2,4]triazolo[4,3-c]pyrimidine (24.4 mg, 71.7 µmol) in methanol (2 mL). The reaction mixture was stirred at room temperature for 2 h. Additional 1.25 N HCl in methanol (57.3 µl, 71.7 µmol) was added and the mixture was stirred for 15 min. The solvent was evaporated. The crude product was purified with preparative HPLC to afford the desired product (20 mg, 82%) as a white solid. MS: m/z=341.2 (M+H+)

Example 76

6-Chloro-8-methoxy-5-methyl-2-[2-(2-methyl-5-pyrrolidin-1-yl-2H-[1,2,4]triazol-3-yl)-ethyl]-[1,2,4] triazolo[1,5-a]pyridine

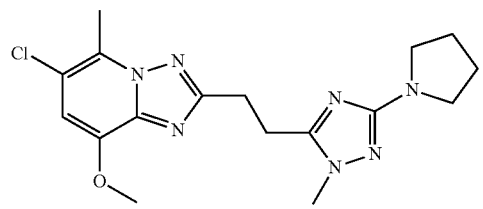 [SMILES: COc1cc(Cl)c(C)n2nc(CCc3nc(N4CCCC4)nn3C)nc12]

The desired product (13 mg) was obtained as a white solid from 3-methoxy-6-methylpyridin-2-amine in analogy to Example 72. MS: m/z=376.4 (M+H+)

Example 77

6-Chloro-8-cyclopropyl-5-methyl-2-[2-(2-methyl-5-pyrrolidin-1-yl-2H-[1,2,4]triazol-3-yl)-ethyl]-[1,2,4] triazolo[1,5-a]pyridine

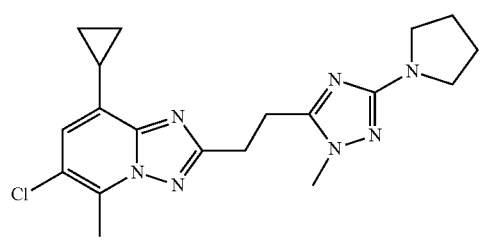 [SMILES: Cc1c(Cl)cc(C2CC2)c2nc(CCc3nc(N4CCCC4)nn3C)nn12]

A mixture of 8-bromo-6-chloro-5-methyl-2-[2-(2-methyl-5-pyrrolidin-1-yl-2H-[1,2,4]triazol-3-yl)-ethyl]-[1,2,4]triazolo[1,5-a]pyridine (30 mg, 70.6 μmol, Eq: 1), cyclopropylboronic acid (9.1 mg, 106 μmol, Eq: 1.5) and cesium carbonate (46.0 mg, 141 μmol, Eq: 2) in dioxane (0.75 mL) and water (0.075 ml) was stirred for 4 min. Dichloro1,1'-bis(diphenylphosphino)ferrocene palladium(II) (11.6 mg, 14.2 μmol, 0.2 Eq) was added, and the mixture was heated at 100° C. for 30 min in a microwave oven. The mixture was separated by preparative HPLC to give the desired product (6.2 mg, 22%) as a white solid. MS: m/z=386.4 (M+H+)

Example 78

5-Methyl-2-[2-(2-methyl-5-pyrrolidin-1-yl-2H-[1,2,4]triazol-3-yl)-ethyl]-[1,2,4]triazolo[1,5-c]pyridine-6,8-dicarbonitrile

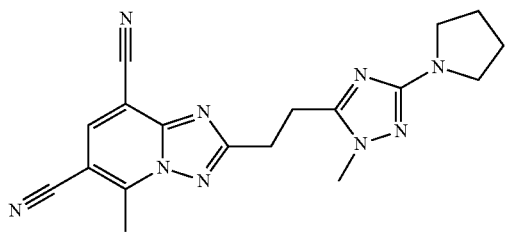 [SMILES: Cc1c(C#N)cc(C#N)c2nc(CCc3nc(N4CCCC4)nn3C)nn12]

A mixture of 8-bromo-6-chloro-5-methyl-2-[2-(2-methyl-5-pyrrolidin-1-yl-2H-[1,2,4]triazol-3-yl)-ethyl]-[1,2,4]triazolo[1,5-a]pyridine (40 mg, 94.2 μmol, Eq: 1.00), dicyanozinc (11.1 mg, 94.2 μmol, Eq: 1) and tetrakis(triphenylphosphine)palladium (10.9 mg, 9.42 μmol, Eq: 0.1) in dimethylformamide (0.9 mL) was heated for 15 min at 170° C. in a microwave oven. Separation of the mixture by preparative HPLC afforded the product (9.9 mg, 29%) as a yellow solid. MS: m/z=362.4 (M+H+)

Example 79

6-Chloro-5-methyl-2-[2-(2-methyl-5-pyrrolidin-1-yl-2H-[1,2,4]triazol-3-yl)-ethyl]-[1,2,4]triazolo[1,5-c]pyridine-8-carbonitrile

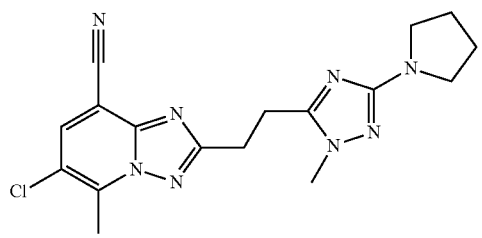 [SMILES: Cc1c(Cl)cc(C#N)c2nc(CCc3nc(N4CCCC4)nn3C)nn12]

The product (2.3 mg, 6.6%) was obtained in the preparative HPLC separation of Example 78. MS: m/z=371.3 (M+H+)

Example 80

2-{6-Chloro-5-methyl-2-[2-(2-methyl-5-pyrrolidin-1-yl-2H-[1,2,4]triazol-3-yl)-ethyl]-[1,2,4]triazolo[1,5-c]pyridin-8-yl}-propan-2-ol

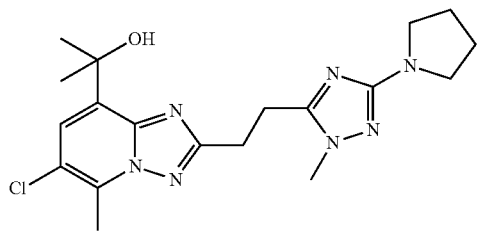 [SMILES: Cc1c(Cl)cc(C(C)(C)O)c2nc(CCc3nc(N4CCCC4)nn3C)nn12]

A 1.6M solution of n-BuLi in hexanes (38.3 μl, 61.2 μmol, Eq: 1.3) was added at −68° C. to a solution of 8-bromo-6-chloro-5-methyl-2-(2-(1-methyl-3-(pyrrolidin-1-yl)-1H-1,2,4-triazol-5-yl)ethyl)-[1,2,4]triazolo[1,5-a]pyridine (20 mg, 47.1 μmol, Eq: 1.00) in tetrahydrofuran (1 mL). This solution was stirred 5 min at −68° C., then propan-2-one (2.73 mg, 1 mL, 47.1 μmol, Eq: 1.00) was added and the cooling bath was removed. The mixture was stirred at room temperature for 10 min. Separation of the mixture by preparative HPLC afforded the desired product (1.7 mg, 8.9%) as a colorless oil. MS: m/z=404.2 (M+H+)

Example 81

2-[(E)-2-(5-Azetidin-1-yl-2-methyl-2H-[1,2,4]triazol-3-yl)-vinyl]-5,8-dimethyl-[1,2,4]triazolo[1,5-c]pyrimidine

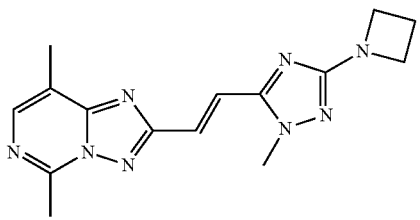 [SMILES: Cc1cnc(C)n2nc(/C=C/c3nc(N4CCC4)nn3C)nc12]

a) 2-[(E)-2-(5-Bromo-2-methyl-2H-[1,2,4]triazol-3-yl)-vinyl]-5,8-dimethyl-[1,2,4]triazolo[1,5-c]pyrimidine

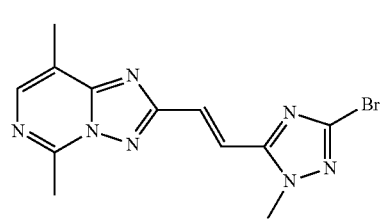 [SMILES: Cc1cnc(C)n2nc(/C=C/c3nc(Br)nn3C)nc12]

To a solution of 3-bromo-1-methyl-1H-1,2,4-triazole-5-carbaldehyde (120 mg, 632 µmol, Eq: 1.00) in tetrahydrofuran (25 ml) were added ((5,8-dimethyl-[1,2,4]triazolo[1,5-c]pyrimidin-2-yl)methyl)triphenylphosphonium chloride (290 mg, 632 µmol, Eq: 1.00) (prepared as described in WO2011150156, pp 123-125, Expl. 24 g) and DBU (106 mg, 105 µl, 695 µmol, Eq: 1.1). The resulting solution was stirred for 18 hours at 25° C. The crude material was applied on silica gel and purified by flash chromatography over a 20 g silica gel column using ethyl acetate methanol 0-10% as eluent affording 2-[(E)-2-(5-bromo-2-methyl-2H-[1,2,4]triazol-3-yl)-vinyl]-5,8-dimethyl-[1,2,4]triazolo[1,5-c]pyrimidine (154 mg, 73%) as a white solid. MS: m/z=336.63537 (M+H+)

b) 2-[(E)-2-(5-Azetidin-1-yl-2-methyl-2H-[1,2,4]triazol-3-yl)-vinyl]-5,8-dimethyl-[1,2,4]triazolo[1,5-c]pyrimidine

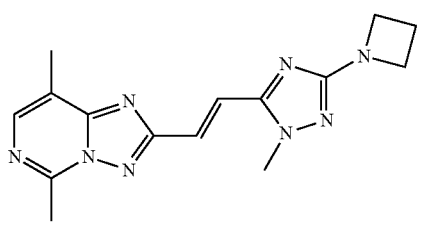 [SMILES: Cc1cnc(C)n2nc(/C=C/c3nc(N4CCC4)nn3C)nc12]

A solution of (E)-2-(2-(3-bromo-1-methyl-1H-1,2,4-triazol-5-yl)vinyl)-5,8-dimethyl-[1,2,4]triazolo[1,5-c]pyrimidine (150 mg, 449 µmol, Eq: 1.00) in dioxane (210.4 ml) was purged with argon, then sodium phenolate (78.2 mg, 673 µmol, Eq: 1.5), 4,5-bis(diphenylphosphino)-9,9-dimethylxanthene (xant-phos) (20.8 mg, 35.9 µmol, Eq: 0.08), tris(dibenzylideneacetone)-dipalladium chloroform complex/Pd$_2$(dba)$_3$CHCl$_3$ (18.6 mg, 18.0 µmol, Eq: 0.04) and azetidine (76.9 mg, 90.5 µl, 1.35 mmol, Eq: 3) were added. The vial was capped and irradiated at 140° C. for 40 minutes in a microwave oven. The crude material was applied on silica gel and purified by flash chromatography over a 20 g silica gel column using ethyl acetate/methanol 0-10% as eluent affording 2-[(E)-2-(5-azetidin-1-yl-2-methyl-2H-[1,2,4]triazol-3-yl)-vinyl]-5,8-dimethyl-[1,2,4]triazolo[1,5-c]pyrimidine (89 mg, 63.9%) as light yellow solid. MS: m/z=311.5 (M+H+), MP: 210.4° C.

Example 82

6-Bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-c]pyridine

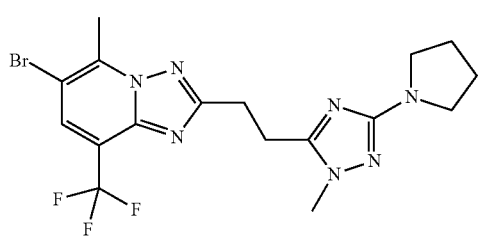 [SMILES: Cc1c(Br)cc(C(F)(F)F)c2nc(CCc3nc(N4CCCC4)nn3C)nn12]

a) 5-Bromo-6-methyl-3-trifluoromethyl-pyridin-2-ylamine

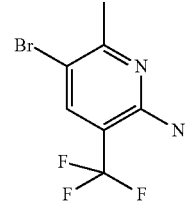

Bromine (1.7 g, 548 µl, 10.6 mmol, Eq: 5) was added to 6-methyl-3-(trifluoromethyl)pyridin-2-amine (375 mg, 2.13 mmol, Eq: 1) in trifluoroacetic acid (7 ml). The mixture was stirred for 30 min and then concentrated to an oil. Water (30 ml) and dichloromethane (10 ml) were added. The mixture was alkalized by addition of sodium bicarbonate and extracted with dichloromethane. The combined organic layers were dried over sodium sulfate and concentrated to an oil. The crude product was purified by chromatography (SiO$_2$, ethyl acetate/n-heptane) to give the desired product (450 mg, 82.9%) as a yellow solid. MS: m/z=255.1 (M+H+)

b) 6-Bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-c]pyridine

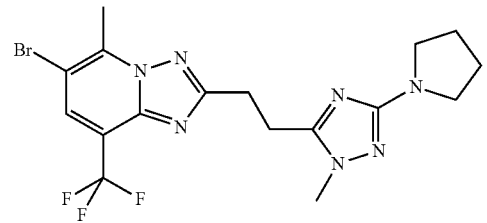 [SMILES: Cc1c(Br)cc(C(F)(F)F)c2nc(CCc3nc(N4CCCC4)nn3C)nn12]

The product (190 mg) was obtained as a white solid in analogy to Example 52 from 5-bromo-6-methyl-3-trifluoromethyl-pyridin-2-ylamine. MS: m/z=458.4 (M+H+)

Example 83

5-Methyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine-6-carbonitrile

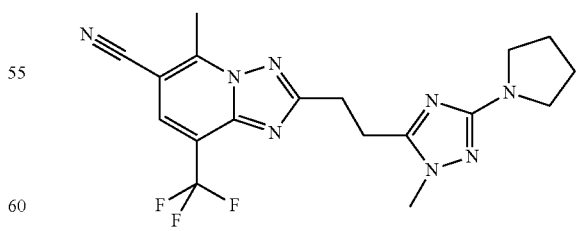

The product (6 mg, 18%) was obtained as a light yellow solid in analogy to Example 78 from 6-bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine. MS: m/z=405.4 (M+H+)

Example 84

5,6-Dimethyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine

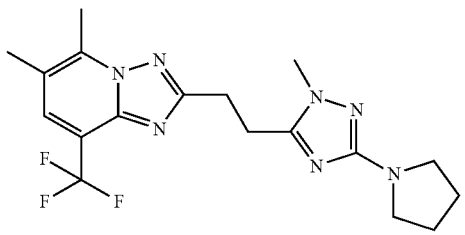 [SMILES: Cc1cc(C(F)(F)F)c2nc(CCc3nc(N4CCCC4)nn3C)nn2c1C]

1 M dimethylzinc in heptane (70 µL, 70 µmol, Eq: 1.00) was added to 6-bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine (30 mg, 65.5 µmol, Eq: 1.00) and 1,3-bis(diphenylphosphino)propane-nickel(II) chloride (13 mg, 24.0 µmol, Eq: 0.366) in dioxane (1 ml). The mixture was heated to 100° C. for 1 h in a microwave oven. Purification by preparative HPLC gave the desired product (16 mg, 61.7%) as a white solid. MS: m/z=394.4 (M+H+)

Example 85

6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-ol

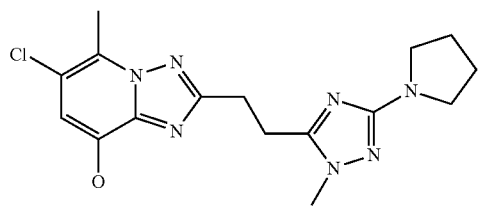 [SMILES: Cc1c(Cl)cc(O)c2nc(CCc3nc(N4CCCC4)nn3C)nn12]

The product (6.3 mg) was obtained as a white solid in analogy to Example 72 from 2-amino-6-methylpyridin-3-ol. MS: m/z=362.3 (M+H+)

Example 86

6-Ethyl-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine

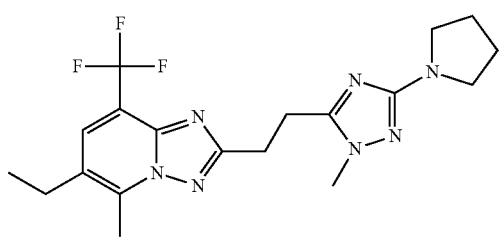 [SMILES: CCc1cc(C(F)(F)F)c2nc(CCc3nc(N4CCCC4)nn3C)nn2c1C]

The product (18 mg, 40%) was obtained as a white powder in analogy to Example 84 using diethylzinc instead of dimethylzinc as starting material. MS: m/z=408.2 (M+H+)

Example 87

1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-2-one

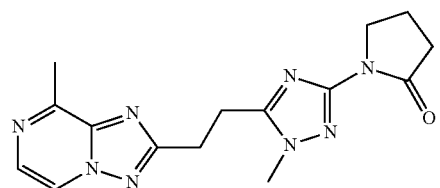

a) 1-{5-[(E)-2-(5,8-Dimethyl-[1,2,4]triazolo[1,5-a]pyrazin-2-yl)-vinyl]-1-methyl-1H-[1,2,4]triazol-3-yl}-pyrrolidin-2-one

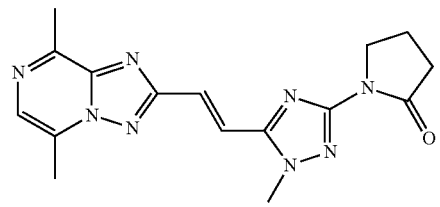 [SMILES: Cc1ncc(C)n2nc(/C=C/c3nc(N4CCCC4=O)nn3C)nc12]

An argon-purged mixture of (E)-2-(2-(3-bromo-1-methyl-1H-1,2,4-triazol-5-yl)vinyl)-5,8-dimethyl-[1,2,4]triazolo[1,5-a]pyrazine (case 30922, Expl. 9a) p 31) (56 mg, 168 µmol, Eq: 1.00), pyrrolidin-2-one (28.6 mg, 25.7 µl, 336 µmol, Eq: 2), cesium carbonate (76.4 mg, 235 µmol, Eq: 1.4), tris(dibenzylideneacetone)-dipalladium(0)/Pd$_2$(dba)$_3$ (3.07 mg, 3.35 µmol, Eq: 0.02) and 4,5-bis(diphenylphosphino)-9,9-dimethylxanthene (xant-phos) (3.88 mg, 6.7 µmol, Eq: 0.04) in dioxane (3 ml) was heated in a closed vessel for 1.5 hours at 140° C. under argon atmosphere. Up to 4 additional portions of Pd$_2$(dba)$_3$ and 4,5-bis(diphenylphosphino)-9,9-dimethylxanthene (xant-phos) are added and heating continued for another 1.5 hours until HPLC shows complete conversion of the Aryl bromide. The crude material was applied on silica gel and purified by flash chromatography over a 20 g silica gel column using ethyl acetate/methanol 5-10% as eluent affording 1-{5-[(E)-2-(5,8-Dimethyl-[1,2,4]triazolo[1,5-a]pyrazin-2-yl)-vinyl]-1-methyl-1H-[1,2,4]triazol-3-yl}-pyrrolidin-2-one (27 mg, 47.6%) as an off-white solid. MS: m/z=339.6 (M+H+), MP: 242.5° C.

b) 1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-2-one

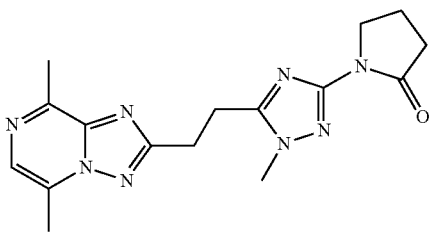 [SMILES: Cc1ncc(C)n2nc(CCc3nc(N4CCCC4=O)nn3C)nc12]

A mixture of (E)-1-(5-(2-(5,8-dimethyl-[1,2,4]triazolo[1,5-a]pyrazin-2-yl)vinyl)-1-methyl-1H-1,2,4-triazol-3-yl)pyrrolidin-2-one (24 mg, 70.9 μmol, Eq: 1.00) and palladium on carbon 10% (7.5 mg, 7.1 μmol, Eq: 0.1) in methanol (15 ml) was stirred for 5 hours at 25° C. under hydrogen atmosphere. Additional catalyst (0.1 eq) was added and hydrogenation continued for another 6 hours until HPLC shows complete conversion. The catalyst was filtered off, the filtrate was evaporated affording 1-{5-[2-(5,8-dimethyl-[1,2,4]triazolo[1,5-a]pyrazin-2-yl)-ethyl]-1-methyl-1H-[1,2,4]triazol-3-yl}-pyrrolidin-2-one (24 mg, 99.4%) as a colorless oil. MS: m/z=341.6 (M+H+)

Example 88

6-Chloro-2-{2-[5-(3,3-difluoro-pyrrolidin-1-yl)-2-methyl-2H-[1,2,4]triazol-3-yl]-ethyl}-5-methyl-8-trifluoromethyl-[1,2,4]triazolo[1,5-c]pyridine

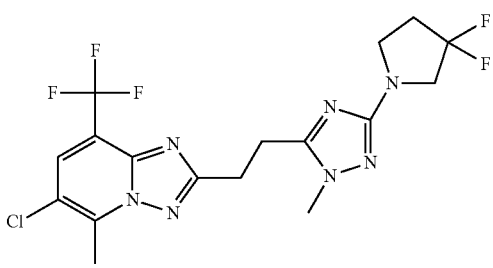 [SMILES: Cc1c(Cl)cc(C(F)(F)F)c2nc(CCc3nc(N4CCC(F)(F)C4)nn3C)nn12]

a) 3-(3,3-Difluoropyrrolidin-1-yl)-1-methyl-1H-1,2,4-triazole-5-carbaldehyde

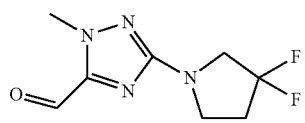

N,N-Diisopropylethylamine (900 mg, 1.22 ml, 6.97 mmol, Eq: 2.00) was added to 3,3-difluoropyrrolidine hydrochloride (500 mg, 3.5 mmol, Eq: 1.00) in diethyl ether (10 ml). A solution of cyanic bromide (369 mg, 3.5 mmol, Eq: 1.00) in diethyl ether (2 mL) was added at 0° C. The mixture was stirred over night at room temperature, filtered and concentrated on a rotatory evaporator at 40° C., keeping the pressure above 100 mbar (product is volatile). 2,2-Dichloroacetyl chloride (510 mg, 0.336 ml, 3.5 mmol, Eq: 1.00) was added to the crude intermediate at 0° C. The mixture was stirred for 15 min. Dichloromethane (6 ml) was added, followed by N,N-diisopropylethylamine (452 mg, 0.61 ml, 3.5 mmol, Eq: 1.00). tert-Butyl 1-methylhydrazinecarboxylate (555 mg, 0.62 ml, 3.8 mmol, Eq: 1.09) was added dropwise at 0° C. The reaction mixture was stirred for 1 h at room temperature. Trifluoroacetic acid (4 g, 2.7 ml, 35 mmol, Eq: 10) was added. The reaction mixture was heated under refluxed for 1.5 h and then concentrated to an oil. The mixture was partitioned between a saturated sodium bicarbonate solution and ethyl acetate. The combined organic layers were washed with a saturated ammonium chloride solution and then dried over sodium sulfate and concentrated to an oil. Ethanol (12 ml) and water (24 ml) were added, followed by sodium acetate (717 mg, 8.75 mmol, Eq: 2.5). The reaction mixture was heated to 60° C. for 1 h. The mixture was extracted with ethyl acetate. The combined organic layers were dried over Na2SO4, filtered and concentrated in vacuo to give the desired product (699 mg, 92%) as a white powder. MS: m/z=217.3 (M+H+)

b) 6-Chloro-2-{2-[5-(3,3-difluoro-pyrrolidin-1-yl)-2-methyl-2H-[1,2,4]triazol-3-yl]-ethyl}-5-methyl-8-trifluoromethyl-[1,2,4]triazolo[1,5-c]pyridine

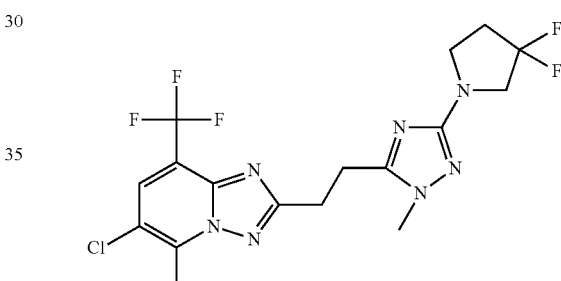

The product (16 mg) was obtained as a light yellow solid in analogy to Example 50 from 3-(3,3-difluoropyrrolidin-1-yl)-1-methyl-1H-1,2,4-triazole-5-carbaldehyde and 5-chloro-6-methyl-3-(trifluoromethyl)pyridin-2-amine. MS: m/z=450.4 (M+H+)

Example 89

5,8-Dimethyl-2-{2-[2-methyl-5-(3-methyl-azetidin-1-yl)-2H-[1,2,4]triazol-3-yl]-ethyl}-[1,2,4]triazolo[1,5-a]pyrazine

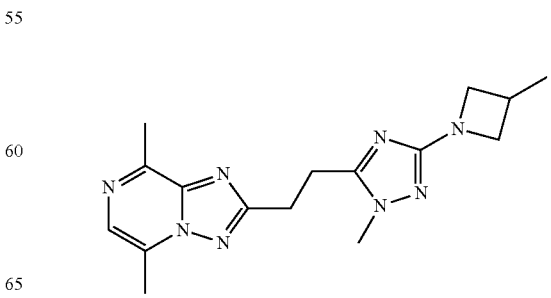

a) 5,8-Dimethyl-2-{(E)-2-[2-methyl-5-(3-methyl-azetidin-1-yl)-2H-[1,2,4]triazol-3-yl]-vinyl}-[1,2,4]triazolo[1,5-a]pyrazine

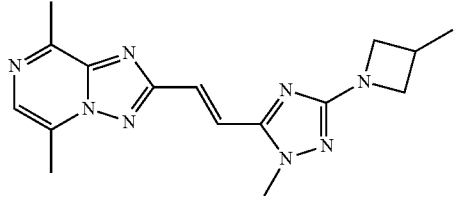 [SMILES: Cc1ncc(C)n2nc(/C=C/c3nc(N4CC(C)C4)nn3C)nc12]

Was prepared in the same manner as described in Example 87a) using 3-methylazetidine benzenesulfonate (206 mg, 898 µmol, Eq: 2) instead of pyrrolidin-2-one affording 5,8-dimethyl-2-{(E)-2-[2-methyl-5-(3-methyl-azetidin-1-yl)-2H-[1,2,4]triazol-3-yl]-vinyl}-[1,2,4]triazolo[1,5-a]pyrazine (51 mg, 35.0%) as a bright yellow viscous oil. MS: m/z=325.6 (M+H+)

b) 5,8-Dimethyl-2-{2-[2-methyl-5-(3-methyl-azetidin-1-yl)-2H-[1,2,4]triazol-3-yl]-ethyl}-[1,2,4]triazolo[1,5-a]pyrazine

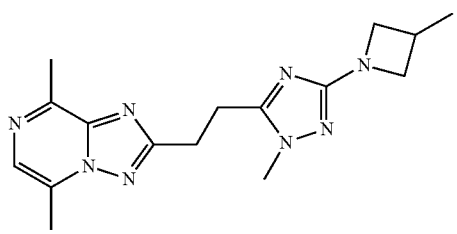 [SMILES: Cc1ncc(C)n2nc(CCc3nc(N4CC(C)C4)nn3C)nc12]

Was prepared in the same manner as described in Example 87 b) from (E)-5,8-dimethyl-2-(2-(1-methyl-3-(3-methylazetidin-1-yl)-1H-1,2,4-triazol-5-yl)vinyl)-[1,2,4]triazolo[1,5-a]pyrazine (50 mg, 154 µmol, Eq: 1.00) affording 5,8-dimethyl-2-{2-[2-methyl-5-(3-methyl-azetidin-1-yl)-2H-[1,2,4]triazol-3-yl]-ethyl}-[1,2,4]triazolo[1,5-a]pyrazine (45 mg, 89.4%) as a colorless oil. MS: m/z=327.5 (M+H+)

Example 90

2-{2-[5-(3,3-Difluoro-azetidin-1-yl)-2-methyl-2H-[1,2,4]triazol-3-yl]-ethyl}-5,8-dimethyl-[1,2,4]triazolo[1,5-a]pyrazine

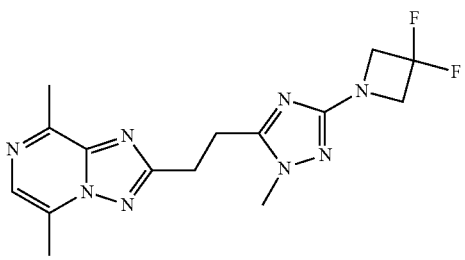 [SMILES: Cc1ncc(C)n2nc(CCc3nc(N4CC(F)(F)C4)nn3C)nc12]

a) 2-{(E)-2-[5-(3,3-Difluoro-azetidin-1-yl)-2-methyl-2H-[1,2,4]triazol-3-yl]-vinyl}-5,8-dimethyl-[1,2,4]triazolo[1,5-a]pyrazine

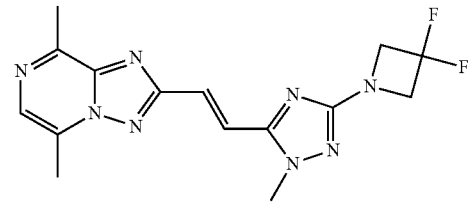 [SMILES: Cc1ncc(C)n2nc(/C=C/c3nc(N4CC(F)(F)C4)nn3C)nc12]

Was prepared in the same manner as described in Example 87a) using 3,3-difluoroazetidine hydrochloride (87.2 mg, 673 µmol, Eq: 1.5) instead of pyrrolidin-2-one affording 2-{(E)-2-[5-(3,3-difluoro-azetidin-1-yl)-2-methyl-2H-[1,2,4]triazol-3-yl]-vinyl}-5,8-dimethyl-[1,2,4]triazolo[1,5-a]pyrazine (57 mg, 36.7%) as a light yellow oil. MS: m/z=347.5 (M+H+)

b) 2-{2-[5-(3,3-Difluoro-azetidin-1-yl)-2-methyl-2H-[1,2,4]triazol-3-yl]-ethyl}-5,8-dimethyl-[1,2,4]triazolo[1,5-a]pyrazine

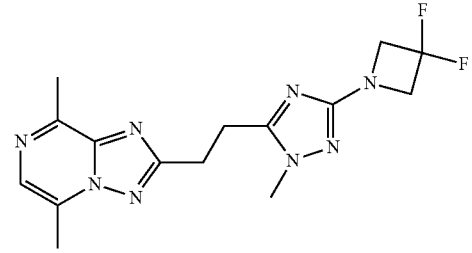 [SMILES: Cc1ncc(C)n2nc(CCc3nc(N4CC(F)(F)C4)nn3C)nc12]

Was prepared in the same manner as described in Example 87 b) from (E)-2-(2-(3-(3,3-difluoroazetidin-1-yl)-1-methyl-1H-1,2,4-triazol-5-yl)vinyl)-5,8-dimethyl-[1,2,4]triazolo[1,5-a]pyrazine (54 mg, 156 µmol, Eq: 1.00) affording 2-{2-[5-(3,3-difluoro-azetidin-1-yl)-2-methyl-2H-[1,2,4]triazol-3-yl]-ethyl}-5,8-dimethyl-[1,2,4]triazolo[1,5-a]pyrazine (51 mg, 93.9%) as an off-white solid. MS: m/z=349.5 (M+H+), MP: 141.3° C.

Example 91

6-Chloro-5-methyl-2-(2-methyl-5-pyrrolidin-1-yl-2H-[1,2,4]triazol-3-ylethynyl)-8-trifluoromethyl-[1,2,4]triazolo[1,5-a]pyridine

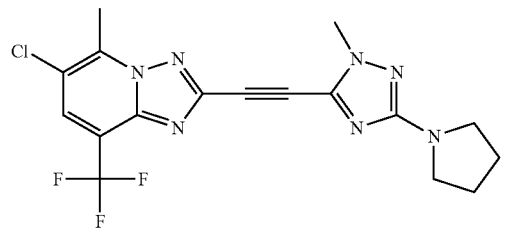 [SMILES: Cc1c(Cl)cc(C(F)(F)F)c2nc(C#Cc3nc(N4CCCC4)nn3C)nn12]

115 a) 6-Chloro-2-iodo-5-methyl-8-trifluoromethyl-[1,2,4]triazolo[1,5-a]pyridine

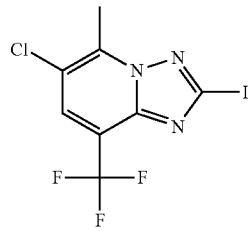 [SMILES: Cc1c(Cl)cc(C(F)(F)F)c2nc(I)nn12]

Ethoxycarbonyl isothiocyanate (111 mg, 0.1 ml, 0.852 mmol, Eq:1.50) was added to 6-methyl-3-(trifluoromethyl)pyridin-2-amine (100 mg, 0.568 mmol, Eq: 1.00) in dioxane (10 ml). The mixture was heated to 60° C. for 1 h. The mixture was filtered. The residue was suspended in ethanol (10 ml), hydroxylamine hydrochloride (197 mg, 2.84 mmol, Eq: 5) and N,N-diisopropylethylamine (220 mg, 0.3 ml, 1.7 mmol, Eq: 3) were added. The mixture was heated under reflux overnight and then concentrated to an oil. Water (15 ml) was added and the mixture was filtered. The residue was washed with water and ether, and then dissolved in acetonitrile (10 ml). Isopentyl nitrite (111 mg, 127 µl, 628 µmol, Eq: 1.1) and copper(I)iodide (160 mg, 838 µmol, Eq: 1.5) were added. The mixture was stirred at 80° C. for 1 h. The mixture was filtered over $SiO_2$ concentrated, suspended in ethyl acetate and filtered again over $SiO_2$ and concentrated to give the product (120 mg, 58%) as a light yellow powder. MS: m/z=362.2 (M+H+)

b) 5-Ethynyl-1-methyl-3-(pyrrolidin-1-yl)-1H-1,2,4-triazole

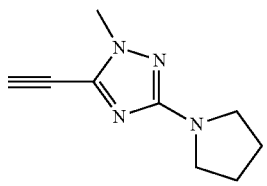

To a stirred mixture of 1-methyl-3-(pyrrolidin-1-yl)-1H-1,2,4-triazole-5-carbaldehyde (2.06 g, 11.4 mmol) and potassium carbonate (3.16 g, 22.9 mmol) at room temperature in methanol (75 ml) under an argon atmosphere was added drop wise a solution of dimethyl 1-diazo-2-oxopropylphosphonate (2.64 g, 2.1 ml, 13.7 mmol) in methanol (15 ml). Stirring at room temperature was then continued for 3 h. The mixture was diluted with diethyl ether and washed with 10% $NaHCO_3$ solution. The aqueous phase was extracted with diethyl ether. The combined organic layers were washed with $H_2O$ and brine, dried over $MgSO_4$, filtered and concentrated. The crude product was purified by silica gel chromatography using a $CH_2Cl_2$MeOH gradient as eluent, providing the title compound (725 mg, 36%) as off-white solid. MS: m/z=177.2 (M+H+)

116 c) 6-Chloro-5-methyl-2-(2-methyl-5-pyrrolidin-1-yl-2H-[1,2,4]triazol-3-ylethynyl)-8-trifluoromethyl-[1,2,4]triazolo[1,5-c]pyridine

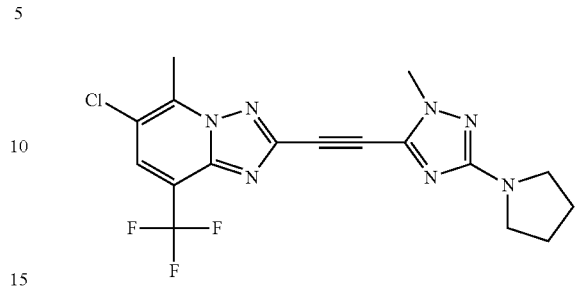

6-Chloro-2-iodo-5-methyl-8-trifluoromethyl-[1,2,4]triazolo[1,5-a]pyridine (13 mg, 36.0 µmol, Eq: 1.00), 5-ethynyl-1-methyl-3-(pyrrolidin-1-yl)-1H-1,2,4-triazole (8 mg, 45.4 µmol, Eq: 1.26), triethylamine (7.26 mg, 10 µl, 71.7 µmol, Eq: 2.00), and bis(triphenylphosphine)palladium (II) chloride (5 mg, 7.12 µmol, Eq: 0.198) were added to dimethylformamide (1 ml). Copper(I)iodide (1 mg, 5.25 µmol, Eq: 0.146) was added and the mixture was stirred for 2 h at 80° C. The crude material was purified by preparative TLC (silica gel, ethyl acetate/n-heptane) to give the product (6.8 mg, 46%) as a white powder. MS: m/z=410.4 (M+H+)

Example 92

2-{2-[5-(5-Aza-spiro[2.4]hept-5-yl)-2-methyl-2H-[1,2,4]triazol-3-yl]-ethyl}-5,8-dimethyl-[1,2,4]triazolo[1,5-a]pyrazine

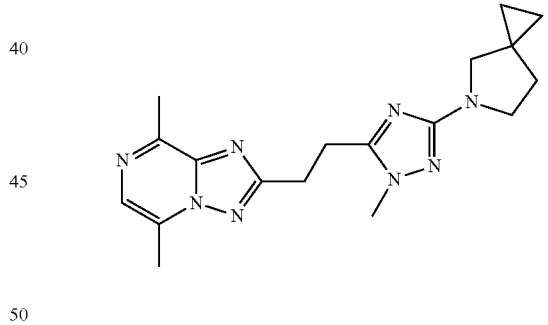

a) 2-{(E)-2-[5-(5-Aza-spiro[2.4]hept-5-yl)-2-methyl-2H-[1,2,4]triazol-3-yl]-vinyl}-5,8-dimethyl-[1,2,4]triazolo[1,5-a]pyrazine

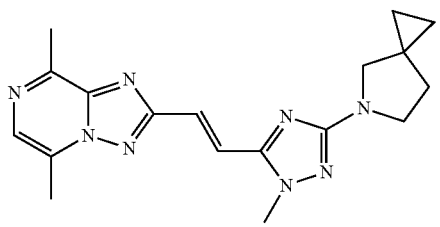 [SMILES: Cc1ncc(C)n2nc(/C=C/c3nc(N4CCC5(CC5)C4)nn3C)nc12]

Was prepared in the same manner as described in Example 87a) using 5-azaspiro[2.4]heptane hydrochloride (120 mg, 898 µmol, Eq: 2) instead of pyrrolidin-2-one affording 2-{(E)-2-[5-(5-aza-spiro[2.4]hept-5-yl)-2-methyl-2H-[1,2,4]triazol-3-yl]-vinyl}-5,8-dimethyl-[1,2,4]triazolo[1,5-a]pyrazine (33 mg, 21%) as yellow amorphous solid. MS: m/z=351.6 (M+H+)

b) 2-{2-[5-(5-Aza-spiro[2.4]hept-5-yl)-2-methyl-2H-[1,2,4]triazol-3-yl]-ethyl}-5,8-dimethyl-[1,2,4]triazolo[1,5-a]pyrazine

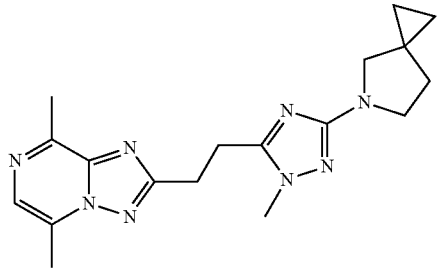 [SMILES: Cc1ncc(C)n2nc(CCc3nc(N4CCC5(CC5)C4)nn3C)nc12]

Was prepared in the same manner as described in Example 87 b) from (E)-5,8-dimethyl-2-(2-(1-methyl-3-(5-azaspiro[2.4]heptan-5-yl)-1H-1,2,4-triazol-5-yl)vinyl)-[1,2,4]triazolo[1,5-a]pyrazine (31 mg, 88.5 µmol, Eq: 1.00) affording 2-{2-[5-(5-aza-spiro[2.4]hept-5-yl)-2-methyl-2H-[1,2,4]triazol-3-yl]-ethyl}-5,8-dimethyl-[1,2,4]triazolo[1,5-a]pyrazine (32 mg, 103%) as a colorless oil. MS: m/z=353.6 (M+H+)

Example 93

2-{2-[5-(3,3-Difluoro-pyrrolidin-1-yl)-2-methyl-2H-[1,2,4]triazol-3-yl]-ethyl}-5,8-dimethyl-[1,2,4]triazolo[1,5-a]pyrazine

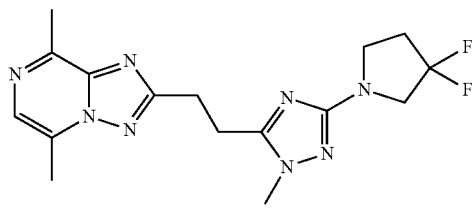 [SMILES: Cc1ncc(C)n2nc(CCc3nc(N4CCC(F)(F)C4)nn3C)nc12]

a) 2-{(E)-2-[5-(3,3-Difluoro-pyrrolidin-1-yl)-2-methyl-2H-[1,2,4]triazol-3-yl]-vinyl}-5,8-dimethyl-[1,2,4]triazolo[1,5-a]pyrazine

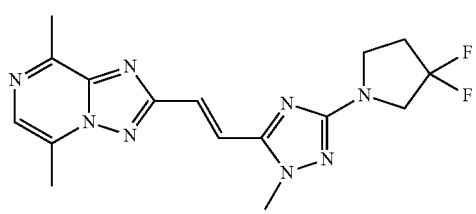 [SMILES: Cc1ncc(C)n2nc(/C=C/c3nc(N4CCC(F)(F)C4)nn3C)nc12]

Was prepared in the same manner as described in Example 49 e) using 3-(3,3-difluoropyrrolidin-1-yl)-1-methyl-1H-1,2,4-triazole-5-carbaldehyde (94.2 mg, 436 µmol, Eq: 1.00) as aldehyde affording 2-{(E)-2-[5-(3,3-difluoro-pyrrolidin-1-yl)-2-methyl-2H-[1,2,4]triazol-3-yl]-vinyl}-5,8-dimethyl-[1,2,4]triazolo[1,5-a]pyrazine (80 mg, 50.9%) as a light yellow solid. MS: m/z=361.5 (M+H+), MP: 207.5° C.

b) 2-{2-[5-(3,3-Difluoro-pyrrolidin-1-yl)-2-methyl-2H-[1,2,4]triazol-3-yl]-ethyl}-5,8-dimethyl-[1,2,4]triazolo[1,5-a]pyrazine

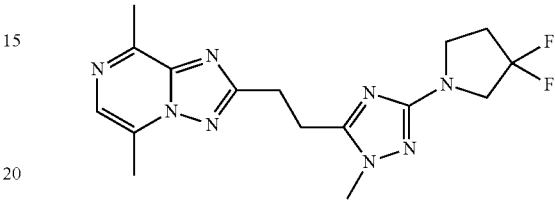

Was prepared in the same manner as described in Example 87 b) using (E)-2-(2-(3-(3,3-difluoropyrrolidin-1-yl)-1-methyl-1H-1,2,4-triazol-5-yl)vinyl)-5,8-dimethyl-[1,2,4]triazolo[1,5-a]pyrazine (71 mg, 197 µmol, Eq: 1.00) affording 2-{2-[5-(3,3-difluoro-pyrrolidin-1-yl)-2-methyl-2H-[1,2,4]triazol-3-yl]-ethyl}-5,8-dimethyl-[1,2,4]triazolo[1,5-a]pyrazine (39 mg, 54.6%) as a white solid. MS: m/z=363.6 (M+H+)

Example 94

2-{2-[5-((S)-3-Fluoro-pyrrolidin-1-yl)-2-methyl-2H-[1,2,4]triazol-3-yl]-ethyl}-5,8-dimethyl-[1,2,4]triazolo[1,5-a]pyrazin

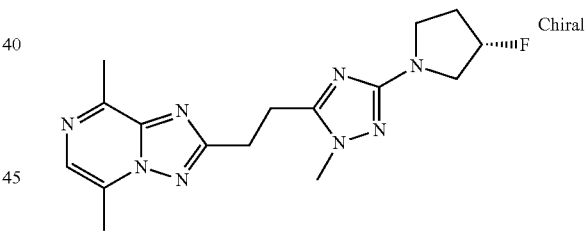

a) 2-{(E)-2-[5-((S)-3-Fluoro-pyrrolidin-1-yl)-2-methyl-2H-[1,2,4]triazol-3-yl]-vinyl}-5,8-dimethyl-[1,2,4]triazolo[1,5-a]pyrazine

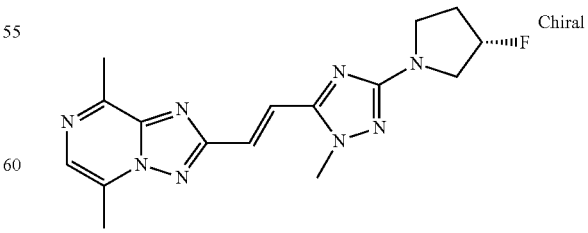

Was prepared in the same manner as described in Example 87a) using (S)-3-fluoropyrrolidine hydrochloride (113 mg, 898 µmol, Eq: 2) instead of pyrrolidin-2-one affording 2-{(E)-2-[5-((S)-3-fluoro-pyrrolidin-1-yl)-2-methyl-2H-[1,2, 4]triazol-3-yl]-vinyl}-5,8-dimethyl-[1,2,4]triazolo-[1,5-a]pyrazine (54 mg, 35.1%) as a light yellow solid. MS: m/z=343.5 (M+H+)

b) 2-{2-[5-((S)-3-Fluoro-pyrrolidin-1-yl)-2-methyl-2H-[1,2,4]triazol-3-yl]-ethyl}-5,8-dimethyl-[1,2,4]triazolo[1,5-a]pyrazin

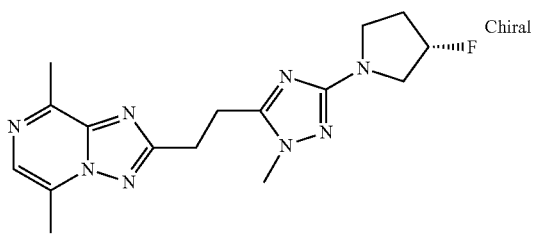 [SMILES: Cc1ncc(C)n2nc(CCc3nc(N4CC[C@H](F)C4)nn3C)nc12]

Was prepared in the same manner as described in Example 87 b) using (S,E)-2-(2-(3-(3-fluoropyrrolidin-1-yl)-1-methyl-1H-1,2,4-triazol-5-yl)vinyl)-5,8-dimethyl-[1,2,4]triazolo[1,5-a]pyrazine (48 mg, 140 μmol, Eq: 1.00) affording 2-{2-[5-((S)-3-fluoro-pyrrolidin-1-yl)-2-methyl-2H-[1,2,4]triazol-3-yl]-ethyl}-5,8-dimethyl-[1,2,4]triazolo[1,5-a]pyrazin (56 mg, 116%) as a colorless oil. MS: m/z=345.6 (M+H+)

Example 95

6-Chloro-8-difluoromethoxy-5-methyl-2-[2-(2-methyl-5-pyrrolidin-1-yl-2H-[1,2,4]triazol-3-yl)-ethyl]-[1,2,4]triazolo[1,5-c]pyridine

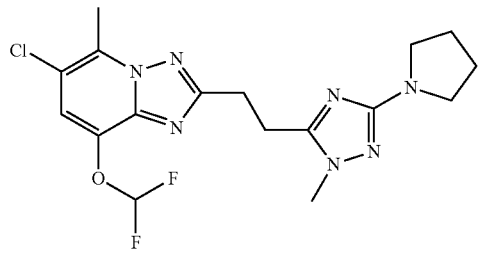 [SMILES: Cc1c(Cl)cc(OC(F)F)c2nc(CCc3nc(N4CCCC4)nn3C)nn12]

The product (37 mg) was obtained as a light brown solid from 3-(difluoromethoxy)-6-methylpyridin-2-amine in analogy to Example 72. MS: m/z=412.4 (M+H+)

Example 96

2-{2-[5-((R)-3-Fluoro-pyrrolidin-1-yl)-2-methyl-2H-[1,2,4]triazol-3-yl]-ethyl}-5,8-dimethyl-[1,2,4]triazolo[1,5-a]pyrazine

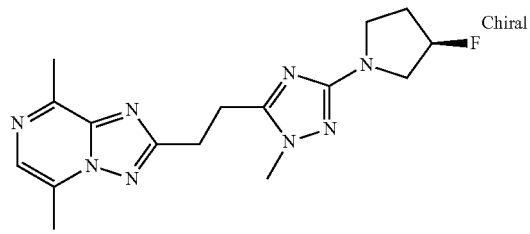 [SMILES: Cc1ncc(C)n2nc(CCc3nc(N4CC[C@@H](F)C4)nn3C)nc12]

a) 2-{(E)-2-[5-((R)-3-Fluoro-pyrrolidin-1-yl)-2-methyl-2H-[1,2,4]triazol-3-yl]-vinyl}-5,8-dimethyl-[1,2,4]triazolo[1,5-a]pyrazine

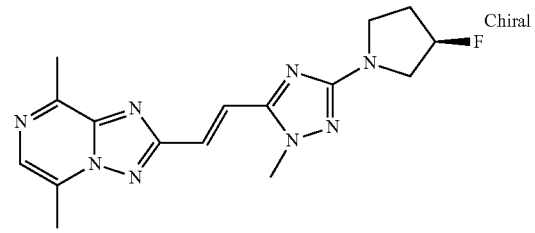 [SMILES: Cc1ncc(C)n2nc(/C=C/c3nc(N4CC[C@@H](F)C4)nn3C)nc12]

Was prepared in the same manner as described in Example 87a) using (R)-3-fluoropyrrolidine hydrochloride (113 mg, 898 μmol, Eq: 2) instead of pyrrolidin-2-one affording 2-{(E)-2-[5-((R)-3-fluoro-pyrrolidin-1-yl)-2-methyl-2H-[1,2,4]triazol-3-yl]-vinyl}-5,8-dimethyl-[1,2,4]triazolo[1,5-a]pyrazine (36 mg, 23.4%) as a light yellow solid. MS: m/z=343.5 (M+H+)

b) 2-{2-[5-((R)-3-Fluoro-pyrrolidin-1-yl)-2-methyl-2H-[1,2,4]triazol-3-yl]-ethyl}-5,8-dimethyl-[1,2,4]triazolo[1,5-a]pyrazine

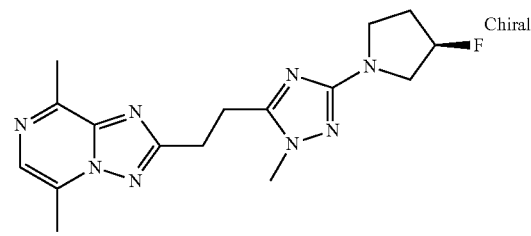 [SMILES: Cc1ncc(C)n2nc(CCc3nc(N4CC[C@@H](F)C4)nn3C)nc12]

Was prepared in the same manner as described in Example 87 b) using (R,E)-2-(2-(3-(3-fluoropyrrolidin-1-yl)-1-methyl-1H-1,2,4-triazol-5-yl)vinyl)-5,8-dimethyl-[1,2,4]triazolo[1,5-a]pyrazine (37 mg, 108 μmol, Eq: 1.00) affording 2-{2-[5-((R)-3-fluoro-pyrrolidin-1-yl)-2-methyl-2H-[1,2,4]-triazol-3-yl]-ethyl}-5,8-dimethyl-[1,2,4]triazolo[1,5-a]pyrazine (16 mg, 43%) as a white solid. MS: m/z=345.5 (M+H+)

Example 97

Cyclopropylmethyl-{5-[(E)-2-(5,8-dimethyl-[1,2,4]triazolo[1,5-a]pyrazin-2-yl)-vinyl]-1-methyl-1H-[1,2,4]triazol-3-yl}-methyl-amine

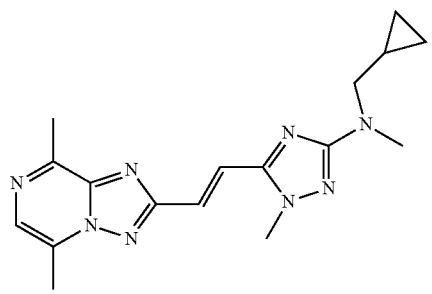 [SMILES: Cc1ncc(C)n2nc(/C=C/c3nc(N(C)CC4CC4)nn3C)nc12]

Was prepared in the same manner as described in Example 87a) using 1-cyclopropyl-N-methylmethanamine hydrochloride (109 mg, 898 μmol, Eq: 2) instead of pyrrolidin-2-one affording cyclopropylmethyl-{5-[(E)-2-(5,8-dimethyl-[1,2,4]triazolo[1,5-a]pyrazin-2-yl)-vinyl]-1-methyl-1H-[1,2,4]triazol-3-yl}-methyl-amine (5 mg, 3.29%) as a yellow viscous oil. MS: m/z=339.5 (M+H+)

Example 98

6-Chloro-5-methyl-2-[2-(2-methyl-5-pyrrolidin-1-yl-2H-[1,2,4]triazol-3-yl)-ethyl]-8-(2,2,2-trifluoro-ethoxy)-[1,2,4]triazolo[1,5-c]pyridine

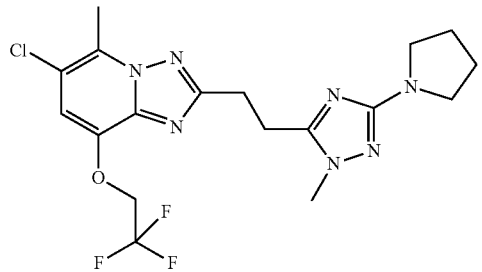 [SMILES: Cc1c(Cl)cc(OCC(F)(F)F)c2nc(CCc3nc(N4CCCC4)nn3C)nn12]

The product (27 mg) was obtained as a light yellow foam from 6-methyl-3-(2,2,2-trifluoroethoxy)-2-pyridinamine in analogy to Example 72. MS: m/z=444.1 (M+H+)

Example 99

2-{2-[5-(3-Aza-bicyclo[3.2.0]hept-3-yl)-2-methyl-2H-[1,2,4]triazol-3-yl]-ethyl}-5,8-dimethyl-[1,2,4]triazolo[1,5-a]pyrazine

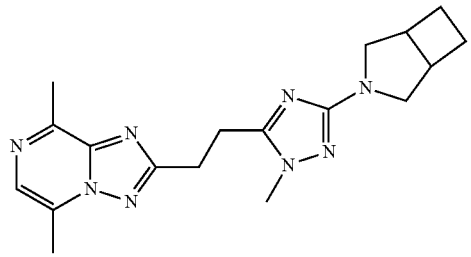 [SMILES: Cc1ncc(C)n2nc(CCc3nc(N4CC5CCC5C4)nn3C)nc12]

a) 2-{(E)-2-[5-(3-Aza-bicyclo[3.2.0]hept-3-yl)-2-methyl-2H-[1,2,4]triazol-3-yl]-vinyl}-5,8-dimethyl-[1,2,4]triazolo[1,5-a]pyrazine

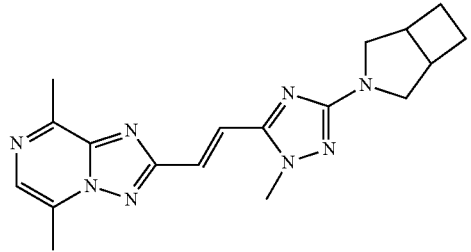 [SMILES: Cc1ncc(C)n2nc(/C=C/c3nc(N4CC5CCC5C4)nn3C)nc12]

Was prepared in the same manner as described in Example 87a) using 3-aza-bicyclo[3.2.0]-heptane hydrochloride (158 mg, 898 µmol, Eq: 2) instead of pyrrolidin-2-one affording 2-{(E)-2-[5-(3-aza-bicyclo[3.2.0]hept-3-yl)-2-methyl-2H-[1,2,4]triazol-3-yl]-vinyl}-5,8-dimethyl-[1,2,4]triazolo-[1,5-a]pyrazine (29 mg, 18.4%) as a yellow oil. MS: m/z=351.5 (M+H+)

b) 2-{2-[5-(3-Aza-bicyclo[3.2.0]hept-3-yl)-2-methyl-2H-[1,2,4]triazol-3-yl]-ethyl}-5,8-dimethyl-[1,2,4]triazolo[1,5-a]pyrazine

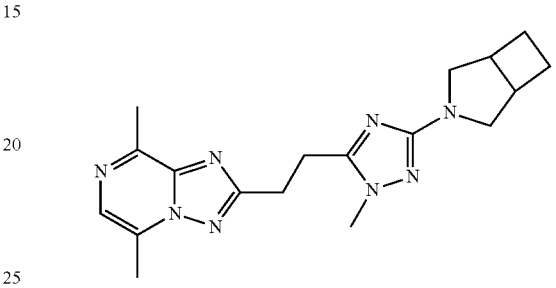

Was prepared in the same manner as described in Example 87 b) using (E)-2-(2-(3-(3-azabicyclo[3.2.0]heptan-3-yl)-1-methyl-1H-1,2,4-triazol-5-yl)vinyl)-5,8-dimethyl-[1,2,4]triazolo[1,5-a]pyrazine (20 mg, 57.1 µmol, Eq: 1.00) affording 2-{2-[5-(3-aza-bicyclo[3.2.0]hept-3-yl)-2-methyl-2H-[1,2,4]triazol-3-yl]-ethyl}-5,8-dimethyl-[1,2,4]triazolo[1,5-a]pyrazine (21 mg, 104%) as a colorless oil. MS: m/z=353.6 (M+H+)

Example 100

5,8-Dimethyl-2-{2-[2-methyl-5-((S)-2-methyl-pyrrolidin-1-yl)-2H-[1,2,4]triazol-3-yl]-ethyl}-[1,2,4]triazolo[1,5-a]pyrazine

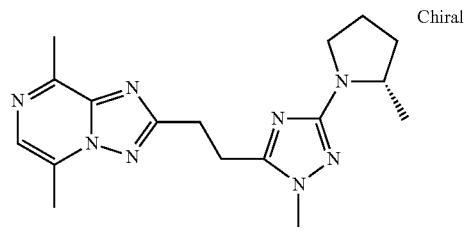 [SMILES: Cc1ncc(C)n2nc(CCc3nc(N4CCC[C@@H]4C)nn3C)nc12]

Chiral HPLC-separation of racemic 5,8-dimethyl-2-(2-(1-methyl-3-(2-methylpyrrolidin-1-yl)-1H-1,2,4-triazol-5-yl)ethyl)-[1,2,4]triazolo[1,5-a]pyrazine (169 mg, 496 µmol, Eq: 1.00) (Example 83c): First Peak A+, afforded 5,8-dimethyl-2-{2-[2-methyl-5-((S)-2-methyl-pyrrolidin-1-yl)-2H-[1,2,4]triazol-3-yl]-ethyl}-[1,2,4]triazolo[1,5-a]pyrazine (67 mg, 39.6%) as a light yellow oil. MS: m/z=341.5 (M+H+)

Example 101

5,8-Dimethyl-2-{2-[2-methyl-5-((R)-2-methyl-pyrrolidin-1-yl)-2H-[1,2,4]triazol-3-yl]-ethyl}-[1,2,4]triazolo[1,5-a]pyrazine

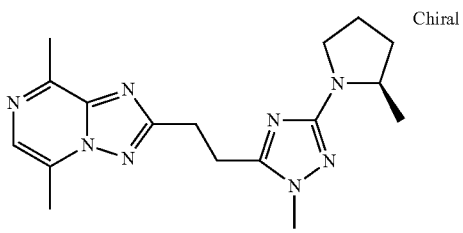 [SMILES: Cc1ncc(C)n2nc(CCc3nc(N4CCC[C@H]4C)nn3C)nc12]

Chiral HPLC-separation of racemic 5,8-dimethyl-2-(2-(1-methyl-3-(2-methylpyrrolidin-1-yl)-1H-1,2,4-triazol-5-yl)ethyl)-[1,2,4]triazolo[1,5-a]pyrazine (169 mg, 496 µmol, Eq: 1.00) (Example 83c): Second Peak B-, afforded 5,8-dimethyl-2-{2-[2-methyl-5-((R)-2-methyl-pyrrolidin-1-yl)-2H-[1,2,4]triazol-3-yl]-ethyl}-[1,2,4]triazolo[1,5-a]pyrazine (66 mg, 39.1%) as a light yellow oil. MS: m/z=341.5 (M+H+)

Example 102

2-[(E)-2-(5-Azepan-1-yl-2-methyl-2H-[1,2,4]triazol-3-yl)-vinyl]-5,8-dimethyl-[1,2,4]triazolo[1,5-a]pyrazine

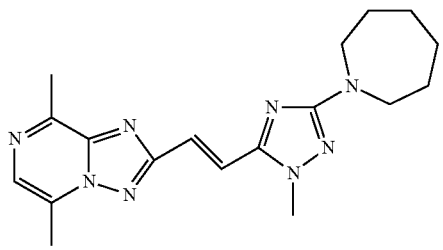 [SMILES: Cc1ncc(C)n2nc(/C=C/c3nc(N4CCCCCC4)nn3C)nc12]

Was prepared in the same manner as described in Example 87a) using azepane (89.0 mg, 101 µl, 898 µmol, Eq: 2.00) instead of pyrrolidin-2-one affording 2-[(E)-2-(5-azepan-1-yl-2-methyl-2H-[1,2,4]triazol-3-yl)-vinyl]-5,8-dimethyl-[1,2,4]triazolo[1,5-a]pyrazine (10.8 mg, 6.83%) as a yellow waxy solid. MS: m/z=353.5 (M+H+)

Example 103

7,8-Dimethyl-2-(2-(1-methyl-3-(pyrrolidin-1-yl)-1H-1,2,4-triazol-5-yl)ethyl)-5-(trifluoromethyl)-[1,2,4]triazolo[1,5-c]pyrimidine

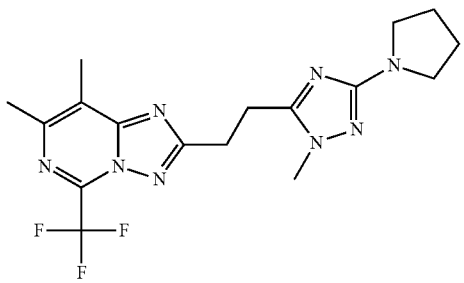 [SMILES: Cc1nc(C(F)(F)F)n2nc(CCc3nc(N4CCCC4)nn3C)nc2c1C]

The product (12 mg) was obtained as a white powder in analogy to Example 75 from 4-chloro-5,6-dimethyl-2-trifluoromethyl-1,3-pyrimidine. MS: m/z=395.6 (M+H+)

Example 104

1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-ol

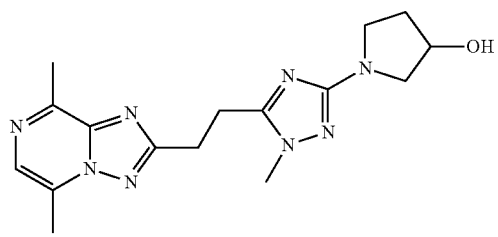 [SMILES: Cc1ncc(C)n2nc(CCc3nc(N4CCC(O)C4)nn3C)nc12]

a) 5,8-Dimethyl-2-((E)-2-{2-methyl-5-[3-(tetrahydro-pyran-2-yloxy)-pyrrolidin-1-yl]-2H-[1,2,4]triazol-3-yl}-vinyl)-[1,2,4]triazolo[1,5-a]pyrazine

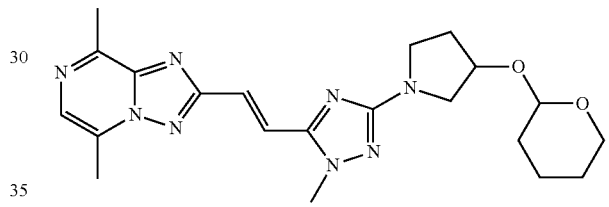

Was prepared in the same manner as described in Example 87a) using 3-(tetrahydro-2H-pyran-2-yloxy)pyrrolidine (154 mg, 898 µmol, Eq: 2) instead of pyrrolidin-2-one affording 5,8-dimethyl-2-((E)-2-{2-methyl-5-[3-(tetrahydro-pyran-2-yloxy)-pyrrolidin-1-yl]-2H-[1,2,4]triazol-3-yl}-vinyl)-[1,2,4]triazolo[1,5-a]pyrazine (37 mg, 19.4%) as a yellow oil. MS: m/z=425.6 (M+H+)

b) 5,8-Dimethyl-2-(2-{2-methyl-5-[3-(tetrahydro-pyran-2-yloxy)-pyrrolidin-1-yl]-2H-[1,2,4]triazol-3-yl}-ethyl)-[1,2,4]triazolo[1,5-a]pyrazine

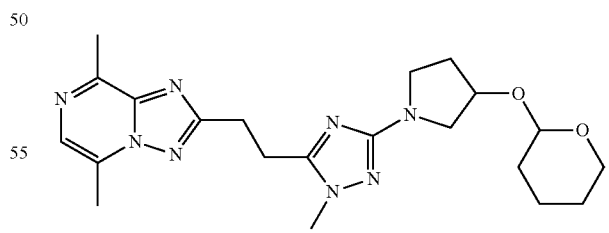

Was prepared in the same manner as described in Example 87 b) using (E)-5,8-dimethyl-2-(2-(1-methyl-3-(3-(tetrahydro-2H-pyran-2-yloxy)pyrrolidin-1-yl)-1H-1,2,4-triazol-5-yl)vinyl)-[1,2,4]triazolo[1,5-a]pyrazine (37 mg, 87.2 µmol, Eq: 1.00) affording 5,8-dimethyl-2-(2-{2-methyl-5-[3-(tetrahydro-pyran-2-yloxy)-pyrrolidin-1-yl]-2H-[1,2,4]triazol-3-yl}-ethyl)-[1,2,4]triazolo[1,5-a]pyrazine (30 mg, 80.7%) as a light yellow viscous oil. MS: m/z=427.6 (M+H+)

c) 1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-ol

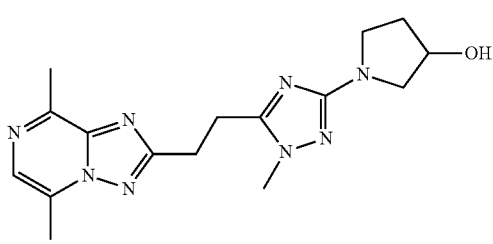 [SMILES: Cc1ncc(C)n2nc(CCc3nc(N4CCC(O)C4)nn3C)nc12]

To a solution of 5,8-dimethyl-2-(2-(1-methyl-3-(3-(tetrahydro-2H-pyran-2-yloxy)pyrrolidin-1-yl)-1H-1,2,4-triazol-5-yl)ethyl)-[1,2,4]triazolo[1,5-a]pyrazine (30 mg, 70.3 μmol, Eq: 1.00) in methanol (3 ml) was added p-toluenesulfonic acid monohydrate (669 μg, 3.52 μmol, Eq: 0.05), the resulting mixture was stirred for 2 hours at 25° C. under nitrogen atmosphere→nearly no reaction, another portion of p-toluenesulfonic acid monohydrate (13.4 mg, 70.3 μmol, Eq: 1.00) was added, stirring at 25° C. was continued overnight. The solvent was evaporated. The residue was diluted with ethyl acetate and washed with sat. sodium hydrogen carbonate. The organic layer was separated, dried over magnesium sulfate, filtrated and evaporated. Purification by HPLC separation afforded 1-{5-[2-(5,8-dimethyl-[1,2,4]triazolo[1,5-a]pyrazin-2-yl)-ethyl]-1-methyl-1H-[1,2,4]triazol-3-yl}-pyrrolidin-3-ol (2.05 mg, 8.51%) as a light yellow viscous oil. MS: m/z=323.5 (M+H+)

Example 105

6-Chloro-5-methyl-2-[2-(1-methyl-5-pyrrolidin-1-yl-1H-[1,2,4]triazol-3-yl)-ethyl]-8-trifluoromethyl-[1,2,4]triazolo[1,5-c]pyridine

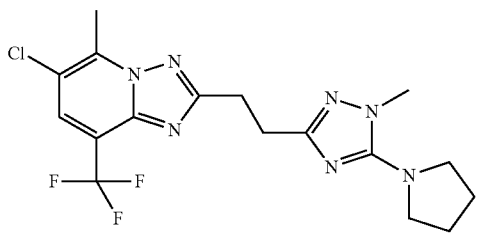 [SMILES: Cc1c(Cl)cc(C(F)(F)F)c2nc(CCc3nc(N4CCCC4)n(C)n3)nn12]

The product (5 mg) was obtained as a white solid in analogy to Example 69 using 1-methyl-5-pyrrolidin-1-yl-1H-[1,2,4]triazole-3-carbaldehyde as starting material. MS: m/z=414.3 (M+H+)

Example 106

6-Chloro-8-difluoromethoxy-5-methyl-2-[2-(1-methyl-5-pyrrolidin-1-yl-1H-[1,2,4]triazol-3-yl)-ethyl]-[1,2,4]triazolo[1,5-c]pyridine

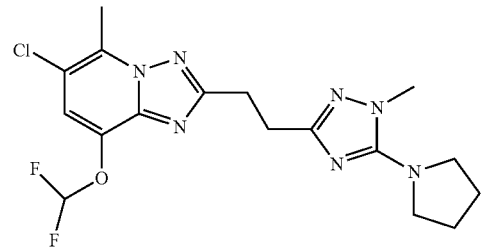 [SMILES: Cc1c(Cl)cc(OC(F)F)c2nc(CCc3nc(N4CCCC4)n(C)n3)nn12]

The product (20 mg) was obtained as a light yellow solid in analogy to Example 95 using 1-methyl-5-pyrrolidin-1-yl-1H-[1,2,4]triazole-3-carbaldehyde as starting material. MS: m/z=412.3 (M+H+)

Example 107

((R)-1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-yl)-carbamic acid tert-butyl ester

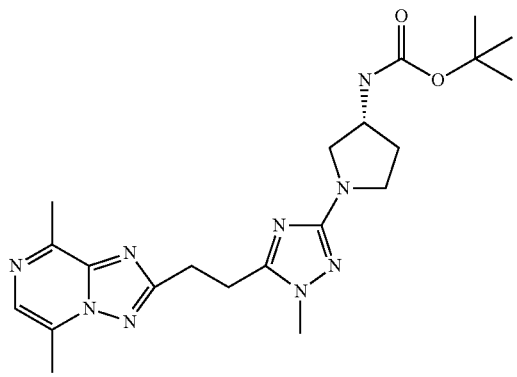 [SMILES: Cc1ncc(C)n2nc(CCc3nc(N4CC[C@@H](NC(=O)OC(C)(C)C)C4)nn3C)nc12]

a) ((R)-1-{5-[(E)-2-(5,8-Dimethyl-[1,2,4]triazolo[1,5-a]pyrazin-2-yl)-vinyl]-1-methyl-1H-[1,2,4]triazol-3-yl}-pyrrolidin-3-yl)-carbamic acid tert-butyl ester

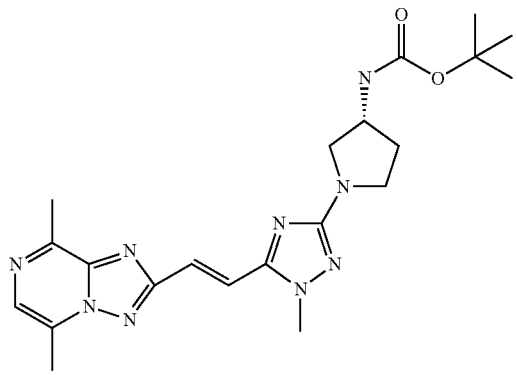 [SMILES: Cc1ncc(C)n2nc(/C=C/c3nc(N4CC[C@@H](NC(=O)OC(C)(C)C)C4)nn3C)nc12]

Was prepared in the same manner as described in Example 87a) using (R)-tert-butyl pyrrolidin-3-ylcarbamate (125 mg, 673 μmol, Eq: 1.50) instead of pyrrolidin-2-one affording ((R)-1-{5-[(E)-2-(5,8-Dimethyl-[1,2,4]triazolo[1,5-a]

pyrazin-2-yl)-vinyl]-1-methyl-1H-[1,2,4]triazol-3-yl}-pyrrolidin-3-yl)-carbamic acid tert-butyl ester (43.7 mg, 20.6%) as a yellow solid. MS: m/z=440.6 (M+H+)

b) ((R)-1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-yl)-carbamic acid tert-butyl ester

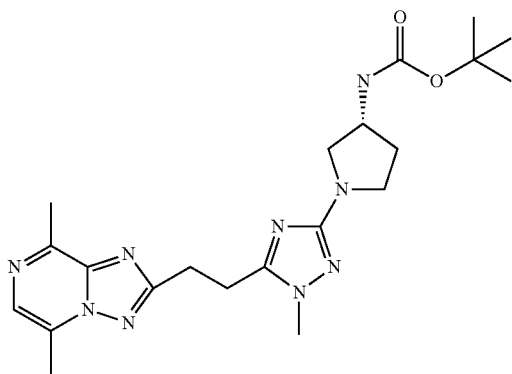 [SMILES: Cc1ncc(C)n2nc(CCc3nc(N4CC[C@@H](NC(=O)OC(C)(C)C)C4)nn3C)nc12]

Was prepared in the same manner as described in Example 87 b) using (R,E)-tert-butyl 1-(5-(2-(5,8-dimethyl-[1,2,4]triazolo[1,5-a]pyrazin-2-yl)vinyl)-1-methyl-1H-1,2,4-triazol-3-yl)pyrrolidin-3-ylcarbamate (38.68 mg, 88.0 μmol, Eq: 1.00) affording ((R)-1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-yl)-carbamic acid tert-butyl ester (31 mg, 79.8%) as an orange solid. MS: m/z=442.5 (M+H+)

Example 108

5,8-Dimethyl-2-(2-methyl-5-pyrrolidin-1-yl-2H-[1,2,4]triazol-3-ylethynyl)-[1,2,4]triazolo[1,5-a]pyrazine

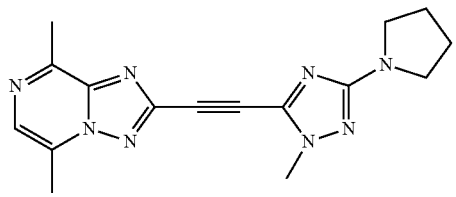 [SMILES: Cc1ncc(C)n2nc(C#Cc3nc(N4CCCC4)nn3C)nc12]

a) 2-Methyl-5-pyrrolidin-1-yl-2H-[1,2,4]triazole-3-carbaldehyde

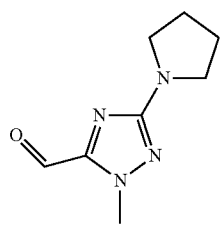

Was prepared in the same manner as described in Example 49 a)-d) using pyrrolidine instead of piperidine, affording 2-methyl-5-pyrrolidin-1-yl-2H-[1,2,4]triazole-3-carbaldehyde (599 mg, 50.9%) as a yellow solid. MS: m/z=181.4 (M+H+), MP: 64.7° C.

b) 5-Ethynyl-1-methyl-3-pyrrolidin-1-yl-1H-[1,2,4]triazole

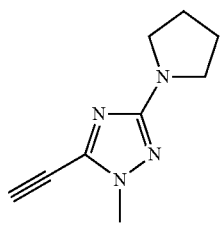

To a stirred mixture of 1-methyl-3-(pyrrolidin-1-yl)-1H-1,2,4-triazole-5-carbaldehyde (1.57 g, 8.71 mmol, Eq: 1.00) and potassium carbonate (2.41 g, 17.4 mmol, Eq: 2) at 25° C. in methanol (60 ml) under an argon atmosphere was added dropwise a solution of dimethyl 1-diazo-2-oxopropylphosphonate (2.01 g, 1.57 ml, 10.5 mmol, Eq: 1.2) in methanol (12 ml). The mixture was stirred at 25° C. for 3 h. The crude material was applied on silica gel and purified by flash chromatography over a 50 g silica gel column using dichloromethane/methanol 0-10% as eluent affording 5-ethynyl-1-methyl-3-pyrrolidin-1-yl-1H-[1,2,4]triazole (785 mg, 51.1%) as an orange solid. MS: m/z=149.2 (M+H+)

c) 5,8-Dimethyl-2-(2-methyl-5-pyrrolidin-1-yl-2H-[1,2,4]triazol-3-ylethynyl)-[1,2,4]triazolo[1,5-a]pyrazine

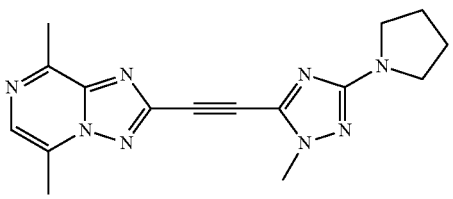

Was prepared in the same manner as described in Example 75e) using 5-ethynyl-1-methyl-3-(pyrrolidin-1-yl)-1H-1,2,4-triazole (62.1 mg, 352 μmol, Eq: 1.00) instead of 1-ethyl-3-ethynyl-5-(pyrrolidin-1-yl)-1H-1,2,4-triazole affording 5,8-dimethyl-2-(2-methyl-5-pyrrolidin-1-yl-2H-[1,2,4]triazol- 3-ylethynyl)-[1,2,4]triazolo[1,5-a]pyrazine (33 mg, 29.1%) as a light brown solid. MS: m/z=323.5 (M+H+)

Example 109

5,8-Dimethyl-2-[2-(2-phenyl-5-pyrrolidin-1-yl-2H-[1,2,4]triazol-3-yl)-ethyl]-[1,2,4]triazolo[1,5-a]pyrazine

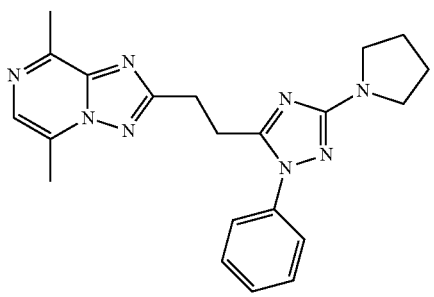 [SMILES: Cc1ncc(C)n2nc(CCc3nc(N4CCCC4)nn3-c3ccccc3)nc12]

a) 3-Methyl-but-2-enoic acid (pyrrolidine-1-carbothioyl)-amide

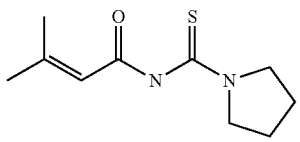

Was prepared in the same manner as described in Example 49 a) using pyrrolidine instead of piperidine affording 3-methyl-but-2-enoic acid (pyrrolidine-1-carbothioyl)-amide (11.55 g, 110%) as a yellow oil. MS: m/z=213.1 (M+H+)

b) 3-Methyl-but-2-enoic acid 1-methylsulfanyl-1-pyrrolidin-1-yl-meth-(Z)-ylideneamide

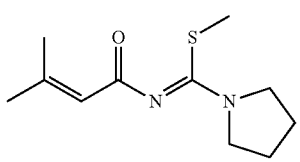

Was prepared in the same manner as described in Example 49 b) using 3-methyl-N-(pyrrolidine-1-carbonothioyl)but-2-enamide (10.5 g, 49.5 mmol, Eq: 1.00) affording 3-methyl-but-2-enoic acid 1-methylsulfanyl-1-pyrrolidin-1-yl-meth-(Z)-ylideneamide (10.94 g, 97.8%) as a yellow oil. MS: m/z=227.4 (M+H+)

c) 5-(2-Methyl-propenyl)-1-phenyl-3-pyrrolidin-1-yl-1H-[1,2,4]triazole

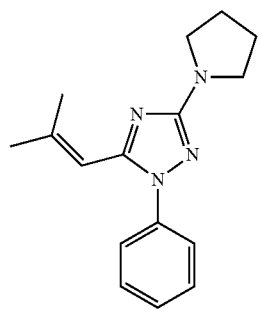 [SMILES: CC(C)=Cc1nc(N2CCCC2)nn1-c1ccccc1]

A mixture of 3-methyl-but-2-enoic acid 1-methylsulfanyl-1-pyrrolidin-1-yl-meth-(Z)-ylideneamide (130 mg, 0.575 mmol) and phenyl hydrazine (0.6 ml, 5.75 mmol) was stirred for 3 hours at 100° C. The mixture was cooled, diluted with ethyl acetate and washed twice with water. The organic layer was separated, dried over sodium sulfate, filtered and concentrated. The crude material was purified by silica gel column chromatography using 50% ethyl acetate in hexane affording 5-(2-methyl-propenyl)-1-phenyl-3-pyrrolidin-1-yl-1H-[1,2,4]triazole (60 mg, 38.87%) as colorless liquid. MS: m/z=268.8 (M+H+)

d) 2-Phenyl-5-pyrrolidin-1-yl-2H-[1,2,4]triazole-3-carbaldehyde

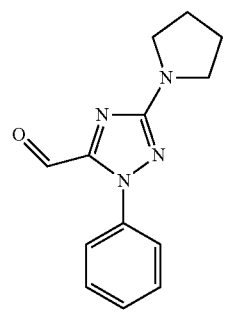 [SMILES: O=Cc1nc(N2CCCC2)nn1-c1ccccc1]

Was prepared in the same manner as described in Example 49 d) using 5-(2-methyl-propenyl)-1-phenyl-3-pyrrolidin-1-yl-1H-[1,2,4]triazole (200 mg, 0.746 mmol) affording 2-phenyl-5-pyrrolidin-1-yl-2H-[1,2,4]triazole-3-carbaldehyde (220 mg, crude) as yellow liquid which was used without further purification.

e) 5,8-Dimethyl-2-[(E)-2-(2-phenyl-5-pyrrolidin-1-yl-2H-[1,2,4]triazol-3-yl)-vinyl]-[1,2,4]triazolo[1,5-a]pyrazine

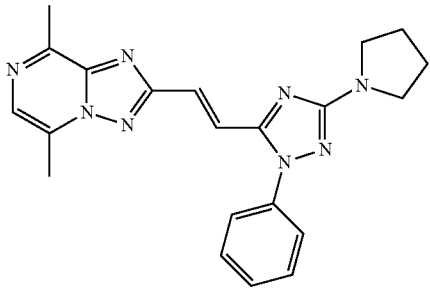 [SMILES: Cc1ncc(C)n2nc(/C=C/c3nc(N4CCCC4)nn3-c3ccccc3)nc12]

Was prepared in the same manner as described in Example 49 e) using 2-phenyl-5-pyrrolidin-1-yl-2H-[1,2,4]triazole-3-carbaldehyde (220 mg, 0.909 mmol) as aldehyde, affording 5,8-dimethyl-2-[(E)-2-(2-phenyl-5-pyrrolidin-1-yl-2H-[1,2,4]triazol-3-yl)-vinyl]-[1,2,4]triazolo[1,5-a]pyrazine (150 mg, 42% with TPPO) as a white solid. MS: m/z=387 (M+H+)

f) 5,8-Dimethyl-2-[2-(2-phenyl-5-pyrrolidin-1-yl-2H-[1,2,4]triazol-3-yl)-ethyl]-[1,2,4]triazolo[1,5-a]pyrazine

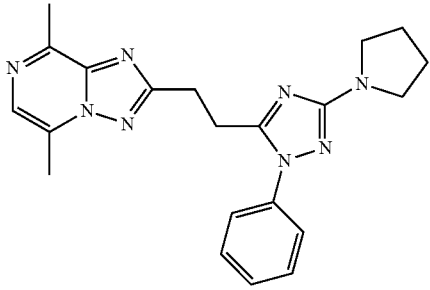 [SMILES: Cc1ncc(C)n2nc(CCc3nc(N4CCCC4)nn3-c3ccccc3)nc12]

Was prepared in the same manner as described in Example 87 b) using (5,8-dimethyl-2-[(E)-2-(2-phenyl-5-pyrrolidin-1-yl-2H-[1,2,4]triazol-3-yl)-vinyl]-[1,2,4]triazolo[1,5-a]pyrazine (150 mg, 0.389 mmol) affording 5,8-dimethyl-2-[2-(2-phenyl-5-pyrrolidin-1-yl-2H-[1,2,4]triazol-3-yl)-ethyl]-[1,2,4]triazolo[1,5-a]pyrazine (85 mg, 56.31%) as a white solid. MS: m/z=388.8 (M+H+)

Example 110

2-{2-[2-(2,2-Difluoro-ethyl)-5-pyrrolidin-1-yl-2H-[1,2,4]triazol-3-yl]-ethyl}-5,8-dimethyl-[1,2,4]triazolo[1,5-a]pyrazine

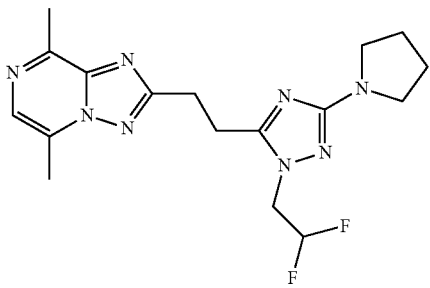 [SMILES: Cc1ncc(C)n2nc(CCc3nc(N4CCCC4)nn3CC(F)F)nc12]

a) 1-(2,2-Difluoro-ethyl)-5-(2-methyl-propenyl)-3-pyrrolidin-1-yl-1H-[1,2,4]triazole

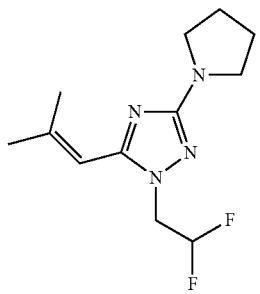 [SMILES: CC(C)=Cc1nc(N2CCCC2)nn1CC(F)F]

Was prepared in the same manner as described in Example 109c) using (2,2-difluoroethyl) hydrazine, hydrochloride (673 mg, 3.98 mmol) and diisopropylethylamine (1.84 ml, 10.619 mmol) as base affording 1-(2,2-difluoro-ethyl)-5-(2-methyl-propenyl)-3-pyrrolidin-1-yl-1H-[1,2,4]triazole (150 mg, 44%) as a colorless liquid. MS: m/z=256.8 (M+H+)

b) 2-(2,2-Difluoro-ethyl)-5-pyrrolidin-1-yl-2H-[1,2,4]triazole-3-carbaldehyde

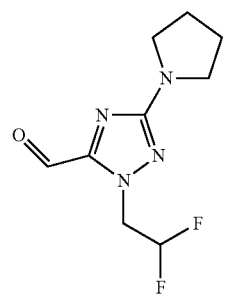 [SMILES: O=Cc1nc(N2CCCC2)nn1CC(F)F]

Was prepared in the same manner as described in Example 49 d) using 1-(2,2-difluoro-ethyl)-5-(2-methyl-propenyl)-3-pyrrolidin-1-yl-1H-[1,2,4]triazole (300 mg, 1.17 mmol) affording 2-(2,2-difluoro-ethyl)-5-pyrrolidin-1-yl-2H-[1,2,4]triazole-3-carbaldehyde (350 mg, crude) as a yellow solid which was used without further purification.

c) 2-{(E)-2-[2-(2,2-Difluoro-ethyl)-5-pyrrolidin-1-yl-2H-[1,2,4]triazol-3-yl]-vinyl}-5,8-dimethyl-[1,2,4]triazolo[1,5-a]pyrazine

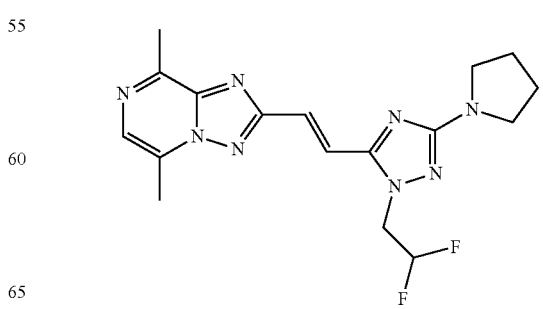

Was prepared in the same manner as described in Example 49 e) using 2-(2,2-difluoro-ethyl)-5-pyrrolidin-1-yl-2H-[1,2,4]triazole-3-carbaldehyde (350 mg, 1.52 mmol) as aldehyde affording 2-{(E)-2-[2-(2,2-difluoro-ethyl)-5-pyrrolidin-1-yl-2H-[1,2,4]triazol-3-yl]-vinyl}-5,8-dimethyl-[1,2,4]triazolo[1,5-a]pyrazine (130 mg, 23%) as a yellow solid. MS: m/z=375 (M+H+)

d) 2-{2-[2-(2,2-Difluoro-ethyl)-5-pyrrolidin-1-yl-2H-[1,2,4]triazol-3-yl]-ethyl}-5,8-dimethyl-[1,2,4]triazolo[1,5-a]pyrazine

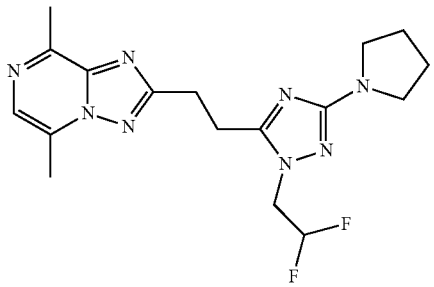 [SMILES: Cc1ncc(C)n2nc(CCc3nc(N4CCCC4)nn3CC(F)F)nc12]

Was prepared in the same manner as described in Example 87 b) using 2-{(E)-2-[2-(2,2-difluoro-ethyl)-5-pyrrolidin-1-yl-2H-[1,2,4]triazol-3-yl]-vinyl}-5,8-dimethyl-[1,2,4]triazolo[1,5-a]pyrazine (130 mg, 0.348 mmol) affording 2-{2-[2-(2,2-difluoro-ethyl)-5-pyrrolidin-1-yl-2H-[1,2,4]triazol-3-yl]-ethyl}-5,8-dimethyl-[1,2,4]triazolo[1,5-a]pyrazine (35 mg, 27%) as a white solid. MS: m/z=349 (M+H+)

Example 111

5,8-Dimethyl-2-{2-[2-methyl-5-(2-methyl-pyrrolidin-1-yl)-2H-[1,2,4]triazol-3-yl]-ethyl}-[1,2,4]triazolo[1,5-c]pyrimidine

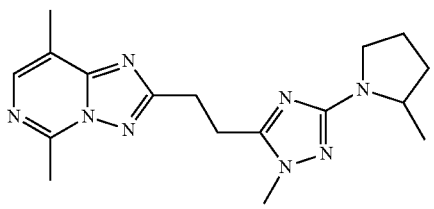 [SMILES: Cc1cnc(C)n2nc(CCc3nc(N4CCCC4C)nn3C)nc12]

a) 5,8-Dimethyl-2-{(E)-2-[2-methyl-5-(2-methyl-pyrrolidin-1-yl)-2H-[1,2,4]triazol-3-yl]-vinyl}-[1,2,4]triazolo[1,5-c]pyrimidine

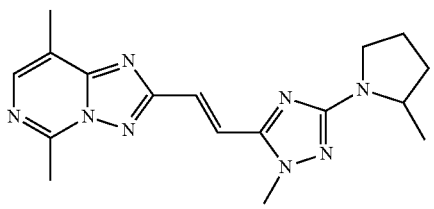 [SMILES: Cc1cnc(C)n2nc(/C=C/c3nc(N4CCCC4C)nn3C)nc12]

Was prepared in the same manner as described in Example 49e) using ((5,8-dimethyl-[1,2,4]triazolo[1,5-c]pyrimidin-2-yl)methyl)triphenylphosphonium chloride (350 mg, 763 µmol, Eq: 1.00) and 1-methyl-3-(2-methylpyrrolidin-1-yl)-1H-1,2,4-triazole-5-carbaldehyde (148 mg, 763 µmol, Eq: 1.00) affording 5,8-dimethyl-2-{(E)-2-[2-methyl-5-(2-methyl-pyrrolidin-1-yl)-2H-[1,2,4]triazol-3-yl]-vinyl}-[1,2,4]triazolo[1,5-c]pyrimidine (190 mg, 73.6%) as a bright yellow solid. MS: m/z=339.5 (M+H+)

b) 5,8-Dimethyl-2-{2-[2-methyl-5-(2-methyl-pyrrolidin-1-yl)-2H-[1,2,4]triazol-3-yl]-ethyl}-[1,2,4]triazolo[1,5-c]pyrimidine

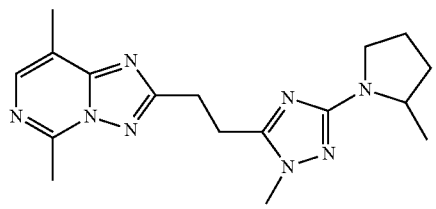 [SMILES: Cc1cnc(C)n2nc(CCc3nc(N4CCCC4C)nn3C)nc12]

Was prepared in the same manner as described in Example 87 b) using (E)-5,8-dimethyl-2-(2-(1-methyl-3-(2-methylpyrrolidin-1-yl)-1H-1,2,4-triazol-5-yl)vinyl)-[1,2,4]triazolo[1,5-c]pyrimidine (190 mg, 561 µmol, Eq: 1.00) affording 5,8-dimethyl-2-{2-[2-methyl-5-(2-methyl-pyrrolidin-1-yl)-2H-[1,2,4]triazol-3-yl]-ethyl}-[1,2,4]triazolo[1,5-c]pyrimidine (197 mg, 103%) as a light yellow oil. MS: m/z=341.5 (M+H+)

Example 112

5,8-Dimethyl-2-{2-[2-methyl-5-((S)-2-methyl-pyrrolidin-1-yl)-2H-[1,2,4]triazol-3-yl]-ethyl}-[1,2,4]triazolo[1,5-c]pyrimidine

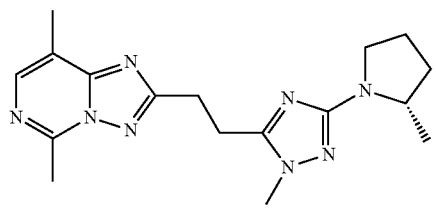 [SMILES: Cc1cnc(C)n2nc(CCc3nc(N4CCC[C@@H]4C)nn3C)nc12]

Chiral HPLC-separation of racemic 5,8-dimethyl-2-(2-(1-methyl-3-(2-methylpyrrolidin-1-yl)-1H-1,2,4-triazol-5-yl)ethyl)-[1,2,4]triazolo[1,5-c]pyrimidine (190 mg, 558 µmol, Eq: 1.00) (Example 181b): First peak A+, afforded 5,8-dimethyl-2-{2-[2-methyl-5-((S)-2-methyl-pyrrolidin-1-yl)-2H-

[1,2,4]triazol-3-yl]-ethyl}-[1,2,4]triazolo[1,5-c]pyrimidine (76.8 mg, 40.4%) as a colorless viscous oil. MS: m/z=341.5 (M+H+)

Example 113

5,8-Dimethyl-2-{2-[2-methyl-5-((R)-2-methyl-pyrrolidin-1-yl)-2H-[1,2,4]triazol-3-yl]-ethyl}-[1,2,4]triazolo[1,5-c]pyrimidine

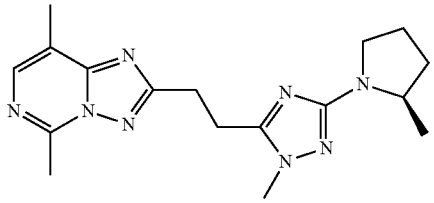 [SMILES: Cc1cnc(C)n2nc(CCc3nc(N4CCC[C@H]4C)nn3C)nc12]

Chiral HPLC-separation of racemic 5,8-dimethyl-2-(2-(1-methyl-3-(2-methylpyrrolidin-1-yl)-1H-1,2,4-triazol-5-yl)ethyl)-[1,2,4]triazolo[1,5-c]pyrimidine (190 mg, 558 µmol, Eq: 1.00) (Example 181b): Second peak B-, afforded 5,8-dimethyl-2-{2-[2-methyl-5-((R)-2-methyl-pyrrolidin-1-yl)-2H-[1,2,4]triazol-3-yl]-ethyl}-[1,2,4]triazolo[1,5-c]pyrimidine (32.9 mg, 38.4%) as a colorless viscous oil. MS: m/z=341.5 (M+H+)

Example 114

5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-a]pyrazine

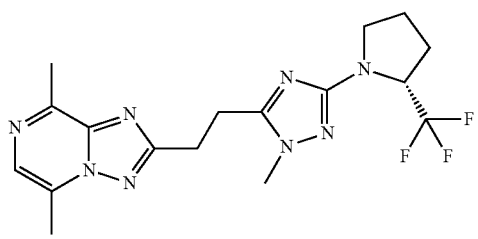 [SMILES: Cc1ncc(C)n2nc(CCc3nc(N4CCC[C@@H]4C(F)(F)F)nn3C)nc12]

a) {5-[(E)-2-(5,8-Dimethyl-[1,2,4]triazolo[1,5-a]pyrazin-2-yl)-vinyl]-1-methyl-1H-[1,2,4]triazol-3-yl}-carbamic acid tert-butyl ester

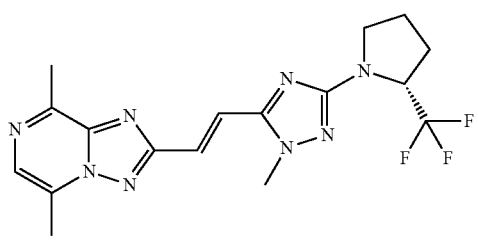 [SMILES: Cc1ncc(C)n2nc(/C=C/c3nc(N4CCC[C@@H]4C(F)(F)F)nn3C)nc12]

Was prepared in the same manner as described in Example 87a) using (R)-2-(trifluoromethyl)-pyrrolidine (83.3 mg, 598 µmol, Eq: 2) instead of pyrrolidin-2-one affording {5-[(E)-2-(5,8-dimethyl-[1,2,4]triazolo[1,5-a]pyrazin-2-yl)-vinyl]-1-methyl-1H-[1,2,4]triazol-3-yl}-carbamic acid tert-butyl ester (20 mg, 17.0%) as an off-white solid. MS: m/z=393.5 (M+H+)

b) 5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-a]pyrazine

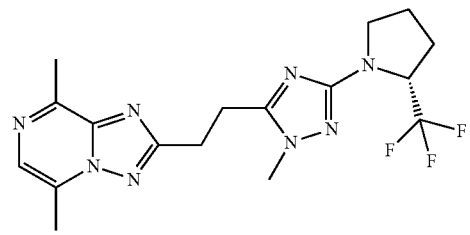 [SMILES: Cc1ncc(C)n2nc(CCc3nc(N4CCC[C@@H]4C(F)(F)F)nn3C)nc12]

Was prepared in the same manner as described in Example 87 b) using (R,E)-5,8-dimethyl-2-(2-(1-methyl-3-(2-(trifluoromethyl)pyrrolidin-1-yl)-1H-1,2,4-triazol-5-yl)vinyl)-[1,2,4]triazolo[1,5-a]pyrazine (20 mg, 51.0 µmol, Eq: 1.00) affording 5,8-dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-a]pyrazine (18 mg, 89.5%) as a light yellow viscous oil. MS: m/z=395.5 (M+H+)

Example 115

5,8-Dimethyl-2-{2-[2-methyl-5-((S)-3-methyl-pyrrolidin-1-yl)-2H-[1,2,4]triazol-3-yl]-ethyl}-[1,2,4]triazolo[1,5-a]pyrazine

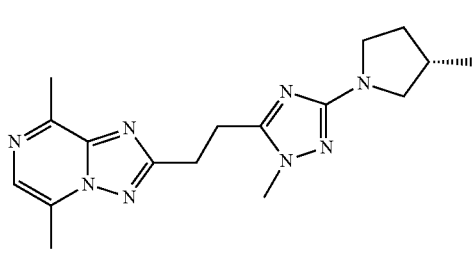 [SMILES: Cc1ncc(C)n2nc(CCc3nc(N4CC[C@H](C)C4)nn3C)nc12]

a) 5,8-Dimethyl-2-{(E)-2-[2-methyl-5-(3-methyl-pyrrolidin-1-yl)-2H-[1,2,4]triazol-3-yl]-vinyl}-[1,2,4]triazolo[1,5-a]pyrazine

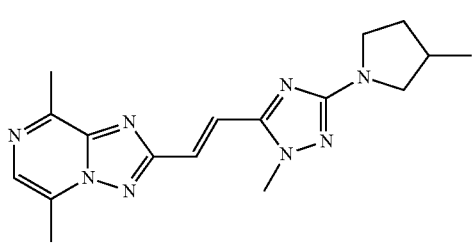 [SMILES: Cc1ncc(C)n2nc(/C=C/c3nc(N4CCC(C)C4)nn3C)nc12]

Was prepared in the same manner as described in Example 87a) using 3-methylpyrrolidine hydrochloride (83 mg, 683 µmol, Eq: 2.28) instead of pyrrolidin-2-one 5,8-Dimethyl-2-{(E)-2-[2-methyl-5-(3-methyl-pyrrolidin-1-yl)-2H-[1,2,4]triazol-3-yl]-vinyl}-[1,2,4]triazolo[1,5-a]pyrazine (65 mg, 64.2%) as an orange solid. MS: m/z=339.2 (M+H⁺)

b) 5,8-Dimethyl-2-{2-[2-methyl-5-((S)-3-methyl-pyrrolidin-1-yl)-2H-[1,2,4]triazol-3-yl]-ethyl}-[1,2,4]triazolo[1,5-a]pyrazine

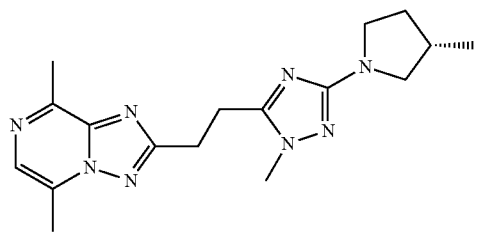 [SMILES: Cc1ncc(C)n2nc(CCc3nc(N4CC[C@H](C)C4)nn3C)nc12]

Was prepared in the same manner as described in Example 87b) from (E)-5,8-dimethyl-2-(2-(1-methyl-3-(3-methylpyrrolidin-1-yl)-1H-1,2,4-triazol-5-yl)vinyl)-[1,2,4]triazolo[1,5-a]pyrazine (60 mg, 177 µmol, Eq: 1.00) after chiral preparative HPLC separation affording 5,8-Dimethyl-2-{2-[2-methyl-5-((S)-3-methyl-pyrrolidin-1-yl)-2H-[1,2,4]triazol-3-yl]-ethyl}-[1,2,4]triazolo[1,5-a]pyrazine (5 mg, 8.28%) as off-white solid. MS: m/z=341.5 (M+H⁺)

Example 116

5,8-Dimethyl-2-{2-[2-methyl-5-((R)-3-methyl-pyrrolidin-1-yl)-2H-[1,2,4]triazol-3-yl]-ethyl}-[1,2,4]triazolo[1,5-a]pyrazine

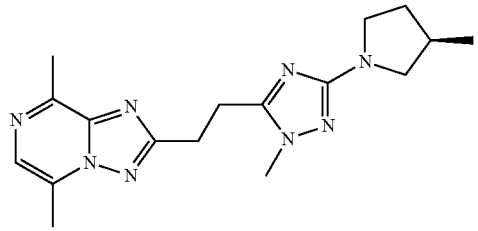 [SMILES: Cc1ncc(C)n2nc(CCc3nc(N4CC[C@@H](C)C4)nn3C)nc12]

Was prepared in the same manner as described in Example 115 b) after chiral preparative HPLC separation affording 5,8-Dimethyl-2-{2-[2-methyl-5-((R)-3-methyl-pyrrolidin-1-yl)-2H-[1,2,4]triazol-3-yl]-ethyl}-[1,2,4]triazolo[1,5-a]pyrazine (7.5 mg, 12.4%) as off-white solid. MS: m/z=341.5 (M+H⁺)

Example 117

2-[2-(2-Cyclopropylmethyl-5-pyrrolidin-1-yl-2H-[1,2,4]triazol-3-yl)-ethyl]-5,8-dimethyl-[1,2,4]triazolo[1,5-a]pyrazine and 2-[2-(1-Cyclopropylmethyl-5-pyrrolidin-1-yl-1H-[1,2,4]triazol-3-yl)-ethyl]-5,8-dimethyl-[1,2,4]triazolo[1,5-a]pyrazine (b)

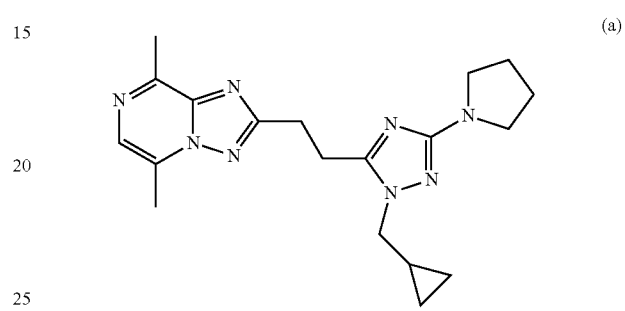

(a)

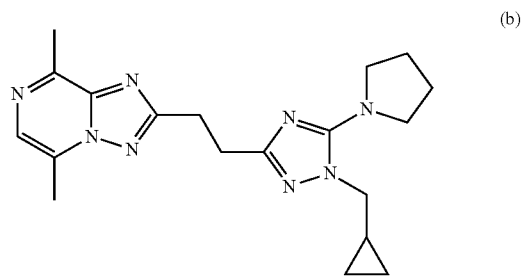

(b)

a) 5-(2-Methyl-propenyl)-3-pyrrolidin-1-yl-1H-[1,2,4]triazole

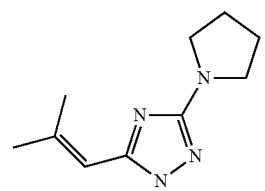

A mixture of 3-methyl-but-2-enoic acid 1-methylsulfanyl-1-pyrrolidin-1-yl-meth-(Z)-ylidene amide (1.2 g, 5.3 mmol) and hydrazine solution was stirred for 2 hours at 100° C. in a sealed tube. The mixture was cooled and concentrated. The crude material was purified by combiflash column chromatography using 50% ethyl acetate in hexane to give 5-(2-methyl-propenyl)-3-pyrrolidin-1-yl-1H-[1,2,4]triazole (300 mg, 29.39%) as a white solid. MS: m/z=193 (M+H+)

b) 1-Cyclopropylmethyl-5-(2-methyl-propenyl)-3-pyrrolidin-1-yl-1H-[1,2,4]triazole (a) with 1-Cyclopropylmethyl-3-(2-methyl-propenyl)-5-pyrrolidin-1-yl-1H-[1,2,4]triazole (b)

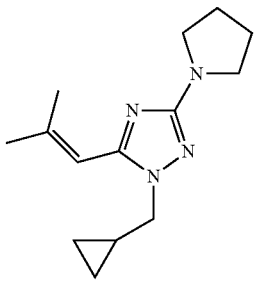
(a)

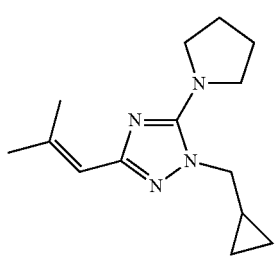
(b)

A solution of 5-(2-methyl-propenyl)-3-pyrrolidin-1-yl-1H-[1,2,4]triazole (300 mg, 1.56 mmol) in dimethyl formamide (10 ml) was cooled to 0° C. Sodium hydride (60% in oil, 0.112 g, 4.68 mmol) was added slowly at 0° C. After that bromomethyl-cyclopropane (0.3 ml, 3.12 mmol) was added drop wise at 0° C. The mixture was allowed to warm to 25° C. and stirred for 4 hours at 25° C. The reaction mass was diluted with water (50 ml) and extracted 3 times with ethyl acetate. The organic layer was washed with water 3 times, brine and dried over sodium sulfate, filtered and evaporated. The crude material was purified by silica gel column chromatography using 20% ethyl acetate in hexane to give a mixture of 1-cyclopropylmethyl-5-(2-methyl-propenyl)-3-pyrrolidin-1-yl-1H-[1,2,4]triazole (a) and 1-cyclopropylmethyl-3-(2-methyl-propenyl)-5-pyrrolidin-1-yl-1H-[1,2,4]triazole (b) (200 mg, 52%) as a white solid. MS: m/z=247.6 (M+H+)

c) 2-Cyclopropylmethyl-5-pyrrolidin-1-yl-2H-[1,2,4]triazole-3-carbaldehyde (a) with 1-Cyclopropylmethyl-5-pyrrolidin-1-yl-1H-[1,2,4]triazole-3-carbaldehyde (b)

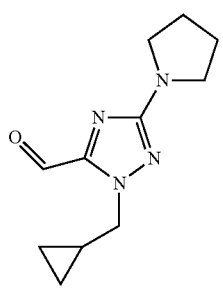
(a)

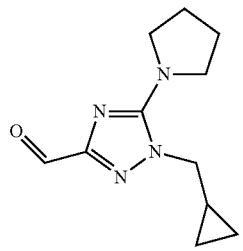
(b)

Was prepared in the same manner as described in Example 49 d) using a mixture of 1-cyclopropylmethyl-5-(2-methyl-propenyl)-3-pyrrolidin-1-yl-1H-[1,2,4]triazole and 1-cyclopropyl methyl-3-(2-methyl-propenyl)-5-pyrrolidin-1-yl-1H-[1,2,4]triazole (200 mg, 0.813 mmol) affording a mixture of 2-cyclopropylmethyl-5-pyrrolidin-1-yl-2H-[1,2,4]triazole-3-carbaldehyde (a) with 1-cyclopropylmethyl-5-pyrrolidin-1-yl-1H-[1,2,4]triazole-3-carbaldehyde (b) (200 mg, crude) which were used without further purification.

d) 2-[(E)-2-(2-Cyclopropylmethyl-5-pyrrolidin-1-yl-2H-[1,2,4]triazol-3-yl)-vinyl]-5,8-dimethyl-[1,2,4]triazolo[1,5-a]pyrazine (a) with 2-[(E)-2-(1-Cyclopropylmethyl-5-pyrrolidin-1-yl-1H-[1,2,4]triazol-3-yl)-vinyl]-5,8-dimethyl-[1,2,4]triazolo[1,5-a]pyrazine (b)

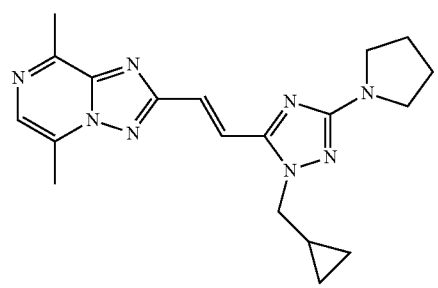
a)

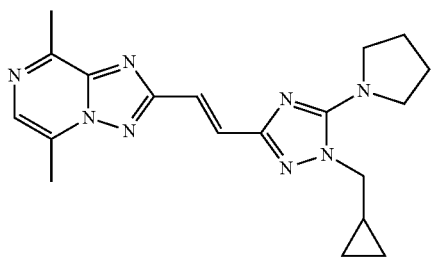
(b)

Was prepared in the same manner as described in Example 49 e) using a mixture of 2-cyclopropylmethyl-5-pyrrolidin-1-yl-2H-[1,2,4]triazole-3-carbaldehyde with 1-cyclopropylmethyl-5-pyrrolidin-1-yl-1H-[1,2,4]triazole-3-carbaldehyde (220 mg, 1.0 mmol) as aldehydes affording a mixture of 2-[(E)-2-(2-cyclopropylmethyl-5-pyrrolidin-1-yl-2H-[1,2,4]triazol-3-yl)-vinyl]-5,8-dimethyl-[1,2,4]triazolo[1,5-a]pyrazine (a) with 2-[(E)-2-(1-cyclopropylmethyl-5-pyrrolidin-1-yl-1H-[1,2,4]triazol-3-yl)-vinyl]-5,8-dimethyl-[1,2,4]triazolo[1,5-a]pyrazine (b) (110 mg, 30%) as a yellow solid. MS: m/z=365 (M+H+)

e) 2-[2-(2-Cyclopropylmethyl-5-pyrrolidin-1-yl-2H-[1,2,4]triazol-3-yl)-ethyl]-5,8-dimethyl-[1,2,4]triazolo[1,5-a]pyrazine (a) with 2-[2-(1-Cyclopropylmethyl-5-pyrrolidin-1-yl-1H-[1,2,4]triazol-3-yl)-ethyl]-5,8-dimethyl-[1,2,4]triazolo[1,5-a]pyrazine (b)

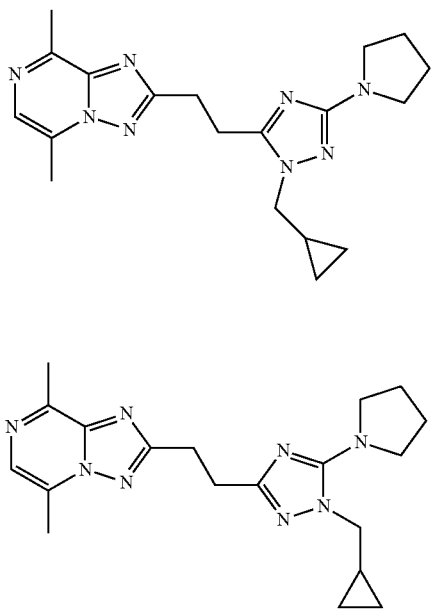

a)

(b)

Was prepared in the same manner as described in Example 87 b) using a mixture of 2-[(E)-2-(2-cyclopropylmethyl-5-pyrrolidin-1-yl-2H-[1,2,4]triazol-3-yl)-vinyl]-5,8-dimethyl-[1,2,4]triazolo[1,5-a]pyrazine and 2-[(E)-2-(1-cyclopropylmethyl-5-pyrrolidin-1-yl-1H-[1,2,4]triazol-3-yl)-vinyl]-5,8-dimethyl-[1,2,4]triazolo[1,5-a]pyrazine (110 mg, 0.302 mmol) affording a mixture of 2-[2-(2-cyclopropylmethyl-5-pyrrolidin-1-yl-2H-[1,2,4]triazol-3-yl)-ethyl]-5,8-dimethyl-[1,2,4]triazolo[1,5-a]pyrazine (a) and 2-[2-(1-Cyclopropylmethyl-5-pyrrolidin-1-yl-1H-[1,2,4]triazol-3-yl)-ethyl]-5,8-dimethyl-[1,2,4]triazolo[1,5-a]pyrazine (b). Separation of the two isomers via preparative HPLC afforded 2-[2-(2-cyclopropylmethyl-5-pyrrolidin-1-yl-2H-[1,2,4]triazol-3-yl)-ethyl]-5,8-dimethyl-[1,2,4]triazolo[1,5-a]pyrazine (a) (20 mg, 18%) as a white solid. MS: m/z=367 (M+H+) and 2-[2-(1-cyclopropylmethyl-5-pyrrolidin-1-yl-1H-[1,2,4]triazol-3-yl)-ethyl]-5,8-dimethyl-[1,2,4]triazolo[1,5-a]pyrazine (b) (18 mg, 16%) as a white solid. MS: m/z=367 (M+H+)

Example 118

5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-c]pyrimidine

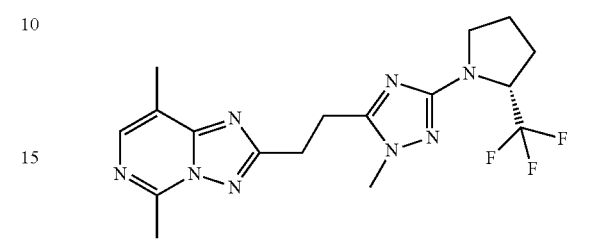

a) 5,8-Dimethyl-2-{(E)-2-[2-methyl-5-((R)-2-trifluoromethyl-pyrrolidin-1-yl)-2H-[1,2,4]triazol-3-yl]-vinyl}-[1,2,4]triazolo[1,5-c]pyrimidine

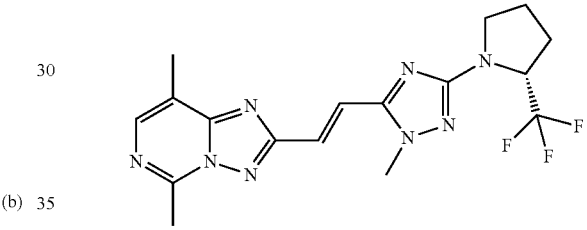

Was prepared in the same manner as described in Example 87a) using (E)-2-(2-(3-bromo-1-methyl-1H-1,2,4-triazol-5-yl)vinyl)-5,8-dimethyl-[1,2,4]triazolo[1,5-c]pyrimidine (100 mg, 299 µmol, Eq: 1.00) instead of 2-[(E)-2-(5-Bromo-2-methyl-2H-[1,2,4]triazol-3-yl)-vinyl]-5,8-dimethyl-[1,2,4]triazolo[1,5-a]pyrazine and (R)-2-(trifluoromethyl)-pyrrolidine (83.3 mg, 598 µmol, Eq: 2) instead of pyrrolidin-2-one affording 5,8-dimethyl-2-{(E)-2-[2-methyl-5-((R)-2-trifluoromethyl-pyrrolidin-1-yl)-2H-[1,2,4]triazol-3-yl]-vinyl}-[1,2,4]triazolo[1,5-c]pyrimidine (17 mg, 14.5%) as a light yellow solid. MS: m/z=393.4 (M+H+)

b) 5,8-Dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-c]pyrimidine

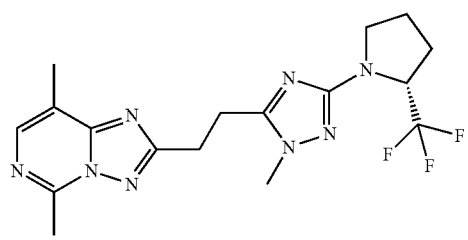 [SMILES: Cc1cnc(C)n2nc(CCc3nc(N4CCC[C@@H]4C(F)(F)F)nn3C)nc12]

Was prepared in the same manner as described in Example 87 b) using (R,E)-5,8-dimethyl-2-(2-(1-methyl-3-(2-(trifluoromethyl)pyrrolidin-1-yl)-1H-1,2,4-triazol-5-yl)vinyl)-[1,2,4]triazolo-[1,5-c]pyrimidine (14 mg, 35.7 µmol, Eq: 1.00) affording 5,8-dimethyl-2-{2-[2-methyl-5-((R)-2-trifluoromethyl-pyrrolidin-1-yl)-2H-[1,2,4]triazol-3-yl]-ethyl}-[1,2,4]triazolo[1,5-c]pyrimidine (14 mg, 98.6%) as a colorless viscous oil. MS: m/z=395.5 (M+H+)

Example 119

6-Chloro-8-(2-methoxyethoxy)-5-methyl-2-[2-(2-methyl-5-pyrrolidin-1-yl-1,2,4-triazol-3-yl)ethyl]-[1,2,4]triazolo[1,5-a]pyridine

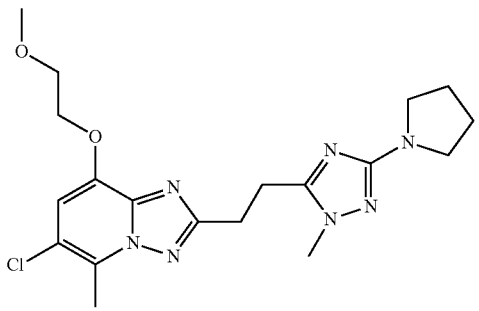 [SMILES: COCCOc1cc(Cl)c(C)n2nc(CCc3nc(N4CCCC4)nn3C)nc12]

1-Bromo-2-methoxyethane (10.7 mg, 7.26 µl, 77.3 µmol, Eq: 1.2) was added to 6-chloro-5-methyl-2-(2-(1-methyl-3-(pyrrolidin-1-yl)-1H-1,2,4-triazol-5-yl)ethyl)-[1,2,4]triazolo[1,5-a]pyridin-8-ol (23.3 mg, 64.4 µmol, Eq: 1.00) and K₂CO₃ (26.7 mg, 193 µmol, Eq: 3) in dimethylformamide (1 ml). The mixture was stirred at 50° C. for 2 h. The crude material was purified by preparative HPLC to give the desired product (7 mg, 25%) as a white powder. MS: m/z=420.6 (M+H+)

Example 120

6-Chloro-5-methyl-2-(2-(1-methyl-3-(pyrrolidin-1-yl)-1H-1,2,4-triazol-5-yl)ethyl)-8-(tetrahydro-2H-pyran-4-yloxy)-[1,2,4]triazolo[1,5-a]pyridine

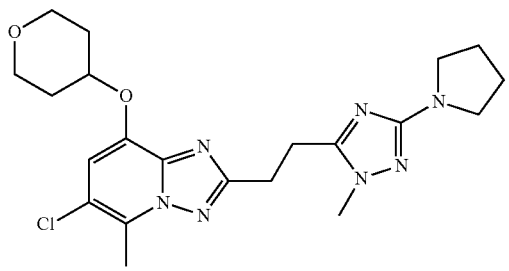 [SMILES: Cc1c(Cl)cc(OC2CCOCC2)c2nc(CCc3nc(N4CCCC4)nn3C)nn12]

The product (3 mg, 10%) was obtained as a white powder in analogy to Example 119 from 4-bromotetrahydro-2H-pyran. MS: m/z=446.6 (M+H+)

Example 121

4-[2-[[6-Chloro-5-methyl-2-[2-(2-methyl-5-pyrrolidin-1-yl-1,2,4-triazol-3-yl)ethyl]-[1,2,4]triazolo[1,5-a]pyridin-8-yl]oxy]ethyl]morpholine

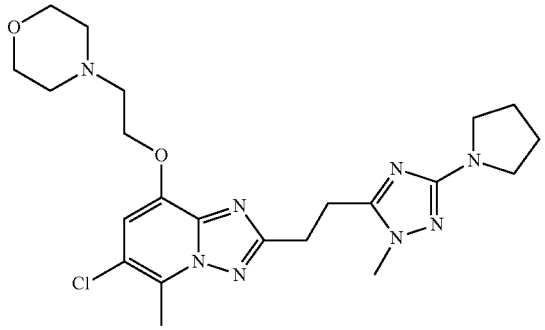 [SMILES: Cc1c(Cl)cc(OCCN2CCOCC2)c2nc(CCc3nc(N4CCCC4)nn3C)nn12]

The product (5 mg, 16%) was obtained as a white powder in analogy to Example 119 from 4-(2-bromoethyl)morpholine hydrobromide. MS: m/z=475.7 (M+H+)

Example 122

6-Chloro-5-methyl-2-(2-(3-(pyrrolidin-1-yl)-1-(tetrahydro-2H-pyran-4-yl)-1H-1,2,4-triazol-5-yl)ethyl)-8-(trifluoromethyl)-[1,2,4]triazolo[1,5-a]pyridine

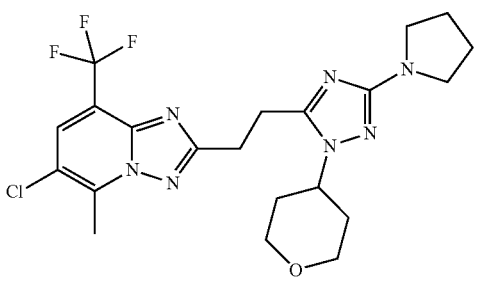 [SMILES: Cc1c(Cl)cc(C(F)(F)F)c2nc(CCc3nc(N4CCCC4)nn3C3CCOCC3)nn12]

a) 5-Chloro-6-methyl-3-(trifluoromethyl)pyridin-1-ium-1,2-diamine; 2,4,6-trimethylbenzenesulfonate

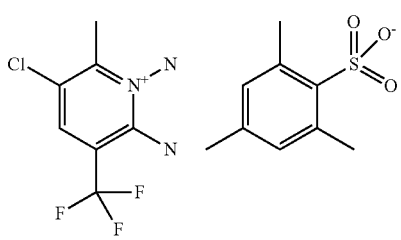

The salt (2 g, 68%) was prepared as a white solid in analogy to Example 26b from 6-methyl-3-(trifluoromethyl)pyridin-2-amine. MS: m/z=226.2 (M+) and 199.2 (M−)

b) 6-Chloro-5-methyl-2-(2-(3-(pyrrolidin-1-yl)-1-(tetrahydro-2H-pyran-4-yl)-1H-1,2,4-triazol-5-yl)ethyl)-8-(trifluoromethyl)-[1,2,4]triazolo[1,5-a]pyridine

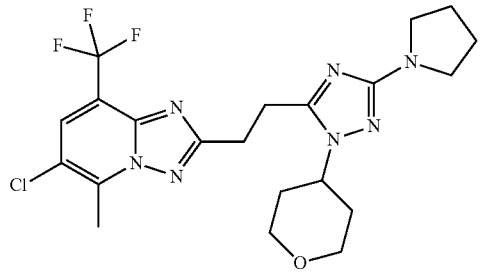 [SMILES: Cc1c(Cl)cc(C(F)(F)F)c2nc(CCc3nc(N4CCCC4)nn3C3CCOCC3)nn12]

The product (14 mg) was prepared as a white solid in analogy to Example 61 using (tetrahydro-2H-pyran-4-yl)hydrazine hydrochloride and 5-chloro-6-methyl-3-(trifluoromethyl)pyridin-1-ium-1,2-diamine; 2,4,6-trimethylbenzenesulfonate as starting materials. MS: m/z=484.2 (M+H+)

Example 123

2-[2-(2-Cyclopropyl-5-pyrrolidin-1-yl-2H-[1,2,4]triazol-3-yl)-ethyl]-5,8-dimethyl-[1,2,4]triazolo[1,5-a]pyrazine (a) and 2-[2-(1-Cyclopropyl-5-pyrrolidin-1-yl-1H-[1,2,4]triazol-3-yl)-ethyl]-5,8-dimethyl-[1,2,4]triazolo[1,5-a]pyrazine (b)

(a)
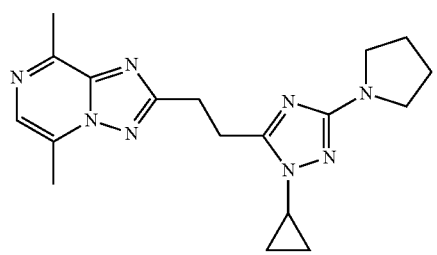

(b)
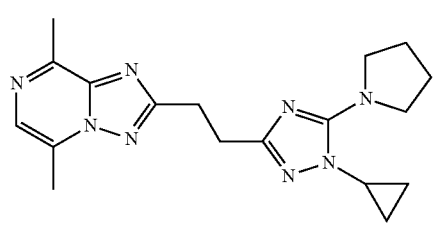

a) 1-Cyclopropyl-5-(2-methyl-propenyl)-3-pyrrolidin-1-yl-1H-[1,2,4]triazole (a) with 1-Cyclopropyl-3-(2-methyl-propenyl)-5-pyrrolidin-1-yl-1H-[1,2,4]triazole (b)

(a)
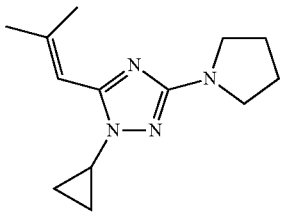

(b)
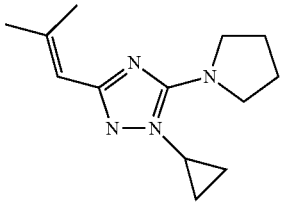

2,2'-Bipyridine (203 mg, 1.30 mmol), copper acetate (236 mg, 1.30 mmol) and sodium carbonate (276 mg, 2.60 mmol) were added to a solution of 5-(2-ethyl-propenyl)-3-pyrrolidin-1-yl-1H-[1,2,4]triazole (250 mg, 1.30 mmol) and cyclopropyl boronic acid (203 mg, 1.30 mmol) in DCE (10 ml). The reaction mixture was heated at 70° C. for 16 hours. After cooling, the mixture was diluted with dichloromethane and washed with a saturated aq. solution of ammonium chloride. The separated organic extracts were washed with brine and dried over Na$_2$SO$_4$, filtration and concentration under reduced pressure. The crude material was purified by silica gel column chromatography using 20% ethyl acetate in hexane affording 1-cyclopropyl-5-(2-methyl-prop enyl)-3-pyrrolidin-1-yl-1H-[1,2,4]triazole (a) with 1-cyclopropyl-3-(2-methyl-propenyl)-5-pyrrolidin-1-yl-1H-[1,2,4]triazole (b) (200 mg, 66%) as a white solid. MS: m/z=232.8 (M+H+)

b) 2-Cyclopropyl-5-pyrrolidin-1-yl-2H-[1,2,4]triazole-3-carbaldehyde (a) with 1-Cyclopropyl-5-pyrrolidin-1-yl-1H-[1,2,4]triazole-3-carbaldehyde (b)

(a)
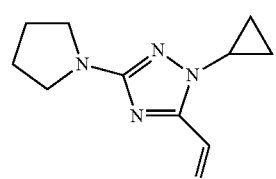

(b)
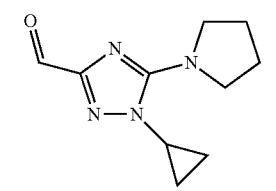

Was prepared in the same manner as described in Example 49 d) using a mixture of 1-cyclopropyl-5-(2-methyl-propenyl)-3-pyrrolidin-1-yl-1H-[1,2,4]triazole with 1-cyclopropyl-3-(2-methyl-propenyl)-5-pyrrolidin-1-yl-1H-[1,2,4]triazole (200 mg, 0.862 mmol) affording a mixture of 2-cyclopropyl-5-pyrrolidin-1-yl-2H-[1,2,4]triazole-3-carbaldehyde (a) with 1-cyclopropyl-5-pyrrolidin-1-yl-1H-[1,2,4]triazole-3-carbaldehyde (b) (220 mg, crude) as a yellow solid which was used without further purification. c) 2-[(E)-2-(2-Cyclopropyl-5-pyrrolidin-1-yl-2H-[1,2,4]triazol-3-yl)-vinyl]-5,8-dimethyl-[1,2,4]triazolo[1,5-a]pyrazine (a) with 2-[(E)-2-(1-Cyclopropyl-5-pyrrolidin-1-yl-1H-[1,2,4]triazol-3-yl)-vinyl]-5,8-dimethyl-[1,2,4]triazolo[1,5-a]pyrazine (b)

(a)
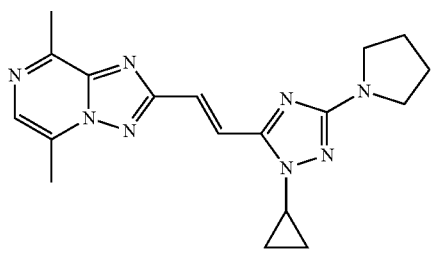

(b)
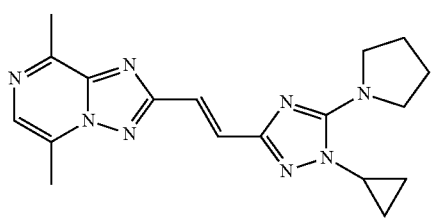

Was prepared in the same manner as described in Example 49 e) using a mixture of 2-cyclopropyl-5-pyrrolidin-1-yl-2H-[1,2,4]triazole-3-carbaldehyde with 1-cyclopropyl-5-pyrrolidin-1-yl-1H-[1,2,4]triazole-3-carbaldehyde (220 mg, 1.068 mmol) as aldehydes affording a mixture of 2-[(E)-2-(2-cyclopropyl-5-pyrrolidin-1-yl-2H-[1,2,4]triazol-3-yl)-vinyl]-5,8-dimethyl-[1,2,4]triazolo[1,5-a]pyrazine (a) with 2-[(E)-2-(1-cyclopropyl-5-pyrrolidin-1-yl-1H-[1,2,4]triazol-3-yl)-vinyl]-5,8-dimethyl-[1,2,4]triazolo[1,5-a]pyrazine (b) (60 mg, 16%) as a yellow solid. MS: m/z=351 (M+H+)

d) 2-[2-(2-Cyclopropyl-5-pyrrolidin-1-yl-2H-[1,2,4]triazol-3-yl)-ethyl]-5,8-dimethyl-[1,2,4]triazolo[1,5-a]pyrazine (a) and 2-[2-(1-Cyclopropyl-5-pyrrolidin-1-yl-1H-[1,2,4]triazol-3-yl)-ethyl]-5,8-dimethyl-[1,2,4]triazolo[1,5-a]pyrazine (b)

(a)
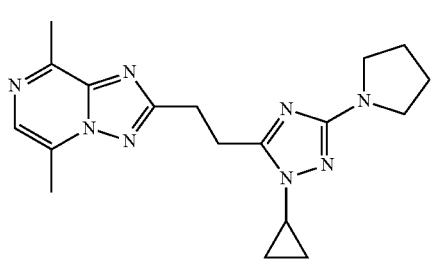

(b)
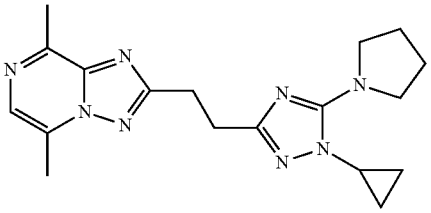

Was prepared in the same manner as described in Example 87 b) using a mixture of 2-[(E)-2-(2-cyclopropyl-5-pyrrolidin-1-yl-2H-[1,2,4]triazol-3-yl)-vinyl]-5,8-dimethyl-[1,2,4]triazolo[1,5-a]pyrazine with 2-[(E)-2-(1-cyclopropyl-5-pyrrolidin-1-yl-1H-[1,2,4]triazol-3-yl)-vinyl]-5,8-dimethyl-[1,2,4]triazolo[1,5-a]pyrazine (110 mg, 0.314 mmol) affording a mixture of 2-[2-(2-cyclopropyl-5-pyrrolidin-1-yl-2H-[1,2,4]triazol-3-yl)-ethyl]-5,8-dimethyl-[1,2,4]triazolo[1,5-a]pyrazine (a) and 2-[2-(1-cyclopropyl-5-pyrrolidin-1-yl-1H-[1,2,4]triazol-3-yl)-ethyl]-5,8-dimethyl-[1,2,4]triazolo[1,5-a]pyrazine (b). Separation of the two isomers via preparative HPLC afforded 2-[2-(2-cyclopropyl-5-pyrrolidin-1-yl-2H-[1,2,4]triazol-3-yl)-ethyl]-5,8-dimethyl-[1,2,4]triazolo[1,5-a]pyrazine (a) (15 mg, 13.5%) as a white solid. MS: m/z=353 (M+H+) and 2-[2-(1-cyclopropyl-5-pyrrolidin-1-yl-1H-[1,2,4]triazol-3-yl)-ethyl]-5,8-dimethyl-[1,2,4]triazolo[1,5-a]pyrazine (b) (18 mg, 16.2%) as a white solid. MS: m/z=353 (M+H+)

Example 124

2-{2-[5-((R)-2-Methoxymethyl-pyrrolidin-1-yl)-2-methyl-2H-[1,2,4]triazol-3-yl]-ethyl}-5,8-dimethyl-[1,2,4]triazolo[1,5-a]pyrazine

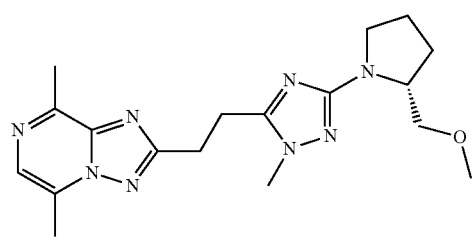 [SMILES: COC[C@H]1CCCN1c1nc(CCc2nc3c(C)ncc(C)n3n2)n(C)n1]

a) 2-{(E)-2-[5-((R)-2-Methoxymethyl-pyrrolidin-1-yl)-2-methyl-2H-[1,2,4]triazol-3-yl]-vinyl}-5,8-dimethyl-[1,2,4]triazolo[1,5-a]pyrazine

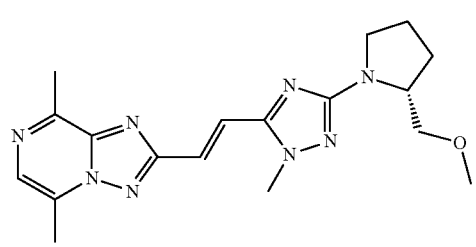 [SMILES: COC[C@H]1CCCN1c1nc(/C=C/c2nc3c(C)ncc(C)n3n2)n(C)n1]

Was prepared in the same manner as described in Example 87a) using (R)-2-(methoxymethyl)-pyrrolidine (68.9 mg, 598 µmol, Eq: 2) instead of pyrrolidin-2-one affording 2-{(E)-2-[5-((R)-2-methoxy-methyl-pyrrolidin-1-yl)-2-methyl-2H-[1,2,4]triazol-3-yl]-vinyl}-5,8-dimethyl-[1,2,4]triazolo[1,5-a]pyrazine (21 mg, 19%) as a yellow solid. MS: m/z=369.5 (M+H+)

b) 2-{2-[5-((R)-2-Methoxymethyl-pyrrolidin-1-yl)-2-methyl-2H-[1,2,4]triazol-3-yl]-ethyl}-5,8-dimethyl-[1,2,4]triazolo[1,5-a]pyrazine

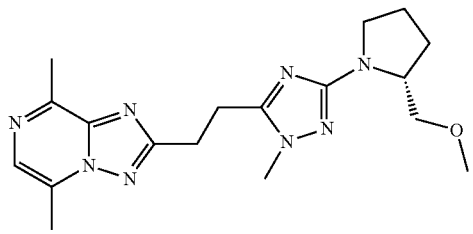 [SMILES: COC[C@H]1CCCN1c1nc(CCc2nc3c(C)ncc(C)n3n2)n(C)n1]

Was prepared in the same manner as described in Example 87 b) using (R,E)-2-(2-(3-(2-(methoxymethyl)pyrrolidin-1-yl)-1-methyl-1H-1,2,4-triazol-5-yl)vinyl)-5,8-dimethyl-[1,2,4]triazolo[1,5-a]pyrazine (20 mg, 54.3 µmol, Eq: 1.00) affording 2-{2-[5-((R)-2-methoxymethyl-pyrrolidin-1-yl)-2-methyl-2H-[1,2,4]triazol-3-yl]-ethyl}-5,8-dimethyl-[1,2,4]triazolo[1,5-a]pyrazine (15.9 mg, 79%) as a colorless oil. MS: m/z=371.5 (M+H+)

Example 125

2-(6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-yloxy)-1-morpholinoethanone

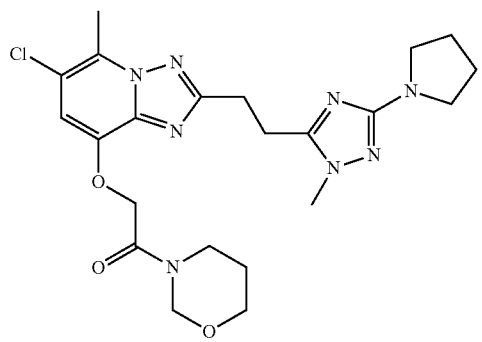 [SMILES: Cc1c(Cl)cc(OCC(=O)N2CCCOC2)c2nc(CCc3nc(N4CCCC4)nn3C)nn12]

The product (12.6 mg, 51.8%) was obtained as an off white solid in analogy to Example 119 from 2-chloro-1-morpholinoethanone. MS: m/z=489.6 (M+H+)

Example 126

(−)-5,8-Dimethyl-2-(2-(1-methyl-3-(pyrrolidin-1-yl)-1H-1,2,4-triazol-5-yl)propyl)-[1,2,4]triazolo[1,5-a]pyrazine

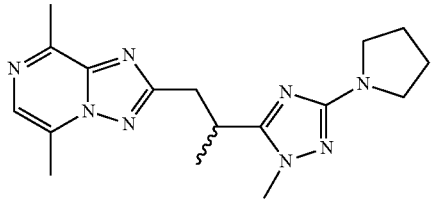 [SMILES: Cc1ncc(C)n2nc(CC(C)c3nc(N4CCCC4)nn3C)nc12]

a) 1-(5-Bromo-2-methyl-2H-[1,2,4]triazol-3-yl)-ethanol

To a solution of 3,5-dibromo-1-methyl-1H-1,2,4-triazole (2.634 g, 10.9 mmol, Eq: 1.00) in tetrahydrofuran (184 ml) was added dropwise at −78° C. under argon atmosphere n-butyllithium 1.6 M in hexanes (6.83 ml, 10.9 mmol, Eq: 1.00). The resulting mixture was stirred for 20 minutes at −75° C. then a solution of acetaldehyde (1.2 g, 1.54 ml, 27.3 mmol, Eq: 2.5) in tetrahydrofuran (36.9 ml) was added slowly and stirring at −75° C. was continued for further 1.5 hours. The mixture was quenched with sat. aq. NH₄Cl solution and was warmed to 25° C. The mixture was diluted with ethyl acetate and washed 2 times with water. The organic layer was separated, dried over magnesium sulfate, filtrated and evaporated affording 1-(5-bromo-2-methyl-2H-[1,2,4]triazol-3-yl)-ethanol (1.639 g, 72.7%) as a light yellow oil. MS: m/z=206209 (M+H+)

b) 1-(5-Bromo-2-methyl-2H-[1,2,4]triazol-3-yl)-ethanone

A solution of 1-(3-bromo-1-methyl-1H-1,2,4-triazol-5-yl)ethanol (1.639 g, 7.95 mmol, Eq: 1.00) and pyridine (944 mg, 965 µl, 11.9 mmol, Eq: 1.5) in dichloromethane (237 ml) was cooled to 0° C. then Dess-Martin periodinane (15% in dichloromethane, 24.7 g, 8.75 mmol, Eq: 1.1) was added. The resulting mixture was stirred for 4 hours at 0° C. under nitrogen atmosphere. The mixture was diluted with dichloromethane and washed with sat. sodium hydrogen carbonate. The organic layer was separated, dried over magnesium sulfate, filtrated and evaporated. The crude material was applied on silica gel and purified by flash chromatography over a 20 g silica gel column using dichloromethane/methanol 0-3% & 5% NH₃ as eluent affording 1-(5-bromo-2-methyl-2H-[1,2,4]triazol-3-yl)-ethanone (948 mg, 58.4%) as a white solid. MS: m/z=203 (EI)

c) 2-[(E)-2-(5-Bromo-2-methyl-2H-[1,2,4]triazol-3-yl)-propenyl]-5,8-dimethyl-[1,2,4]triazolo[1,5-a]pyrazine

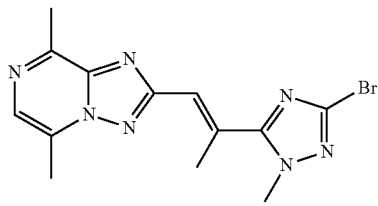 [SMILES: C/C(=C\c1nc2c(C)ncc(C)n2n1)c1nc(Br)nn1C]

Was prepared in the same manner as described in Example 49 e) using 1-(3-bromo-1-methyl-1H-1,2,4-triazol-5-yl)ethanone (667 mg, 3.27 mmol, Eq: 1) instead of aldehyde affording 2-[2-(5-bromo-2-methyl-2H-[1,2,4]triazol-3-yl)-propyl]-5,8-dimethyl-[1,2,4]triazolo[1,5-a]pyrazine (488 mg, 39.4%) as a white solid. MS: m/z=350.3 (M+H+)

d) 5,8-Dimethyl-2-[(E)-2-(2-methyl-5-pyrrolidin-1-yl-2H-[1,2,4]triazol-3-yl)-propenyl]-[1,2,4]triazolo[1,5-a]pyrazine

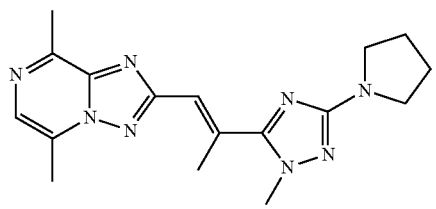 [SMILES: C/C(=C\c1nc2c(C)ncc(C)n2n1)c1nc(N2CCCC2)nn1C]

Was prepared in the same manner as described in Example 87a) using (E)-2-(2-(3-bromo-1-methyl-1H-1,2,4-triazol-5-yl)prop-1-enyl)-5,8-dimethyl-[1,2,4]triazolo[1,5-a]pyrazine (448 mg, 1.29 mmol, Eq: 1.00) instead of 2-[(E)-2-(5-bromo-2-methyl-2H-[1,2,4]triazol-3-yl)-vinyl]-5,8-dimethyl-[1,2,4]triazolo[1,5-a]pyrazine and pyrrolidine (183 mg, 213 µl, 2.57 mmol, Eq: 2) instead of pyrrolidin-2-one affording 5,8-dimethyl-2-[(E)-2-(2-methyl-5-pyrrolidin-1-yl-2H-[1,2,4]triazol-3-yl)-propenyl]-[1,2,4]triazolo[1,5-a]pyrazine (109 mg, 41.1%) as a white solid. MS: m/z=339.5 (M+H+)

e) 5,8-Dimethyl-2-[2-(2-methyl-5-pyrrolidin-1-yl-2H-[1,2,4]triazol-3-yl)-propyl]-[1,2,4]triazolo[1,5-a]pyrazine

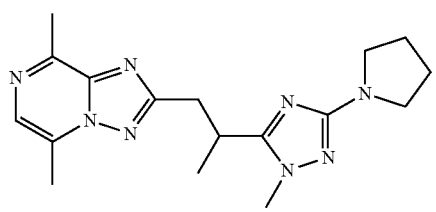 [SMILES: Cc1ncc(C)n2nc(CC(C)c3nc(N4CCCC4)nn3C)nc12]

Was prepared in the same manner as described in Example 87 b) using (E)-5,8-dimethyl-2-(2-(1-methyl-3-(pyrrolidin-1-yl)-1H-1,2,4-triazol-5-yl)prop-1-enyl)-[1,2,4]triazolo[1,5-a]pyrazine (173 mg, 511 µmol, Eq: 1.00) affording 5,8-dimethyl-2-[2-(2-methyl-5-pyrrolidin-1-yl-2H-[1,2,4]triazol-3-yl)-propyl]-[1,2,4]triazolo[1,5-a]pyrazine (170 mg, 97.7%) as a light brown solid. MS: m/z=341.5 (M+H+)

f) (−)-5,8-Dimethyl-2-(2-(1-methyl-3-(pyrrolidin-1-yl)-1H-1,2,4-triazol-5-yl)propyl)-[1,2,4]triazolo[1,5-a]pyrazine

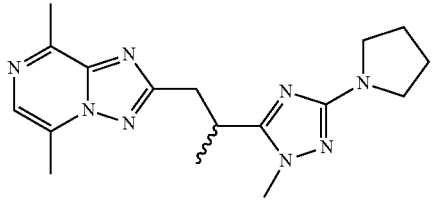 [SMILES: Cc1ncc(C)n2nc(CC(C)c3nc(N4CCCC4)nn3C)nc12]

Chiral HPLC-separation of racemic 5,8-dimethyl-2-(2-(1-methyl-3-(pyrrolidin-1-yl)-1H-1,2,4-triazol-5-yl)propyl)-[1,2,4]triazolo[1,5-a]pyrazine (170 mg, 499 µmol, Eq: 1.00) afforded (−)-5,8-dimethyl-2-(2-(1-methyl-3-(pyrrolidin-1-yl)-1H-1,2,4-triazol-5-yl)propyl)-[1,2,4]triazolo[1,5-a]pyrazine (63 mg, 37.1%), as the second elution enantiomer with negative rotation as a white solid. MS: m/z=341.5 (M+H+).

Example 127

(R)-6-Chloro-2-(2-(3-(3-fluoropyrrolidin-1-yl)-1-methyl-1H-1,2,4-triazol-5-yl)ethyl)-5-methyl-8-(trifluoromethyl)-[1,2,4]triazolo[1,5-a]pyridine

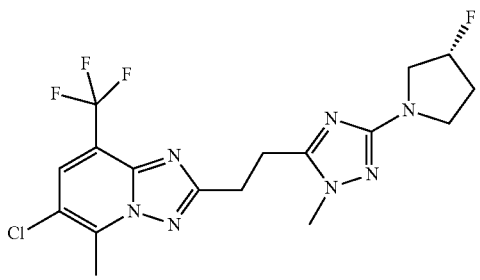 [SMILES: Cc1c(Cl)cc(C(F)(F)F)c2nc(CCc3nc(N4CC[C@@H](F)C4)nn3C)nn12]

The product (28 mg) was obtained as a white solid in analogy to Example 88 from (R)-3-fluoropyrrolidine hydrochloride. MS: m/z=432.2 (M+H+).

Example 128

6-Chloro-5-methyl-2-(2-(3-(pyrrolidin-1-yl)-1H-1,2,4-triazol-5-yl)ethyl)-8-(trifluoromethyl)-[1,2,4]triazolo[1,5-a]pyridine

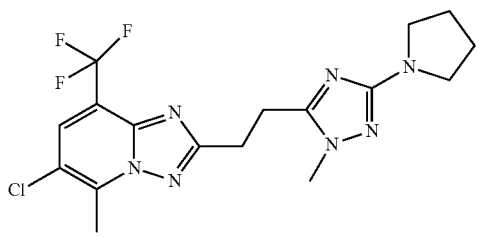 [SMILES: Cc1c(Cl)cc(C(F)(F)F)c2nc(CCc3nc(N4CCCC4)nn3C)nn12]

a) 6-Chloro-2-(2-(1-(4-methoxybenzyl)-3-(pyrrolidin-1-yl)-1H-1,2,4-triazol-5-yl)ethyl)-5-methyl-8-(trifluoromethyl)-[1,2,4]triazolo[1,5-a]pyridine

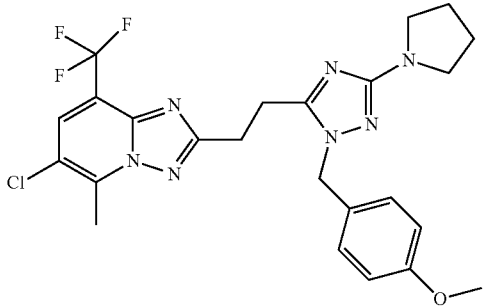 [SMILES: COc1ccc(Cn2nc(N3CCCC3)nc2CCc2nc3c(C(F)(F)F)cc(Cl)c(C)n3n2)cc1]

The product (450 mg) was obtained as a light brown oil in analogy to Example 61 from 5-chloro-6-methyl-3-(trifluoromethyl)pyridin-1-ium-1,2-diamine; 2,4,6-trimethylbenzenesulfonate. MS: m/z=520.3 (M+H+)

b) 6-Chloro-5-methyl-2-(2-(3-(pyrrolidin-1-yl)-1H-1,2,4-triazol-5-yl)ethyl)-8-(trifluoromethyl)-[1,2,4]triazolo[1,5-a]pyridine

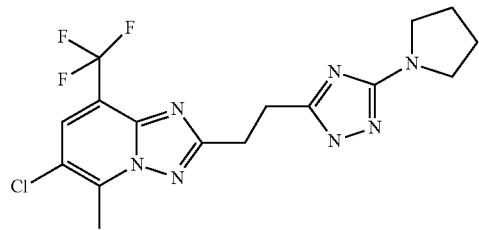 [SMILES: Cc1c(Cl)cc(C(F)(F)F)c2nc(CCc3nc(N4CCCC4)n[nH]3)nn12]

Trifluoroacetic acid (9.87 g, 6.67 ml, 86.5 mmol, Eq: 100) was added to 6-chloro-2-(2-(1-(4-methoxybenzyl)-3-(pyrrolidin-1-yl)-1H-1,2,4-triazol-5-yl)ethyl)-5-methyl-8-(trifluoromethyl)-[1,2,4]triazolo[1,5-a]pyridine (450 mg, 865 µmol, Eq: 1.00). The mixture was heated under reflux for 4 h and then concentrated to an oil. Water (15 ml) was added and the mixture was alkalized by addition of sodium bicarbonate. The mixture was extracted with dichloromethane. The combined organic layers were dried over sodium sulfate and concentrated to an oil. The crude product was purified by chromatography (SiO$_2$, methanol ethyl acetate) to afford the product (140 mg, 40.5%) as an off white solid. MS: m/z=400.2 (M+H+)

Example 129

2-{2-[5-(3-Difluoromethyl-pyrrolidin-1-yl)-2-methyl-2H-[1,2,4]triazol-3-yl]-ethyl}-5,8-dimethyl-[1,2,4]triazolo[1,5-a]pyrazine

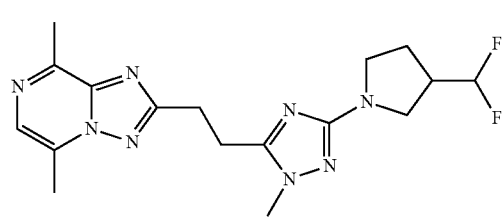 [SMILES: Cc1ncc(C)n2nc(CCc3nc(N4CCC(C(F)F)C4)nn3C)nc12]

a) 2-{(E)-2-[5-(3-Difluoromethyl-pyrrolidin-1-yl)-2-methyl-2H-[1,2,4]triazol-3-yl]-vinyl}-5,8-dimethyl-[1,2,4]triazolo[1,5-a]pyrazine

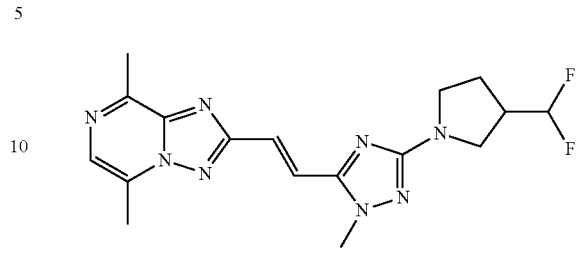

Was prepared in the same manner as described in Example 87a) using 3-(difluoromethyl)-pyrrolidine hydrochloride (94.3 mg, 598 µmol, Eq: 2) instead of pyrrolidin-2-one affording 2-{(E)-2-[5-(3-difluoromethyl-pyrrolidin-1-yl)-2-methyl-2H-[1,2,4]triazol-3-yl]-vinyl}-5,8-dimethyl-[1,2,4]triazolo[1,5-a]pyrazine (74 mg, 66.1%) as a light yellow solid. MS: m/z=375.5 (M+H+)

b) 2-{2-[5-(3-Difluoromethyl-pyrrolidin-1-yl)-2-methyl-2H-[1,2,4]triazol-3-yl]-ethyl}-5,8-dimethyl-[1,2,4]triazolo[1,5-a]pyrazine

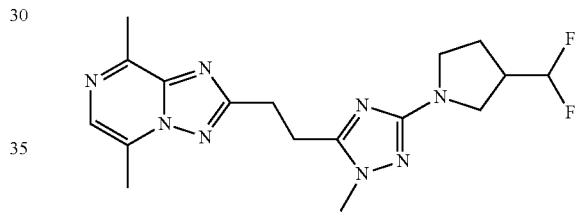

Was prepared in the same manner as described in Example 87 b) using (E)-2-(2-(3-(3-(difluoro-methyl)pyrrolidin-1-yl)-1-methyl-1H-1,2,4-triazol-5-yl)vinyl)-5,8-dimethyl-[1,2,4]triazolo[1,5-a]pyrazine (74 mg, 198 µmol, Eq: 1.00) affording 2-{2-[5-(3-Difluoromethyl-pyrrolidin-1-yl)-2-methyl-2H-[1,2,4]triazol-3-yl]-ethyl}-5,8-dimethyl-[1,2,4]triazolo[1,5-a]pyrazine (66 mg, 88.7%) as a light yellow solid. MS: m/z=349.5 (M+H+)

Example 130

6-Chloro-8-(difluoromethyl)-5-methyl-2-(2-(1-methyl-3-(pyrrolidin-1-yl)-1H-1,2,4-triazol-5-yl)ethyl)-[1,2,4]triazolo[1,5-a]pyridine

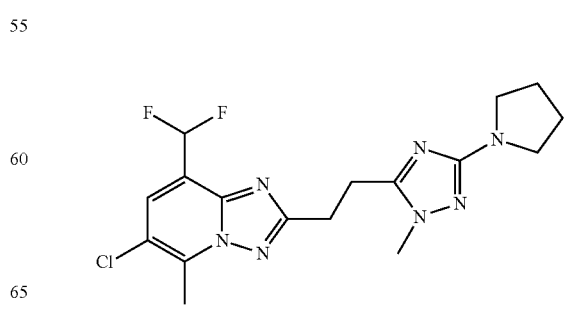

a) 5-Chloro-3-(difluoromethyl)-6-methylpyridin-2-amine

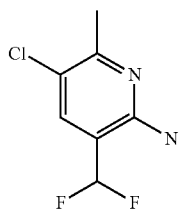

Diethylaminosulfur trifluoride (DAST, 355 mg, 291 µl, 2.2 mmol, Eq: 3) was added to 2-amino-6-methylnicotinaldehyde (100 mg, 734 µmol, Eq: 1.00) in dichloromethane (5 ml) at 0° C. The mixture was stirred overnight at room temperature. The mixture was washed with saturated aqueous sodium bicarbonate solution, dried over sodium sulfate and then concentrated to an oil. Acetonitrile (5 ml) was added, followed by N-chlorosuccinimide (196 mg, 1.47 mmol, Eq: 2). The mixture was stirred overnight at room temperature and then concentrated to an oil.

The mixture was purified by column chromatography (SiO2, MeOH/25% NH4OH aq/dichloromethane) to give the desired product (30 mg, 21%) as a white solid. MS: m/z=193.3 (M+H+)

b) 6-Chloro-8-(difluoromethyl)-5-methyl-2-(2-(1-methyl-3-(pyrrolidin-1-yl)-1H-1,2,4-triazol-5-yl)ethyl)-[1,2,4]triazolo[1,5-a]pyridine

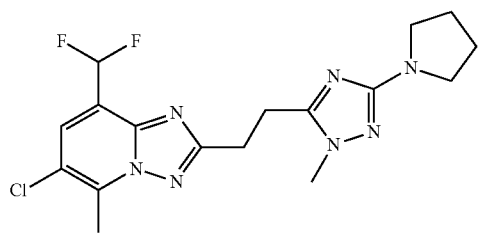 [SMILES: Cc1c(Cl)cc(C(F)F)c2nc(CCc3nc(N4CCCC4)nn3C)nn12]

The product (4 mg) was obtained as a light yellow oil in analogy to Example 52 from 5-chloro-3-(difluoromethyl)-6-methylpyridin-2-amine. MS: m/z=396.6 (M+H+)

Example 131

6-Chloro-2-(2-(1-cyclopropyl-5-(pyrrolidin-1-yl)-1H-1,2,4-triazol-3-yl)ethyl)-5-methyl-8-(trifluoromethyl)-[1,2,4]triazolo[1,5-a]pyridine

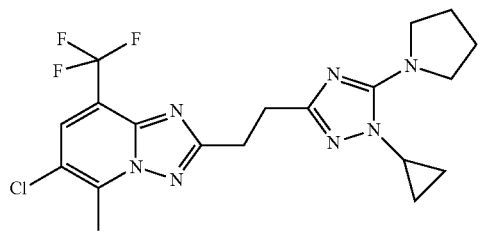 [SMILES: Cc1c(Cl)cc(C(F)(F)F)c2nc(CCc3nc(N4CCCC4)n(C4CC4)n3)nn12]

A mixture of 6-chloro-5-methyl-2-(2-(3-(pyrrolidin-1-yl)-1H-1,2,4-triazol-5-yl)ethyl)-8-(trifluoromethyl)-[1,2,4]triazolo[1,5-a]pyridine (30 mg, 75.0 µmol, Eq: 1.00), cyclopropyl-boronic acid (19.3 mg, 225 µmol, Eq: 3), copper (II) acetate (27.3 mg, 150 µmol, Eq: 2), molecular sieves, pyridine (47.5 mg, 48.6 µl, 600 µmol, Eq: 8), triethylamine (38.0 mg, 52.3 µl, 375 µmol, Eq: 5) in tetrahydrofuran (4 ml) was heated under air in a sealed tube for 2 h at 100° C. The mixture was filtered and concentrated to an oil. Water was added and extracted with dichloromethane. The combined organic layers were dried over sodium sulfate and then concentrated. The mixture was separated by preparative HPLC to give the product (4.8 mg, 14.5%) as a colorless oil. MS: m/z=440.2 (M+H+)

Example 132

6-Chloro-2-(2-(1-cyclopropyl-3-(pyrrolidin-1-yl)-1H-1,2,4-triazol-5-yl)ethyl)-5-methyl-8-(trifluoromethyl)-[1,2,4]triazolo[1,5-a]pyridine

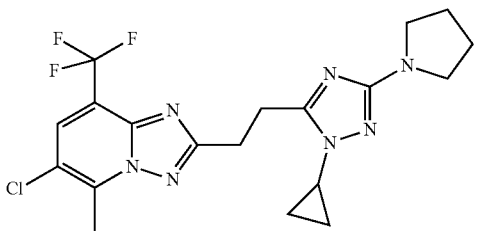 [SMILES: Cc1c(Cl)cc(C(F)(F)F)c2nc(CCc3nc(N4CCCC4)nn3C3CC3)nn12]

The desired product (5.1 mg, 15.5%) was obtained as a white solid in the chromatographic separation of Example 131. MS: m/z=440.2 (M+H+)

Example 133

7-chloro-2-((1-(4-methoxybenzyl)-5-(pyrrolidin-1-yl)-1H-1,2,4-triazol-3-yl)ethynyl)quinoxaline

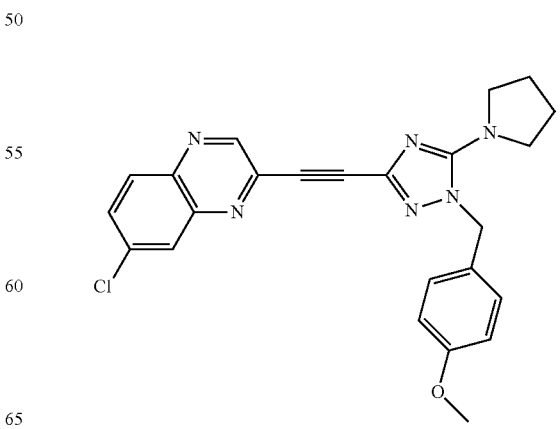

157 a) 2-{(E)-2-[5-(3-Fluoro-azetidin-1-yl)-2-methyl-2H-[1,2,4]triazol-3-yl]-vinyl}-5,8-dimethyl-[1,2,4]triazolo[1,5-a]pyrazine

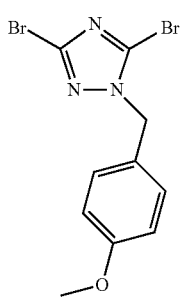 [SMILES: COc1ccc(Cn2nc(Br)nc2Br)cc1]

3,5-dibromo-1H-1,2,4-triazole (1.5 g, 6.61 mmol, Eq: 1.00), potassium iodide (110 mg, 661 µmol, Eq: 0.10), 4-methoxybenzyl chloride (1.14 g, 990 µl, 7.27 mmol, Eq: 1.1) and N,N-diisopropylethylamine (1.71 g, 2.31 ml, 13.2 mmol, Eq: 2.0) was stirred in acetonitrile (23.0 ml) overnight at room temperature. The crude material was applied on silica gel and purified by column to give 3,5-Dibromo-1-(4-methoxy-benzyl)-1H-[1,2,4]triazole (1.79 g, 78%) as white solid. MS: m/z=348.1 (M+H$^+$)

b) 3-Ethynyl-1-(4-methoxy-benzyl)-5-pyrrolidin-1-yl-1H-[1,2,4]triazole

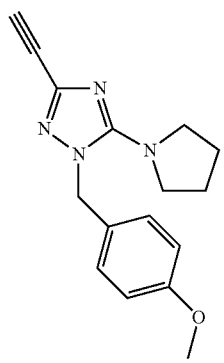 [SMILES: C#Cc1nc(N2CCCC2)n(Cc2ccc(OC)cc2)n1]

Was prepared in the same manner as described in Example 47 (b-d) from 1-(4-methoxybenzyl)-5-(pyrrolidin-1-yl)-3-((trimethylsilyl)ethynyl)-1H-1,2,4-triazole (153 mg, 432 µmol, Eq: 1.00) affording 3-Ethynyl-1-(4-methoxy-benzyl)-5-pyrrolidin-1-yl-1H-[1,2,4]triazole (118 mg, 96.8%) as light brown solid. MS: m/z=283.4 (M+H$^+$)

158 c) 7-chloro-2-((1-(4-methoxybenzyl)-5-(pyrrolidin-1-yl)-1H-1,2,4-triazol-3-yl)ethynyl)quinoxaline

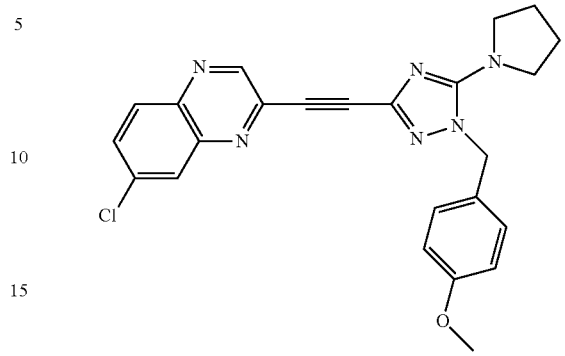

A mixture of 3-ethynyl-1-(4-methoxybenzyl)-5-(pyrrolidin-1-yl)-1H-1,2,4-triazole (115 mg, 407 µmol, Eq: 1.00), 2,7-dichloroquinoxaline (89.2 mg, 448 µmol, Eq: 1.1) and triethylamine (61.8 mg, 85.2 µl, 611 µmol, Eq: 1.5) in tetrahydrofuran (3 ml) was purged with argon, then copper (I) iodide (3.1 mg, 16.3 µmol, Eq: 0.04), bis(triphenylphosphine)palladium(II) chloride (11.4 mg, 16.3 µmol, Eq: 0.04) and triphenylphosphine (4.27 mg, 16.3 µmol, Eq: 0.04) were added, the vessel was capped and heated for 18 hours to 75° C. The crude material was applied on silica gel and purified by flash chromatography to give 7-Chloro-2-[1-(4-methoxy-benzyl)-5-pyrrolidin-1-yl-1H-[1,2,4]triazol-3-ylethynyl]-quinoxaline (89 mg, 49.1%) as yellow solid. MS: m/z=445.4 (M+H$^+$)

Example 134

7-chloro-2-(2-(5-(pyrrolidin-1-yl)-1H-1,2,4-triazol-3-yl)ethyl)quinoxaline

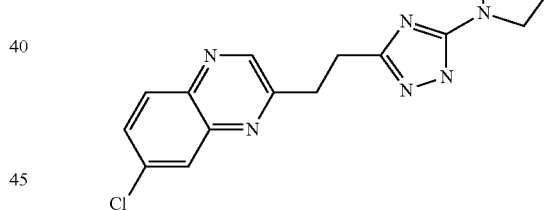

a) 7-Chloro-2-{2-[1-(4-methoxy-benzyl)-5-pyrrolidin-1-yl-1H-[1,2,4]triazol-3-yl]-ethyl}-quinoxaline

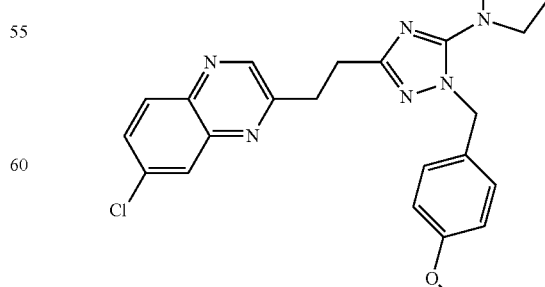

7-chloro-2-((1-(4-methoxybenzyl)-5-(pyrrolidin-1-yl)-1H-1,2,4-triazol-3-yl)ethynyl)quinoxaline (33 mg, 74.2 µmol, Eq: 1.00) was stirred in ethyl acetate (12 ml) with palladium, 5 wt % on barium sulfate, reduced (33.0 mg, 310 µmol, Eq: 4.18) under a hydrogen atmosphere for 2.5 h. Then 3 drops of acetic acid were added and stirring was continued for 1.5 h. The crude material was applied on silica gel and purified by column chromatography to give 7-chloro-2-{2-[1-(4-methoxy-benzyl)-5-pyrrolidin-1-yl-1H-[1,2,4]triazol-3-yl]-ethyl}-quinoxaline (17 mg, 51.1%) as light red oil. MS: m/z=449.4 (M+H$^+$)

b) 7-Chloro-2-[2-(5-pyrrolidin-1-yl-1H-[1,2,4]triazol-3-yl)-ethyl]-quinoxaline

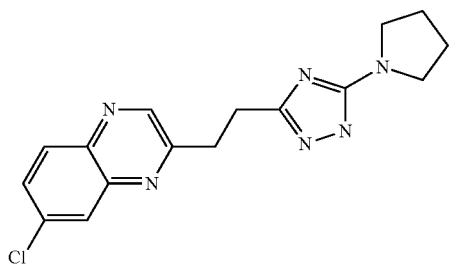 [SMILES: Clc1ccc2ncc(CCc3n[nH]c(N4CCCC4)n3)nc2c1]

7-chloro-2-(2-(1-(4-methoxybenzyl)-5-(pyrrolidin-1-yl)-1H-1,2,4-triazol-3-yl)ethyl)quinoxaline (17 mg, 37.9 µmol, Eq: 1.00) was stirred in trifluoroacetic acid (173 mg, 117 µl, 1.51 mmol, Eq: 40) with anisole (81.9 mg, 82.7 µl, 757 µmol, Eq: 20) at 120° C. overnight. The mixture was made basic by addition of sodium hydroxide 2N aq. and extracted three times with 1,2-dichloromethane, dried over magnesium sulfate, filtered and evaporated. The crude material was applied on silica gel and purified by column chromatography to give 7-Chloro-2-[2-(5-pyrrolidin-1-yl-1H-[1,2,4]triazol-3-yl)-ethyl]-quinoxaline (2.2 mg, 17.7%) as off-white solid. MS: m/z=329.12 (M+H$^+$)

Example 135

6-Chloro-3-methyl-2-(2-methyl-5-pyrrolidin-1-yl-2H-[1,2,4]triazol-3-ylethynyl)-quinoxaline

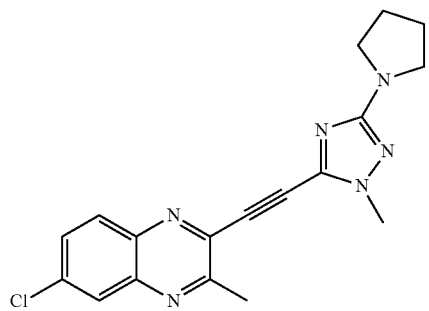 [SMILES: Cc1nc2cc(Cl)ccc2nc1C#Cc1nc(N2CCCC2)nn1C]

a) 6-Chloro-3-methyl-1H-quinoxalin-2-one with 7-Chloro-3-methyl-1H-quinoxalin-2-one

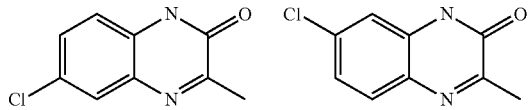

4-chlorobenzene-1,2-diamine (5 g, 35.1 mmol, Eq: 1.00) was stirred in water (50 ml) at room temperature. 2-Oxopropanoic acid (3.09 g, 2.44 ml, 35.1 mmol, Eq: 1.00) in water (20 ml) was added drop wise. The dark mixture was stirred at room temperature for 30 min. The precipitate was filtered off and washed with water and dried under high vacuum to give 6-chloro-3-methyl-1H-quinoxalin-2-one with 7-chloro-3-methyl-1H-quinoxalin-2-one (5.06 g, 37.1%) as brown solid. MS: m/z=195.03 (M+H$^+$)

b) 3-Bromo-6-chloro-2-methyl-quinoxaline with 2-bromo-6-chloro-3-methyl-quinoxaline

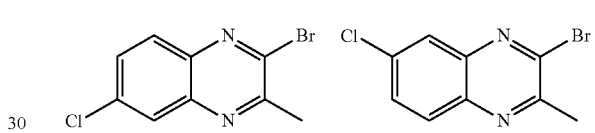

6-Chloro-3-methylquinoxalin-2(1H)-one compound with 7-chloro-3-methylquinoxalin-2(1H)-one (300 mg, 771 µmol, Eq: 1.00) was stirred neat in phosphoryl tribromide (1.6 g, 5.58 mmol, Eq: 7.24). N,N-Dimethylformamide (1 drop) (771 µmol, Eq: 1.00) was added and the mixture was stirred at 105° C. for 1.5 h. The mixture was added to ice water and neutralized with aqueous 25% ammonium hydroxide. The precipitated solid was filtered and dried under high vacuum followed by preparative HPLC to give 3-Bromo-6-chloro-2-methyl-quinoxaline with 2-bromo-6-chloro-3-methyl-quinoxaline (40 mg, 10.1%) as a light brown solid. MS: m/z=195.03 (M+H$^+$)

c) 6-Chloro-3-methyl-2-(2-methyl-5-pyrrolidin-1-yl-2H-[1,2,4]triazol-3-ylethynyl)-quinoxaline

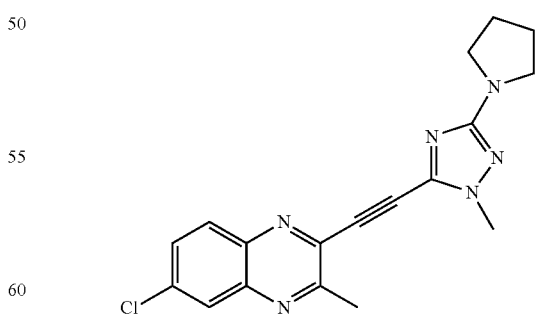

To a stirred solution of 2-bromo-6-chloro-3-methylquinoxaline with 3-bromo-6-chloro-2-methylquinoxaline (250 mg, 485 µmol, Eq: 1.00) and 5-Ethynyl-1-methyl-3-pyrrolidin-1-yl-1H-[1,2,4]triazole (94.1 mg, 534 µmol, Eq: 1.1) at room temperature in N,N-dimethylformamide (7.5 ml) under an argon atmosphere were added triethylamine (98.2 mg, 135 µl, 971 µmol, Eq: 2), copper (I) iodide (4.62 mg, 24.3 µmol, Eq: 0.05) and bis(triphenylphosphine)palladium (II) chloride (17.0 mg, 24.3 µmol, Eq: 0.05). The mixture was purged with argon before it was stirred over weekend at room temperature (dark sol.). The mixture was stirred over an additional night at 80° C. The crude material was applied on silica gel and purified by column chromatography. After separation of the isomers by preparative HPLC gave 6-chloro-3-methyl-2-(2-methyl-5-pyrrolidin-1-yl-2H-[1,2,4]triazol-3-ylethynyl)-quinoxaline (9.3 mg, 5.4%) as a yellow solid. MS: m/z=353.5 (M+H+)

Example 136

6-Chloro-2-methyl-3-(2-methyl-5-pyrrolidin-1-yl-2H-[1,2,4]triazol-3-ylethynyl)-quinoxaline

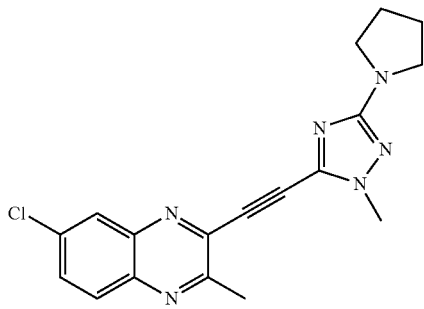 [SMILES: Cc1nc2ccc(Cl)cc2nc1C#Cc1nc(N2CCCC2)nn1C]

Was prepared in the same manner as described in Example 135 c) after chiral preparative HPLC separation affording 6-Chloro-2-methyl-3-(2-methyl-5-pyrrolidin-1-yl-2H-[1,2,4]triazol-3-ylethynyl)-quinoxaline (5.3 mg, 3.1%) as yellow solid. MS: m/z=353.5 (M+H+)

The invention claimed is:
1. A compound of formula (Ia) or (Ib)

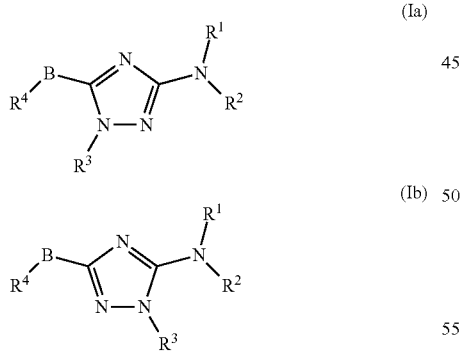

wherein
B is $C_2$-alkylene, $C_2$-alkenylene, or $C_2$-alkynylene;
$R^1$ and $R^2$ together with the nitrogen atom to which they are attached, form a 4 to 7 membered heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$ alkoxy, $C_1$-$C_7$ haloalkyl, hydroxyl, and oxo;
$R^3$ is selected from hydrogen, $C_1$-$C_7$-alkyl, $C_3$-$C_5$-cycloalkyl, $C_1$-$C_7$-alkoxyalkyl, $C_1$-$C_7$-haloalkyl, —$(CH_2)_{1,2}$-aryl optionally substituted by $C_1$-$C_7$ alkoxy, and —$(CH_2)_{1,2}$—$C_3$-$C_5$-cycloalkyl;
$R^4$ is a heteroaryl group selected from (a), (b), (c), (d) or (e)

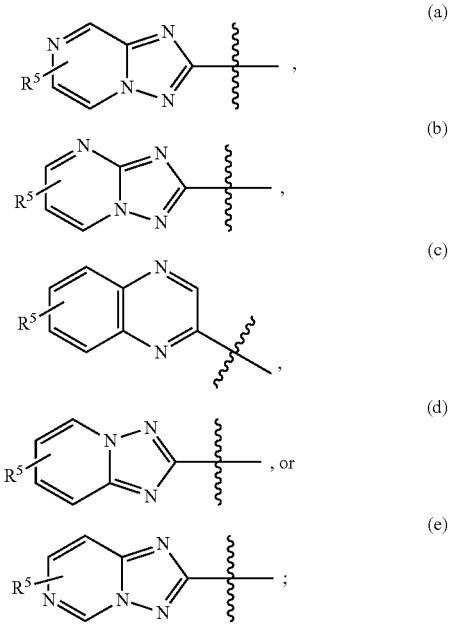

each optionally substituted by 1 to 3 $R^5$, wherein $R^5$ is selected from halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, —$SO_2R^8$, or $C_1$-$C_2$-alkoxy optionally substituted by $C_1$-$C_2$-alkoxy, heterocycloalkyl;
$R^6$ and $R^8$ are each $C_1$-$C_7$-alkyl;
$R^7$ is heterocycloalkyl.
2. The compound of claim 1, wherein B is ethylene or ethenylene.
3. The compound of claim 1, wherein $R^1$ and $R^2$, together with the nitrogen atom to which they are attached form a azetidinyl, pyrrolidinyl, piperidinyl, or azepanyl ring.
4. The compound of claim 2, wherein $R^5$ is selected from halogen, $C_1$-$C_7$-alkyl, $C_1$-$C_7$-haloalkyl, $C_1$-$C_2$-alkoxy, or cyano.
5. The compound of claim 2 wherein $R^4$ is selected from the group consisting of:

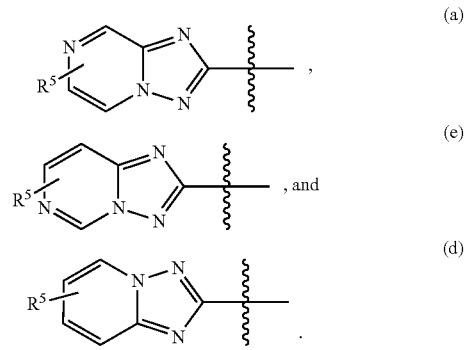

6. The compound of claim 1 selected from the group consisting of:

2-[2-(2-Ethyl-5-pyrrolidin-1-yl-2H-[1,2,4]triazol-3-yl)-vinyl]-5,8-dimethyl-[1,2,4]triazolo[1,5-a]pyrazine,
2[2-(2-Ethyl-5-pyrrolidin-1-yl-2H-[1,2,4]triazol-3-yl)-ethyl]-5,8-dimethyl-[1,2,4]triazolo[1,5-a]pyrazine,
2[2-(2-Ethyl-5-pyrrolidin-1-yl-2H-[1,2,4]triazol-3-yl)-vinyl]-5,8-dimethyl-[1,2,4]triazolo[1,5-a]pyrimidine,
2[2-(2-Ethyl-5-pyrrolidin-1-yl-2H-[1,2,4]triazol-3-yl)-ethyl]-5,7-dimethyl-[1,2,4]triazolo[1,5-a]pyrimidine,
5,8-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrazine,
5,8-Dimethyl-2-[2-(5-pyrrolidin-1-yl-2H-[1,2,4]triazol-3-yl)-ethyl]-[1,2,4]triazolo[1,5-a]pyrazine,
2-[2-(5-Azetidin-1-yl-2-methyl-2H-[1,2,4]triazol-3-yl)-vinyl]-5,8-dimethyl-[1,2,4]triazolo[1,5-a]pyrazine,
2-[2-(5-Azetidin-1-yl-2-methyl-2H-[1,2,4]triazol-3-yl)-ethyl]-5,8-dimethyl-[1,2,4]triazolo[1,5-a]pyrazine,
5,8-Dimethyl-2-[2-(2-methyl-5-pyrrolidin-1-yl-2H-[1,2,4]triazol-3-yl)-vinyl]-[1,2,4]triazolo[1,5-a]pyrazine,
5,8-Dimethyl-2-[2-(2-methyl-5-pyrrolidin-1-yl-2H-[1,2,4]triazol-3-yl)-ethyl]-[1,2,4]triazolo[1,5-a]pyrazine,
2-Methyl-3-[2-(2-methyl-5-pyrrolidin-1-yl-2H-[1,2,4]triazol-3-yl)-vinyl]-quinoxaline,
2-Methyl-3-[2-(2-methyl-5-pyrrolidin-1-yl-2H-[1,2,4]triazol-3-yl)-ethyl]-quinoxaline,
5,8-Dimethyl-2-[2-(1-methyl-5-pyrrolidin-1-yl-1H-[1,2,4]triazol-3-yl)-vinyl]-[1,2,4]triazolo[1,5-a]pyrazine,
5,8-Dimethyl-2-[2-(1-methyl-5-pyrrolidin-1-yl-1H-[1,2,4]triazol-3-yl)-ethyl]-[1,2,4]triazolo[1,5-a]pyrazine,
7-Chloro-2-[1-(4-methoxy-benzyl)-5-pyrrolidin-1-yl-1H-[1,2,4]triazol-3-ylethynyl]-[1,2,4]triazolo[1,5-a]pyridine,
2-{2-[2-(4-Methoxy-benzyl)-5-pyrrolidin-1-yl-2H-[1,2,4]triazol-3-yl]-ethyl}-5,8-dimethyl-[1,2,4]triazolo[1,5-a]pyrazine,
2-[2-(5-Azetidin-1-yl-2-methyl-2H-[1,2,4]triazol-3-yl)-ethyl]-5,7-dimethyl-[1,2,4]triazolo[1,5-a]pyrimidine,
5,7-Dimethyl-2-{2-[5-pyrrolidin-1-yl-2-(2,2,2-trifluoro-ethyl)-2H-[1,2,4]triazol-3-yl]-ethyl}-[1,2,4]triazolo[1,5-a]pyrimidine,
5,7-dimethyl-2-(2-(1-methyl-3-(pyrrolidin-1-yl)-1H-1,2,4-triazol-5-yl)ethyl)-[1,2,4]triazolo[1,5-a]pyrimidine,
6-Chloro-2-(2-(1-methyl-3-(pyrrolidin-1-yl)-1H-1,2,4-triazol-5-yl)ethyl)-[1,2,4]triazolo[1,5-a]pyridine,
6-Chloro-5-methyl-2-(2-(1-methyl-3-(pyrrolidin-1-yl)-1H-1,2,4-triazol-5-yl)ethyl)-[1,2,4]triazolo[1,5-a]pyridine,
6-Chloro-5-methyl-2[2-(1-methyl-5-pyrrolidin-1-yl-1H-[1,2,4]triazol-3-yl)-ethyl]-[1,2,4]triazolo[1,5-a]pyridine,
5-Methyl-2-(2-(1-methyl-3-(pyrrolidin-1-yl)-1H-1,2,4-triazol-5-yl)ethyl)-[1,2,4]triazolo[1,5-a]pyridine,
7,8-Dimethyl-2-(2-(1-methyl-3-(pyrrolidin-1-yl)-1H-1,2,4-triazol-5-yl)ethyl)-[1,2,4]triazolo[1,5-a]pyridine,
7,8-Dimethyl-2-(2-(1-methyl-5-(pyrrolidin-1-yl)-1H-1,2,4-triazol-3-yl)ethyl)-[1,2,4]triazolo[1,5-a]pyridine,
2[2-(2-Ethyl-5-pyrrolidin-1-yl-2H-[1,2,4]triazol-3-yl)-ethyl]-3-methyl-quinoxaline,
6-Chloro-5,8-dimethyl-2-(2-(1-methyl-5-(pyrrolidin-1-yl)-1H-1,2,4-triazol-3-yl)vinyl)-[1,2,4]triazolo[1,5-a]pyridine,
6-Chloro-5,8-dimethyl-2-(2-(1-methyl-5-(pyrrolidin-1-yl)-1H-1,2,4-triazol-3-yl)ethyl)-[1,2,4]triazolo[1,5-a]pyridine,
5,8-Dimethyl-2-(2-(1-methyl-3-(pyrrolidin-1-yl)-1H-1,2,4-triazol-5-yl)ethyl)-[1,2,4]triazolo[1,5-a]pyridine,
6-Chloro-5,8-dimethyl-2-(2-(1-methyl-3-(pyrrolidin-1-yl)-1H-1,2,4-triazol-5-yl)ethyl)-[1,2,4]triazolo[1,5-a]pyridine,
2-{2-[5-(3-Fluoro-azetidin-1-yl)-2-methyl-2H-[1,2,4]triazol-3-yl]-ethyl}-5,8-dimethyl-[1,2,4]triazolo[1,5-a]pyrazine,
5,6-Dimethyl-2-(2-(1-methyl-3-(pyrrolidin-1-yl)-1H-1,2,4-triazol-5-yl)ethyl)-[1,2,4]triazolo[1,5-a]pyridine,
5,6, 8-Trimethyl-2-(2-(1-methyl-3-(pyrrolidin-1-yl)-1H-1,2,4-triazol-5-yl)ethyl)-[1,2,4]triazolo[1,5-a]pyrazine,
5,7, 8-Trimethyl-2-(2-(1-methyl-3-(pyrrolidin-1-yl)-1H-1,2,4-triazol-5-yl)ethyl)-[1,2,4]triazolo[1,5-c]pyrimidine,
2-{2-[5-(3-Methoxy-pyrrolidin-1-yl)-2-methyl-2H-[1,2,4]triazol-3-yl]-ethyl}-5,8-dimethyl-[1,2,4]triazolo[1,5-a]pyrazine,
8-Chloro-5,7-dimethyl-2-(2-(1-methyl-3-(pyrrolidin-1-yl)-1H-1,2,4-triazol-5-yl)ethyl)-[1,2,4]triazolo[1,5-c]pyrimidine,
5,7-Dimethyl-2-(2-(1-methyl-3-(pyrrolidin-1-yl)-1H-1,2,4-triazol-5-yl)ethyl)-[1,2,4]triazolo[1,5-c]pyrimidine,
6-Chloro-5,8-dimethyl-2-[(1 S,2 S)-2-(2-methyl-5-pyrrolidin-1-yl-2H-[1,2,4]triazol-3-yl)-cyclopropyl]-[1,2,4]triazolo[1,5-a]pyridine,
2-((1-Ethyl-5-(pyrrolidin-1-yl)-1H-1,2,4-triazol-3-yl)ethynyl)-5,8-dimethyl-[1,2,4]triazolo[1,5-a]pyrazine,
2-(2-(1-Ethyl-5-(pyrrolidin-1-yl)-1H-1,2,4-triazol-3-yl)ethyl)-5,8-dimethyl-[1,2,4]triazolo[1,5-a]pyrazine,
5,8-Dimethyl-2[2-(2-methyl-5-piperidin-1-yl-2H-[1,2,4]triazol-3-yl)-ethyl]-[1,2,4]triazolo[1,5-a]pyrazine,
5-Ethyl-8-methyl-2-(2-(1-methyl-3-(pyrrolidin-1-yl)-1H-1,2,4-triazol-5-yl)ethyl)-[1,2,4]triazolo[1,5-c]pyrimidine,
5,8-Dimethyl-2-{2[2-methyl-5-(2-methyl-pyrrolidin-1-yl)-2H-[1,2,4]triazol-3-yl]-ethyl}-[1,2,4]triazolo[1,5-a]pyrazine,
6,8-Dichloro-5-methyl-2[2-(2-methyl-5-pyrrolidin-1-yl-2H-[1,2,4]triazol-3-yl)-ethyl]-[1,2,4]triazolo[1,5-a]pyridine,
2-(2-(1-Methyl-3-(pyrrolidin-1-yl)-1H-1,2,4-triazol-5-yl)ethyl)-[1,2,4]triazolo[1,5-a]pyridine-6-carbonitrile,
8-Chloro-2-(2-(1-methyl-3-(pyrrolidin-1-yl)-1H-1,2,4-triazol-5-yl)ethyl)-6-(trifluoromethyl)-[1,2,4]triazolo[1,5-a]pyridine,
7-Methyl-2-(2-(1-methyl-3-(pyrrolidin-1-yl)-1H-1,2,4-triazol-5-yl)ethyl)-8-nitro-[1,2,4]triazolo[1,5-a]pyridine,
2-(2-(1-Methyl-3-(pyrrolidin-1-yl)-1H-1,2,4-triazol-5-yl)ethyl)-[1,2,4]triazolo[1,5-a]quinoline,
5-Methyl-2-(2-(1-methyl-3-(pyrrolidin-1-yl)-1H-1,2,4-triazol-5-yl)ethyl)-[1,2,4]triazolo[1,5-a]pyrazine,
5,8-Dimethyl-2[2-(2-methyl-5-pyrrolidin-1-yl-2H-[1,2,4]triazol-3-yl)-ethyl]-[1,2,4]triazolo[1,5-c]pyrimidine,
6,8-Dichloro-2-{2[2-(4-methoxy-benzyl)-5-pyrrolidin-1-yl-2H-[1,2,4]triazol-3-yl]-ethyl}-5-methyl-[1,2,4]triazolo[1,5-a]pyridine,
6,8-Dichloro-2-(2-(1-(4-methoxybenzyl)-5-(pyrrolidin-1-yl)-1H-1,2,4-triazol-3-yl)ethyl)-5-methyl-[1,2,4]triazolo[1,5-a]pyridine,
6-Fluoro-2-(2-(1-methyl-3-(pyrrolidin-1-yl)-1H-1,2,4-triazol-5-yl)ethyl)-7-(trifluoromethyl)-[1,2,4]triazolo[1,5-a]pyridin-5-amine,
2-(2-(1-Methyl-3-(pyrrolidin-1-yl)-1H-1,2,4-triazol-5-yl)ethyl)-5-(trifluoromethyl)-[1,2,4]triazolo[1,5-a]pyridine, 8-Bromo-2-(2-(1-methyl-3-(pyrrolidin-1-yl)-1H-1,2,4-triazol-5-yl)ethyl)-6-(trifluoromethyl)-[1,2,4]triazolo[1,5-a]pyridine, 2-(2-(1-Methyl-3-(pyrrolidin-1-yl)-1H-1,2,4-triazol-5-yl)ethyl)-7-(trifluoromethyl)-[1,2,4]triazolo[1,5-a]pyridine, 2-(2-(1-Methyl-3-(pyrrolidin-1-yl)-1H-1,2,4-triazol-5-yl)ethyl)-[1,2,4]triazolo[1,5-a]pyridine-7-carbonitrile, 6,8-Dichloro-5-methyl-2[2-(5-pyrrolidin-1-yl-1H-[1,2,4]triazol-3-yl)-ethyl]-[1,2,4]triazolo[1,5-a]pyridine, 6-Chloro-5-methyl-2[2-(2-methyl-5-pyrrolidin-1-yl-2H-[1,2,4]triazol-3-yl)-ethyl]-8-trifluoromethyl-[1,2,4]triazolo[1,5-a]pyridine, 5-Methyl-2-(2-(1-methyl-3-(pyrrolidin-1-yl)-1H-1,2,4-triazol-5-yl)ethyl)-[1,2,4]triazolo[1,5-a]pyridine-6-carbonitrile, 8-Bromo-6-chloro-5-methyl-2[2-(2-methyl-5-pyrrolidin-1-yl-2H-[1,2,4]triazol-3-yl)-ethyl]-[1,2,4]triazolo[1,5-a]pyridine, 6-Bromo-8-chloro-5-methyl-2-(2-(1-methyl-3-(pyrrolidin-1-yl)-1H-1,2,4-triazol-5-yl)ethyl)-[1,2,4]triazolo[1,5-a]pyridine, 6-Chloro-8-methanesulfonyl-5-methyl-2-[2-(2-methyl-5-pyrrolidin-1-yl-2H-[1,2,4]triazol-3-yl)-ethyl]-[1,2,4]triazolo[1,5-a]pyridine, 8-Chloro-5-methyl-2[2-(2-methyl-5-pyrrolidin-1-yl-2H-[1,2,4]triazol-3-yl)-ethyl]-[1,2,4]triazolo[1,5-a]pyridine-6-carbonitrile, 8-Ethyl-5-methyl-2-(2-(1-methyl-3-(pyrrolidin-1-yl)-1H-1,2,4-triazol-5-yl)ethyl)-[1,2,4]triazolo[1,5-c]pyrimidine, 6-Chloro-8-methoxy-5-methyl-2-[2-(2-methyl-5-pyrrolidin-1-yl-2H-[1,2,4]triazol-3-yl)-ethyl]-[1,2,4]triazolo[1,5-a]pyridine, 6-Chloro-8-cyclopropyl-5-methyl-2-[2-(2-methyl-5-pyrrolidin-1-yl-2H-[1,2,4]triazol-3-yl)-ethyl]-[1,2,4]triazolo[1,5-a]pyridine, 5-Methyl-2-[2-(2-methyl-5-pyrrolidin-1-yl-2H-[1,2,4]triazol-3-yl)-ethyl]-[1,2,4]triazolo[1,5-a]pyridine-6,8-dicarbonitrile, 6-Chloro-5-methyl-2[2-(2-methyl-5-pyrrolidin-1-yl-2H-[1,2,4]triazol-3-yl)-ethyl]-[1,2,4]triazolo[1,5-a]pyridine-8-carbonitrile, 2-{6-Chloro-5-methyl-2-[2-(2-methyl-5-pyrrolidin-1-yl-2H-[1,2,4]triazol-3-yl)-ethyl]-[1,2,4]triazolo[1,5-a]pyridin-8-yl}-propan-2-ol, 2-[(E)-2-(5-Azetidin-1-yl-2-methyl-2H-[1,2,4]triazol-3-yl)-vinyl]-5,8-dimethyl-[1,2,4]triazolo[1,5-c]pyrimidine, 6-Bromo-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine, 5-Methyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine-6-carbonitrile, 5,6-Dimethyl-2-(2-(1-methyl-3-(pyrrolidin-1-yl)-1H-1,2,4-triazol-5-yl)ethyl)-8-(trifluoromethyl)-[1,2,4]triazolo[1,5-a]pyridine, 6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-ol, 6-Ethyl-5-methyl-2-[2-(2-methyl-5-pyrrolidin-1-yl-2H-[1,2,4]triazol-3-yl)-ethyl]-8-trifluoromethyl-[1,2,4]triazolo[1,5-a]pyridine, 1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-2-one, 6-Chloro-2-{2-[5-(3,3-difluoro-pyrrolidin-1-yl)-2-methyl-2H-[1,2,4]triazol-3-yl]-ethyl}-5-methyl-8-trifluoromethyl-[1,2,4]triazolo[1,5-a]pyridine, 5,8-Dimethyl-2-{2-[2-methyl-5-(3-methyl-azetidin-1-yl)-2H-[1,2,4]triazol-3-yl]-ethyl}-[1,2,4]triazolo[1,5-a]pyrazine, 2-{2-[5-(3,3-Difluoro-azetidin-1-yl)-2-methyl-2H-[1,2,4]triazol-3-yl]-ethyl}-5,8-dimethyl-[1,2,4]triazolo[1,5-a]pyrazine, 6-Chloro-5-methyl-2-(2-methyl-5-pyrrolidin-1-yl-2H-[1,2,4]triazol-3-ylethynyl)-8-trifluoromethyl-[1,2,4]triazolo[1,5-a]pyridine, 2-{2-[5-(3,3-Difluoro-pyrrolidin-1-yl)-2-methyl-2H-[1,2,4]triazol-3-yl]-ethyl}-5,8-dimethyl-[1,2,4]triazolo[1,5-a]pyrazine, 2-{2-[5-((S)-3-Fluoro-pyrrolidin-1-yl)-2-methyl-2H-[1,2,4]triazol-3-yl]-ethyl}-5,8-dimethyl-[1,2,4]triazolo[1,5-a]pyrazin, 6-Chloro-8-difluoromethoxy-5-methyl-2-[2-(2-methyl-5-pyrrolidin-1-yl-2H-[1,2,4]triazol-3-yl)-ethyl]-[1,2,4]triazolo[1,5-a]pyridine, 2-{2-[5-((R)-3-Fluoro-pyrrolidin-1-yl)-2-methyl-2H-[1,2,4]triazol-3-yl]-ethyl}-5,8-dimethyl-[1,2,4]triazolo[1,5-a]pyrazine, 6-Chloro-5-methyl-2[2-(2-methyl-5-pyrrolidin-1-yl-2H-[1,2,4]triazol-3-yl)-ethyl]-8-(2,2,2-trifluoro-ethoxy)-[1,2,4]triazolo[1,5-a]pyridine, 5,8-Dimethyl-2-{2[2-methyl-5-((S)-2-methyl-pyrrolidin-1-yl)-2H-[1,2,4]triazol-3-yl]-ethyl}-[1,2,4]triazolo[1,5-a]pyrazine, 5,8-Dimethyl-2-{2[2-methyl-5-((R)-2-methyl-pyrrolidin-1-yl)-2H-[1,2,4]triazol-3-yl]-ethyl}-[1,2,4]triazolo[1,5-a]pyrazine, 2-[(E)-2-(5-Azepan-1-yl-2-methyl-2H-[1,2,4]triazol-3-yl)-vinyl]-5,8-dimethyl-[1,2,4]triazolo[1,5-a]pyrazine, 7,8-Dimethyl-2-(2-(1-methyl-3-(pyrrolidin-1-yl)-1H-1,2,4-triazol-5-yl)ethyl)-5-(trifluoromethyl)-[1,2,4]triazolo[1,5-c]pyrimidine, 1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-ol, 6-Chloro-5-methyl-2-[2-(1-methyl-5-pyrrolidin-1-yl-1H-[1,2,4]triazol-3-yl)-ethyl]-8-trifluoromethyl-[1,2,4]triazolo[1,5-a]pyridine, 6-Chloro-8-difluoromethoxy-5-methyl-2[2-(1-methyl-5-pyrrolidin-1-yl-1H-[1,2,4]triazol-3-yl)-ethyl]-[1,2,4]triazolo[1,5-a]pyridine, ((R)-1-{5-[2-(5,8-Dimethyl-[1,2,4]triazolo[1,5-a]pyrazin-2-yl)-ethyl]-1-methyl-1H-[1,2,4]triazol-3-yl}-pyrrolidin-3-yl)-carbamic acid tert-butyl ester, 5,8-Dimethyl-2-(2-methyl-5-pyrrolidin-1-yl-2H-[1,2,4]triazol-3-ylethynyl)-[1,2,4]triazolo[1,5-a]pyrazine, 5,8-Dimethyl-2[2-(2-phenyl-5-pyrrolidin-1-yl-2H-[1,2,4]triazol-3-yl)-ethyl]-[1,2,4]triazolo[1,5-a]pyrazine, 2-{2-[2-(2,2-Difluoro-ethyl)-5-pyrrolidin-1-yl-2H-[1,2,4]triazol-3-yl]-ethyl}-5,8-dimethyl-[1,2,4]triazolo[1,5-a]pyrazine, 5,8-Dimethyl-2-{2[2-methyl-5-(2-methyl-pyrrolidin-1-yl)-2H-[1,2,4]triazol-3-yl]-ethyl}-[1,2,4]triazolo[1,5-c]pyrimidine, 5,8-Dimethyl-2-{2[2-methyl-5-((S)-2-methyl-pyrrolidin-1-yl)-2H-[1,2,4]triazol-3-yl]-ethyl}-[1,2,4]triazolo[1,5-c]pyrimidine, 5,8-Dimethyl-2-{2[2-methyl-5-((R)-2-methyl-pyrrolidin-1-yl)-2H-[1,2,4]triazol-3-yl]-ethyl}-[1,2,4]triazolo[1,5-c]pyrimidine, 5,8-Dimethyl-2-{2[2-methyl-5-((R)-2-trifluoromethyl-pyrrolidin-1-yl)-2H-[1,2,4]triazol-3-yl]-ethyl}-[1,2,4]triazolo[1,5-a]pyrazine, 5,8-Dimethyl-2-{2[2-methyl-5-((S)-3-methyl-pyrrolidin-1-yl)-2H-[1,2,4]triazol-3-yl]-ethyl}-[1,2,4]triazolo[1,5-a]pyrazine, 5,8-Dimethyl-2-{2[2-methyl-5-((R)-3-methyl-pyrrolidin-1-yl)-2H-[1,2,4]triazol-3-yl]-thyl}-[1,2,4]triazolo[1,5-a]pyrazine, 2[2-(2-Cyclopropylmethyl-5-pyrrolidin-1-yl-2H-[1,2,4]triazol-3-yl)-ethyl]-5, 8-dimethyl-[1,2,4]triazolo[1,5-a]pyrazine, 2-[2-(1-Cyclopropylmethyl-5-pyrrolidin-1-yl-1H-[1,2,4]triazol-3-yl)-ethyl]-5, 8-dimethyl-[1,2,4]triazolo[1,5-a]pyrazine (b), 5,8-Dimethyl-2-{2[2-methyl-5-((R)-2-trifluoromethyl-pyrrolidin-1-yl)-2H-[1,2,4]triazol-3-yl]-ethyl}-[1,2,4]triazolo[1,5-c]pyrimidine, 6-Chloro-8-(2-methoxyethoxy)-5-methyl-2-[2-(2-methyl-5-pyrrolidin-1-yl-1,2,4-triazol-3-yl)ethyl]-[1,2,4]triazolo[1,5-a]pyridine, 6-Chloro-5-methyl-2-(2-(1-methyl-3-(pyrrolidin-1-yl)-1H-1,2,4-triazol-5-yl)ethyl)-8-(tetrahydro-2H-pyran-4-yloxy)-[1,2,4]triazolo[1,5-a]pyridine, 4-[2-[[6-Chloro-5-methyl-2-[2-(2-methyl-5-pyrrolidin-1-yl-1,2,4-triazol-3-yl)ethyl]-[1,2,4]triazolo[1,5-a]pyridin-8-yl]oxy]ethyl]morpholine, 6-Chloro-5-methyl-2-(2-(3-(pyrrolidin-1-yl)-1-(tetrahydro-2H-pyran-4-yl)-1H-1,2,4-triazol-5-yl)ethyl)-8-(trifluoromethyl)-[1,2,4]triazolo[1,5-a]pyridine, 2[2-(2-Cyclopropyl-5-pyrrolidin-1-yl-2H-[1,2,4]triazol-3-yl)-ethyl]-5, 8-dimethyl-[1,2,4]triazolo[1,5-a]pyrazine, 2-[2-(1-Cyclopropyl-5-pyrrolidin-1-yl-1H-[1,2,4]triazol-3-yl)-ethyl]-5, 8-dimethyl-[1,2,4]triazolo[1,5-a]pyrazine (b, 2-{2-[5-((R)-2-Methoxymethyl-pyrrolidin-1-yl)-2-methyl-2H-[1,2,4]triazol-3-yl]-ethyl}-5,8-dimethyl-[1,2,4]triazolo[1,5-a]pyrazine, 2-(6-Chloro-5-methyl-2-(2-(1-methyl-3-(pyrrolidin-1-yl)-1H-1,2,4-triazol-5-yl)ethyl)-[1,2,4]triazolo[1,5-a]pyridin-8-yloxy)-1-morpholinoethanone, (−)-5,8-Dimethyl-2-(2-(1-methyl-3-(pyrrolidin-1-yl)-1H-1,2,4-triazol-5-yl)propyl)-[1,2,4]triazolo[1,5-a]pyrazine, (R)-6-Chloro-2-(2-(3-(3-fluoropyrrolidin-1-yl)-1-methyl-1H-1,2,4-triazol-5-yl)ethyl)-5-methyl-8-(trifluoromethyl)-[1,2,4]triazolo[1,5-a]pyridine, 6-Chloro-5-methyl-2-(2-(3-(pyrrolidin-1-yl)-1H-1,2,4-triazol-5-yl)ethyl)-8-(trifluoromethyl)-[1,2,4]triazolo[1,5-a]pyridine, 2-{2-[5-(3-Difluoromethyl-pyrrolidin-1-yl)-2-methyl-2H-[1,2,4]triazol-3-yl]-ethyl}-5,8-dimethyl-[1,2,4]triazolo[1,5-a]pyrazine, 6-Chloro-8-(difluoromethyl)-5-methyl-2-(2-(1-methyl-3-(pyrrolidin-1-yl)-1H-1,2,4-triazol-5-yl)ethyl)-[1,2,4]triazolo[1,5-a]pyridine, 6-Chloro-2-(2-(1-cyclopropyl-5-(pyrrolidin-1-yl)-1H-1,2,4-triazol-3-yl)ethyl)-5-methyl-8-(trifluoromethyl)-[1,2,4]triazolo[1,5-a]pyridine, 6-Chloro-2-(2-(1-cyclopropyl-3-(pyrrolidin-1-yl)-1H-1,2,4-triazol-5-yl)ethyl)-5-methyl-8-(trifluoromethyl)-[1,2,4]triazolo[1,5-a]pyridine, 7-chloro-2-((1-(4-methoxybenzyl)-5-(pyrrolidin-1-yl)-1H-1,2,4-triazol-3-yl)ethynyl)quinoxaline, 7-chloro-2-(2-(5-(pyrrolidin-1-yl)-1H-1,2,4-triazol-3-yl)ethyl)quinoxaline, 6-Chloro-3-methyl-2-(2-methyl-5-pyrrolidin-1-yl-2H-[1,2,4]triazol-3-ylethynyl)-quinoxaline, and, 6-Chloro-2-methyl-3-(2-methyl-5-pyrrolidin-1-yl-2H-[1,2,4]triazol-3-ylethynyl)-quinoxaline.

7. A method comprising administering an effective amount of a compound according to formula I for the treatment of schizophrenia, positive, negative and/or cognitive symptoms associated with schizophrenia, delusional disorder, substance-induced psychotic disorder, panic disorder, obsessive/compulsive disorders, acute stress disorder, generalized anxiety disorder, drug addictions, Parkinson's disease, restless leg syndrome, Alzheimer's disease, multi-infarct dementia, depression, bipolar disorders, psychosis, attention-deficit/hyperactivity disorder, attentional disorders, Huntington's disease, or multiple sclerosis.

8. A process for the preparation of compounds of formula (Ia) or (Ib)

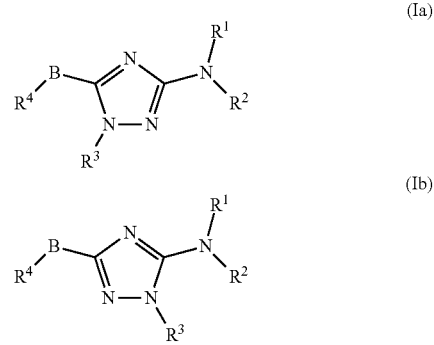

which process comprises
a) reacting a compound of formula (Id)

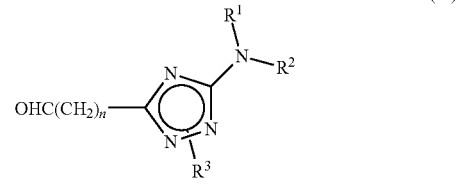

with
b) compound of formula (4a)

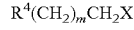

(4a)

to a compound of formula (Ie)

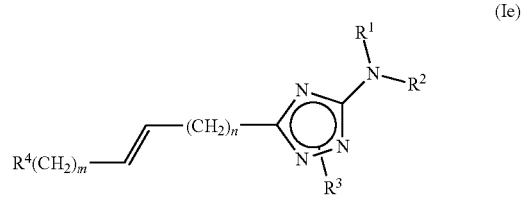

wherein
n and m are 0 or 1;
X is an alkylsulfonate, iodide or bromide;
B is $C_2$-alkenylene, or $C_2$-alkynylene;
$R^1$ and $R^2$ together with the nitrogen atom to which they are attached, form a 4 to 7 membered heterocycloalkyl which can be substituted by 1 to 3 substituents independently selected from the group consisting of halogen, $C_1$-$C_7$-alkyl, $C_1$-$C_7$-hydroxyalkyl, $C_1$-$C_7$-alkoxy, $C_1$-$C_7$-haloalkyl, hydroxyl, and oxo;

$R^3$ is selected from hydrogen, $C_1$-$C_7$-alkyl, $C_3$-$C_5$-cycloalkyl, $C_1$-$C_7$-alkoxyalkyl, $C_1$-$C_7$-haloalkyl, —$(CH_2)_{1,2}$-aryl optionally substituted by $C_1$-$C_7$ alkoxy, and —$(CH_2)_{1,2}$—$C_3$-$C_5$-cycloalkyl;

$R^4$ is an optionally substituted heteroaryl group selected from (a), (b), (c), (d) or (e)

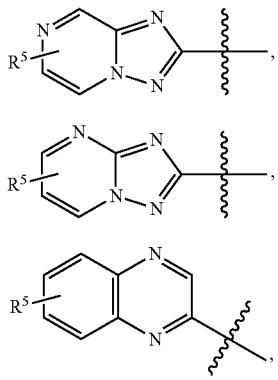

(a)

(b)

(c)

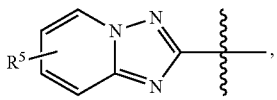

(d)

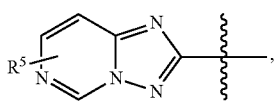

(e)

wherein $R^5$ is selected from halogen, $C_1$-$C_7$-alkyl, $C_1$-$C_7$-hydroxyalkyl, $C_1$-$C_7$-haloalkoxy, $C_1$-$C_7$-haloalkyl, $C_3$-$C_5$-cycloalkyl, cyano, amino, nitro, —O—$R^6$—C(O)—$R^7$, —$SO_2R^8$ or $C_1$-$C_2$-alkoxy optionally substituted by $C_1$-$C_2$-alkoxy, heterocycloalkyl;

$R^6$ and $R^8$ are each from $C_1$-$C_7$-alkyl;

$R_7$ is heterocycloalkyl.

9. The process of claim 8, wherein n=0 and m=0.

* * * * *